United States Patent
Zavoronkovs et al.

(10) Patent No.: US 11,530,199 B2
(45) Date of Patent: Dec. 20, 2022

(54) ANALOGS FOR THE TREATMENT OF DISEASE

(71) Applicant: Insilico Medicine IP Limited, Hong Kong (HK)

(72) Inventors: Aleksandrs Zavoronkovs, Pak Shek Kok (HK); Aleksandr Aliper, Ramenskoye (RU); Vladimir Aladinskiy, Kaliningrad (RU); Andrey Kukharenko, Moscow (RU)

(73) Assignee: Insilico Medicine IP Limited, Hong Kong (HK)

( * ) Notice: Subject to any disclaimer, the term of this patent is extended or adjusted under 35 U.S.C. 154(b) by 11 days.

(21) Appl. No.: 17/678,315

(22) Filed: Feb. 23, 2022

(65) Prior Publication Data
US 2022/0289723 A1 Sep. 15, 2022

(30) Foreign Application Priority Data

Feb. 24, 2021 (WO) ............... PCT/CN2021/077706
Dec. 29, 2021 (WO) ............... PCT/CN2021/142622

(51) Int. Cl.
| | |
|---|---|
| *C07D 403/06* | (2006.01) |
| *C07D 403/14* | (2006.01) |
| *C07D 233/90* | (2006.01) |
| *C07D 401/04* | (2006.01) |
| *A61P 11/00* | (2006.01) |
| *C07D 405/04* | (2006.01) |
| *A61P 13/12* | (2006.01) |
| *C07D 487/08* | (2006.01) |

(52) U.S. Cl.
CPC ............ *C07D 403/14* (2013.01); *A61P 11/00* (2018.01); *A61P 13/12* (2018.01); *C07D 233/90* (2013.01); *C07D 401/04* (2013.01); *C07D 405/04* (2013.01); *C07D 487/08* (2013.01)

(58) Field of Classification Search
CPC ... C07D 403/06; C07D 403/14; A61K 31/496
USPC .................................. 544/370; 514/254.05
See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 5,013,556 | A | 5/1991 | Woodle et al. |
| 5,846,514 | A | 12/1998 | Foster et al. |
| 6,334,997 | B1 | 1/2002 | Foster et al. |
| 7,314,885 | B2 | 1/2008 | Aronov et al. |
| 9,556,179 | B2 | 1/2017 | Velaparthi et al. |
| 2007/0105900 | A1 | 5/2007 | Berdini et al. |
| 2009/0227588 | A1 | 9/2009 | Fleck et al. |
| 2020/0270231 | A1 | 8/2020 | Aliper et al. |
| 2020/0270234 | A1 | 8/2020 | Aliper et al. |

FOREIGN PATENT DOCUMENTS

| | | |
|---|---|---|
| CN | 1505625 A | 6/2004 |
| CN | 1505628 A | 6/2004 |
| WO | WO-9847894 A1 | 10/1998 |
| WO | WO-0157022 A2 | 8/2001 |
| WO | WO-0240468 A1 | 5/2002 |
| WO | WO-02088097 A1 | 11/2002 |
| WO | WO-2010090716 A1 | 8/2010 |
| WO | WO-2016038583 A1 | 3/2016 |
| WO | WO-2020170202 A1 | 8/2020 |
| WO | WO-2020170203 A1 | 8/2020 |

OTHER PUBLICATIONS

Patani, et. al. Chem. Rev. 1996, 96, 3147-3176. (Year: 1996).*
International search report with written opinion dated May 19, 2022 for PCT/CN2022/077477.
Registry No. 2215364-32-0, File Registry on STN, entered STN: Apr. 19, 2018.
Aschcroft, et al. Simple method of estimating severity of pulmonary fibrosis on a numerical scale. J Clin Pathol. Apr. 1988; 41(4): 467-470. doi: 10.1136/jcp.41.4.467.
Carlson, et al. Systematically Mitigating the p38α Activity of Triazole-based BET Inhibitors. ACS Med Chem Lett. Aug. 2, 2019;10(9):1296-1301. doi: 10.1021/acsmedchemlett.9b00227. eCollection Sep. 12, 2019.
Clark, et al. Chemistry of micrococcin P. VII. Dimethyl micrococcinate and some synthetic pyridine-polythiazole carboxylic esters. J Chem Soc Perkin 1. 1966;16:1354-1356. doi: 10.1039/j39660001354.
Co-pending U.S. Appl. No. 17/678,301, inventors Zavoronkovs; Aleksandrs et al., filed Feb. 23, 2022.
Eppstein, et al. Biological activity of liposome-encapsulated murine interferon gamma is mediated by a cell membrane receptor. Proc Natl Acad Sci USA. Jun. 1985; 82(11): 3688-3692. doi: 10.1073/pnas.82.11.3688.
Evans. Synthesis of radiolabeled compounds. J Radioanal Chem 64(1-2):9-32 (1981).
Fedorak, et al. A novel colon-specific steroid prodrug enhances sodium chloride absorption in rat colitis. Am J Physiol. Aug. 1995;269(2 Pt 1):G210-8.
Hochhaus et al. A selective HPLC/RIA for dexamethasone and its prodrug dexamethasone-21-sulphobenzoate sodium in biological fluids. Biomed. Chrom. 6:283-286 (1992).

(Continued)

*Primary Examiner* — Jeffrey H Murray
(74) *Attorney, Agent, or Firm* — Wilson Sonsini Goodrich & Rosati

(57) ABSTRACT

The disclosure provides TNIK and/or MAP4K4 kinases inhibitors for the treatment of disease. In one aspect, disclosed herein are kinase inhibitors having a structure of Formula (A), (A*), (I), (IIA), or (IIB). Further described herein are pharmaceutical composition comprising these compounds and methods of using these compounds. In one aspect, disclosed herein are methods of treating a disease or condition by administering the kinases inhibitors described herein.

30 Claims, No Drawings

(56) References Cited

OTHER PUBLICATIONS

Hubner et al. Standardized Quantification of Pulmonary Fibrosis in Histological Samples. BioTechniques 44(4):507-17 (2008).
Hwang, et al. Hepatic uptake and degradation of unilamellar sphingomyelin/cholesterol liposomes: A kinetic study. Proc Natl Acad Sci USA. Jul. 1980;77(7):4030-4034. doi: 10.1073/pnas.77.7.4030.
Kabalka et al. The Synthesis of Radiolabeled Compounds via Organometallic Intermediates. Tetrahedron 45(21):6601-6621 (1989).
Larsen et al. Prodrug forms for the sulfonamide group. I. Evaluation of N-acyl derivatives, N-sulfonylamindes, N-sulfonylsulfilimines and sulfonylureas as possible prodrug derivatives. Int. J. Pharmaceutics 37:87-95 (1987).
Larsen et al. Prodrug forms for the sulfonamide group. II. water-soluble amino acid derivatives of N-methylsulfonylamindes as possible prodrug derivatives. Int'l J of Pharmaceutics 47:103-110 (1988).
McLeod et al. A glucocorticoid prodrug facilitates normal mucosal function in rat colitis without adrenal suppression. Gastroenterol 106:405-413 (1994).
Registry No. 1349069-58-4, File Registry on STN, entered STN: Dec. 5, 2011.
Registry No. 1357751-66-6, File Registry on STN, entered STN: Feb. 28, 2012.
Registry No. 1359379-48-8, File Registry on STN, entered STN: Mar. 2, 2012.
Registry No. 214408-80-7, File Registry on STN, entered STN: Nov. 18, 1998.
Registry No. 254964-43-7, File Registry on STN, entered STN: Feb. 6, 2000.
Sinkula et al. Rationale for design of biologically reversible drug derivatives: prodrugs. J. Pharm. Sci. 64:181-210 (1975).
STN search results, RN 1359379-48-8 . . . , RN951603-22-8, etc., entered STN: Mar. 2, 2012-Oct. 26, 2007 Structure formula. (46 pages).

* cited by examiner

ANALOGS FOR THE TREATMENT OF DISEASE

CROSS REFERENCE

This application claims the benefit of International Application No. PCT/CN2021/077706, filed Feb. 24, 2021 and International Application No. PCT/CN2021/142622, filed Dec. 29, 2021, each of which is hereby incorporated by reference in its entirety.

BACKGROUND OF THE INVENTION

A biologically active enzyme known as Traf2- and Nck-interacting protein kinase is an enzyme commonly known as the TNIK in humans, and which is encoded by the TNIK gene. TNIK as a serine/threonine kinase is involved in various biological processes. There is a need for new drug candidates that can target TNIK.

SUMMARY OF THE INVENTION

TNIK is a serine/threonine kinase that is involved in various biological processes including acting as an essential regulatory component of the Wnt signaling pathway. TNIK directly binds TCF4 and b-catenin and phosphorylates TCF4. Additionally, TNIK plays an activator of Wnt target gene expression and modulates the actin cytoskeleton and activates the c-Jun N-terminal kinase pathway, which is responsive to stress. It is also part of a signaling complex composed of NEDD4, RAP2A, and TNIK, which regulates neuronal dendrite extension and arbonization during development. More generally, TNIK may play a role in cytoskeletal rearrangement and regulate cell spreading. TNIK also causes weak Smad1 T322 phosphorylation, involved in TGF-b1 signaling transduction.

TNIK is considered to be a germinal center kinase (GCK), which can be characterized by an N-terminal kinase domain and a C-terminal GCK domain that serves a regulatory function.

TNIK activation of Wnt signaling plays important roles in carcinogenesis and embryonic development. Mutations in this gene are associated with an autosomal recessive form of cognitive disability.

Additionally, TNIK is linked to cancer, including for example, colorectal cancer. As such, TNIK has been identified as an attractive candidate for drugs targeting certain cancers.

The current data imply TNIK is a potential target for the generation of small molecule inhibitors to specifically block the Wnt pathway in disease states such as colorectal cancer or the autosomal recessive form of cognitive disability.

Also, it is known that TGF-β-activated EMT can be identified through the attenuation of Smad and non-Smad signaling pathways, including the Wnt, FF-kB, FAK-Src-paxillin-related focal adhesion, and MAP kinase (ERK and JNK) signaling pathways. As such, therapeutic targets associated with EMT, such as TNIK being target for inhibition, can be used for therapies for treating and/or preventing EMT-based disorders, such as cancer metastasis and fibrosis.

Accordingly, it would be advantageous to have a TNIK inhibitor that can inhibit the kinase activity of TNIK, as a member of the Ste20 family of MAP kinase kinase kinase (MAP4K).

The present disclosure addresses the above need and provides additional advantages as well.

In some aspects, the present disclosure provides a compound represented by Formula (A):

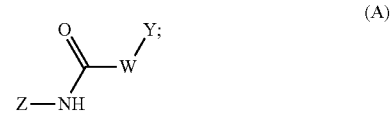

or a pharmaceutically acceptable salt thereof, wherein:

Z is selected from optionally substituted 3- to 12-membered heterocycle and optionally substituted $C_3$-$C_{12}$ carbocycle, wherein the substituents on each are independently selected at each occurrence from one or more —N($R^{10}$)$_2$, halogen, —OH, —CN, —NO$_2$, —NH$_2$, oxo, =S, —$C_{1-10}$ haloalkyl, —O—$C_{1-10}$ alkyl, $C_{2-10}$ alkenyl, $C_{2-10}$ alkynyl, $C_1$-$C_{10}$ alkyl, $C_{3-12}$ carbocycle, 3- to 12-membered heterocycle;

wherein the $C_1$-$C_{10}$ alkyl is optionally substituted with one or more substituents independently selected at each occurrence from halogen, —OH, —CN, —NO$_2$, —NH$_2$, oxo, =S, —$C_{1-10}$ haloalkyl, —O—$C_{1-10}$ alkyl, —O—$C_{1-6}$alkyl-O—C(O)(O—$C_{1-10}$ alkyl), $C_{2-10}$ alkenyl, $C_{2-10}$ alkynyl, $C_{3-12}$ carbocycle, 3- to 12-membered heterocycle;

wherein the $C_{3-12}$ carbocycle and 3- to 12-membered heterocycle are each optionally substituted at each occurrence from one or more substituents independently selected from halogen, —OH, —CN, —NO$_2$, —NH$_2$, oxo, =S, —S(O$_2$)NH$_2$, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, and optionally substituted $C_{1-10}$ alkyl, wherein the optional substituents on the $C_{1-10}$ alkyl are independently selected at each occurrence from one or more hydroxy, halogen, oxo, —$C_{1-10}$ haloalkyl, —NH$_2$, —CN, and —NO$_2$;

$R^{10}$ is selected from optionally substituted $C_1$-$C_6$ alkyl, wherein the optional substituents on $C_1$-$C_6$ alkyl are independently selected at each occurrence from one or more halogen, —OH, —CN, —NO$_2$, —NH$_2$, oxo, =S, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle;

W is selected from optionally substituted 5- to 8-membered heterocycle and optionally substituted $C_3$-$C_8$ carbocycle, wherein the substituents on each are independently selected at each occurrence from one or more halogen, —OH, —CN, —NO$_2$, —NH$_2$, oxo, =S, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, wherein the $C_{3-12}$ carbocycle and 3- to 12-membered heterocycle are each optionally substituted with one or more substituents independently selected at each occurrence from halogen, —OH, —CN, —NO$_2$, —NH$_2$, oxo, =S, $C_{1-10}$ alkyl, —$C_{1-10}$ haloalkyl, and —O—$C_{1-10}$ alkyl; and Y is selected from optionally substituted 5- to 8-membered heterocycle and optionally substituted $C_3$-$C_8$ carbocycle, wherein the substituents on each are independently selected at each occurrence from one or more halogen, —OH, —CN, —NO$_2$, —NH$_2$, oxo, =S, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, wherein the $C_{3-12}$ carbocycle and 3- to 12-membered heterocycle are each optionally substituted with one or more substituents independently selected at each occurrence from halogen, —OH, —CN, —NO$_2$, —NH$_2$, oxo, =S, C$_{1-10}$ alkyl, —C$_{1-10}$ haloalkyl, and —O—C$_{1-10}$ alkyl.

In some aspects, the disclosure provides a compound represented by Formula (A*):

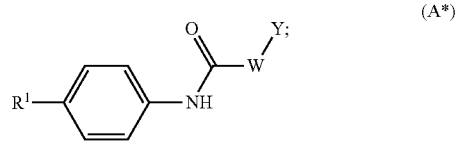

(A*)

R$^1$ is selected from:
- —N(R$^5$)$_2$, wherein R$^5$ is selected from hydrogen, and optionally substituted C$_1$-C$_6$ alkyl, wherein the optional substituents on C$_1$-C$_6$ alkyl are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle;
- optionally substituted C$_1$-C$_6$ alkyl, wherein the substituents on C$_1$-C$_6$ alkyl are independently selected at each occurrence from one or more halogen, —OH, —CN, —NO$_2$, —NH$_2$, oxo, =S, —C$_{1-10}$ haloalkyl, —O—C$_{1-10}$ alkyl, —O—C$_{1-6}$alkyl-O—C(O)(O—C$_{1-10}$ alkyl), C$_{2-10}$ alkenyl, C$_{2-10}$ alkynyl, C$_{3-12}$ carbocycle, 3- to 12-membered heterocycle;
- optionally substituted 3 to 8-membered heterocycle; wherein the optional substituents on the 3 to 8-membered heterocycle are independently selected at each occurrence from one or more halogen, —OH, —CN, —NO$_2$, —NH$_2$, oxo, =S, —S(O$_2$)NH$_2$, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, and optionally substituted C$_{1-10}$ alkyl, wherein the optional substituents on the C$_{1-10}$ alkyl are independently selected at each occurrence from one or more hydroxy, halogen, oxo, —C$_{1-10}$ haloalkyl, —NH$_2$, —CN, and —NO$_2$;

W is selected from optionally substituted 5- to 8-membered heterocycle and optionally substituted C$_3$-C$_8$ carbocycle, wherein the substituents on each are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, wherein the C$_{3-12}$ carbocycle and 3- to 12-membered heterocycle are each optionally substituted with one or more substituents independently selected at each occurrence from halogen, —OH, —CN, —NO$_2$, —NH$_2$, oxo, =S, C$_{1-10}$ alkyl, —C$_{1-10}$ haloalkyl, and —O—C$_{1-10}$ alkyl; and Y is selected from optionally substituted 5- to 8-membered heterocycle and optionally substituted C$_3$-C$_8$ carbocycle, wherein the substituents on each are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, wherein the C$_{3-12}$ carbocycle and 3- to 12-membered heterocycle are each optionally substituted with one or more substituents independently selected at each occurrence from halogen, —OH, —CN, —NO$_2$, —NH$_2$, oxo, =S, C$_{1-10}$ alkyl, —C$_{1-10}$ haloalkyl, and —O—C$_{1-10}$ alkyl.

In certain embodiments, the disclosure provides a compound represented by Formula (I):

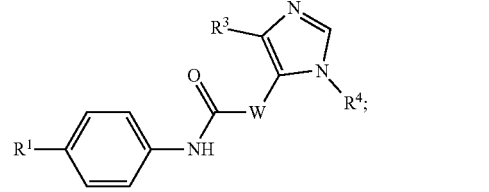

(I)

or a pharmaceutically acceptable salt thereof, wherein:

R$^1$ is selected from:
- —N(R$^5$)$_2$, wherein R$^5$ is selected from hydrogen, and optionally substituted C$_1$-C$_6$ alkyl, wherein the optional substituents on C$_1$-C$_6$ alkyl are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle;
- substituted C$_1$-C$_6$ alkyl, wherein the substituents on C$_1$-C$_6$ alkyl are independently selected at each occurrence from one or more halogen, —OH, —CN, —NO$_2$, —NH$_2$, oxo, =S, —C$_{1-10}$ haloalkyl, —O—C$_{1-10}$ alkyl, —O—C$_{1-6}$alkyl-O—C(O)(O—C$_{1-10}$ alkyl), C$_{2-10}$ alkenyl, C$_{2-10}$ alkynyl, C$_{3-12}$ carbocycle, 3- to 12-membered heterocycle;
- optionally substituted 3 to 8-membered heterocycle; wherein the optional substituents on the 3 to 8-membered heterocycle are independently selected at each occurrence from one or more halogen, —OH, —CN, —NO$_2$, —NH$_2$, oxo, =S, —S(O$_2$)NH$_2$, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, and optionally substituted C$_{1-10}$ alkyl, wherein the optional substituents on the C$_{1-10}$ alkyl are independently selected at each occurrence from one or more hydroxy, halogen, oxo, —C$_{1-10}$ haloalkyl, —NH$_2$, —CN, and —NO$_2$;

R$^3$ is selected from optionally substituted C$_1$-C$_6$ alkyl, optionally substituted 3- to 10-membered heterocycle and optionally substituted C$_{3-10}$ carbocycle, wherein the optional substituents on each are independently selected at each occurrence from one or more halogen, —OH, —CN, —NO$_2$, —NH$_2$, oxo, =S, C$_{1-6}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle;

R$^4$ is selected from:
- hydrogen;
- optionally substituted C$_1$-C$_6$ alkyl, wherein the optional substituents on C$_1$-C$_6$ alkyl are independently selected at each occurrence from one or more halogen, —OH, —CN, —NO$_2$, —NH$_2$, oxo, =S, —O—C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle;
- optionally substituted C$_{3-10}$ carbocycle, wherein the optional substituents on C$_{3-10}$ carbocycle are independently selected at each occurrence from one or more halogen, —OH, —CN, —NO$_2$, —NH$_2$, oxo, =S, C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle; and W is selected from optionally substituted 5- to 8-membered heteroaryl, wherein the substituents on the optionally substituted 5- to 8-membered heteroaryl are independently selected at each occurrence from one or more halogen, —OH, —CN, —NO$_2$, —NH$_2$, oxo, =S, —S(O$_2$)NH$_2$, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle.

In some aspects, the disclosure provides a pharmaceutical composition comprising a compound or salt of Formula (A), Formula (A*), or Formula (I) and a pharmaceutically acceptable excipient.

In some aspects, the disclosure provides a method of treating or preventing disease comprising administering a compound or salt of Formula (A), Formula (A*), or Formula (I) or a pharmaceutical composition comprising a compound or salt of Formula (A), Formula (A*), or Formula (I) and a pharmaceutically acceptable excipient to a subject in need thereof. In some aspects, the disease is a cancer. In some cases, the cancer is selected from colorectal cancer, gastric cancer, breast cancer, lung cancer, pancreatic cancer, prostate cancer, multiple myeloma, chronic myelogenous leukemia, cancer metastasis, fibrosis and psychiatric disorders. In some cases, the pharmaceutical composition can be used as an inhibitor of tumor immunosuppression in combination with chemotherapy or immune checkpoint inhibitor therapy for cancer. In some cases, the pharmaceutical composition can be used to treat a fibrotic disease or condition including but not limited to chronic kidney fibrosis ("CKD"), liver cirrhosis, pulmonary fibrosis, renal interstitial fibrosis, myocardial infarction, skin fibrosis, systemic sclerosis ("SSc"), and graft-versus-host disease ("GVHD"). In some cases, the pharmaceutical composition can be used to treat kidney fibrosis. In some cases, the pharmaceutical composition can be used to treat skin fibrosis. In some cases, the pharmaceutical composition can be used to treat idiopathic pulmonary fibrosis (IPF). In some cases, the pharmaceutical composition can be used to treat a disease is associated with TNIK kinase.

In some aspects, the disclosure provides a method of inhibiting TNIK kinase comprising administering a compound or salt of Formula (A), Formula (A*), or Formula (I) or a pharmaceutical composition comprising a compound or salt of Formula (A), Formula (A*), or Formula (I) and a pharmaceutically acceptable excipient to a subject in need thereof.

In some aspects, the disclosure provides a method of inhibiting MAP4K4 kinase comprising administering a compound or salt of Formula (A), Formula (A*), or Formula (I) or a pharmaceutical composition comprising a compound or salt of Formula (A), Formula (A*), or Formula (I) and a pharmaceutically acceptable excipient to a subject in need thereof.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

DETAILED DESCRIPTION OF THE INVENTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

A. Definitions

Unless defined otherwise, all technical and scientific terms used herein have the same meaning as is commonly understood by one of skill in the art to which this invention belongs. All patents and publications referred to herein are incorporated by reference.

"Alkyl" refers to a straight or branched hydrocarbon chain radical consisting solely of carbon and hydrogen atoms, containing no unsaturation, and preferably having from one to fifteen carbon atoms (i.e., $C_1$-$C_{15}$ alkyl). In certain embodiments, an alkyl comprises one to thirteen carbon atoms (i.e., $C_1$-$C_{13}$ alkyl). In certain embodiments, an alkyl comprises one to eight carbon atoms (i.e., $C_1$-$C_8$ alkyl). In other embodiments, an alkyl comprises one to five carbon atoms (i.e., $C_1$-$C_5$ alkyl). In other embodiments, an alkyl comprises one to four carbon atoms (i.e., $C_1$-$C_4$ alkyl). In other embodiments, an alkyl comprises one to three carbon atoms (i.e., $C_1$-$C_3$ alkyl). In other embodiments, an alkyl comprises one to two carbon atoms (i.e., $C_1$-$C_2$ alkyl). In other embodiments, an alkyl comprises one carbon atom (i.e., $C_1$ alkyl). In other embodiments, an alkyl comprises five to fifteen carbon atoms (i.e., $C_5$-$C_{15}$ alkyl). In other embodiments, an alkyl comprises five to eight carbon atoms (i.e., $C_5$-$C_8$ alkyl). In other embodiments, an alkyl comprises two to five carbon atoms (i.e., $C_2$-$C_5$ alkyl). In other embodiments, an alkyl comprises three to five carbon atoms (i.e., $C_3$-$C_5$ alkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkyl is optionally substituted with oxo, halogen, —CN, —COOH, —COOMe, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

The term "$C_{x-y}$" when used in conjunction with a chemical moiety, such as alkyl, alkenyl, or alkynyl is meant to include groups that contain from x to y carbons in the chain. For example, the term "$C_{1-6}$alkyl" refers to an alkyl group that may consist of 1 carbon atom, 2 carbon atoms, 3 carbon atoms, 4 carbon atoms, 5 carbon atoms or 6 carbon atoms, including straight-chain alkyl and branched-chain alkyl groups.

"Alkoxy" refers to a radical bonded through an oxygen atom of the formula —O-alkyl, where alkyl is an alkyl chain as defined above. Unless stated otherwise specifically in the specification, an alkoxy group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkoxy is optionally substituted with halogen, —CN, —COOH, COOMe, —OH, —OMe, —$NH_2$, or —$NO_2$. In some embodiments, the alkoxy is optionally substituted with halogen, —CN, —OH, or —OMe. In some embodiments, the alkoxy is optionally substituted with halogen.

"Alkenyl" refers to a straight or branched hydrocarbon chain radical group consisting solely of carbon and hydrogen atoms, containing at least one carbon-carbon double bond, and preferably having from two to twelve carbon atoms (i.e., $C_2$-$C_{12}$ alkenyl). In certain embodiments, an alkenyl comprises two to eight carbon atoms (i.e., $C_2$-$C_8$ alkenyl). In certain embodiments, an alkenyl comprises two to six carbon atoms (i.e., $C_2$-$C_6$ alkenyl). In other embodiments, an alkenyl comprises two to four carbon atoms (i.e., $C_2$-$C_4$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkenyl is optionally substituted with oxo, halogen, —CN, —COOH, —COOMe, —OH, —OMe, —$NH_2$, or —$NO_2$. In some embodiments, the alkenyl is optionally substituted with halogen, —CN, —OH, or —OMe. In some embodiments, the alkenyl is optionally substituted with halogen.

"Alkynyl" refers to a straight or branched hydrocarbon chain radical group consisting solely of carbon and hydrogen atoms, containing at least one carbon-carbon triple bond, and preferably having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl comprises two to six carbon atoms (i.e., $C_2$-$C_6$ alkynyl). In other embodiments, an alkynyl comprises two to four carbon atoms (i.e., $C_2$-$C_4$ alkynyl). The alkynyl is attached to the rest of the molecule by a single bond, for example, ethynyl, propynyl, butynyl, pentynyl, hexynyl, and the like. Unless stated otherwise specifically in the specification, an alkynyl group may be optionally substituted, for example, with oxo, halogen, amino, nitrile, nitro, hydroxyl, haloalkyl, alkoxy, carboxyl, carboxylate, aryl, cycloalkyl, heterocycloalkyl, heteroaryl, and the like. In some embodiments, the alkynyl is optionally substituted with oxo, halogen, —CN, —COOH, COOMe, —OH, —OMe, —$NH_2$, or —$NO_2$. In some embodiments, the alkynyl is optionally substituted with halogen, —CN, —OH, or —OMe. In some embodiments, the alkynyl is optionally substituted with halogen.

The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond, respectively. The term —$C_{x-y}$alkenylene- refers to a substituted or unsubstituted alkenylene chain with from x to y carbons in the alkenylene chain. For example, —$C_{2-6}$alkenylene- may be selected from ethenylene, propenylene, butenylene, pentenylene, and hexenylene, any one of which is optionally substituted. An alkenylene chain may have one double bond or more than one double bond in the alkenylene chain. The term —$C_{x-y}$alkynylene- refers to a substituted or unsubstituted alkynylene chain with from x to y carbons in the alkenylene chain. For example, —$C_{2-6}$alkenylene- may be selected from ethynylene, propynylene, butynylene, pentynylene, and hexynylene, any one of which is optionally substituted. An alkynylene chain may have one triple bond or more than one triple bond in the alkynylene chain.

"Alkylene" or "alkylene chain" refers to a straight or branched divalent hydrocarbon chain linking the rest of the molecule to a radical group, consisting solely of carbon and hydrogen, containing no unsaturation, and preferably having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group may be through any two carbons within the chain. In certain embodiments, an alkylene comprises one to ten carbon atoms (i.e., $C_1$-$C_8$ alkylene). In certain embodiments, an alkylene comprises one to eight carbon atoms (i.e., $C_1$-$C_8$ alkylene). In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). In other embodiments, an alkylene comprises five to eight carbon atoms (i.e., $C_5$-$C_8$ alkylene). In other embodiments, an alkylene comprises two to five carbon atoms (i.e., $C_2$-$C_5$ alkylene). In other embodiments, an alkylene comprises three to five carbon atoms (i.e., $C_3$-$C_5$ alkylene). The term —$C_{x-y}$alkylene- refers to a substituted or unsubstituted alkylene chain with from x to y carbons in the alkylene chain. For example —$C_{1-6}$alkylene- may be selected from methylene, ethylene, propylene, butylene, pentylene, and hexylene, any one of which is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group may be through any two carbons within the chain. In certain embodiments, an alkenylene comprises two to ten carbon atoms (i.e., $C_2$-$C_{10}$ alkenylene). In certain embodiments, an alkenylene comprises two to eight carbon atoms (i.e., $C_2$-$C_8$ alkenylene). In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). In other embodiments, an alkenylene comprises five to eight carbon atoms (i.e., $C_5$-$C_8$ alkenylene). In other embodiments, an alkenylene comprises three to five carbon atoms (i.e., $C_3$-$C_5$ alkenylene).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group may be through any two carbons within the chain. In certain embodiments, an alkynylene comprises two to ten carbon atoms (i.e., $C_2$-$C_{10}$ alkynylene). In certain embodiments, an alkynylene comprises two to eight carbon atoms (i.e., $C_2$-$C_8$ alkynylene). In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). In other embodiments, an alkynylene comprises five to eight carbon atoms (i.e., $C_5$-$C_8$ alkynylene). In other embodiments, an alkynylene comprises three to five carbon atoms (i.e., $C_3$-$C_5$ alkynylene).

"Aryl" refers to a radical derived from an aromatic monocyclic or aromatic multicyclic hydrocarbon ring system by removing a hydrogen atom from a ring carbon atom, wherein the ring system contains at least one aromatic ring. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. The aryl radical may be a monocyclic, bicyclic, tricyclic or tetracyclic ring system, which may include fused or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the aryl is optionally substituted with halogen, methyl, ethyl, —CN, —COOH, COOMe, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Heteroalkyl" refers to an alkyl group in which one or more skeletal atoms of the alkyl are selected from an atom other than carbon, e.g., oxygen, nitrogen (e.g., —NH—, —N(alkyl)-), sulfur, phosphorus, or combinations thereof. A heteroalkyl is attached to the rest of the molecule at a carbon atom of the heteroalkyl. In one aspect, a heteroalkyl is a $C_1$-$C_6$ heteroalkyl wherein the heteroalkyl is comprised of 1 to 6 carbon atoms and one or more atoms other than carbon, e.g., oxygen, nitrogen (e.g. —NH—, —N(alkyl)-), sulfur, phosphorus, or combinations thereof wherein the heteroalkyl is attached to the rest of the molecule at a carbon atom of the heteroalkyl. Examples of such heteroalkyl are, for example, —CH$_2$OCH$_3$, —CH$_2$CH$_2$OCH$_3$, —CH$_2$CH$_2$OCH$_2$CH$_2$OCH$_3$, —CH(CH$_3$)OCH$_3$, —CH$_2$NHCH$_3$, —CH$_2$N(CH$_3$)$_2$, —CH$_2$CH$_2$NHCH$_3$, or —CH$_2$CH$_2$N(CH$_3$)$_2$. Unless stated otherwise specifically in the specification, a heteroalkyl is optionally substituted for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a heteroalkyl is optionally substituted with oxo, halogen, methyl, ethyl, —CN, —CF$_3$, —OH, —OMe, —NH$_2$, or —NO$_2$. In some embodiments, a heteroalkyl is optionally substituted with oxo, halogen, methyl, ethyl, —CN, —CF$_3$, —OH, or —OMe. In some embodiments, the heteroalkyl is optionally substituted with halogen.

"Aralkyl" refers to a radical of the formula —$R^c$-aryl where $R^c$ is an alkylene chain as defined above, for example, methylene, ethylene, and the like.

"Aralkenyl" refers to a radical of the formula —$R^d$-aryl where $R^d$ is an alkenylene chain as defined above. "Aralkynyl" refers to a radical of the formula —$R^e$-aryl, where $R^e$ is an alkynylene chain as defined above.

"Carbocycle" refers to a saturated, unsaturated or aromatic ring system in which each ring atom of the ring system is carbon. Carbocycle may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. An aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. In some embodiments, the carbocycle is an aryl. In some embodiments, the carbocycle is a cycloalkyl. In some embodiments, the carbocycle is a cycloalkenyl. In some embodiments, the carbocycle contains a triple bond. Unless stated otherwise specifically in the specification, a carbocycle can be optionally substituted.

"Cycloalkyl" refers to a fully saturated monocyclic or polycyclic hydrocarbon radical consisting solely of carbon and hydrogen atoms, which includes fused or bridged ring systems, and preferably having from three to twelve carbon atoms. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, a cycloalkyl is optionally substituted with oxo, halogen, methyl, ethyl, —CN, —COOH, COOMe, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Heterocycloalkyl" refers to a cycloalkyl group, as defined above, wherein one or more ring carbons are replaced with one or more heteroatoms, such as N, O, P, and S. A heterocycloalkyl may be optionally substituted.

"Cycloalkenyl" refers to an unsaturated non-aromatic monocyclic or polycyclic hydrocarbon radical consisting solely of carbon and hydrogen atoms, which includes fused or bridged ring systems, preferably having from three to twelve carbon atoms and comprising at least one double bond. In certain embodiments, a cycloalkenyl comprises one double bond. In certain embodiments, a cycloalkenyl comprises more than one double bond. In certain embodiments, a cycloalkenyl comprises three to ten carbon atoms. In other embodiments, a cycloalkenyl comprises five to seven carbon atoms. The cycloalkenyl may be attached to the rest of the molecule by a single bond. Examples of monocyclic cycloalkenyls includes, e.g., cyclopentenyl, cyclohexenyl, cycloheptenyl, and cyclooctenyl.

"Heterocycloalkenyl" refers to a cycloalkenyl group, as defined above, wherein one or more ring carbons are replaced with one or more heteroatoms, such as N, O, P, and S. A heterocycloalkenyl may be optionally substituted.

"Cycloalkylalkyl" refers to a radical of the formula —R$^c$-cycloalkyl where R$^c$ is an alkylene chain as described above.

"Cycloalkylalkoxy" refers to a radical bonded through an oxygen atom of the formula —O—R$^c$-cycloalkyl where R$^c$ is an alkylene chain as described above.

"Halo" or "halogen" refers to halogen substituents such as bromo, chloro, fluoro and iodo substituents.

As used herein, the term "haloalkyl" or "haloalkane" refers to an alkyl radical, as defined above, that is substituted by one or more halogen radicals, for example, trifluoromethyl, dichloromethyl, bromomethyl, 2,2,2-trifluoroethyl, 1-fluoromethyl-2-fluoroethyl, and the like. In some embodiments, the alkyl part of the fluoroalkyl radical is optionally further substituted. Examples of halogen substituted alkanes ("haloalkanes") include halomethane (e.g., chloromethane, bromomethane, fluoromethane, iodomethane), di- and trihalomethane (e.g., trichloromethane, tribromomethane, trifluoromethane, triiodomethane), 1-haloethane, 2-haloethane, 1,2-dihaloethane, 1-halopropane, 2-halopropane, 3-halopropane, 1,2-dihalopropane, 1,3-dihalopropane, 2,3-dihalopropane, 1,2,3-trihalopropane, and any other suitable combinations of alkanes (or substituted alkanes) and halogens (e.g., Cl, Br, F, I, etc.). When an alkyl group is substituted with more than one halogen radicals, each halogen may be independently selected e.g., 1-chloro,2-fluoroethane.

"Fluoroalkyl" refers to an alkyl radical, as defined above, that is substituted by one or more fluoro radicals, for example, trifluoromethyl, difluoromethyl, fluoromethyl, 2,2,2-trifluoroethyl, 1-fluoromethyl-2-fluoroethyl, and the like.

"Heterocycle" refers to a saturated, unsaturated or aromatic ring comprising one or more heteroatoms. Exemplary heteroatoms include N, O, Si, P, B, and S atoms. Heterocycles include e.g., 3- to 10-membered monocyclic rings, 6- to 12-membered bicyclic rings, and 6- to 12-membered bridged rings. Each ring of a bicyclic heterocycle may be selected from saturated, unsaturated, and aromatic rings. "Heterocyclene" refers to a divalent heterocycle linking the rest of the molecule to a radical group. Unless stated otherwise specifically in the specification, a heterocycle is optionally substituted, for example, with oxo, halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heterocycle is optionally substituted with halogen, methyl, ethyl, —CN, —CF$_3$, —OH, or —OMe. In some embodiments, the heterocycloalkyl is optionally substituted with halogen. In some embodiments, a heterocycle is a heteroaryl. In some embodiments, a heterocycle is a heterocycloalkyl. In some embodiments, a heterocycle is a heterocycloalkenyl. In some embodiments, a heterocycle contains one or more triple bonds.

In some embodiments, the heterocycle comprises one to three heteroatoms selected from the group consisting of nitrogen, oxygen, and sulfur. In some embodiments, the heterocycle comprises one to three heteroatoms selected from the group consisting of nitrogen and oxygen. In some embodiments, the heterocycle comprises one to three nitrogens. In some embodiments, the heterocycle comprises one or two nitrogens. In some embodiments, the heterocycle comprises one nitrogen. In some embodiments, the heterocycle comprises one nitrogen and one oxygen. Unless stated otherwise specifically in the specification, the heterocycle radical may be a monocyclic, bicyclic, tricyclic or tetracyclic ring system, which may include fused, spiro, or bridged ring systems; and the nitrogen, carbon, or sulfur atoms in the heterocycle radical may be optionally oxidized; the nitrogen atom may be optionally quaternized. Representative heterocycles include, the heteroaryl groups described below. Representative heterocycle also include, but are not limited to, heterocycles having from two to fifteen carbon atoms (C$_2$-C$_{15}$ heterocycloalkyl or C$_2$-C$_{15}$ heterocycloalkenyl), from two to ten carbon atoms (C$_2$-C$_{10}$ heterocycloalkyl or C$_2$-C$_{10}$ heterocycloalkenyl), from two to eight carbon atoms (C$_2$-C$_8$ heterocycloalkyl or C$_2$-C$_8$ heterocycloalkenyl), from two to seven carbon atoms (C$_2$-C$_7$ heterocycloalkyl or C$_2$-C$_7$ heterocycloalkenyl), from two to six carbon atoms (C$_2$-C$_6$ heterocycloalkyl or C$_2$-C$_7$ heterocycloalkenyl), from two to five carbon atoms (C$_2$-C$_5$ heterocycloalkyl or C$_2$-C$_5$ heterocycloalkenyl), or two to four carbon atoms (C$_2$-C$_4$ heterocycloalkyl or C$_2$-C$_4$ heterocycloalkenyl). Examples of such heterocycle radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycle also includes all ring forms of the carbohydrates, including but not limited to the monosaccharides, the disaccharides and the oligosaccharides. In some embodiments, heterocycles have from 2 to 10 carbons in the ring. It is understood that when referring to the number of carbon atoms in a heterocycle, the number of carbon atoms in the heterocycle is not the same as the total number of atoms (including the heteroatoms) that make up the heterocycle (i.e. skeletal atoms of the heterocycle ring). In some embodiments, the heterocycle is a 3- to 8-membered. In some embodiments, the heterocycle is a 3- to 7-membered. In some embodiments, the heterocycle is a 3- to 6-membered. In some embodiments, the heterocycle is a 4- to 6-membered. In some embodiments, the heterocycle is a 5- to 6-membered.

"Heteroaryl" or "aromatic heterocycle" refers to a radical derived from a heteroaromatic ring radical that comprises one to thirteen carbon atoms, at least one heteroatom wherein each heteroatom may be selected from N, O, and S, and at least one aromatic ring. As used herein, the heteroaryl ring may be selected from monocyclic or bicyclic and fused or bridged ring systems rings wherein at least one of the rings in the ring system is aromatic, i.e., it contains a cyclic, delocalized (4n+2) π-electron system in accordance with the Hückel theory. The heteroatom(s) in the heteroaryl radical may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryls include, but are not limited to, pyridine, pyrimidine, oxazole, furan, thiophene, benzthiazole, and imdazopyridine. An "X-membered heteroaryl" refers to the number of endocylic atoms, i.e., X, in the ring. For example, a 5-membered heteroaryl ring or 5-membered aromatic heterocycle has 5 endocylic atoms, e.g., triazole, oxazole, thiophene, etc. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted, for example, with halogen, amino, nitrile, nitro, hydroxyl, alkyl, alkenyl, alkynyl, haloalkyl, alkoxy, carboxyl, carboxylate, aryl, cycloalkyl, heterocycloalkyl, heteroaryl, and the like. In some embodiments, the heteroaryl is optionally substituted with halogen, methyl, ethyl, —CN, —COOH, COOMe, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroaryl is optionally substituted with halogen.

The term "substituted" refers to moieties having substituents replacing a hydrogen on one or more carbons or substitutable heteroatoms, e.g., NH, of the structure. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

In some embodiments, substituents may include any substituents described herein, for example: halogen, hydroxy, oxo (=O), thioxo (=S), cyano (—CN), nitro (—NO$_2$), imino (=N—H), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, and heterocycle, any of which may be optionally substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); wherein each R$^a$ is independently selected from hydrogen, alkyl, cycloalkyl, cycloalkylalkyl, aryl, aralkyl, and heterocycle, wherein each R$^a$, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$R$^a$ (where t is 1 or 2), —R$^b$—S(O)$_t$OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^c$ is a straight or branched alkylene, alkenylene or alkynylene chain.

As used in the specification and claims, the singular form "a", "an" and "the" includes plural references unless the context clearly dictates otherwise.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

The terms "treat," "treating" or "treatment," as used herein, may include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

B. Compounds of the Disclosure

In certain embodiments, the disclosure provides a compound represented by Formula (A):

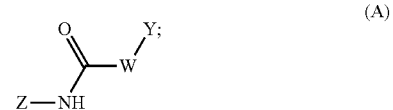

(A)

or a pharmaceutically acceptable salt thereof, wherein:

Z is selected from optionally substituted 3- to 12-membered heterocycle and optionally substituted $C_3$-$C_{12}$ carbocycle, wherein the substituents on each are independently selected at each occurrence from one or more —N($R^{10}$)$_2$, halogen, —OH, —CN, —NO$_2$, —NH$_2$, oxo, =S, —$C_{1-10}$ haloalkyl, —O—$C_{1-10}$ alkyl, $C_{2-10}$ alkenyl, $C_{2-10}$ alkynyl, $C_1$-$C_{10}$ alkyl, $C_{3-12}$ carbocycle, 3- to 12-membered heterocycle;

wherein the $C_1$-$C_{10}$ alkyl is optionally substituted with one or more substituents independently selected at each occurrence from halogen, —OH, —CN, —NO$_2$, —NH$_2$, oxo, =S, —$C_{1-10}$ haloalkyl, —O—$C_{1-10}$ alkyl, —O—$C_{1-6}$alkyl-O—C(O)(O—$C_{1-10}$ alkyl), $C_{2-10}$ alkenyl, $C_{2-10}$ alkynyl, $C_{3-12}$ carbocycle, 3- to 12-membered heterocycle;

wherein the $C_{3-12}$ carbocycle and 3- to 12-membered heterocycle are each optionally substituted at each occurrence from one or more substituents independently selected from halogen, —OH, —CN, —NO$_2$, —NH$_2$, oxo, =S, —S(O$_2$)NH$_2$, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, and optionally substituted $C_{1-10}$ alkyl, wherein the optional substituents on the $C_{1-10}$ alkyl are independently selected at each occurrence from one or more hydroxy, halogen, oxo, —$C_{1-10}$ haloalkyl, —NH$_2$, —CN, and —NO$_2$;

$R^{10}$ is selected from optionally substituted $C_1$-$C_6$ alkyl, wherein the optional substituents on $C_1$-$C_6$ alkyl are independently selected at each occurrence from one or more halogen, —OH, —CN, —NO$_2$, —NH$_2$, oxo, =S, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle;

W is selected from optionally substituted 5- to 8-membered heterocycle and optionally substituted $C_3$-$C_8$ carbocycle, wherein the substituents on each are independently selected at each occurrence from one or more halogen, —OH, —CN, —NO$_2$, —NH$_2$, oxo, =S, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, wherein the $C_{3-12}$ carbocycle and 3- to 12-membered heterocycle are each optionally substituted with one or more substituents independently selected at each occurrence from halogen, —OH, —CN, —NO$_2$, —NH$_2$, oxo, =S, C$_{1-10}$ alkyl, —C$_{1-10}$ haloalkyl, and —O—C$_{1-10}$ alkyl; and Y is selected from optionally substituted 5- to 8-membered heterocycle and optionally substituted C$_3$-C$_8$ carbocycle, wherein the substituents on each are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, wherein the C$_{3-12}$ carbocycle and 3- to 12-membered heterocycle are each optionally substituted with one or more substituents independently selected at each occurrence from halogen, —OH, —CN, —NO$_2$, —NH$_2$, oxo, =S, C$_{1-10}$ alkyl, —C$_{1-10}$ haloalkyl, and —O—C$_{1-10}$ alkyl.

In some aspects, the compound of Formula (A) is represented by Formula (A*).

In some embodiments, for a compound or salt of Formula (A), Z is selected from optionally substituted 3- to 12-membered heterocycle and optionally substituted C$_3$-C$_{12}$ carbocycle, wherein the substituents on each are independently selected at each occurrence from one or more halogen, —OH, —CN, —NO$_2$, —NH$_2$, oxo, =S, —C$_{1-10}$ haloalkyl, —O—C$_{1-10}$ alkyl. In some cases, for Z, the heterocycle includes at least one nitrogen atom. In some cases, Z is selected from optionally substituted phenyl and optionally substituted pyridine. In some cases, the optional substituents of the optionally substituted phenyl of Z are selected from one or more substituents selected from halogen, —OH, —CN, —NO$_2$, —NH$_2$, oxo, =S, C$_{1-10}$ alkyl, —C$_{1-10}$ haloalkyl, and —O—C$_{1-10}$ alkyl. In some cases, the optional substituents of the optionally substituted phenyl of Z are selected from one or more substituents selected from halogen and C$_{1-10}$ alkyl. In some cases, the heterocycle is unsubstituted. In some cases, Z is selected from substituted phenyl and unsubstituted pyridine. In some cases, the heterocycle has 1 or 2 nitrogen atoms. In some cases, the heterocycle has only 1 nitrogen atom. In some cases, the heterocycle has only 2 nitrogen atoms. In some cases, the heterocycle is a 6-membered heterocycle. In some cases, Z is selected from

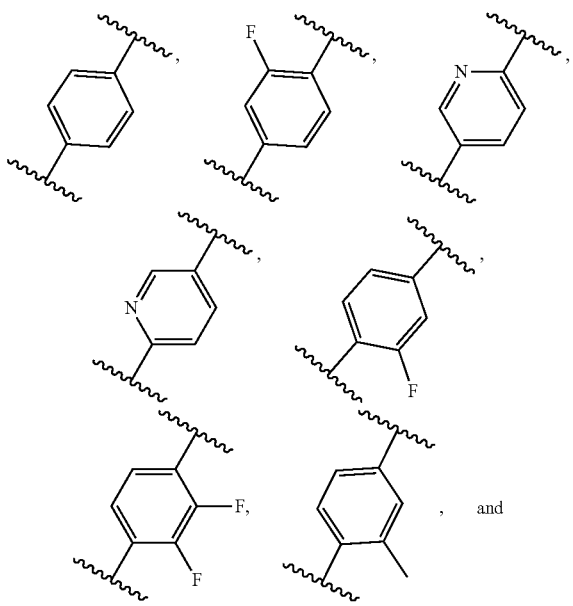

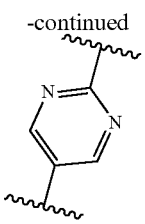

In some cases, the optional substituents of the optionally substituted phenyl of Z is halogen. In some cases, Z is selected from

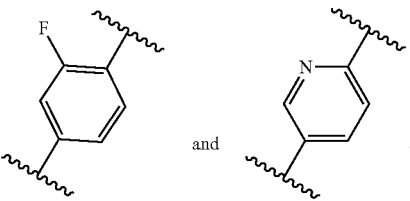

In some cases, Z is substituted phenyl. In some cases, Z is phenyl substituted with halogen.

In some aspects, the disclosure provides a compound represented by Formula (A*):

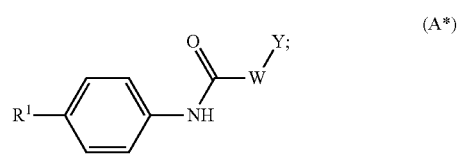

(A*)

R$^1$ is selected from:
—N(R$^5$)$_2$, wherein R$^5$ is selected from hydrogen, and optionally substituted C$_1$-C$_6$ alkyl, wherein the optional substituents on C$_1$-C$_6$ alkyl are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle;
optionally substituted C$_1$-C$_6$ alkyl, wherein the substituents on C$_1$-C$_6$ alkyl are independently selected at each occurrence from one or more halogen, —OH, —CN, —NO$_2$, —NH$_2$, oxo, =S, —C$_{1-10}$ haloalkyl, —O—C$_{1-10}$ alkyl, —O—C$_{1-6}$alkyl-O—C(O)(O—C$_{1-10}$ alkyl), C$_{2-10}$ alkenyl, C$_{2-10}$ alkynyl, C$_{3-12}$ carbocycle, 3- to 12-membered heterocycle;
optionally substituted 3 to 8-membered heterocycle; wherein the optional substituents on the 3 to 8-membered heterocycle are independently selected at each occurrence from one or more halogen, —OH, —CN, —NO$_2$, —NH$_2$, oxo, =S, —S(O$_2$)NH$_2$, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, and optionally substituted C$_{1-10}$ alkyl, wherein the optional substituents on the C$_{1-10}$ alkyl are independently selected at each occurrence from one or more hydroxy, halogen, oxo, —C$_{1-10}$ haloalkyl, —NH$_2$, —CN, and —NO$_2$;

W is selected from optionally substituted 5- to 8-membered heterocycle and optionally substituted C$_3$-C$_8$ carbocycle, wherein the substituents on each are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, wherein the C$_{3-12}$ carbocycle and 3- to 12-membered heterocycle are each optionally substituted with one or more substituents independently selected at each occurrence from halogen, —OH, —CN, —NO$_2$, —NH$_2$, oxo, =S, C$_{1-10}$ alkyl, —C$_{1-10}$ haloalkyl, and —O—C$_{1-10}$ alkyl; and Y is selected from optionally substituted 5- to 8-membered heterocycle and optionally substituted C$_3$-C$_8$ carbocycle, wherein the substituents on each are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, wherein the C$_{3-12}$ carbocycle and 3- to 12-membered heterocycle are each optionally substituted with one or more substituents independently selected at each occurrence from halogen, —OH, —CN, —NO$_2$, —NH$_2$, oxo, =S, C$_{1-10}$ alkyl, —C$_{1-10}$ haloalkyl, and —O—C$_{1-10}$ alkyl.

In some aspects, the compound of Formula (A) or Formula (A*) are represented by Formula (I).

In some aspects, the disclosure provides a compound represented by Formula (A*):

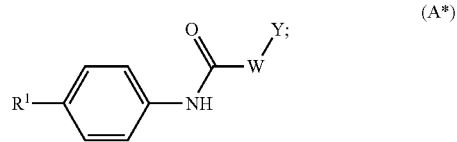

(A*)

R$^1$ is selected from:
—N(R$^5$)$_2$, wherein R$^5$ is selected from hydrogen, and optionally substituted C$_1$-C$_6$ alkyl, wherein the optional substituents on C$_1$-C$_6$ alkyl are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle;
optionally substituted C$_1$-C$_6$ alkyl, wherein the substituents on C$_1$-C$_6$ alkyl are independently selected at each occurrence from one or more halogen, —OH, —CN, —NO$_2$, —NH$_2$, oxo, =S, —C$_{1-10}$ haloalkyl, —O—C$_{1-10}$ alkyl, —O—C$_{1-6}$alkyl-O—C(O)(O—C$_{1-10}$ alkyl), C$_{2-10}$ alkenyl, C$_{2-10}$ alkynyl, C$_{3-12}$ carbocycle, 3- to 12-membered heterocycle;
optionally substituted 3 to 14-membered heterocycle; wherein the optional substituents on the 3 to 8-membered heterocycle are independently selected at each occurrence from one or more halogen, —OH, —CN, —NO$_2$, —NH$_2$, oxo, =S, —S(O$_2$)NH$_2$, —C$_{1-10}$ heteroalkyl, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, and optionally substituted C$_{1-10}$ alkyl, wherein the optional substituents on the C$_{1-10}$ alkyl are independently selected at each occurrence from one or more hydroxy, halogen, oxo, —C$_{1-10}$ haloalkyl, —NH$_2$, —CN, and —NO$_2$;
W is selected from optionally substituted 5- to 8-membered heterocycle and optionally substituted C$_3$-C$_8$ carbocycle, wherein the substituents on each are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, wherein the C$_{3-12}$ carbocycle and 3- to 12-membered heterocycle are each optionally substituted with one or more substituents independently selected at each occurrence from halogen, —OH, —CN, —NO$_2$, —NH$_2$, oxo, =S, C$_{1-10}$ alkyl, —C$_{1-10}$ haloalkyl, and —O—C$_{1-10}$ alkyl; and Y is selected from optionally substituted 5- to 8-membered heterocycle and optionally substituted C$_3$-C$_8$ carbocycle, wherein the substituents on each are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, wherein the C$_{3-12}$ carbocycle and 3- to 12-membered heterocycle are each optionally substituted with one or more substituents independently selected at each occurrence from halogen, —OH, —CN, —NO$_2$, —NH$_2$, oxo, =S, C$_{1-10}$ alkyl, —C$_{1-10}$ haloalkyl, and —O—C$_{1-10}$ alkyl.

In some aspects, the disclosure provides a compound represented by Formula (A*):

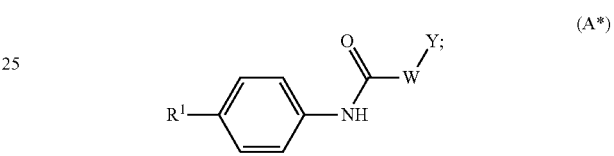

(A*)

R$^1$ is selected from:
—N(R$^5$)$_2$, wherein R$^5$ is selected from hydrogen and optionally substituted C$_1$-C$_6$ alkyl; optionally substituted C$_1$-C$_6$ alkyl;
optionally substituted 3 to 14-membered heterocycle or optionally substituted 3 to 14-membered carbocycle;
W is selected from optionally substituted 5- to 8-membered heterocycle and optionally substituted C$_3$-C$_8$ carbocycle; and Y is selected from optionally substituted 5- to 8-membered heterocycle and optionally substituted C$_3$-C$_8$ carbocycle.

In some embodiments, R is optionally substituted 3 to 14-membered heterocycle.

In certain embodiments, the disclosure provides a compound represented by Formula (I):

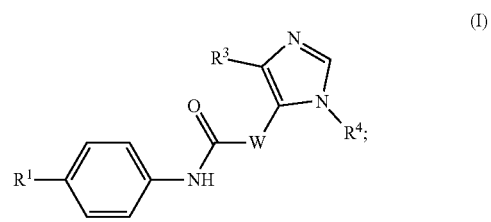

(I)

or a pharmaceutically acceptable salt thereof, wherein:
R$^1$ is selected from:
—N(R$^5$)$_2$, wherein R$^5$ is selected from hydrogen, and optionally substituted C$_1$-C$_6$ alkyl, wherein the optional substituents on C$_1$-C$_6$ alkyl are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle;
substituted C$_1$-C$_6$ alkyl, wherein the substituents on C$_1$-C$_6$ alkyl are independently selected at each occurrence from one or more halogen, —OH, —CN, —NO$_2$, —NH$_2$, oxo, =S, —C$_{1-10}$ haloalkyl, —O—C$_1$. 10 alkyl, —O—C$_{1-6}$alkyl-O—C(O)(O—C$_{1-10}$ alkyl), C$_{2-10}$ alkenyl, C$_{2-10}$ alkynyl, C$_{3-12}$ carbocycle, 3- to 12-membered heterocycle;

optionally substituted 3 to 8-membered heterocycle; wherein the optional substituents on the 3 to 8-membered heterocycle are independently selected at each occurrence from one or more halogen, —OH, —CN, —NO$_2$, —NH$_2$, oxo, =S, —S(O$_2$)NH$_2$, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, and optionally substituted C$_{1-10}$ alkyl, wherein the optional substituents on the C$_{1-10}$ alkyl are independently selected at each occurrence from one or more hydroxy, halogen, oxo, —C$_{1-10}$ haloalkyl, —NH$_2$, —CN, and —NO$_2$;

R$^3$ is selected from optionally substituted C$_1$-C$_6$ alkyl, optionally substituted 3- to 10-membered heterocycle and optionally substituted C$_{3-10}$ carbocycle, wherein the optional substituents on each are independently selected at each occurrence from one or more halogen, —OH, —CN, —NO$_2$, —NH$_2$, oxo, =S, C$_{1-6}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle;

R$^4$ is selected from:

hydrogen;

optionally substituted C$_1$-C$_6$ alkyl, wherein the optional substituents on C$_1$-C$_6$ alkyl are independently selected at each occurrence from one or more halogen, —OH, —CN, —NO$_2$, —NH$_2$, oxo, =S, —O—C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle;

optionally substituted C$_{3-10}$ carbocycle, wherein the optional substituents on C$_{3-10}$ carbocycle are independently selected at each occurrence from one or more halogen, —OH, —CN, —NO$_2$, —NH$_2$, oxo, =S, C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle; and W is selected from optionally substituted 5- to 8-membered heteroaryl, wherein the substituents on the optionally substituted 5- to 8-membered heteroaryl are independently selected at each occurrence from one or more halogen, —OH, —CN, —NO$_2$, —NH$_2$, oxo, =S, —S(O$_2$)NH$_2$, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle.

In certain embodiments, the disclosure provides a compound represented by Formula (I):

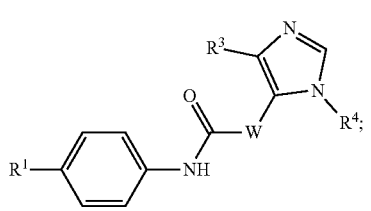

(I)

or a pharmaceutically acceptable salt thereof, wherein:

R$^1$ is selected from:
—N(R$^5$)$_2$, wherein R$^5$ is selected from hydrogen and optionally substituted C$_1$-C$_6$ alkyl; substituted C$_1$-C$_6$ alkyl; and
optionally substituted 3 to 14-membered heterocycle (such as 5-6 membered heterocycloalkyl);

R$^3$ is selected from optionally substituted C$_1$-C$_6$ alkyl, optionally substituted 3- to 10-membered heterocycle and optionally substituted C$_{3-10}$ carbocycle;

R$^4$ is selected from:
hydrogen;
optionally substituted C$_1$-C$_6$ alkyl or optionally substituted C$_1$-C$_6$ heteroalkyl;
optionally substituted C$_{3-10}$ carbocycle or optionally substituted 3- to 12-membered heterocycle; and W is selected from optionally substituted 5- to 8-membered heteroaryl (such as 5-6 membered heteroaryl).

In some embodiments, R$^4$ is optionally substituted C$_1$-C$_6$ alkyl. In some embodiments, R$^4$ is optionally substituted C$_{3-10}$ carbocycle.

In some embodiments, for a compound or salt of Formula (A), (A*), or (I), when R$^1$ is methylpiperazine and W is pyridine, R$^4$ is not methyl. In some cases, when R$^1$ is

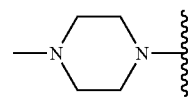

and W is pyridine, R$^4$ is not methyl.

In some embodiments, for a compound or salt of Formula (A), (A*), or (I), when W is furan, R$^4$ is not ethan-1-one. In some cases, when W is furan and R$^4$ is cyclopentyl or cyclohexyl, R$^1$ is not ethan-1-one. In some cases, when W is furan and R$^4$ is cyclopentyl or cyclohexyl, R$^1$ is not ethan-1-one. In some cases, R$^1$ is not

.

In some embodiments, for a compound or salt of Formula (A), (A*), or (I), W is selected from optionally substituted 5- to 8-membered heterocycle. In some cases, the heterocycle of W is a 5- to 8-membered heteroaryl. In some cases, the heterocycle of W is an unsubstituted 5- to 8-membered heteroaryl. In some cases, the heterocycle of W is an unsubstituted 5-membered heteroaryl. In some cases, the heterocycle of W has at least 2 heteroatoms. In some cases, the heterocycle of W has at most 2 heteroatoms. In some cases, the heterocycle of W has only 2 heteroatoms. In some cases, the heterocycle of W is unsubstituted. In some cases, the heterocycle of W has 2 heteroatoms selected from nitrogen, sulfur, and oxygen. In some cases, the heterocycle of W has at least 2 different heteroatoms. In some cases, the heterocycle of W has 2 nitrogen atoms. In some cases, the heterocycle of W has 1 nitrogen atom and 1 oxygen atom.

In some embodiments, for a compound or salt of Formula (A), (A*), (I), (IIA), or (IIB), R$^1$ is optionally substituted. In some embodiments, R$^1$ is optionally substituted with 1 to 4 substituents. In some embodiments, R$^1$ is optionally substituted with 1 to 3 substituents. In some embodiments, R$^1$ is optionally substituted with 1 to 2 substituents. In some embodiments, R$^1$ is optionally substituted with 1 substituent.

In some embodiments, $R^1$ is optionally substituted with 2 substituents. In some embodiments, $R^1$ is optionally substituted with 3 substituents. In some embodiments, $R^1$ is monocyclic. In some embodiments, $R^1$ is bicyclic. In some embodiments, $R^1$ is a bridged ring. In some embodiments, $R^1$ is a fused ring. In some embodiments, $R^1$ is a spiro ring. In some embodiments, $R^1$ is optionally substituted 3-12 membered ring. In some embodiments, $R^1$ is optionally substituted 5-8 membered ring.

In some embodiments, for a compound or salt of Formula (A), (A*), (I), (IIA), or (IIB), $R^1$ is optionally substituted with an oxide.

In some embodiments, for a compound or salt of Formula (A), (A*), (I), (IIA), or (IIB), $R^1$ is selected from substituted $C_1$-$C_6$ alkyl, wherein the substituents on $C_1$-$C_6$ alkyl are independently selected at each occurrence from one or more halogen, —OH, —CN, —NO$_2$, —NH$_2$, =S, —$C_{1-10}$ haloalkyl, —O—$C_{1-10}$ alkyl, —O—$C_{1-6}$alkyl-O—C(O)(O—$C_{1-10}$ alkyl), $C_{2-10}$ alkenyl, $C_{2-10}$ alkynyl, $C_{3-12}$ carbocycle, and 3- to 12-membered heterocycle. In some embodiments, for a compound or salt of Formula (A), (A*), (I), (IIA), or (IIB), $R^1$ is selected from substituted $C_1$-$C_6$ alkyl, wherein the substituents on $C_1$-$C_6$ alkyl are independently selected at each occurrence from one or more halogen, —OH, —CN, —NO$_2$, —NH$_2$, =S, —$C_{1-6}$ haloalkyl, —O—$C_{1-6}$ alkyl, —O—$C_{1-6}$alkyl-O—C(O)(O—$C_{1-6}$alkyl), $C_{2-6}$ alkenyl, $C_{2-6}$ alkynyl, $C_{3-6}$ carbocycle, and 3- to 12-membered heterocycle. In some embodiments, $R^1$ is optionally substituted $C_1$-$C_3$ alkyl. In some embodiments, $R^1$ is optionally substituted with one or more substituents selected from oxo, halogen, —O—$C_{1-10}$ alkyl, —$C_{1-10}$ haloalkyl, and —OH.

In some embodiments, for a compound or salt of Formula (A), (A*), (I), (IIA), or (IIB), $R^1$ is optionally substituted $C_1$-$C_{10}$ heteroalkyl. In some embodiments, for a compound or salt of Formula (A), (A*), (I), (IIA), or (IIB), $R^1$ is optionally substituted $C_1$-$C_6$ heteroalkyl wherein the substituents on $C_1$-$C_6$ heteroalkyl are independently selected at each occurrence from one or more halogen, —OH, —CN, —NO$_2$, —NH$_2$, =S, —$C_{1-10}$ haloalkyl, —$C_{2-10}$ alkenyl, $C_{2-10}$ alkynyl, $C_{3-12}$ carbocycle, and 3- to 12-membered heterocycle. In some embodiments, for a compound or salt of Formula (A), (A*), (I), (IIA), or (IIB), $R^1$ is optionally substituted $C_1$-$C_6$ heteroalkyl wherein the substituents on $C_1$-$C_6$ heteroalkyl are independently selected at each occurrence from one or more halogen, —OH, —CN, —NO$_2$, —NH$_2$, =S, —$C_{1-3}$ haloalkyl, —$C_{2-6}$ alkenyl, $C_{2-6}$ alkynyl, $C_{3-6}$ carbocycle, and 3- to 12-membered heterocycle.

In some cases, when W is furan, $R^1$ is selected from substituted $C_1$-$C_6$ alkyl, wherein the substituents on $C_1$-$C_6$ alkyl are independently selected at each occurrence from one or more halogen, —OH, —CN, —NO$_2$, —NH$_2$, oxo, =S, —$C_{1-10}$ haloalkyl, —O—$C_{1-10}$ alkyl, —O—$C_{1-6}$alkyl-O—C(O)(O—$C_{1-10}$ alkyl), $C_{2-10}$ alkenyl, $C_{2-10}$ alkynyl, $C_{3-12}$ carbocycle, and 3- to 12-membered heterocycle.

In some embodiments, for a compound or salt of Formula (A), (A*), (I), (IIA), or (IIB), $R^1$ is selected from —N($R^5$)$_2$, In some embodiments, for a compound or salt of Formula (A), (A*), (I), (IIA), or (IIB), $R^1$ is selected from —N($R^5$)$_2$, wherein $R^5$ is selected from optionally substituted $C_1$-$C_6$ alkyl, wherein the optional substituents on $C_1$-$C_6$ alkyl are selected from hydroxy.

In some embodiments, for a compound or salt of Formula (A), (A*), (I), (IIA), or (IIB), $R^1$ is selected from substituted $C_1$-$C_6$ alkyl and optionally substituted 3 to 8-membered heterocycle.

In some embodiments, for a compound or salt of Formula (A), (A*), (I), (IIA), or (IIB), $R^1$ is substituted $C_1$-$C_6$ alkyl.

In some embodiments, for a compound or salt of Formula (A), (A*), (I), (IIA), or (IIB), $R^1$ is selected from substituted $C_1$-$C_6$ alkyl, wherein the substituents are selected from hydroxy, oxo, and —O—$C_{1-10}$ alkyl.

In some embodiments, for a compound or salt of Formula (A), (A*), (I), (IIA), or (IIB), $R^1$ is optionally substituted 3 to 8-membered heterocycle. In some embodiments, for a compound or salt of Formula (A), (A*), (I), (IIA), or (IIB), $R^1$ is selected from optionally substituted 5 to 6-membered heterocycle. In some embodiments, $R^1$ is monocyclic. In some embodiments, $R^1$ is bicyclic. In some embodiments, $R^1$ is a fused bicyclic group. In some embodiments, $R^1$ is a bridged bicyclic group. In some embodiments, $R^1$ is optionally substituted 5 membered heterocycle. In some embodiments, $R^1$ is optionally substituted heteroaryl. In some embodiments, $R^1$ is optionally substituted heterocycloalkyl. In some embodiments, $R^1$ contains 0-3 nitrogen and 0-1 oxygen atoms on the ring.

In some embodiments, $R^1$ contains 1-2 nitrogen and 0-1 oxygen atoms on the ring. In some embodiments, $R^1$ contains 1-2 ring nitrogen atoms. In some embodiments, $R^1$ contains 2 ring nitrogen atoms. In some embodiments, $R^1$ contains 1 ring nitrogen atom.

In some embodiments, for a compound or salt of Formula (A), (A*), (I), (IIA), or (IIB), $R^1$ is an optionally substituted 6-membered heterocycle.

In some embodiments, for a compound or salt of Formula (A), (A*), (I), (IIA), or (IIB), $R^1$ is an optionally substituted piperazine. In some embodiments, $R^1$ is an optionally substituted piperazine, wherein the piperazine is attached to the rest of the compound (e.g., attached to the phenyl) via a nitrogen. In some embodiments, for a compound or salt of Formula (A), (A*), (I), (IIA), or (IIB), $R^1$ is piperazine optionally substituted with one or more $_{1-6}$ alkyl. In some embodiments, for a compound or salt of Formula (A), (A*), (I), (IIA), or (IIB), $R^1$ is piperazine optionally substituted with one or more substituents selected from methyl, ethyl and propyl. In some embodiments, for a compound or salt of Formula (A), (A*), (I), (IIA), or (IIB), $R^1$ is piperazine optionally substituted with one or more methyl. In some embodiments, for a compound or salt of Formula (A), (A*), (I), (IIA), or (IIB), $R^1$ is piperazine optionally substituted with one or more $_{1-6}$ alkyl, wherein the alkyl is optionally substituted with hydroxy, halogen, oxo, and —NH$_2$. In some embodiments, for a compound or salt of Formula (A), (A*), (I), (IIA), or (IIB), $R^1$ is piperazine optionally substituted with an oxide.

In some embodiments, for a compound or salt of Formula (A), (A*), (I), (IIA), or (IIB), the optional substituents on the optionally substituted piperazine of $R^1$ are selected from oxo, —S(O$_2$)NH$_2$, and optionally substituted $C_{1-10}$ alkyl, wherein the optional substituents on the $C_{1-10}$ alkyl are independently selected at each occurrence from one or more hydroxy, halogen, oxo, and —NH$_2$. In some embodiments, for a compound or salt of Formula (A), (A*), (I), (IIA), or (IIB), the optional substituents on the optionally substituted piperazine of $R^1$ are selected from oxo, —S(O$_2$)NH$_2$, —S(O$_2$)N(C$_{1-6}$ alkyl)$_2$, —S(O$_2$)NH(C$_{1-6}$ alkyl), and optionally substituted $C_{1-6}$ alkyl. In some embodiments, for a compound or salt of Formula (A), (A*), (I), (IIA), or (IIB), $R^1$ is optionally substituted with a heteroalkyl. In some embodiments, $R^1$ is optionally substituted with one or more substituents selected from halogen, —CN, —OH, —S(=O)CH$_3$, —S(=O)$_2$CH$_3$, —S(=O)$_2$NH$_2$, —S(=O)$_2$NHCH$_3$, —S(=O)$_2$N(CH$_3$)$_2$, —NH$_2$, —NHCH$_3$, —N(CH$_3$)$_2$, —C(=O)CH$_3$, —C(=O)OH, —C(=O)OCH$_3$, $C_1$-$C_6$alkyl, $C_1$-$C_6$alkoxy, $C_1$-$C_6$haloalkyl, $C_1$-$C_6$hydroxyalkyl, $C_1$-$C_6$aminoalkyl, $C_1$-$C_6$heteroalkyl, and $C_3$-$C_6$cycloalkyl.

In some embodiments, for a compound or salt of Formula (A), (A*), (I), (IIA), or (IIB), $R^1$ is an optionally substituted 3 to 10-membered heterocycle. In some cases, $R^1$ is an optionally substituted 4- to 8-membered heterocycle. In some cases, $R^1$ is an optionally substituted 4-membered heterocycle. In some cases, $R^1$ is an optionally substituted 6-membered heterocycle. In some cases, when $R^1$ is piperazine, the piperazine is substituted. In some cases, $R^1$ is not unsubstituted piperazine. In some cases, $R^1$ is a substituted 3 to 10-membered heterocycle.

In some embodiments, for a compound or salt of Formula (A), (A*), (I), (IIA), or (IIB), for $R^1$, the optional substituents of the heterocycle are independently selected at each occurrence from one or more substituents selected from halogen, —OH, —CN, —NO$_2$, —NH$_2$, —N(H)C$_1$-C$_6$ alkyl, —N(C$_1$-C$_6$ alkyl)$_2$, oxo, =S, —S(O$_2$)NH$_2$, —C$_{1-10}$ haloalkyl, —O—C$_{1-10}$ alkyl, and optionally substituted C$_{1-10}$ alkyl, wherein the optional substituents on the C$_{1-10}$ alkyl are independently selected at each occurrence from one or more hydroxy, halogen, oxo, —C$_{1-10}$ haloalkyl, —NH$_2$, —CN, —O—C$_{1-10}$ alkyl, and —NO$_2$.

In some embodiments, for a compound or salt of Formula (A), (A*), (I), (IIA), or (IIB), the optional substituents of $R^1$ are independently selected at each occurrence from one or more substituents selected from —NH$_2$, —N(H)C$_1$-C$_6$ alkyl, —N(C$_1$-C$_6$ alkyl)$_2$, oxo, and optionally substituted C$_{1-10}$ alkyl, wherein the optional substituents on the C$_{1-10}$ alkyl are independently selected at each occurrence from one or more oxo and —O—C$_{1-10}$ alkyl.

In some embodiments, for a compound or salt of Formula (A), (A*), (I), (IIA), or (IIB), the optional substituents of $R^1$ are independently selected at each occurrence from one or more substituents selected from —NH$_2$, —N(H)C$_1$-C$_6$ alkyl, —N(C$_1$-C$_6$ alkyl)$_2$, oxo, and optionally substituted C$_{1-10}$ alkyl, wherein the optional substituents on the C$_{1-10}$ alkyl are independently selected at each occurrence from one or more oxo and —O—C$_{1-10}$ alkyl.

In some embodiments, for a compound or salt of Formula (A), (A*), (I), (IIA), or (IIB), for $R^1$, the heterocycle has at least one nitrogen atom, phosphorous atom, or oxygen atom. In some cases, for $R^1$, the heterocycle has at least one nitrogen atom. In some cases, for $R^1$, the heterocycle has at least two nitrogen atoms. In some cases, for $R^1$, the heterocycle has at most two nitrogen atoms. In some cases, for $R^1$, the heterocycle has at most one nitrogen atom. In some cases, for $R^1$, the heterocycle has two nitrogen atoms. In some cases, for $R^1$, the heterocycle is a spiro-heterocycle. In some cases, for $R^1$, the heterocycle is a bridged heterocycle. In some cases, for $R^1$, the heterocycle is unsaturated. In some cases, for $R^1$, the heterocycle is saturated.

In some embodiments, for a compound or salt of Formula (A), (A*), (I), (IIA), or (IIB), $R^1$ is selected from

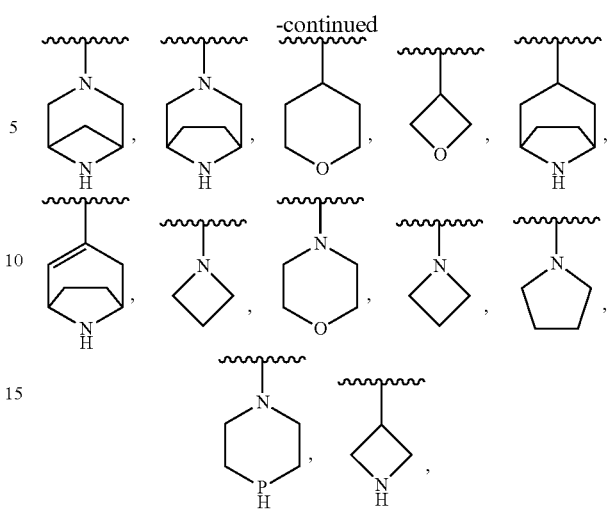

any of which are optionally substituted.

In some embodiments, for a compound or salt of Formula (A), (A*), (I), (IIA), or (IIB), $R^1$ is selected from

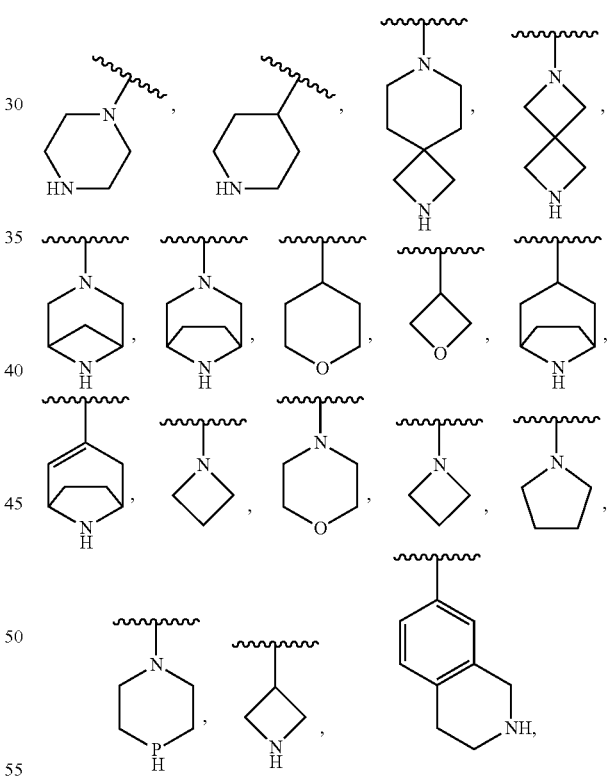

any of which are optionally substituted with one or more substituents selected from —NH$_2$, —N(H)C$_1$-C$_6$ alkyl, —N(C$_1$-C$_6$ alkyl)$_2$, oxo, and optionally substituted C$_{1-10}$ alkyl, wherein the optional substituents on the C$_{1-10}$ alkyl are independently selected at each occurrence from one or more oxo and —O—C$_{1-10}$ alkyl. In some embodiments, $R^1$ is optionally substituted with one or more substituents selected from —NH$_2$, —N(H)C$_1$-C$_6$ alkyl, —N(C$_1$-C$_6$ alkyl)$_2$, oxo, optionally substituted C$_{1-10}$ heteroalkyl, and optionally substituted C$_{1-10}$ alkyl.

In some embodiments, for a compound or salt of Formula (A), (A*), (I), (IIA), or (IIB), $R^1$ is selected from
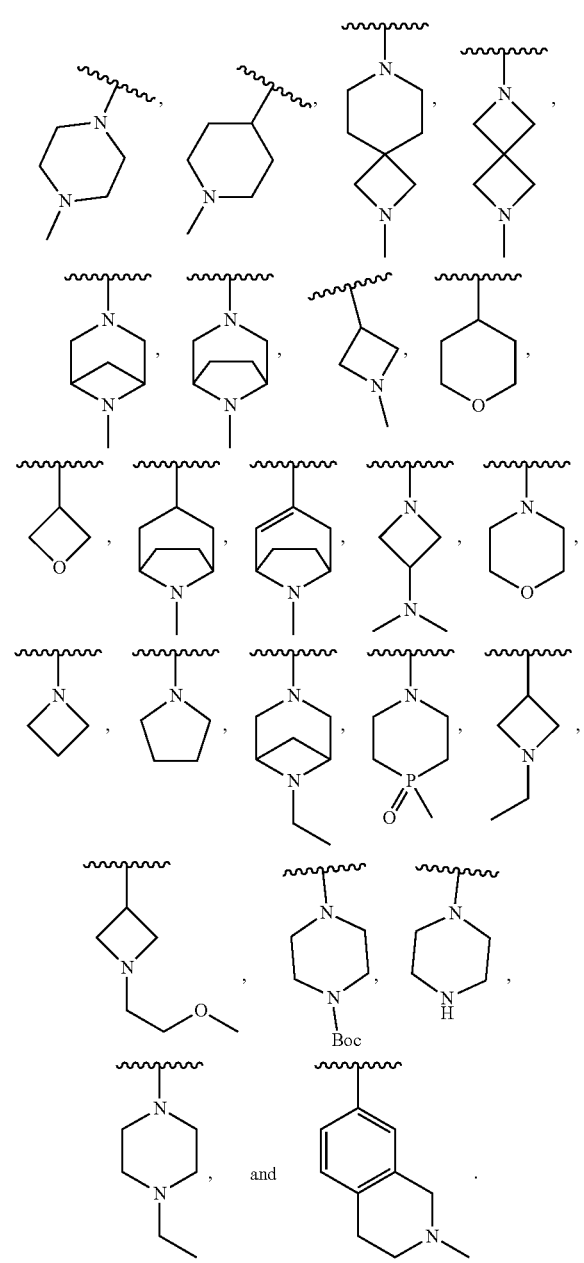
In some embodiments, for a compound or salt of Formula (A), (A*), (I), (IIA), or (IIB), $R^1$ is selected from
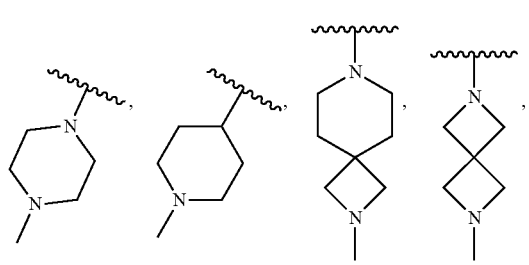
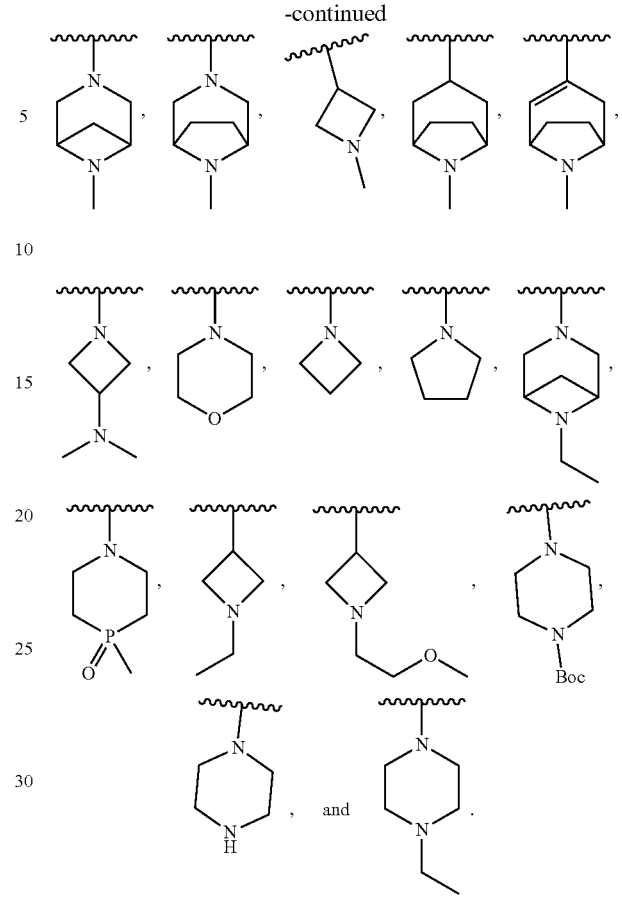
In some embodiments, for a compound or salt of Formula (A), (A*), (I), (IIA), or (IIB), $R^1$ is selected from
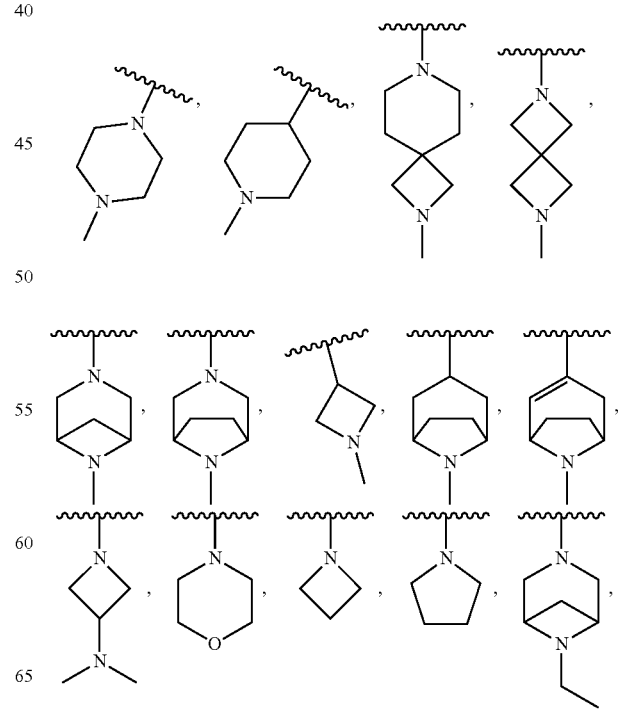

In some embodiments, for a compound or salt of Formula (A), (A*), (I), (IIA), or (IIB), $R^1$ is selected from

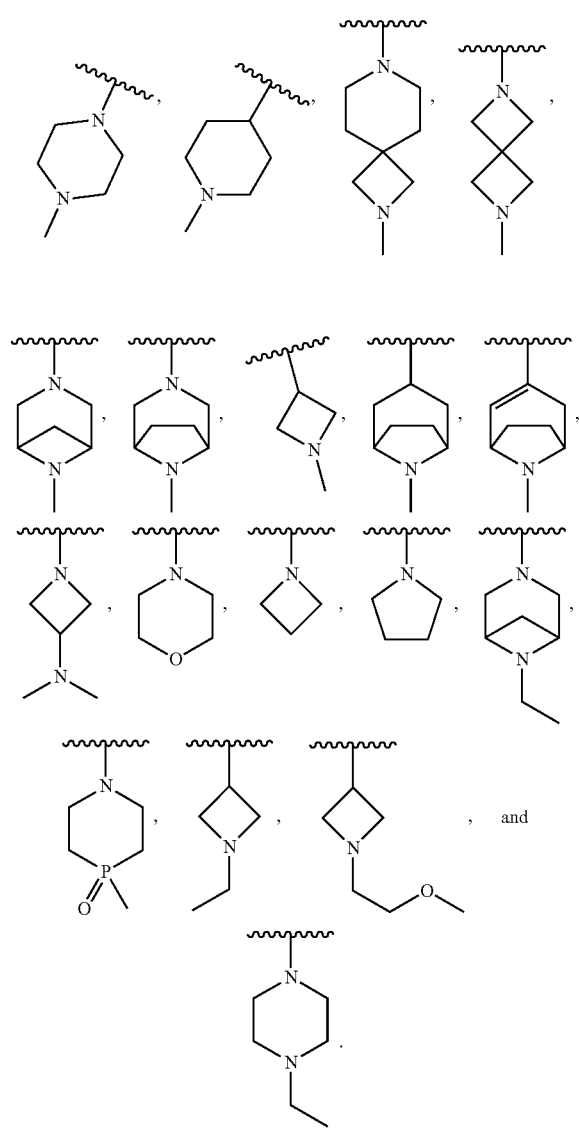

and

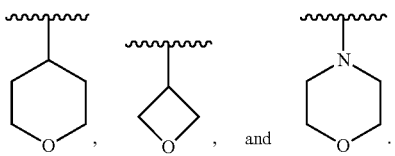

In some embodiments, for a compound or salt of Formula (A), (A*), (I), (IIA), or (IIB), $R^1$ is an optionally substituted 6- to 10-membered heterocycloalkyl. In some cases, the optional substituents of the optionally substituted 6- to 10-membered heterocycloalkyl for $R^1$ are selected from $C_{1-6}$ alkyl. In some cases, the 6- to 10-membered heterocycloalkyl is a spiro heterocycloalkyl. In some cases, $R^1$ is selected from optionally substituted piperazine, optionally substituted diazabicyclo [3.2.1]octane, optionally substituted diazabicyclo[3.1.1]heptane, optionally substituted diazaspiro[3.5]nonane, and optionally substituted diazaspiro[3.3]heptane. In some cases, the optional are selected from $C_{1-6}$ alkyl.

In some embodiments, for a compound or salt of Formula (A), (A*), (I), (IIA), or (IIB), $R^3$ is optionally substituted. In some embodiments, $R^3$ is optionally substituted with 1 to 4 substituents. In some embodiments, $R^3$ is optionally substituted with 1 to 3 substituents. In some embodiments, $R^3$ is optionally substituted with 1 to 2 substituents. In some embodiments, $R^3$ is optionally substituted with 1 substituent. In some embodiments, $R^3$ is optionally substituted with 2 substituents. In some embodiments, $R^3$ is optionally substituted with 3 substituents.

In some embodiments, for a compound or salt of Formula (A), (A*), (I), (IIA), or (IIB), $R^3$ is selected from optionally substituted $C_{3-6}$ carbocycle. In some embodiments, for a compound or salt of Formula (A), (A*), (I), (IIA), or (IIB), $R^3$ is selected from optionally substituted $C_{3-6}$ cycloalkyl.

In some embodiments, for a compound or salt of Formula (A), (A*), (I), (IIA), or (IIB), $R^3$ is optionally substituted phenyl. In some embodiments, for a compound or salt of Formula (A), (A*), (I), (IIA), or (IIB), $R^3$ is a phenyl optionally substituted with one or more halogen. In some embodiments, for a compound or salt of Formula (A), (A*), (I), (IIA), or (IIB), $R^3$ is a phenyl optionally substituted with 1-3 halogen. In some embodiments, for a compound or salt of Formula (A), (A*), (I), (IIA), or (IIB), $R^3$ is a phenyl optionally substituted with 1-2 halogen. In some embodiments, for a compound or salt of Formula (A), (A*), (I), (IIA), or (IIB), $R^3$ is a phenyl optionally substituted with one halogen.

In some embodiments, for a compound or salt of Formula (A), (A*), (I), (IIA), or (IIB), the optional substituents of phenyl of $R^3$ are selected from halogen and —$C_{1-10}$ haloalkyl. In some embodiments, for a compound or salt of Formula (A), (A*), (I), (IIA), or (IIB), the optional substituents of phenyl of $R^3$ are selected from halogen and —$C_{1-3}$ haloalkyl.

In some embodiments, for a compound or salt of Formula (A), (A*), (I), (IIA), or (IIB), $R^4$ is unsubstituted. In some embodiments, for a compound or salt of Formula (A), (A*), (I), (IIA), or (IIB), $R^4$ is substituted. In some embodiments, for a compound or salt of Formula (A), (A*), (I), (IIA), or (IIB), $R^4$ is substituted with one or more substituents selected from halogen, —OH, —CN, —NO$_2$, —NH$_2$, oxo, =S, —O—$C_{1-10}$ alkyl, —$C_{1-10}$ haloalkyl, —O—$C_{1-10}$ alkyl, $C_{2-10}$ alkenyl, $C_{2-10}$ alkynyl, $C_{3-12}$ carbocycle, and 3- to 12-membered heterocycle. In some embodiments, $R^4$ is substituted with one or more substituents selected from halogen, —OH, —CN, —NO$_2$, —NH$_2$, oxo, =S, —O—C$_{1-6}$ alkyl, —C$_{1-6}$ haloalkyl, —O—C$_{1-6}$ alkyl, C$_{2-6}$ alkenyl, C$_{2-6}$ alkynyl, C$_{3-6}$ carbocycle, and 3- to 12-membered heterocycle. In some embodiments, R$^4$ is substituted with one or more substituents selected from halogen, —OH, —CN, —NO$_2$, —NH$_2$, oxo, =S, —O—C$_{1-6}$ alkyl, —C$_{1-6}$ haloalkyl, and —O—C$_{1-6}$ alkyl. In some embodiments, R$^4$ is substituted with one or more substituents selected from halogen, —OH, —NO$_2$, —NH$_2$, oxo, —C$_{1-6}$ haloalkyl, and —O—C$_{1-6}$ alkyl. In some embodiments, R$^4$ is substituted with one or more halogen. In some embodiments, R$^4$ is substituted with 1 halogen. In some embodiments, R$^4$ is substituted with 2 halogens. In some embodiments, R$^4$ is substituted with 3 halogens.

In some embodiments, for a compound or salt of Formula (A), (A*), (I), (IIA), or (IIB), R$^4$ is hydrogen.

In some embodiments, for a compound or salt of Formula (A), (A*), (I), (IIA), or (IIB), R$^4$ is selected from optionally substituted C$_1$-C$_6$ alkyl and optionally substituted C$_{3-6}$ carbocycle. In some embodiments, for a compound or salt of Formula (A), (A*), (I), (IIA), or (IIB), R$^4$ is optionally substituted cycloalkyl. In some embodiments, for a compound or salt of Formula (A), (A*), (I), (IIA), or (IIB), R$^4$ is optionally substituted aryl.

In some embodiments, for a compound or salt of Formula (A), (A*), (I), (IIA), or (IIB), the optional substituents of C$_1$-C$_6$ alkyl of R$^4$ are selected from halogen.

In some embodiments, for a compound or salt of Formula (A), (A*), (I), (IIA), or (IIB), the optional substituents of C$_3$-C$_6$ carbocycle of R$^4$ are selected from hydroxy. In In some embodiments, for a compound or salt of Formula (A), (A*), or (I), W is selected from 5- to 6-membered heteroaryl.

In some embodiments, for a compound or salt of Formula (A), (A*), or (I), the 5- to 6-membered heteroaryl of W are selected from imidazole, furan, thiophene, oxazole, isoxazole, thiazole, oxadiazole, thiadiazole, pyridine, pyridazine, pyrimidine, and pyrazine.

In some embodiments, for a compound or salt of Formula (A), (A*), or (I), the 5- to 6-membered heteroaryl of W are selected from imidazole, furan, and pyridine.

In some embodiments, for a compound or salt of Formula (A), (A*), or (I), W is imidazole.

In some embodiments, for a compound or salt of Formula (A), (A*), or (I), W is pyridine.

In some embodiments, for a compound or salt of Formula (A), (A*), or (I), W is selected from optionally substituted 5- to 6-membered heteroaryl.

In some embodiments, for a compound or salt of Formula (A), (A*), or (I), W is selected from pyridine, imidazole, thiazole, and furan.

In some embodiments, for a compound or salt of Formula (A), (A*), or (I), W is selected from pyridine and imidazole.

In some aspects, the compound or salt of Formula (I) is represented by formula (IIA):

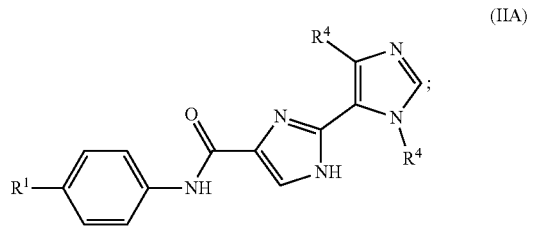

(IIA)

or a pharmaceutically acceptable salt thereof.

In some aspects, the compound or salt of Formula (I) is represented by formula (IIB),

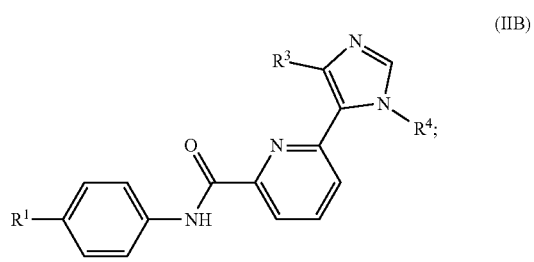

(IIB)

or a pharmaceutically acceptable salt thereof.

In some embodiments, for a compound or salt of Formula (A), (A*), (I), (IIA), or (IIB), R$^3$ is selected from optionally substituted C$_1$-C$_6$ alkyl and optionally substituted C$_6$ carbocycle.

In some embodiments, for a compound or salt of Formula (A), (A*), (I), (IIA), or (IIB), for a compound or salt of Formula (A), (A*), (I), (IIA), or (IIB), R$^3$ is selected from C$_1$-C$_6$ alkyl and wherein the C$_6$ carbocycle is substituted with one or more substituents selected from halogen and —C$_{1-10}$ haloalkyl.

In some embodiments, for a compound or salt of Formula (A), (A*), (I), (IIA), or (IIB), R$^3$ is selected from

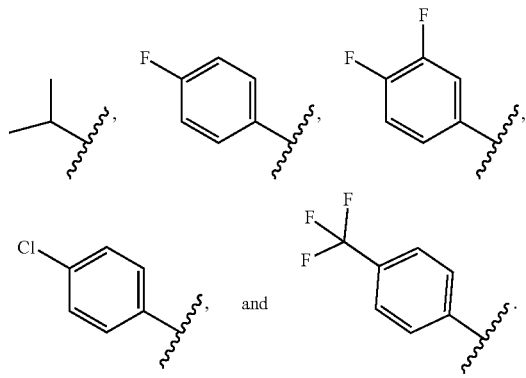

In some embodiments, for a compound or salt of Formula (A), (A*), (I), (IIA), or (IIB), R$^3$ is C$_6$ carbocycle substituted with one or more substituents selected from halogen.

In some embodiments, for a compound or salt of Formula (A), (A*), (I), (IIA), or (IIB), R$^3$ is phenyl, wherein the phenyl is optionally substituted with one or more halogen.

In some embodiments, for a compound or salt of Formula (A), (A*), (I), (IIA), or (IIB), R$^3$ is selected from

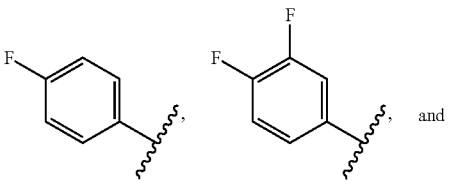

-continued

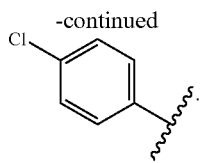

In some embodiments, for a compound or salt of Formula (A), (A*), (I), (IIA), or (IIB), $R^3$ is

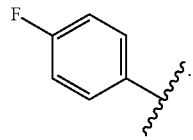

In some embodiments, for a compound or salt of Formula (A), (A*), (I), (IIA), or (IIB), $R^4$ is selected from hydrogen, $C_1$-$C_6$ alkyl optionally substituted with one or more substituents selected from halogen, and $C_{5-6}$ carbocycle optionally substituted with one or more substituents selected from hydroxy and amine.

In some embodiments, for a compound or salt of Formula (A), (A*), (I), (IIA), or (IIB), $R^4$ is unsubstituted $C_1$-$C_6$ alkyl.

In some embodiments, for a compound or salt of Formula (A), (A*), (I), (IIA), or (IIB), $R^4$ is substituted $C_1$-$C_6$ alkyl, wherein the $C_1$-$C_6$ alkyl is substituted with one or more halogen.

In some embodiments, for a compound or salt of Formula (A), (A*), (I), (IIA), or (IIB), $R^4$ is selected from

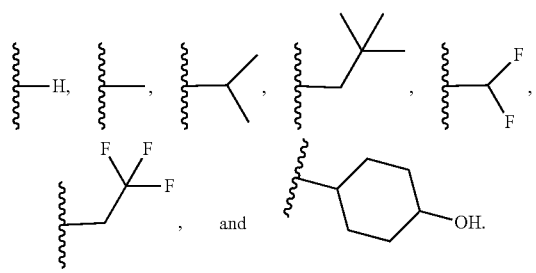

In some embodiments, for a compound or salt of Formula (A), (A*), (I), (IIA), or (IIB), $R^4$ is selected from $C_1$-$C_6$ alkyl optionally substituted with one or more substituents selected from fluorine, and $C_6$ cycloalkyl substituted with hydroxy.

In some embodiments, for a compound or salt of Formula (A), (A*), (I), (IIA), or (IIB), $R^4$ is selected from

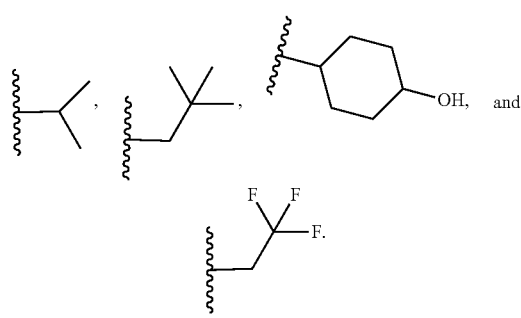

In some embodiments, for a compound or salt of Formula (A), (A*), (I), (IIA), or (IIB), $R^4$ is selected from

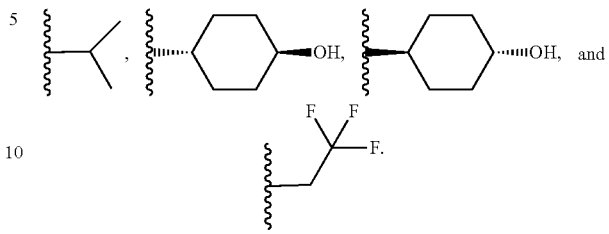

In certain embodiments, $R^4$ is

In some embodiments, for a compound or salt of Formula (A), (A*), (I), (IIA), or (IIB), $R^4$ is selected from

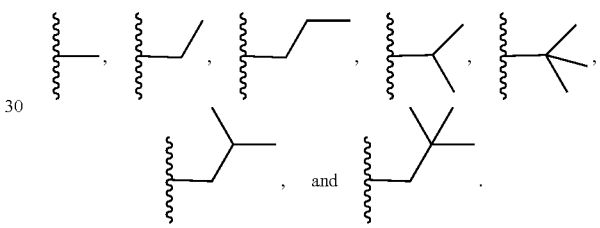

In some embodiments, for a compound or salt of Formula (A), (A*), (I), (IIA), or (IIB), $R^4$ is selected from

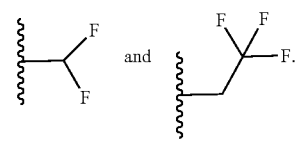

In some cases, $R^4$ is selected from unsubstituted $C_{1-10}$ alkyl, unsubstituted 3- to 6-membered heterocycle, and optionally substituted $C_3$-$C_6$ carbocycle.

In some embodiments, for a compound or salt of Formula (A), (A*), (I), (IIA), or (IIB), each $R^4$ is selected at each occurrence from $C_{1-10}$ alkyl, $C_{3-12}$ carbocycle, and 3- to 12-membered heterocycle, wherein the $C_{1-10}$ alkyl, $C_{3-12}$ carbocycle and 3- to 12-membered heterocycle are each optionally substituted with one or more substituents independently selected at each occurrence from halogen, —OH, —CN, —NO$_2$, —NH$_2$, oxo, =S, $C_{1-10}$ alkyl, —$C_{1-10}$ haloalkyl, and —O—$C_{1-10}$ alkyl.

In some embodiments, for a compound or salt of Formula (A), (A*), (I), (IIA), or (IIB), $R^4$ is selected from unsubstituted $C_{1-10}$ alkyl, unsubstituted 3- to 6-membered heterocycle, and optionally substituted $C_3$-$C_6$ carbocycle, wherein the optional substituents are independently selected from one or more halogen —$C_{1-10}$ haloalkyl.

In some embodiments, f for a compound or salt of Formula (A), (A*), (I), (IIA), or (IIB), each $R^4$ is selected at each occurrence from $C_{1-10}$ alkyl, unsubstituted 4-membered heterocycle, and optionally substituted $C_3$-$C_5$ carbocycle, wherein the optional substituents are independently selected from one or more halogen —$C_{1-10}$ haloalkyl. In some cases, $R^4$ is selected from a $C_{1-10}$ alkyl. In some cases, $R^4$ is selected from a 4-membered heterocycle. In some cases, $R^4$ is a 4-membered heterocycle. In some cases, $R^4$ is a saturated 4-membered heterocycle.

In some embodiments, for a compound or salt of Formula (A), (A*), (I), (IIA), or (IIB), $R^4$ is selected from

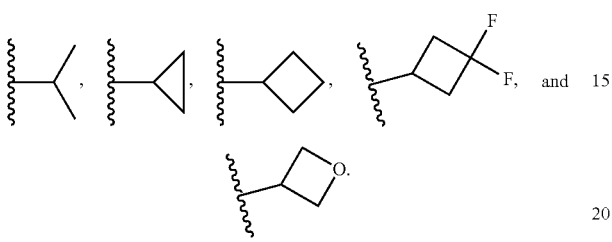

In some cases, $R^4$ is selected from

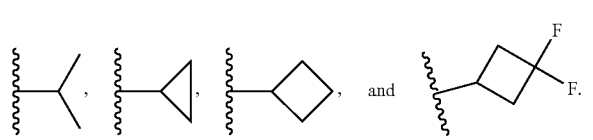

In some cases, $R^4$ is selected from

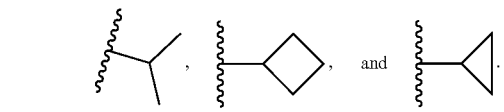

In some embodiments, for a compound or salt of Formula (A), (A*), (I), (IIA), or (IIB), $R^1$ is selected from:

—N($R^5$)$_2$, wherein $R^5$ is selected from optionally substituted $C_1$-$C_6$ alkyl, wherein the substituents on $C_1$-$C_6$ alkyl are independently selected at each occurrence from one or more halogen, —OH, —CN, —NO$_2$, —NH$_2$, oxo, —$C_{1-10}$ haloalkyl, —O—$C_{1-10}$ alkyl, substituted $C_1$-$C_6$ alkyl, wherein the substituents on $C_1$-$C_6$ alkyl are independently selected at each occurrence from one or more halogen, —OH, —NH$_2$, oxo, —$C_{1-10}$ haloalkyl, —O—$C_{1-10}$ alkyl, —O—$C_{1-6}$alkyl-O—C(O)(O—$C_{1-10}$ alkyl);

optionally substituted 6 to 8-membered heterocycle; wherein the optional substituents on the 6 to 8-membered heterocycle are independently selected at each occurrence from one or more oxo, —S(O$_2$)NH$_2$, —NH$_2$, —$C_{1-10}$ haloalkyl, —O—$C_{1-10}$ alkyl, and optionally substituted $C_{1-10}$ alkyl, wherein the optional substituents on the $C_{1-10}$ alkyl are independently selected at each occurrence from one or more hydroxy, halogen, oxo, —$C_{1-10}$ haloalkyl, —NH$_2$, —CN, and —NO$_2$.

In some embodiments, for a compound or salt of Formula (A), (A*), (I), (IIA), or (IIB), $R^1$ is selected from

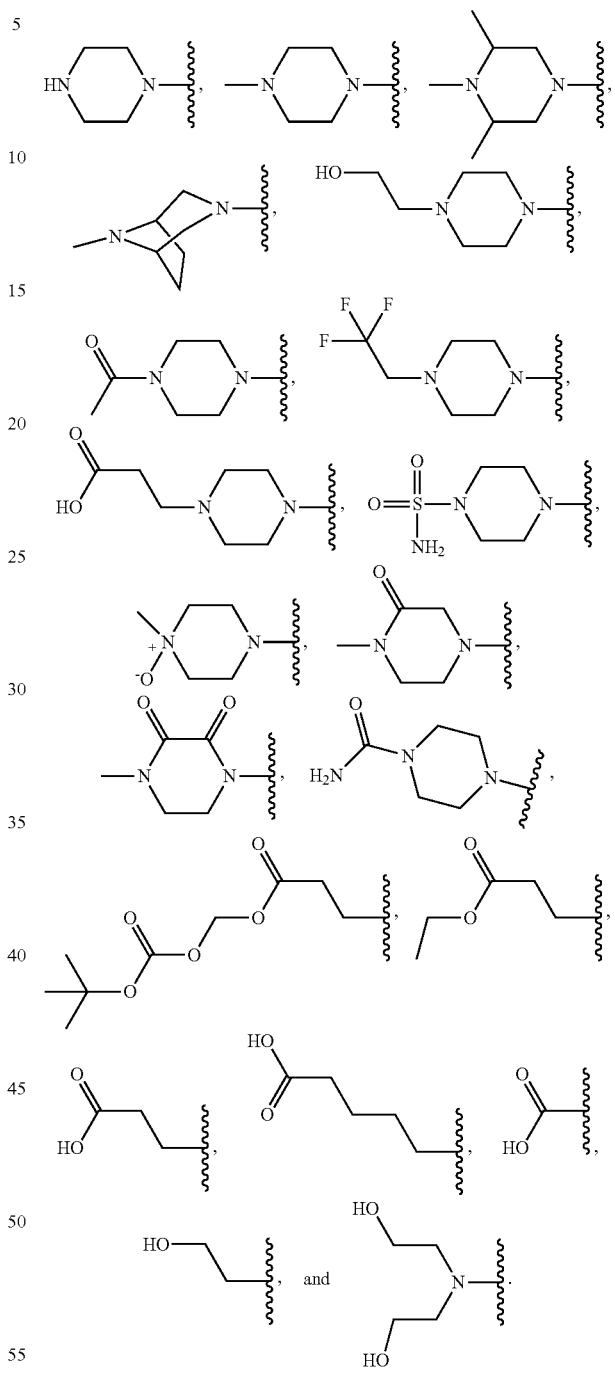

In some embodiments, for a compound or salt of Formula (A), (A*), (I), (IIA), or (IIB), $R^1$ is selected from

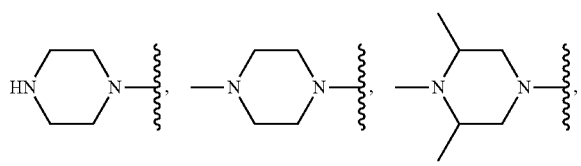

-continued

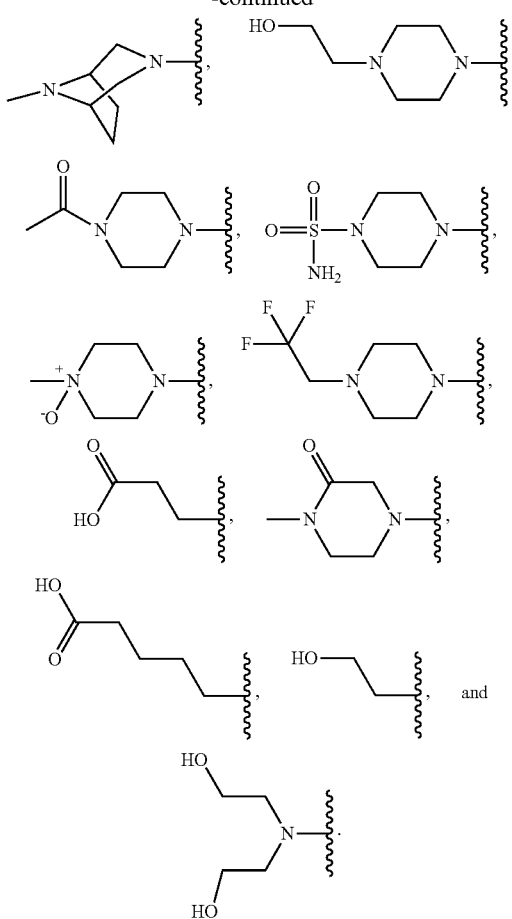

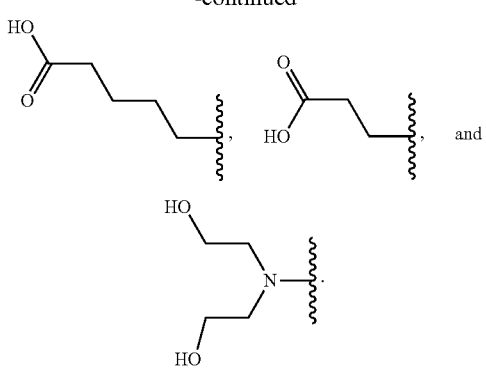

In some embodiments, for a compound or salt of Formula (A), (A*), (I), (IIA), or (IIB), $R^1$ is selected from:

substituted $C_1$-$C_6$ alkyl, wherein the substituents on $C_1$-$C_6$ alkyl are independently selected at each occurrence from one or more halogen, —OH, oxo, —$C_{1-10}$ haloalkyl, and —O—$C_{1-10}$ alkyl;

optionally substituted 6 to 8-membered saturated heterocycle; wherein the optional substituents are independently selected at each occurrence from one or more —S(O$_2$)NH$_2$, and optionally substituted $C_{1-10}$ alkyl, wherein the optional substituents on the $C_{1-10}$ alkyl are independently selected at each occurrence from one or more hydroxy, halogen, oxo, —$C_{1-10}$ haloalkyl, and —NH$_2$.

In some embodiments, for a compound or salt of Formula (A), (A*), (I), (IIA), or (IIB), $R^1$ is selected from

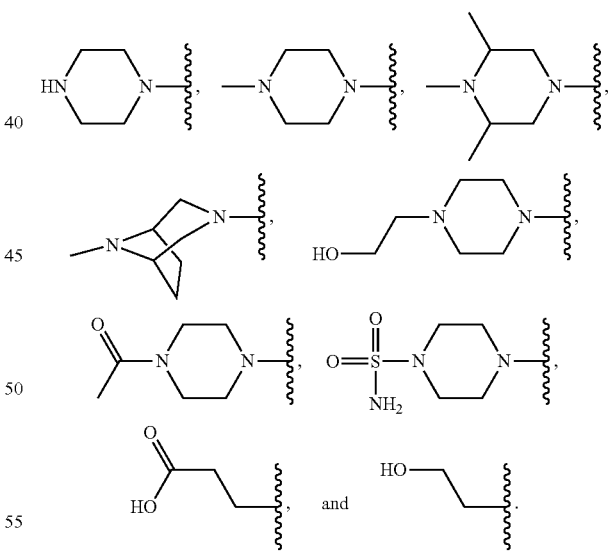

In some embodiments, for a compound or salt of Formula (A), (A*), (I), (IIA), or (IIB), $R^1$ is selected from optionally substituted 6 to 8-membered saturated heterocycle; wherein the optional substituents are independently selected at each occurrence from one or more —S(O$_2$)NH$_2$, and optionally substituted $C_{1-10}$ alkyl, wherein the optional substituents on the $C_{1-10}$ alkyl are independently selected at each occurrence from one or more hydroxy, halogen, oxo, —$C_{1-10}$ haloalkyl, and —NH$_2$.

In some embodiments, for a compound or salt of Formula (A), (A*), (I), (IIA), or (IIB), $R^1$ is selected from:

In some embodiments, for a compound or salt of Formula (A), (A*), (I), (IIA), or (IIB), $R^1$ is selected from

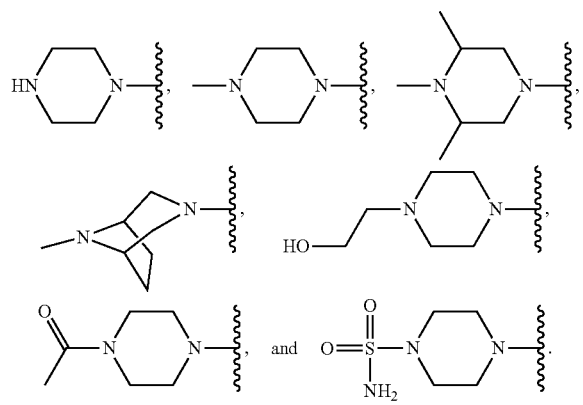

In some embodiments, for a compound or salt of Formula (A), (A*), (I), (IIA), or (IIB), $R^1$ is selected from substituted $C_1$-$C_6$ alkyl, wherein the substituents on $C_1$-$C_6$ alkyl are independently selected at each occurrence from one or more halogen, —OH, oxo, —$C_{1-10}$ haloalkyl, and —O—$C_{1-10}$ alkyl.

In some embodiments, for a compound or salt of Formula (A), (A*), (I), (IIA), or (IIB), $R^1$ is selected from

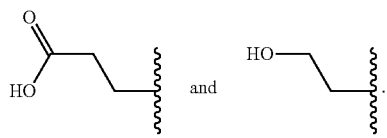

In some embodiments, for a compound or salt of Formula (A), (A*), (I), (IIA), or (IIB), $R^1$ is selected from:
substituted $C_1$-$C_6$ alkyl, wherein the substituents on $C_1$-$C_6$ alkyl are independently selected at each occurrence from one or more —OH, oxo, and —O—$C_{1-10}$ alkyl;
optionally substituted 6 to 8-membered saturated heterocycle; wherein the optional substituents are independently selected at each occurrence from one or more optionally substituted $C_{1-10}$ alkyl, wherein the optional substituents on the $C_{1-10}$ alkyl are independently selected at each occurrence from one or more hydroxy, oxo, —$C_{1-10}$ haloalkyl, and —$NH_2$.

In some embodiments, for a compound or salt of Formula (A), (A*), (I), (IIA), or (IIB), $R^1$ is selected from:

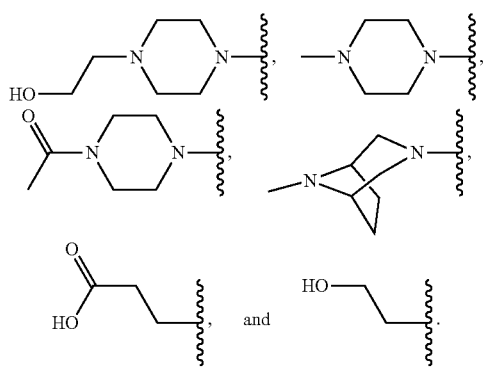

In some embodiments, for a compound or salt of Formula (A), (A*), (I), (IIA), or (IIB), $R^1$ is piperazine, wherein the piperazine is optionally substituted with one or more substituents independently selected at each occurrence from oxo, —$S(O_2)NH_2$, and $C_{1-10}$ alkyl, wherein the $C_{1-10}$ alkyl is optionally substituted with one or more substituents independently selected at each occurrence from hydroxy, halogen, oxo, and —$NH_2$. In some embodiments, $R^1$ is piperazine substituted with one or more $C_{1-3}$ alkyl, wherein the $C_{1-3}$ alkyl is optionally substituted with one or more substituents independently selected at each occurrence from hydroxy, halogen, oxo, and —$NH_2$.

In some embodiments, for a compound or salt of Formula (A), (A*), (I), (IIA), or (IIB), $R^1$ is selected from

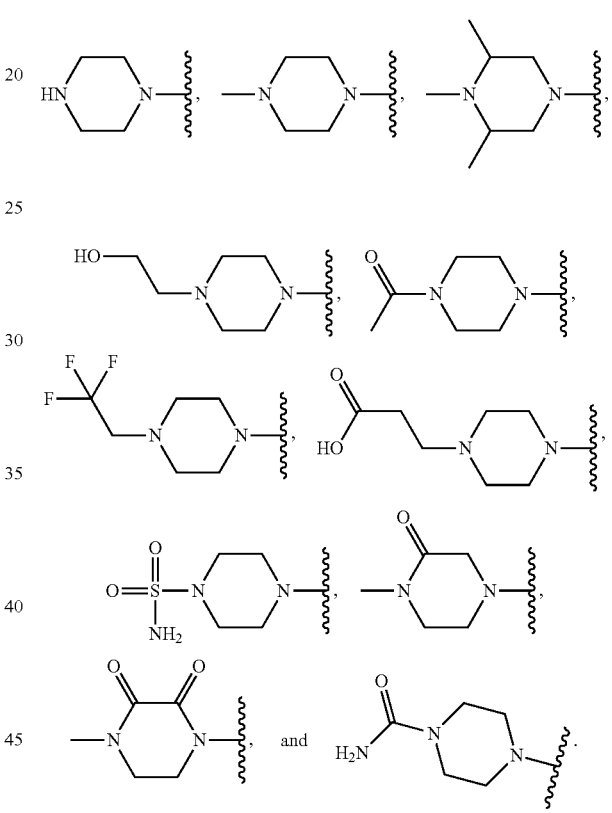

In some embodiments, for a compound or salt of Formula (A), (A*), or (I), the compound is not

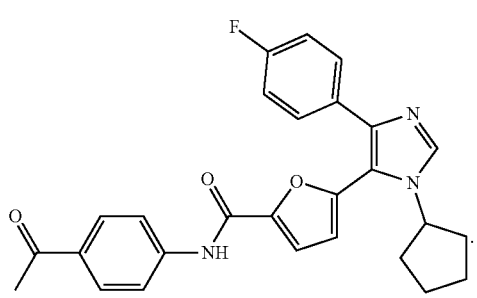 [SMILES: CC(=O)c1ccc(NC(=O)c2ccc(-c3c(-c4ccc(F)cc4)ncn3C3CCCC3)o2)cc1]

In some cases, the compound is not

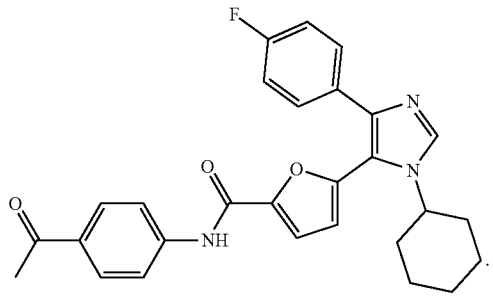 [SMILES: CC(=O)c1ccc(NC(=O)c2ccc(-c3c(-c4ccc(F)cc4)ncn3C3CCCCC3)o2)cc1]

In some embodiments, for a compound or salt of Formula (A), (A*), or (I), $R^1$ is selected from —$N(R^5)_2$, wherein $R^5$ is selected from optionally substituted $C_1$-$C_6$ alkyl, wherein the optional substituents on $C_1$-$C_6$ alkyl are selected from hydroxy;

substituted $C_1$-$C_6$ alkyl wherein the substituents are selected from hydroxy, oxo, and —O—$C_{1-10}$ alkyl; and optionally substituted 5 to 6-membered heterocycle wherein the optional substituents are selected from oxo, —$S(O_2)NH_2$, and optionally substituted $C_{1-10}$ alkyl, wherein the optional substituents on the $C_{1-10}$ alkyl are independently selected at each occurrence from one or more hydroxy, halogen, oxo, and —$NH_2$;

$R^3$ is optionally substituted phenyl wherein the optional substituents of phenyl of $R^3$ are selected from halogen and —$C_{1-10}$ haloalkyl;

$R^4$ is selected from optionally substituted $C_1$-$C_6$ alkyl and optionally substituted $C_{3-6}$ carbocycle wherein the optional substituents of $C_1$-$C_6$ alkyl of $R^4$ are selected from halogen and wherein the optional substituents of $C_3$-$C_6$ carbocycle of $R^4$ are selected from hydroxy; and W is selected from imidazole, furan, and pyridine.

In some embodiments, for a compound or salt of Formula (A), (A*), or (I), $R^1$ is selected from —$N(R^5)_2$, wherein $R^5$ is selected from optionally substituted $C_1$-$C_6$ alkyl, wherein the optional substituents on $C_1$-$C_6$ alkyl are selected from hydroxy;

substituted $C_1$-$C_6$ alkyl wherein the substituents are selected from hydroxy, oxo, and —O—$C_{1-10}$ alkyl; and optionally substituted 5 to 6-membered heterocycle wherein the optional substituents are selected from oxo, —$S(O_2)NH_2$, and optionally substituted $C_{1-10}$ alkyl, wherein the optional substituents on the $C_{1-10}$ alkyl are independently selected at each occurrence from one or more hydroxy, halogen, oxo, and —$NH_2$;

$R^3$ is optionally substituted phenyl wherein the optional substituents of phenyl of $R^3$ are selected from halogen and —$C_{1-10}$ haloalkyl;

$R^4$ is selected from optionally substituted $C_1$-$C_6$ alkyl and optionally substituted $C_{3-6}$ carbocycle wherein the optional substituents of $C_1$-$C_6$ alkyl of $R^4$ are selected from halogen and wherein the optional substituents of $C_3$-$C_6$ carbocycle of $R^4$ are selected from hydroxy; and W are selected from imidazole.

In some embodiments, for a compound or salt of Formula (A), (A*), (IIA), (IIB), or (I), $R^1$ is selected from

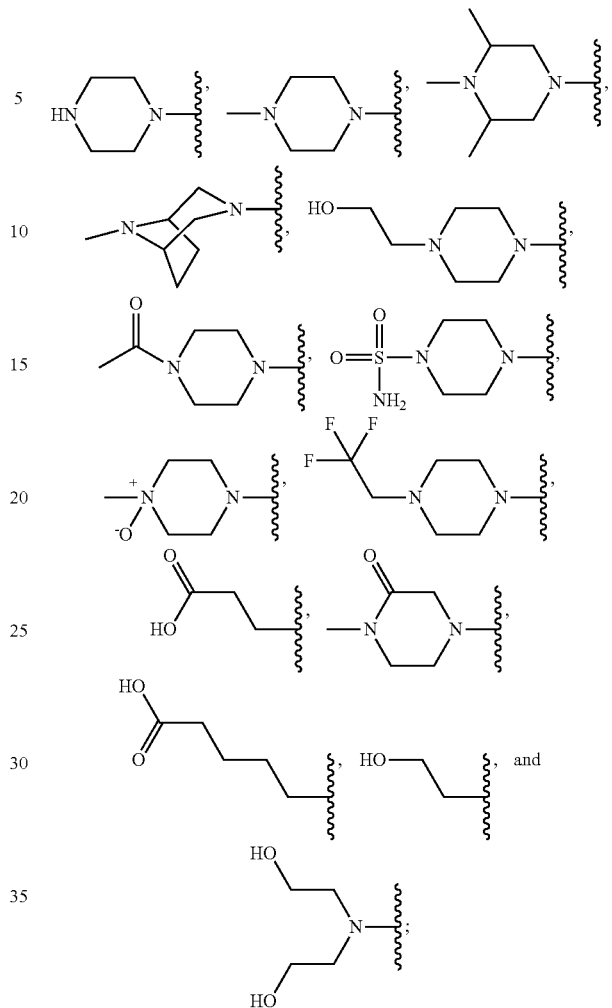

$R^3$ is

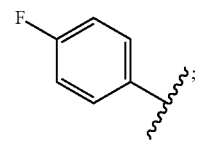 [SMILES: *c1ccc(F)cc1]

and $R^4$ is selected from

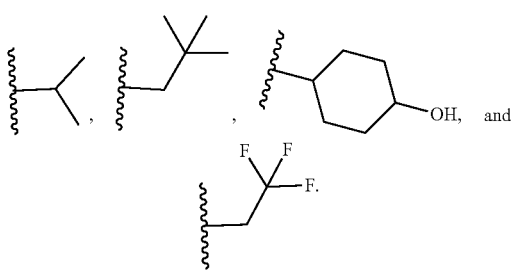

Included in the present disclosure are salts, particularly pharmaceutically acceptable salts, of the compounds described herein. The compounds of the present invention that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

Chemical entities having carbon-carbon double bonds or carbon-nitrogen double bonds may exist in Z- or E-form (or cis- or trans-form). Furthermore, some chemical entities may exist in various tautomeric forms. Unless otherwise specified, compounds described herein are intended to include all Z-, E- and tautomeric forms as well.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, and $^{125}$I are all contemplated. All isotopic variations of the compounds of the present invention, whether radioactive or not, are encompassed within the scope of the present invention. In some embodiments, where isotopic variations are illustrated, the remaining atoms of the compound may optionally contain unnatural portions of atomic isotopes.

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetra-

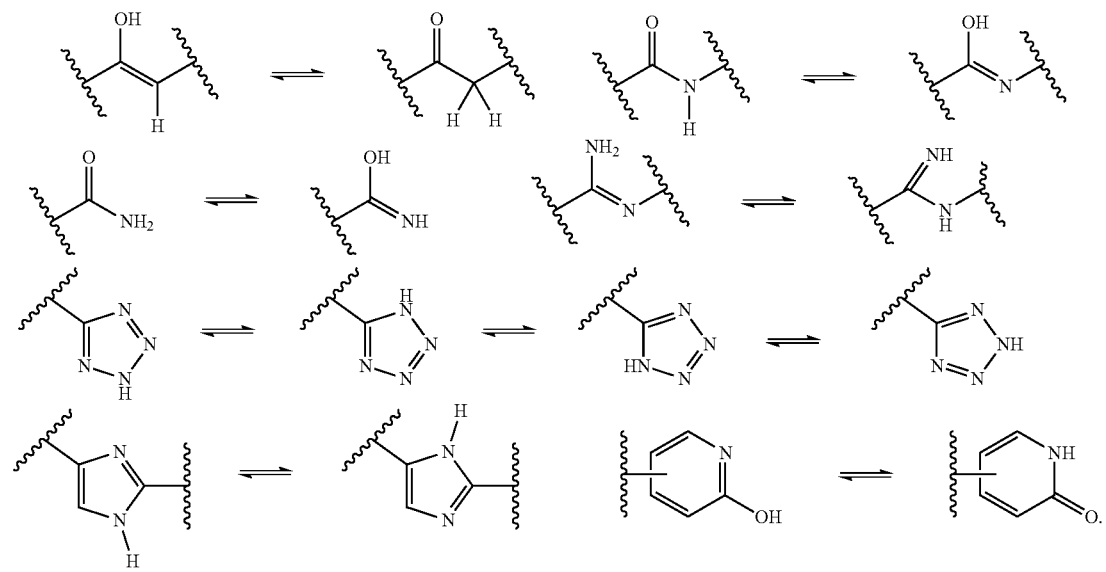

hedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

In some embodiments of a compound disclosed herein, one or more of $R^1$, $R^3$, $R^4$, $R^5$, W, Z, Y, and $R^{10}$ groups comprise deuterium at a percentage higher than the natural abundance of deuterium.

In some embodiments of a compound disclosed herein, one or more hydrogens are replaced with one or more deuteriums in one or more of the following groups $R^1$, $R^3$, $R^4$, $R^5$, W, Z, Y, and $R^{10}$.

In some embodiments of a compound disclosed herein, the abundance of deuterium in each of $R^1$, $R^3$, $R^4$, $R^5$, W, Z, The compounds disclosed herein, in some embodiments, are used in different enriched isotopic forms, e.g., enriched in the content of $^2$H, $^3$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, compounds described herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the Y, and R¹⁰ is independently at least 1%, at least 10%, at least 20%, at least 30%, at least 40%, at least 50%, at least 60%, at least 70%, at least 80%, at least 90%, or 100% of a total number of hydrogen and deuterium.

In some embodiments of a compound disclosed herein, one or more hydrogens of ring W are replaced with one or more deuteriums.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

The compounds described herein may in some cases exist as diastereomers, enantiomers, or other stereoisomeric forms. Where absolute stereochemistry is not specified, the compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

In certain embodiments, compounds or salts of the compounds may be prodrugs, e.g., wherein a hydroxyl in the parent compound is presented as an ester or a carbonate, or carboxylic acid present in the parent compound is presented as an ester. The term "prodrug" is intended to encompass compounds which, under physiologic conditions, are converted into pharmaceutical agents of the present disclosure. One method for making a prodrug is to include one or more selected moieties which are hydrolyzed under physiologic conditions to reveal the desired molecule. In other embodiments, the prodrug is converted by an enzymatic activity of the host animal such as specific target cells in the host animal. For example, esters or carbonates (e.g., esters or carbonates of alcohols or carboxylic acids and esters of phosphonic acids) are preferred prodrugs of the present disclosure.

Prodrug forms of the herein described compounds, wherein the prodrug is metabolized in vivo to produce a compound as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. Prodrugs may help enhance the cell permeability of a compound relative to the parent drug. The prodrug may also have improved solubility in pharmaceutical compositions over the parent drug. Prodrugs may be designed as reversible drug derivatives, for use as modifiers to enhance drug transport to site-specific tissues or to increase drug residence inside of a cell.

In some embodiments, the design of a prodrug increases the lipophilicity of the pharmaceutical agent. In some embodiments, the design of a prodrug increases the effective water solubility. See, e.g., Fedorak et al., *Am. J. Physiol.*, 269:G210-218 (1995); McLoed et al., *Gastroenterol*, 106: 405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103 (1988); Sinkula et al., *J. Pharm. Sci.*, 64:181-210 (1975); T. Higuchi and V. Stella, *Pro-drugs as Novel Delivery Systems*, Vol. 14 of the A.C.S. Symposium Series; and Edward B. Roche, *Bioreversible Carriers in Drug Design*, American Pharmaceutical Association and Pergamon Press, 1987, all incorporated herein for such disclosure). According to another embodiment, the present disclosure provides methods of producing the above-defined compounds. The compounds may be synthesized using conventional techniques. Advantageously, these compounds are conveniently synthesized from readily available starting materials.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis*, 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

C. Pharmaceutical Compositions

Provided herein, in certain embodiments, are compositions comprising a therapeutically effective amount of any compound or salt of any one of Formulas (A), (A*), (I), (IIA), or (IIB), (also referred to herein as "a pharmaceutical agent").

Pharmaceutical compositions may be formulated using one or more physiologically acceptable carriers including excipients and auxiliaries which facilitate processing of the pharmaceutical agent into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa., Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

The compositions and methods of the present disclosure may be utilized to treat an individual in need thereof. In certain embodiments, the individual is a mammal such as a human, or a non-human mammal. When administered to an animal, such as a human, the composition or the pharmaceutical agent, is preferably administered as a pharmaceutical composition comprising, for example, a pharmaceutical agent and a pharmaceutically acceptable carrier or excipient. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration, e.g., routes, such as injection or implantation, that circumvent transport or diffusion through an epithelial barrier, the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule, granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

The pharmaceutical composition can be used as an inhibitor of tumor immunosuppresion in combination with chemotherapy or an immune checkpoint inhibitor therapy for cancer. In some case the pharmaceutical composition can be used to treat a fibrotic disease or condition including but not limited to chronic kidney fibrosis ("CKD"), liver cirrhosis, pulmonary fibrosis, renal interstitial fibrosis, myocardial infarction, skin fibrosis, systemic sclerosis ("SSc"), and graft-versus-host disease ("GVHD). In some cases, the pharmaceutical composition can be used to treat kidney fibrosis. In some cases, the pharmaceutical composition can be used to treat skin fibrosis. In some cases, the pharmaceutical composition can be used to treat idiopathic pulmonary fibrosis (IPF). In some cases, the pharmaceutical composition can be used to treat a disease associated with TNIK kinase.

A pharmaceutically acceptable excipient can contain physiologically acceptable agents that act, for example, to stabilize, increase solubility or to increase the absorption of a compound such as a pharmaceutical agent. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable excipient, including a physiologically acceptable agent, depends, for example, on the route of administration of the composition. The preparation or pharmaceutical composition can be a self-emulsifying drug delivery system or a self microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

A pharmaceutical composition (preparation) can be administered to a subject by any of a number of routes of administration including, for example, orally, for example, drenches as in aqueous or non-aqueous solutions or suspensions, tablets, capsules, including sprinkle capsules and gelatin capsules, boluses, powders, granules, pastes for application to the tongue; absorption through the oral mucosa, e.g., sublingually; anally, rectally or vaginally, for example, as a pessary, cream or foam; parenterally, including intramuscularly, intravenously, subcutaneously or intrathecally as, for example, a sterile solution or suspension; nasally; intraperitoneally; subcutaneously; transdermally, for example, as a patch applied to the skin; and topically, for example, as a cream, ointment or spray applied to the skin, or as an eye drop. The compound may also be formulated for inhalation. In certain embodiments, a compound may be simply dissolved or suspended in sterile water.

A pharmaceutical composition may be a sterile aqueous or non-aqueous solution, suspension or emulsion, e.g., a microemulsion. The excipients described herein are examples and are in no way limiting. An effective amount or therapeutically effective amount refers to an amount of the one or more pharmaceutical agents administered to a subject, either as a single dose or as part of a series of doses, which is effective to produce a desired therapeutic effect.

Subjects may generally be monitored for therapeutic effectiveness using assays and methods suitable for the condition being treated, which assays will be familiar to those having ordinary skill in the art and are described herein. Pharmacokinetics of a pharmaceutical agent, or one or more metabolites thereof, that is administered to a subject may be monitored by determining the level of the pharmaceutical agent or metabolite in a biological fluid, for example, in the blood, blood fraction, e.g., serum, and/or in the urine, and/or other biological sample or biological tissue from the subject. Any method practiced in the art and described herein to detect the agent may be used to measure the level of the pharmaceutical agent or metabolite during a treatment course.

The dose of a pharmaceutical agent described herein for treating a disease or disorder may depend upon the subject's condition, that is, stage of the disease, severity of symptoms caused by the disease, general health status, as well as age, gender, and weight, and other factors apparent to a person skilled in the medical art. Pharmaceutical compositions may be administered in a manner appropriate to the disease to be treated as determined by persons skilled in the medical arts. In addition to the factors described herein and above related to use of pharmaceutical agent for treating a disease or disorder, suitable duration and frequency of administration of the pharmaceutical agent may also be determined or adjusted by such factors as the condition of the patient, the type and severity of the patient's disease, the particular form of the active ingredient, and the method of administration. Optimal doses of an agent may generally be determined using experimental models and/or clinical trials. The optimal dose may depend upon the body mass, weight, or blood volume of the subject. The use of the minimum dose that is sufficient to provide effective therapy is usually preferred. Design and execution of pre-clinical and clinical studies for a pharmaceutical agent, including when administered for prophylactic benefit, described herein are well within the skill of a person skilled in the relevant art. When two or more pharmaceutical agents are administered to treat a disease or disorder, the optimal dose of each pharmaceutical agent may be different, such as less than when either agent is administered alone as a single agent therapy. In certain particular embodiments, two pharmaceutical agents in combination may act synergistically or additively, and either agent may be used in a lesser amount than if administered alone. An amount of a pharmaceutical agent that may be administered per day may be, for example, between about 0.01 mg/kg and 100 mg/kg, e.g., between about 0.1 to 1 mg/kg, between about 1 to 10 mg/kg, between about 10-50 mg/kg, between about 50-100 mg/kg body weight. In other embodiments, the amount of a pharmaceutical agent that may be administered per day is between about 0.01 mg/kg and 1000 mg/kg, between about 100-500 mg/kg, or between about 500-1000 mg/kg body weight. The optimal dose, per day or per course of treatment, may be different for the disease or disorder to be treated and may also vary with the administrative route and therapeutic regimen.

Pharmaceutical compositions comprising a pharmaceutical agent can be formulated in a manner appropriate for the delivery method by using techniques routinely practiced in the art. The composition may be in the form of a solid, e.g., tablet, capsule, semi-solid, e.g., gel, liquid, or gas, e.g., aerosol. In other embodiments, the pharmaceutical composition is administered as a bolus infusion.

Pharmaceutical acceptable excipients are well known in the pharmaceutical art and described, for example, in Rowe et al., Handbook of Pharmaceutical Excipients: A Comprehensive Guide to Uses, Properties, and Safety, 5$^{th}$ Ed., 2006, and in *Remington: The Science and Practice of Pharmacy* (Gennaro, 21st Ed. Mack Pub. Co., Easton, Pa. (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used. In general, the type of excipient is selected based on the mode of administration, as well as the chemical composition of the active ingredient(s). Alternatively, compositions described herein may be formulated as a lyophilizate. A composition described herein may be lyophilized or otherwise formulated as a lyophilized product using one or more appropriate excipient solutions for solubilizing and/or diluting the pharmaceutical agent(s) of the composition upon administration. In other embodiments, the pharmaceutical agent may be encapsulated within liposomes using technology known and practiced in the art. In certain particular embodiments, a pharmaceutical agent is not formulated within liposomes for application to a stent that is used for treating highly, though not totally, occluded arteries. Pharmaceutical compositions may be formulated for any appropriate manner of administration described herein and in the art.

A pharmaceutical composition, e.g., for oral administration or for injection, infusion, subcutaneous delivery, intramuscular delivery, intraperitoneal delivery or other method, may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition may be applied to the eye in the form of eye drops. A liquid pharmaceutical composition may be delivered orally.

For oral formulations, at least one of the pharmaceutical agents described herein can be used alone or in combination with appropriate additives to make tablets, powders, granules or capsules, and if desired, with diluents, buffering agents, moistening agents, preservatives, coloring agents, and flavoring agents. The pharmaceutical agents may be formulated with a buffering agent to provide for protection of the compound from low pH of the gastric environment and/or an enteric coating. A pharmaceutical agent included in a pharmaceutical composition may be formulated for oral delivery with a flavoring agent, e.g., in a liquid, solid or semi-solid formulation and/or with an enteric coating.

A pharmaceutical composition comprising any one of the pharmaceutical agents described herein may be formulated for sustained or slow release, also called timed release or controlled release. Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of pharmaceutical agent contained within a sustained release formulation depends upon the site of implantation, the rate and expected duration of release, and the nature of the condition, disease or disorder to be treated or prevented.

In certain embodiments, the pharmaceutical compositions comprising a pharmaceutical agent are formulated for transdermal, intradermal, or topical administration. The compositions can be administered using a syringe, bandage, transdermal patch, insert, or syringe-like applicator, as a powder/talc or other solid, liquid, spray, aerosol, ointment, foam, cream, gel, paste. This preferably is in the form of a controlled release formulation or sustained release formulation administered topically or injected directly into the skin adjacent to or within the area to be treated, e.g., intradermally or subcutaneously. The active compositions can also be delivered via iontophoresis. Preservatives can be used to prevent the growth of fungi and other microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, thimerosal, and combinations thereof.

Pharmaceutical compositions comprising a pharmaceutical agent can be formulated as emulsions for topical application. An emulsion contains one liquid distributed in the body of a second liquid. The emulsion may be an oil-in-water emulsion or a water-in-oil emulsion. Either or both of the oil phase and the aqueous phase may contain one or more surfactants, emulsifiers, emulsion stabilizers, buffers, and other excipients. The oil phase may contain other oily pharmaceutically approved excipients. Suitable surfactants include, but are not limited to, anionic surfactants, non-ionic surfactants, cationic surfactants, and amphoteric surfactants. Compositions for topical application may also include at least one suitable suspending agent, antioxidant, chelating agent, emollient, or humectant.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays may be delivered from pressurized packs, for example, via a specially shaped closure. Oil-in-water emulsions can also be used in the compositions, patches, bandages and articles. These systems are semisolid emulsions, micro-emulsions, or foam emulsion systems.

In some embodiments, the pharmaceutical agent described herein can be formulated as in inhalant. Inhaled methods can deliver medication directly to the airway. The pharmaceutical agent can be formulated as aerosols, microspheres, liposomes, or nanoparticles. The pharmaceutical agent can be formulated with solvents, gases, nitrates, or any combinations thereof. Compositions described herein are optionally formulated for delivery as a liquid aerosol or inhalable dry powder. Liquid aerosol formulations are optionally nebulized predominantly into particle sizes that can be delivered to the terminal and respiratory bronchioles. Liquid aerosol and inhalable dry powder formulations are preferably delivered throughout the endobronchial tree to the terminal bronchioles and eventually to the parenchymal tissue.

Aerosolized formulations described herein are optionally delivered using an aerosol forming device, such as a jet, vibrating porous plate or ultrasonic nebulizer, preferably selected to allow the formation of aerosol particles having with a mass medium average diameter predominantly between 1 to 5μ. Further, the formulation preferably has balanced osmolarity ionic strength and chloride concentration, and the smallest aerosolizable volume able to deliver effective dose of the pharmaceutical agent. Additionally, the aerosolized formulation preferably does not negatively impair the functionality of the airways and does not cause undesirable side effects.

Aerosolization devices suitable for administration of aerosol formulations described herein include, for example, jet, vibrating porous plate, ultrasonic nebulizers and energized dry powder inhalers, that are able to nebulize the formulation into aerosol particle size predominantly in the size range from 1-5μ. Predominantly in this application means that at least 70% but preferably more than 90% of all generated aerosol particles are within 1-5 μrange. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb™ and AeroDose™ vibrating porous plate nebulizers (AeroGen, Inc., Sunnyvale, Calif.), Sidestream® nebulizers (Medic-Aid Ltd., West Sussex, England), Pari LC® and Pari LC Star® jet nebulizers (Pari Respiratory Equipment, Inc., Richmond, Va.), and Aerosonic™ (DeVilbiss Medizinische Produkte (Deutschland) GmbH, Heiden, Germany) and UltraAire® (Omron Healthcare, Inc., Vernon Hills, Ill.) ultrasonic nebulizers.

In some embodiments, the pharmaceutical agent(s) can be formulated with oleaginous bases or ointments to form a semisolid composition with a desired shape. In addition to the pharmaceutical agent, these semisolid compositions can contain dissolved and/or suspended bactericidal agents, preservatives and/or a buffer system. A petrolatum component that may be included may be any paraffin ranging in viscosity from mineral oil that incorporates isobutylene, colloidal silica, or stearate salts to paraffin waxes. Absorption bases can be used with an oleaginous system. Additives may include cholesterol, lanolin (lanolin derivatives, beeswax, fatty alcohols, wool wax alcohols, low HLB (hydrophobel-lipophobe balance) emulsifiers, and assorted ionic and nonionic surfactants, singularly or in combination.

Controlled or sustained release transdermal or topical formulations can be achieved by the addition of time-release additives, such as polymeric structures, matrices, that are available in the art. For example, the compositions may be administered through use of hot-melt extrusion articles, such as bioadhesive hot-melt extruded film. The formulation can comprise a cross-linked polycarboxylic acid polymer formulation. A cross-linking agent may be present in an amount that provides adequate adhesion to allow the system to remain attached to target epithelial or endothelial cell surfaces for a sufficient time to allow the desired release of the compound.

An insert, transdermal patch, bandage or article can comprise a mixture or coating of polymers that provide release of the pharmaceutical agents at a constant rate over a prolonged period of time. In some embodiments, the article, transdermal patch or insert comprises water-soluble pore forming agents, such as polyethylene glycol (PEG) that can be mixed with water insoluble polymers to increase the durability of the insert and to prolong the release of the active ingredients.

Transdermal devices (inserts, patches, bandages) may also comprise a water insoluble polymer. Rate controlling polymers may be useful for administration to sites where pH change can be used to effect release. These rate controlling polymers can be applied using a continuous coating film during the process of spraying and drying with the active compound. In one embodiment, the coating formulation is used to coat pellets comprising the active ingredients that are compressed to form a solid, biodegradable insert.

A polymer formulation can also be utilized to provide controlled or sustained release. Bioadhesive polymers described in the art may be used. By way of example, a sustained-release gel and the compound may be incorporated in a polymeric matrix, such as a hydrophobic polymer matrix. Examples of a polymeric matrix include a microparticle. The microparticles can be microspheres, and the core may be of a different material than the polymeric shell. Alternatively, the polymer may be cast as a thin slab or film, a powder produced by grinding or other standard techniques, or a gel such as a hydrogel. The polymer can also be in the form of a coating or part of a bandage, stent, catheter, vascular graft, or other device to facilitate delivery of the pharmaceutical agent. The matrices can be formed by solvent evaporation, spray drying, solvent extraction and other methods known to those skilled in the art.

Kits with unit doses of one or more of the agents described herein, usually in oral or injectable doses, are provided. Such kits may include a container containing the unit dose, an informational package insert describing the use and attendant benefits of the drugs in treating disease, and optionally an appliance or device for delivery of the composition.

D. Methods of Treatment

The compounds described herein can be used in the preparation of medicaments for the prevention or treatment of diseases or conditions. In addition, a method for treating any of the diseases or conditions described herein in a subject in need of such treatment, involves administration of pharmaceutical compositions containing at least one compound described herein, or a pharmaceutically acceptable salt, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day. In some embodiments, compounds and pharmaceutical compositions described herein are administered once daily. In some embodiments, compounds and pharmaceutical compositions described herein are administered twice daily. In some embodiments, compounds and pharmaceutical compositions described herein are administered 3 times a day. In some embodiments, compounds and pharmaceutical compositions described herein are administered once weekly. In some embodiments, compounds and pharmaceutical compositions described herein are administered twice weekly. In some embodiments, compounds and pharmaceutical compositions described herein are administered 3 to 7 times a week. In some embodiments, compounds and pharmaceutical compositions described herein are administered orally. In some embodiments, compounds and pharmaceutical compositions described herein are administered intravenously. In some embodiments, compounds and pharmaceutical compositions described herein are administered topically. For example, a compound described herein can be administered topically at doses of 0.001% to 10%.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

In an aspect provided herein, the invention provides for inhibitors of TNIK kinase. Accordingly, the TNIK kinase inhibitors can be used to inhibit a biological pathway downstream from inhibiting TNIK. In some aspects, the TNIK inhibitor can inhibit fibrillar collagen, and thereby can inhibit biological activity related to regulation of the extracellular matrix, and regulation of remodeling the extracellular matrix. The TNIK inhibitor can inhibit regulation of cell growth, differentiation, cell migration, proliferation, and metabolism.

In certain embodiments, inhibiting the TNIK can inhibit certain TNIK related biological pathways. In certain aspects, the inhibiting of TNIK inhibits the Wnt pathway.

In certain embodiments, the inhibiting of TNIK inhibits cytoskeletal rearrangements. The inhibition of TNIK can inhibit the c-Jun N-terminal kinase pathway. The inhibition of TNIK can inhibit the phosphorylation of Gelsolin. The inhibition of TNIK can inhibit the regulation of the cytoskeleton, such as cytoskeletal rearrangements.

In certain embodiments, the inhibiting of TNIK inhibits carcinogenesis. In certain aspect, the administering of the TNIK inhibitor includes a therapeutically effective amount of the compound sufficient to treat cancer by: inhibiting cancer cell growth; inhibiting cancer cell migration; inhibiting cancer cell proliferation; or inhibiting cancer cell migration.

In certain embodiments, the invention provides a method of treating or preventing a disease, state or condition in a patient in need thereof comprising administering to the patient an effective amount of a compound of any one of embodiments of the invention or a pharmaceutically acceptable salt thereof. The disease, state or condition may be selected from the group consisting of colorectal cancer, gastric cancer, breast cancer, lung cancer, pancreatic cancer, prostate cancer, multiple myeloma, chronic myelogenous leukemia, cancer metastasis, fibrosis and psychiatric disorders. In some embodiments, the cancer is colorectal cancer. In some embodiments, the cancer is gastric cancer. In some embodiments, the cancer is breast cancer. In some embodiments, the cancer is lung cancer. In some embodiments, the cancer is pancreatic cancer. In some embodiments, the cancer is prostate cancer. In some embodiments, the cancer is multiple myeloma. In some embodiments, the cancer is chronic myelogenous leukemia. In some embodiments, the cancer is cancer metastasis.

In certain embodiments, the cancer is a solid tumor. In certain embodiments, the cancer is not a solid tumor.

In certain embodiments, the inhibiting of TNIK inhibits embryonic development. As such, the TNIK inhibitor can inhibit pregnancy progression and thereby be used for terminating a pregnancy.

In some embodiments, the inhibiting of TNIK inhibits TGF beta signaling. The TGF beta signaling pathway is involved in a various processes, and thereby inhibiting the TGF beta signaling pathway can inhibit these processes, some of which are described herein. This can include inhibiting development of an embryo as described herein for inhibiting progression of pregnancy. This can include inhibiting cell growth, cell differentiation, which may be used to inhibit pregnancy progression as well as inhibiting cancer.

In certain embodiments, inhibiting the TGF beta signaling can be used for inhibiting formation of extracellular matrix or over formation of extracellular matrix and the problems associated therewith (e.g., fibrosis). In some aspects, the inhibiting of TGF beta signaling by inhibiting TNIK inhibits glycosaminoglycan formation. In some aspects, the inhibiting of TGF beta by inhibiting TNIK inhibits collagen formation. In some aspects, the inhibiting of TNIK inhibits fibrosis. In some aspects, the inhibited fibrosis is selected from pulmonary fibrosis (e.g., idiopathic or radiation induced), cystic fibrosis, liver fibrosis (e.g., cirrhosis), myocardial fibrosis (e.g., atrial fibrosis, endomyocardial fibrosis, old myocardial infarction), kidney fibrosis, brain fibrosis (e.g., glial scar), arterial fibrosis, arthrofibrosis (e.g., knee, shoulder, other joints), intestinal fibrosis (e.g., Crohn's disease), Dupytren's contracture fibrosis (e.g., hands, fingers), keloid fibrosis (e.g., skin), mediastinal fibrosis (e.g., soft tissue of the mediastinum), myelofibrosis (e.g., bone marrow), peyronie's disease fibrosis (e.g., penis), progressive massive fibrosis (e.g., lungs, complication of coal worker's pneumoconiosis), retroperitoneal fibrosis (e.g., soft tissue of the retroperitoneum), scleroderma sclerosis fibrosis (e.g., skin, lungs), adhesive capsulitis fibrosis (e.g., shoulder), or combinations thereof. In some aspects, the fibrosis is skin fibrosis.

In certain embodiments, the TNIK inhibitor can be used to inhibit the epithelial to mesenchymal transition of cancer cells and/or development of fibrosis. In some aspects, this can include inhibiting the Smad signaling pathways. In some aspects, this can include inhibiting the non-Smad signaling pathways. In some aspects, this can include inhibiting Wnt, NF-KB, FAC-Src-paxillin-related focal adhesion, and MAP kinases (e.g., ERK and INK) signaling pathways.

In certain embodiments, the disclosure provides for methods of treating or preventing a fibrotic disease or condition. In some embodiments, the fibrotic disease or condition is selected from pulmonary fibrosis, cystic fibrosis, liver fibrosis, myocardial fibrosis, kidney fibrosis, brain fibrosis, arterial fibrosis, arthrofibrosis, intestinal fibrosis, Dupytren's contracture fibrosis, keloid fibrosis, mediastinal fibrosis, myelofibrosis, peyronie's disease fibrosis, progressive massive fibrosis, retroperitoneal fibrosis, scleroderma sclerosis fibrosis, adhesive capsulitis fibrosis, or combinations thereof. In some embodiments, the fibrotic disease is selected from liver cirrhosis, pulmonary fibrosis, renal interstitial fibrosis, myocardial infarction, systemic sclerosis (SSc), and graft-versus-host disease (GVHD). In some embodiments, the fibrotic disease is kidney fibrosis.

In certain embodiments, the disclosure provides for methods of treating a kidney disease. In some embodiments, the kidney disease is chronic kidney fibrosis (CKD). In some embodiments, the kidney disease is a kidney fibrosis.

In some embodiments, the fibrotic disease is liver cirrhosis. In some embodiments, the fibrotic disease is pulmonary fibrosis. In some embodiments, the fibrotic disease is idiopathic pulmonary fibrosis (IPF).

In some embodiments, the fibrotic disease is kidney fibrosis wherein the disease is chronic or acute. In some embodiments, the kidney fibrosis causes glomerulosclerosis or tubulointerstitial fibrosis. In some embodiments, the fibrotic disease is renal interstitial fibrosis. In some embodiments, the fibrotic disease is acute interstitial nephritis (AIN).

In some embodiments, the fibrotic disease is systemic sclerosis (SSc). In some embodiments, the fibrotic disease is graft-versus-host disease (GVHD). In some embodiments, the fibrotic disease is hypertrophic scarring (HTS).

In some embodiments, provided herein are methods of suppressing fibrosis markers in a subject such as alpha-smooth muscle actin, or α-SMA, and collagen by administering compounds and pharmaceutical compositions of the present disclosure.

In some embodiments, provided herein are methods of antagonizing fibroblast-to-myofibroblast transition (FMT) in primary human lung fibroblasts. In some embodiments, provided herein are methods of antagonizing epithelial-mesenchymal transition (EMT) in primary human epithelial cells.

In some embodiments, provided herein are methods of reducing collagen and hydroxyproline in the skin by administering compounds and pharmaceutical compositions of the present disclosure, e.g., via oral or topical administration.

In some embodiments, compounds and pharmaceutical compositions described herein are administered with a second therapeutic agent. In some embodiments, the second therapeutic agent is Pirfenidone. In some embodiments, compounds and pharmaceutical compositions described herein are administered with sub-therapeutic doses of Pirfenidone.

Compounds and pharmaceutical compositions described herein can be administered to a subject for a period of about 1 day to about 30 years or more. In some embodiments, compounds and pharmaceutical compositions described herein are administered to a subject for a period of over a year. In some embodiments, compounds and pharmaceutical compositions described herein are administered to a subject for a period of 3 months to 5 years. In some embodiments, compounds and pharmaceutical compositions described herein are administered to a subject for a period of 1 month to 1 year or any numbers or ranges therebetween (e.g., 2-3 months, 1-6 months, 6-12 months, 1-3 months, etc.).

E. Further Embodiments

In an aspect, provided herein is a compound represented by Formula (IIA):

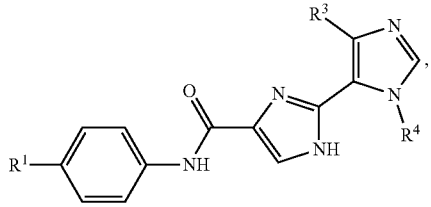

(IIA)

or a pharmaceutically acceptable salt thereof, wherein:

$R^1$ is piperazine, wherein the piperazine is optionally substituted with one or more substituents independently selected at each occurrence from oxo, —S(O$_2$)NH$_2$, and C$_{1-10}$ alkyl, wherein the C$_{1-10}$ alkyl is optionally substituted with one or more substituents independently selected at each occurrence from hydroxy, halogen, oxo, and —NH$_2$;

$R^3$ is phenyl, wherein the phenyl is optionally substituted with one or more halogen; and $R^4$ is unsubstituted C$_1$-C$_6$ alkyl.

In some embodiments, $R^4$ is selected from

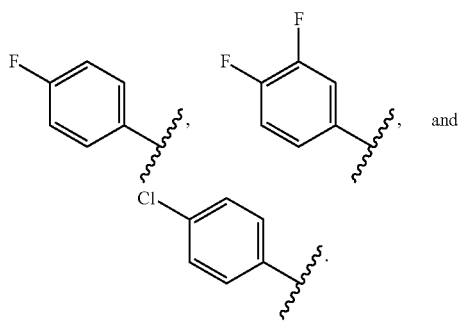

In some embodiments, $R^3$ is selected from

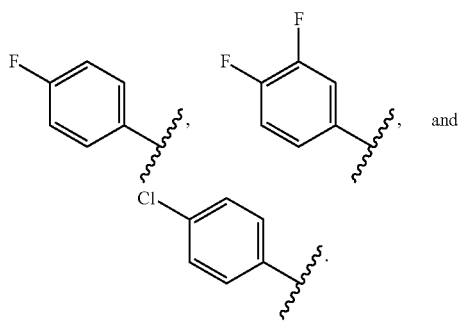

In some embodiments, $R^1$ is piperazine substituted with one or more C$_{1-3}$ alkyl, wherein the C$_{1-3}$ alkyl is optionally substituted with one or more substituents independently selected at each occurrence from hydroxy, halogen, oxo, and —NH$_2$.

In some embodiments, $R^1$ is selected from

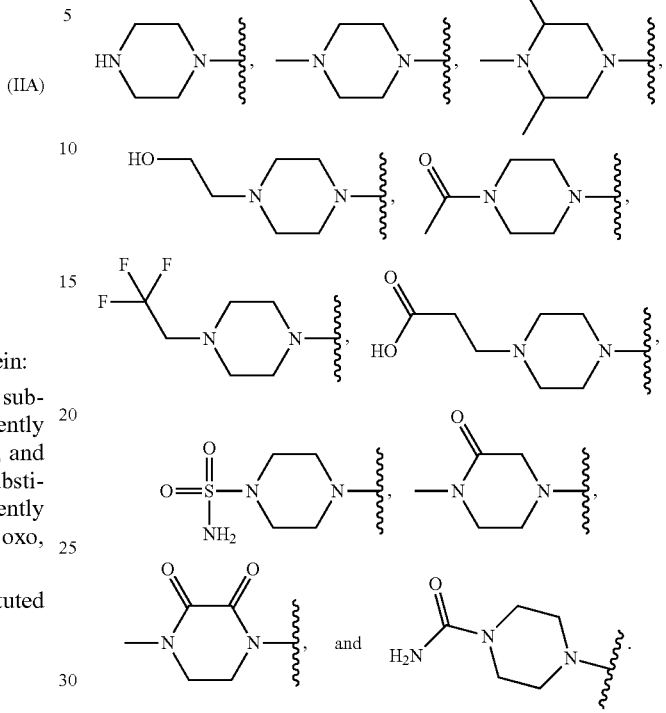

In some embodiments, the compound is:

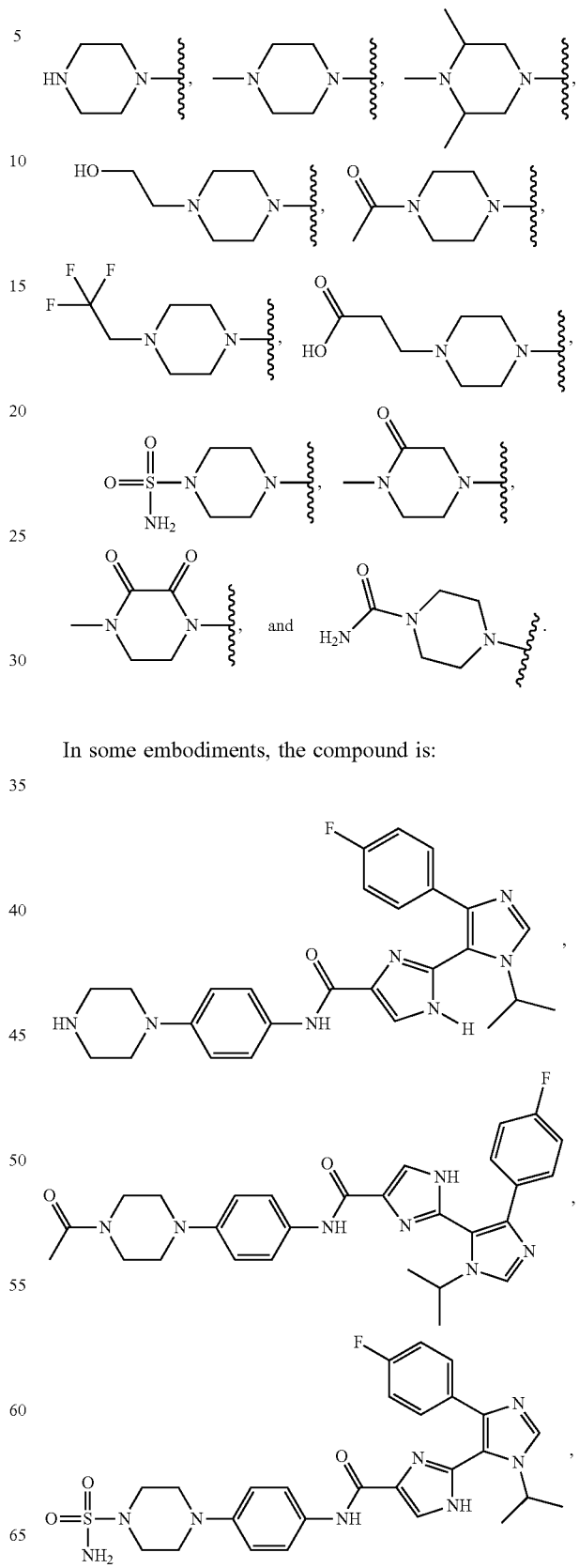

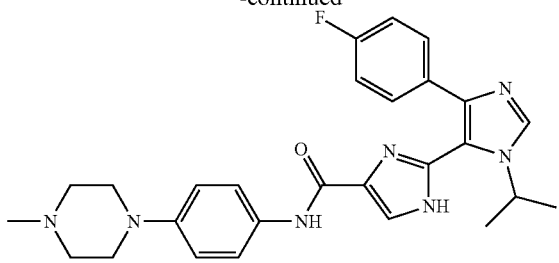

,

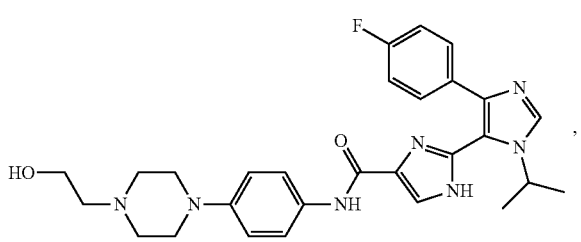

,

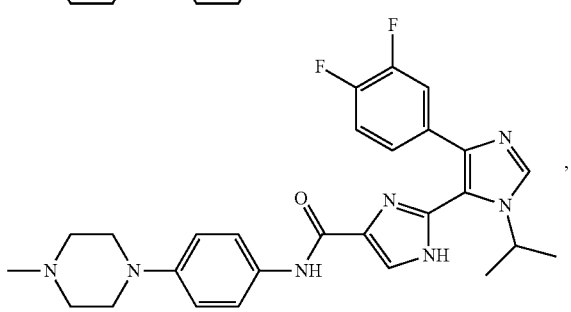

,

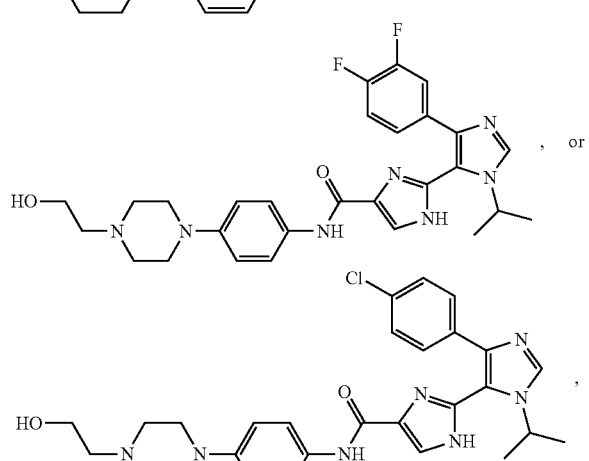

, or

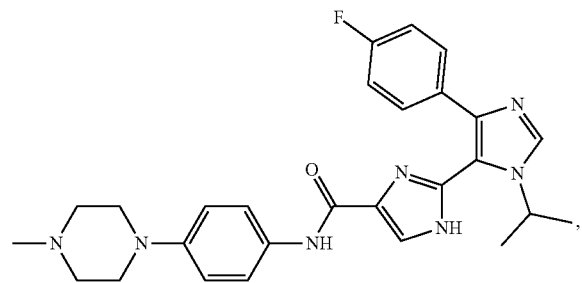

or a pharmaceutically acceptable salt thereof.

In some embodiments, the compound is

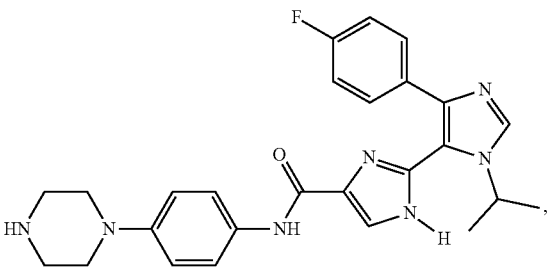 [SMILES: CC(C)n1cnc(-c2ccc(F)cc2)c1-c1nc(C(=O)Nc2ccc(N3CCNCC3)cc2)c[nH]1]

or a pharmaceutically acceptable salt thereof.

In some embodiments, the compound is

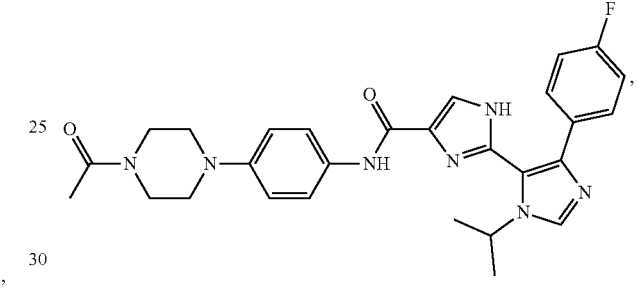

or a pharmaceutically acceptable salt thereof.

In some embodiments, the compound is

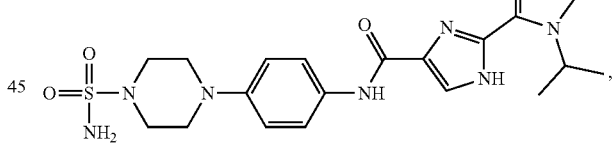

or a pharmaceutically acceptable salt thereof.

In some embodiments, the compound is or a pharmaceutically acceptable salt thereof.

In some embodiments, the compound is

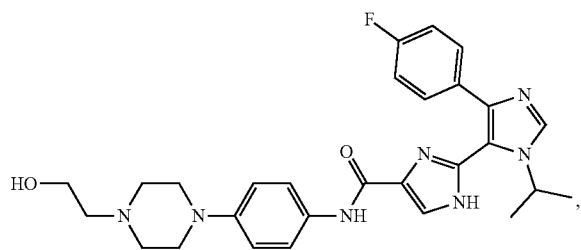 [SMILES: CC(C)n1cnc(-c2ccc(F)cc2)c1-c1nc(C(=O)Nc2ccc(N3CCN(CCO)CC3)cc2)c[nH]1]

or a pharmaceutically acceptable salt thereof.

In some embodiments, the compound is

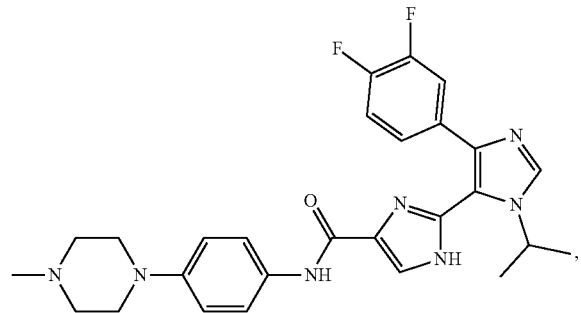 [SMILES: CC(C)n1cnc(-c2ccc(F)c(F)c2)c1-c1nc(C(=O)Nc2ccc(N3CCN(C)CC3)cc2)c[nH]1]

or a pharmaceutically acceptable salt thereof.

In some embodiments, the compound is

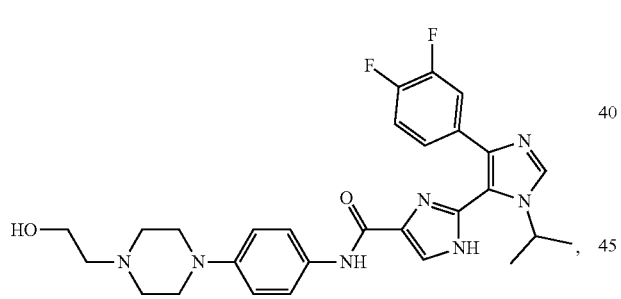

or a pharmaceutically acceptable salt thereof.

In some embodiments, the compound is

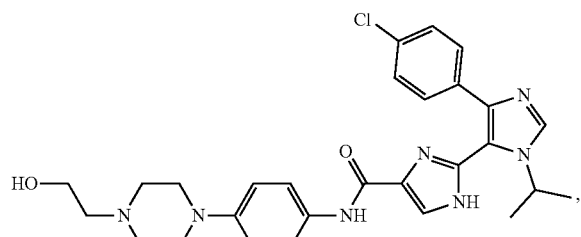

or a pharmaceutically acceptable salt thereof.

In some embodiments, the compound is

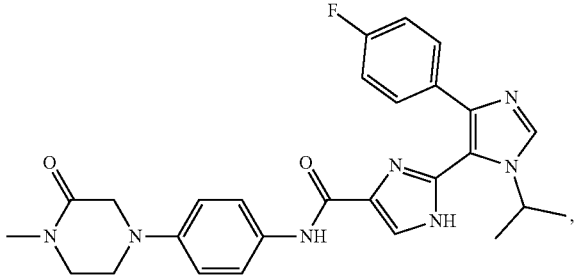 [SMILES: CC(C)n1cnc(-c2ccc(F)cc2)c1-c1nc(C(=O)Nc2ccc(N3CCN(C)C(=O)C3)cc2)c[nH]1]

or a pharmaceutically acceptable salt thereof.

In another aspect, provide herein is a method of treating a fibrotic disease or condition, comprising administering a compound described herein, or a pharmaceutically acceptable salt thereof, to a subject in need thereof In some embodiments, the fibrotic disease or condition is idiopathic pulmonary fibrosis (IPF).

In some embodiments, the fibrotic disease or condition is skin fibrosis.

In another aspect, provided herein is a pharmaceutical composition comprising (i) a compound represented by Formula (IIA):

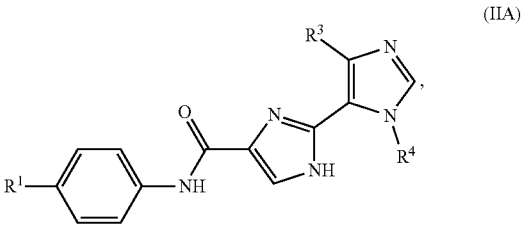

or a pharmaceutically acceptable salt thereof, wherein:

$R^1$ is piperazine, wherein the piperazine is optionally substituted with one or more substituents independently selected at each occurrence from oxo, —S(O$_2$)NH$_2$, and C$_{1-10}$ alkyl, wherein the C$_{1-10}$ alkyl is optionally substituted with one or more substituents independently selected at each occurrence from hydroxy, halogen, oxo, and —NH$_2$;

$R^3$ is phenyl, wherein the phenyl is optionally substituted with one or more halogen; and $R^4$ is unsubstituted C$_1$-C$_6$ alkyl; and (ii) a pharmaceutically acceptable excipient.

In some embodiments, $R^1$ is selected from

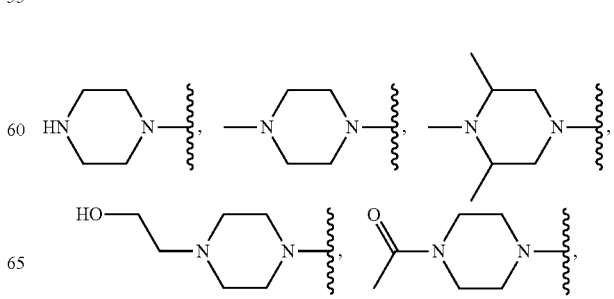

-continued
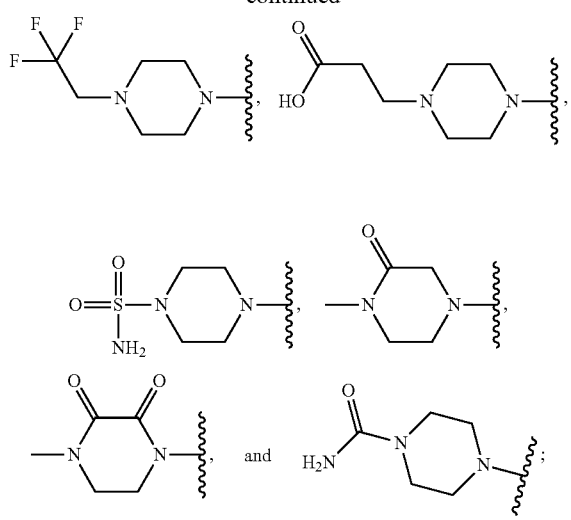
R³ is selected from
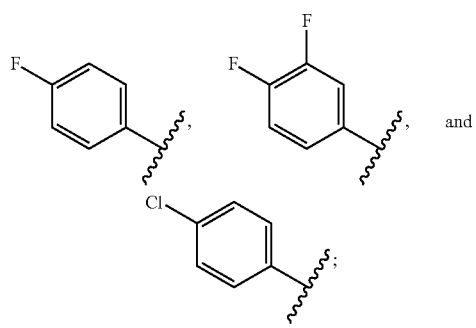
and
R⁴ is selected from
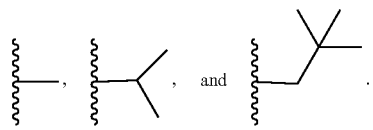
In some embodiments, the compound represented by Formula (IIA) is:
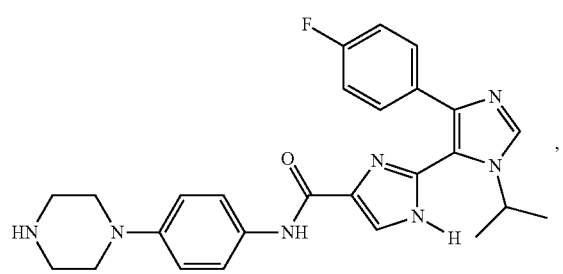
-continued
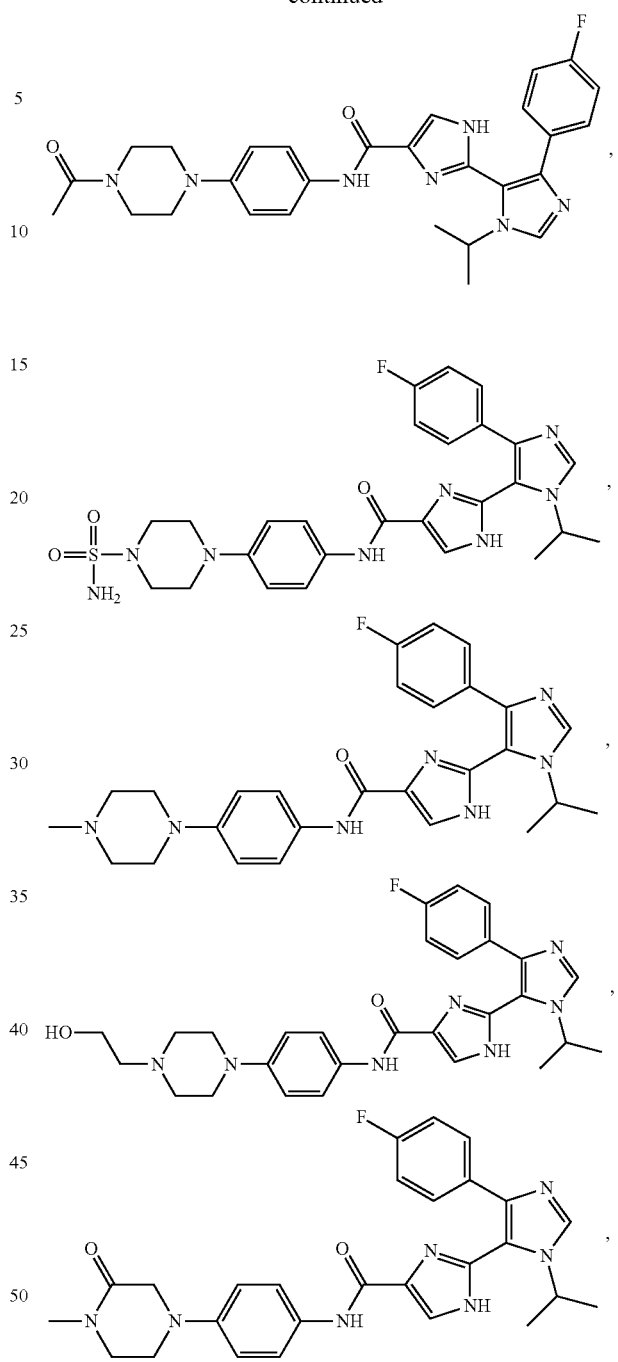

-continued

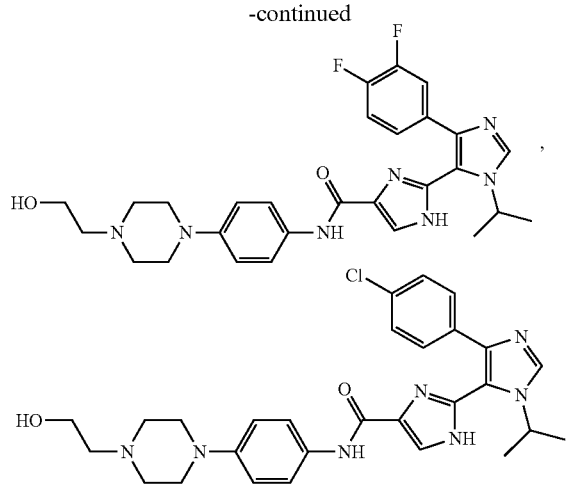

, or or a pharmaceutically acceptable salt thereof.

In some embodiments, the compound represented by Formula (IIA) is

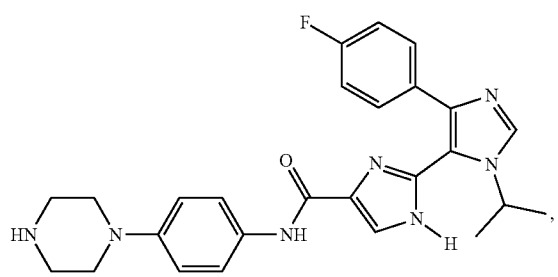 [SMILES: CC(C)n1cnc(-c2ccc(F)cc2)c1-c1nc(C(=O)Nc2ccc(N3CCNCC3)cc2)c[nH]1]

or a pharmaceutically acceptable salt thereof.

In some embodiments, the compound represented by Formula (IIA) is

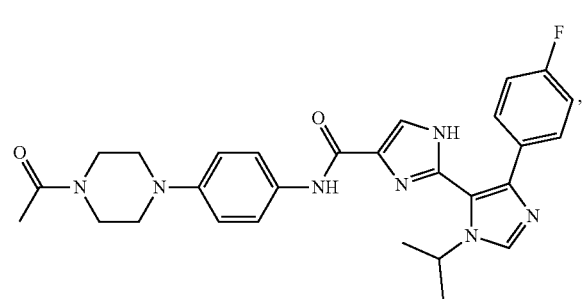 [SMILES: CC(=O)N1CCN(c2ccc(NC(=O)c3c[nH]c(-c4c(-c5ccc(F)cc5)ncn4C(C)C)n3)cc2)CC1]

or a pharmaceutically acceptable salt thereof.

In some embodiments, the compound represented by Formula (IIA) is

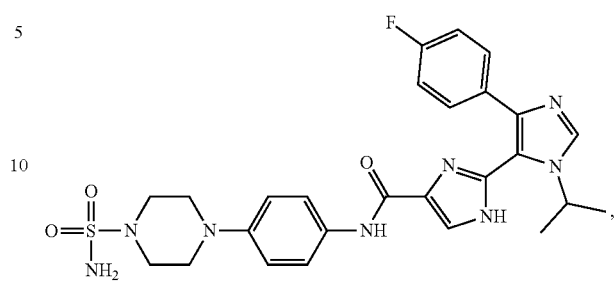

or a pharmaceutically acceptable salt thereof.

In some embodiments, the compound represented by Formula (IIA) is

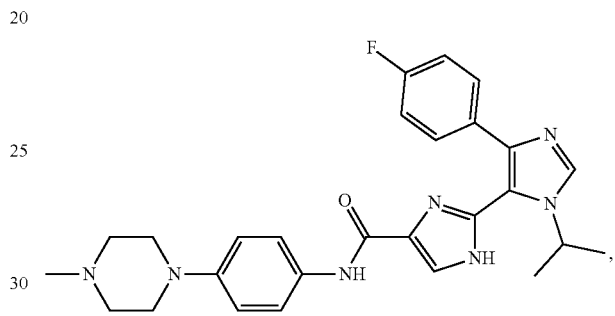

or a pharmaceutically acceptable salt thereof.

In some embodiments, the compound represented by Formula (IIA) is

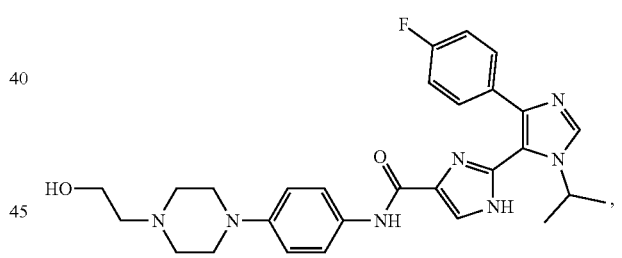

or a pharmaceutically acceptable salt thereof.

In some embodiments, the compound represented by Formula (IIA) is

In some embodiments, the compound represented by Formula (IIA) is

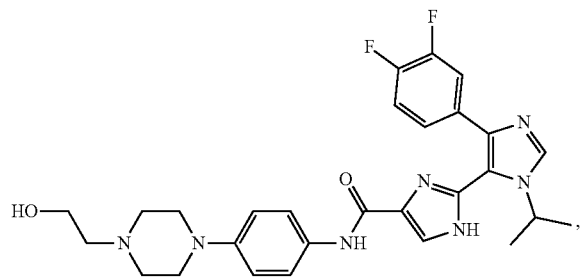 [SMILES: CC(C)n1cnc(-c2ccc(F)c(F)c2)c1-c1nc(C(=O)Nc2ccc(N3CCN(CCO)CC3)cc2)c[nH]1]

or a pharmaceutically acceptable salt thereof.

In some embodiments, the compound represented by Formula (IIA) is

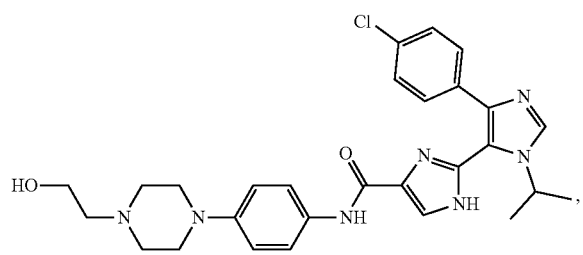 [SMILES: CC(C)n1cnc(-c2ccc(Cl)cc2)c1-c1nc(C(=O)Nc2ccc(N3CCN(CCO)CC3)cc2)c[nH]1]

or a pharmaceutically acceptable salt thereof.

In some embodiments, the compound represented by Formula (IIA) is

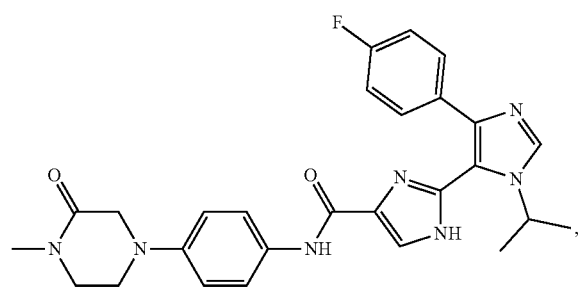 [SMILES: CC(C)n1cnc(-c2ccc(F)cc2)c1-c1nc(C(=O)Nc2ccc(N3CCN(C)C(=O)C3)cc2)c[nH]1]

or a pharmaceutically acceptable salt thereof.

In another aspect, provided herein is a compound represented by Formula (I),

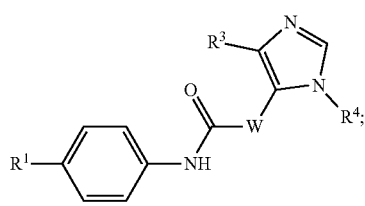

or a pharmaceutically acceptable salt thereof, wherein:
$R^1$ is selected from:
—N($R^5$)$_2$, wherein each $R^5$ is independently selected from hydrogen, and optionally substituted $C_1$-$C_6$ alkyl, wherein the $C_1$-$C_6$ alkyl is optionally substituted with one or more substituents independently selected at each occurrence from halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, and 3- to 12-membered heterocycle;

substituted $C_1$-$C_6$ alkyl, wherein the $C_1$-$C_6$ alkyl is optionally substituted with one or more substituents independently selected at each occurrence from halogen, —OH, —CN, —NO$_2$, —NH$_2$, oxo, =S, —C$_{1-10}$ haloalkyl, —O—C$_{1-10}$ alkyl, —O—C$_{1-6}$alkyl-O—C(O)(O—C$_{1-10}$ alkyl), C$_{2-10}$ alkenyl, C$_{2-10}$ alkynyl, C$_{3-12}$ carbocycle, and 3- to 12-membered heterocycle; and optionally substituted 3 to 8-membered heterocycle; wherein the 3 to 8-membered heterocycle is optionally substituted with one or more substituents independently selected at each occurrence from halogen, —OH, —CN, —NO$_2$, —NH$_2$, oxo, =S, —S(O$_2$)NH$_2$, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, and optionally substituted C$_{1-10}$ alkyl, wherein the C$_{1-10}$ alkyl is optionally substituted with one or more substituents independently selected at each occurrence from hydroxy, halogen, oxo, —C$_{1-10}$ haloalkyl, —NH$_2$, —CN, and —NO$_2$;

$R^3$ is selected from optionally substituted $C_1$-$C_6$ alkyl, optionally substituted 3- to 10-membered heterocycle and optionally substituted C$_{3-10}$ carbocycle, wherein each of the alkyl, heterocycle and carbocycle is optionally substituted with one or more substituents independently selected at each occurrence from halogen, —OH, —CN, —NO$_2$, —NH$_2$, oxo, =S, C$_{1-6}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, and 3- to 12-membered heterocycle;

$R^4$ is selected from:
hydrogen;
optionally substituted $C_1$-$C_6$ alkyl, wherein the $C_1$-$C_6$ alkyl is optionally substituted with one or more substituents independently selected at each occurrence from halogen, —OH, —CN, —NO$_2$, —NH$_2$, oxo, =S, —O—C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, and 3- to 12-membered heterocycle; and optionally substituted C$_{3-10}$ carbocycle, wherein the C$_{3-10}$ carbocycle is optionally substituted with one or more substituents independently selected at each occurrence from halogen, —OH, —CN, —NO$_2$, —NH$_2$, oxo, =S, C$_{1-10}$ alkyl, —C$_{1-10}$ haloalkyl, —O—C$_{1-10}$ alkyl, C$_{2-10}$ alkenyl, C$_{2-10}$ alkynyl, C$_{3-12}$ carbocycle, and 3- to 12-membered heterocycle;

W is selected from optionally substituted 5- to 8-membered heteroaryl, wherein the 5- to 8-membered heteroaryl is optionally substituted with one or more substituents independently selected at each occurrence from halogen, —OH, —CN, —NO$_2$, —NH$_2$, oxo, =S, —S(O$_2$)NH$_2$, —C$_{1-10}$ haloalkyl, —O—C$_{1-10}$ alkyl, C$_{2-10}$ alkenyl, C$_{2-10}$ alkynyl, C$_{3-12}$ carbocycle, and 3- to 12-membered heterocycle; and wherein when $R^1$ is methylpiperazine and W is pyridine, then $R^4$ is not methyl; and when W is furan and $R^4$ is cyclopentyl or cyclohexyl, then $R^1$ is not ethan-1-one.

In some embodiments, $R^1$ is selected from —N($R^5$)$_2$, wherein each $R^5$ is independently selected from optionally substituted $C_1$-$C_6$ alkyl, wherein the optional substituents on $C_1$-$C_6$ alkyl are selected from hydroxy, $R^1$ is selected from substituted $C_1$-$C_6$ alkyl and optionally substituted 3 to 8-membered heterocycle.

In some embodiments, $R^1$ is selected from substituted $C_1$-$C_6$ alkyl, wherein the optional substituents are selected from hydroxy, oxo, and —O—$C_{1-10}$ alkyl.

In some embodiments, $R^1$ is selected from optionally substituted 5 to 6-membered heterocycle.

In some embodiments, $R^1$ is an optionally substituted 6-membered heterocycle.

In some embodiments, $R^1$ is an optionally substituted piperazine.

In some embodiments, the optional substituents on the piperazine are selected from oxo, —S($O_2$)$NH_2$, and optionally substituted $C_{1-10}$ alkyl, wherein the optional substituents on the $C_{1-10}$ alkyl are independently selected at each occurrence from one or more hydroxy, halogen, oxo, and —$NH_2$.

In some embodiments, $R^3$ is selected from optionally substituted $C_{3-6}$ carbocycle.

In some embodiments, $R^3$ is optionally substituted phenyl.

In some embodiments, the optional substituents of the phenyl are selected from halogen and —$C_{1-10}$ haloalkyl.

In some embodiments, $R^4$ is selected from optionally substituted $C_1$-$C_6$ alkyl and optionally substituted $C_{3-6}$ carbocycle.

In some embodiments, $R^4$ is $C_1$-$C_6$ alkyl and is optionally substituted with one or more halogen.

In some embodiments, $R^4$ is $C_{3-6}$ carbocycle and is optionally substituted with one or more hydroxy.

In some embodiments, W is selected from 5- to 6-membered heteroaryl.

In some embodiments, the 5- to 6-membered heteroaryl of W are selected from imidazole, thiophene, oxazole, isoxazole, thiazole, oxadiazole, thiadiazole, pyridazine, pyrimidine, pyrazine, and triazine.

In some embodiments, the 5- to 6-membered heteroaryl of W are selected from imidazole, furan, and pyridine.

In some embodiments, W is imidazole.

In some embodiments, W is selected from optionally substituted 5- to 6-membered heteroaryl.

In some embodiments, W is selected from optionally substituted pyridine, imidazole, thiazole, and furan.

In some embodiments, W is selected from optionally substituted pyridine and imidazole.

In some embodiments, the compound is represented by formula (IIA):

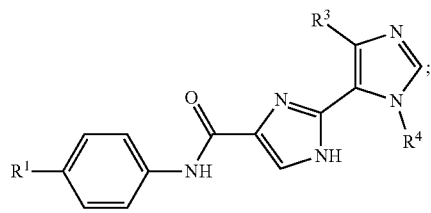

(IIA)

or a pharmaceutically acceptable salt thereof.

In some embodiments, the compound is represented by formula (IIB).

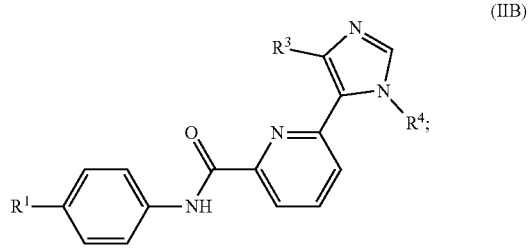

(IIB)

or a pharmaceutically acceptable salt thereof.

In some embodiments, $R^3$ is selected from optionally substituted $C_1$-$C_6$ alkyl and optionally substituted $C_6$ carbocycle.

In some embodiments, $R^3$ is selected from $C_1$-$C_6$ alkyl and substituted $C_6$ carbocycle, and wherein the $C_6$ carbocycle is substituted with one or more substituents selected from halogen and —$C_{1-10}$ haloalkyl.

In some embodiments, $R^3$ is selected from

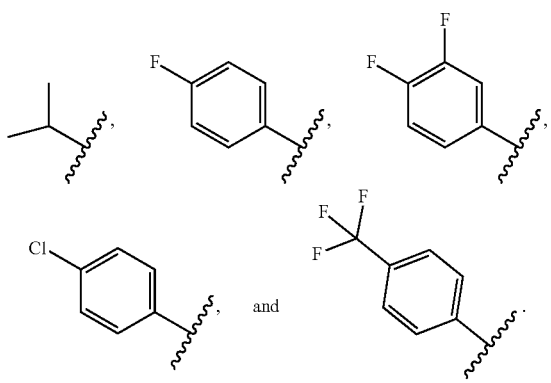

In some embodiments, $R^3$ is $C_6$ carbocycle substituted with one or more substituents selected from halogen.

In some embodiments, $R^3$ is selected from

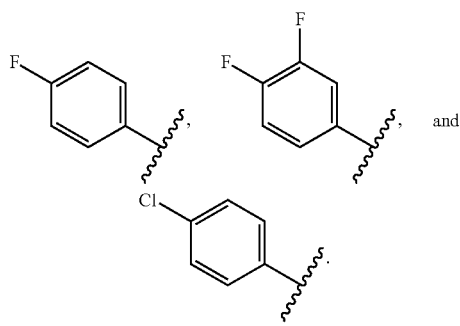

In some embodiments, $R^3$ is

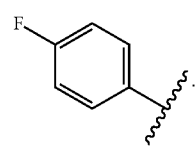

In some embodiments, $R^4$ is selected from hydrogen, $C_1$-$C_6$ alkyl optionally substituted with one or more substituents selected from halogen, and $C_{5-6}$ carbocycle optionally substituted with one or more substituents selected from hydroxy and amine.

In some embodiments, $R^4$ is selected from

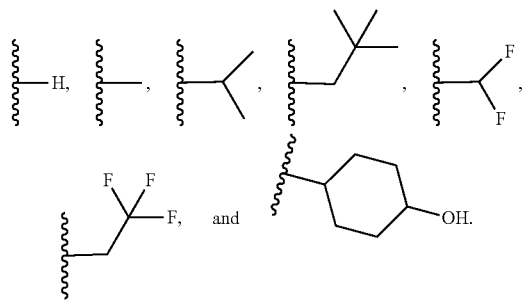

In some embodiments, $R^4$ is selected from $C_1$-$C_6$ alkyl optionally substituted with one or more substituents selected from fluorine, and $C_6$ cycloalkyl substituted with hydroxy.

In some embodiments, $R^4$ is selected from

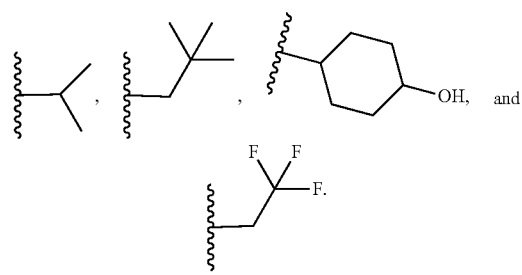

In some embodiments, $R^4$ is selected from

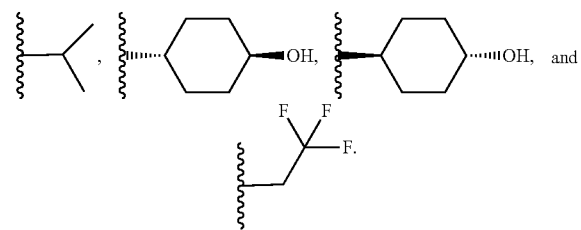

In some embodiments, $R^4$ is

In some embodiments, $R^1$ is selected from:
—N($R^5$)$_2$, wherein $R^5$ is selected from optionally substituted $C_1$-$C_6$ alkyl, wherein the substituents on $C_1$-$C_6$ alkyl are independently selected at each occurrence from one or more halogen, —OH, —CN, —NO$_2$, —NH$_2$, oxo, —C$_{1-10}$ haloalkyl, —O—C$_{1-10}$ alkyl,
substituted $C_1$-$C_6$ alkyl, wherein the substituents on $C_1$-$C_6$ alkyl are independently selected at each occurrence from one or more halogen, —OH, —NH$_2$, oxo, —C$_{1-10}$ haloalkyl, —O—C$_{1-10}$ alkyl, —O—C$_{1-6}$alkyl-O—C(O)(O—C$_{1-10}$ alkyl);

optionally substituted 6 to 8-membered heterocycle; wherein the optional substituents on the 6 to 8-membered heterocycle are independently selected at each occurrence from one or more oxo, —S(O$_2$)NH$_2$, —NH$_2$, —C$_{1-10}$ haloalkyl, —O—C$_{1-10}$ alkyl, and optionally substituted C$_{1-10}$ alkyl, wherein the optional substituents on the C$_{1-10}$ alkyl are independently selected at each occurrence from one or more hydroxy, halogen, oxo, —C$_{1-10}$ haloalkyl, —NH$_2$, —CN, and —NO$_2$.

In some embodiments, $R^1$ is selected from

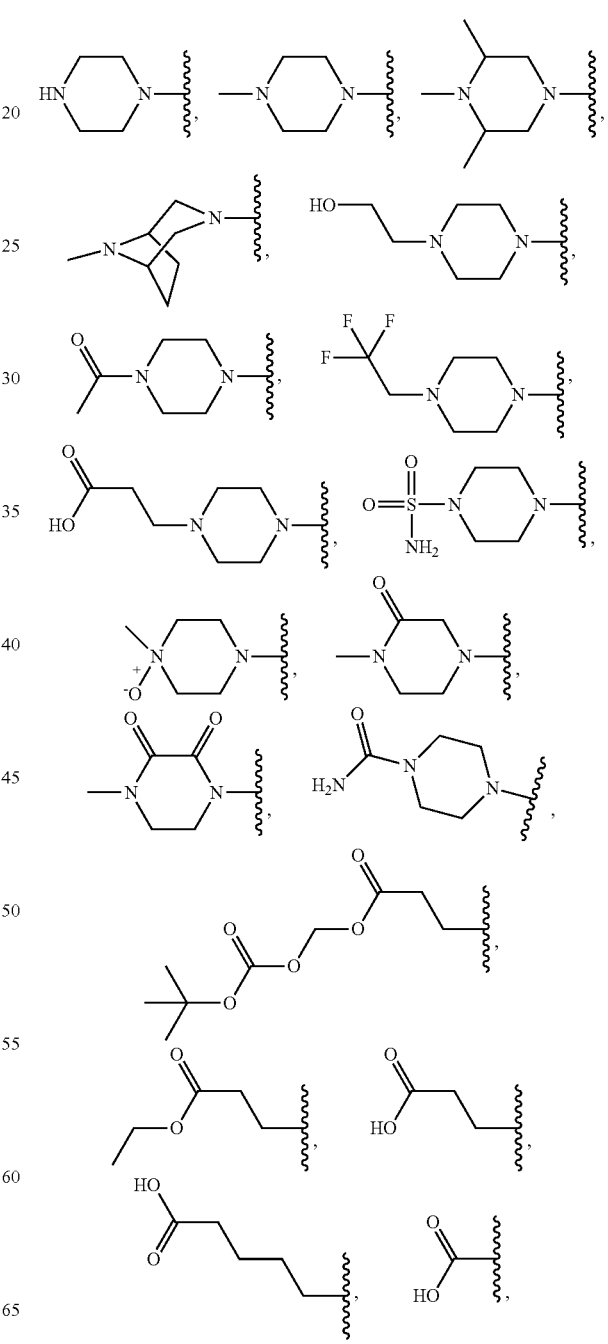

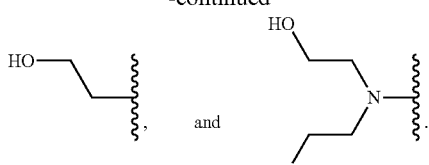

In some embodiments, R¹ is selected from

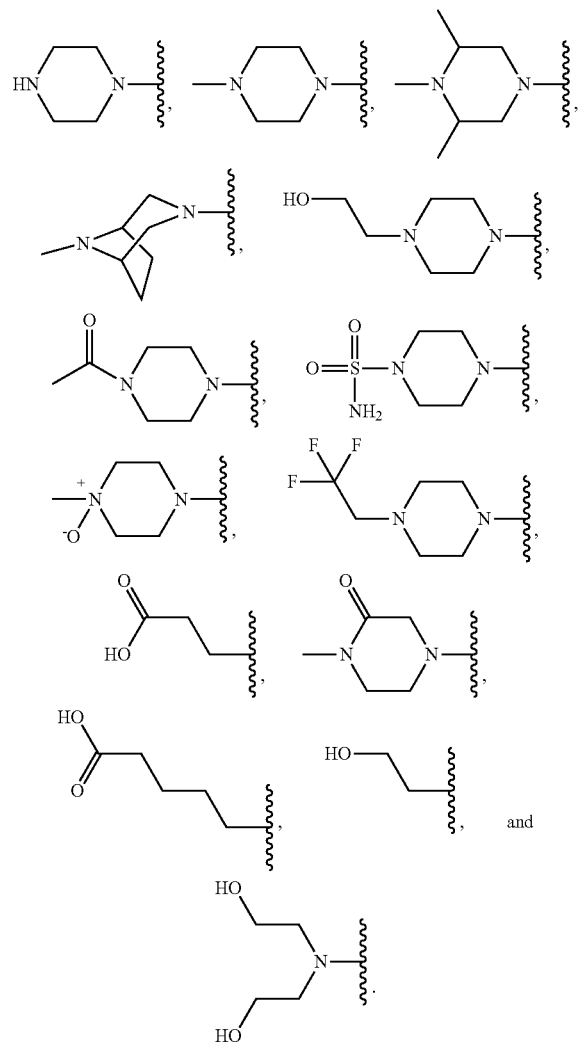

In some embodiments, R¹ is selected from

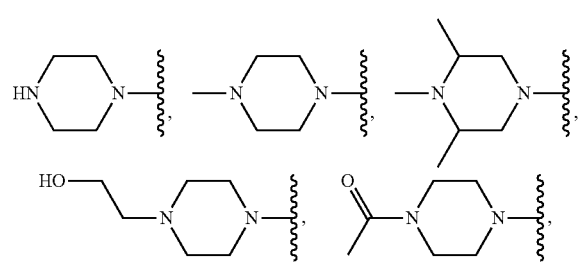

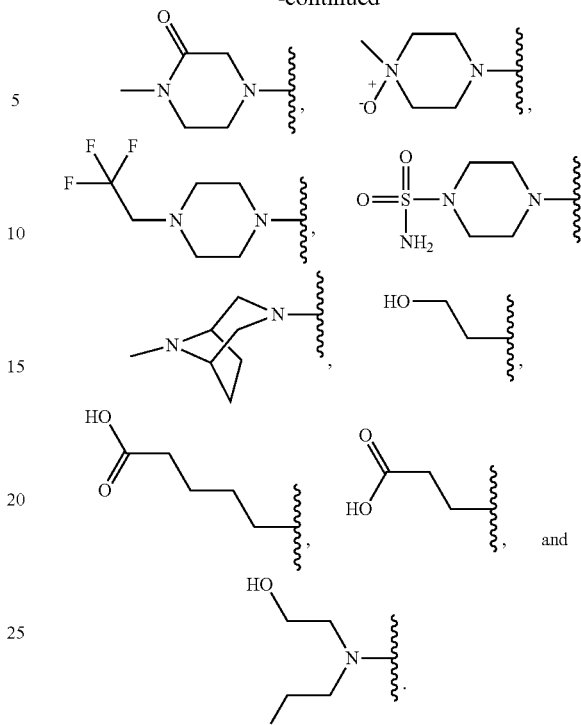

In some embodiments, R¹ is selected from:
substituted $C_1$-$C_6$ alkyl, wherein the substituents on $C_1$-$C_6$ alkyl are independently selected at each occurrence from one or more halogen, —OH, oxo, —$C_{1-10}$ haloalkyl, and —O—$C_{1-10}$ alkyl;

optionally substituted 6 to 8-membered saturated heterocycle; wherein the optional substituents are independently selected at each occurrence from one or more —S($O_2$)N$H_2$, and optionally substituted $C_{1-10}$ alkyl, wherein the optional substituents on the $C_{1-10}$ alkyl are independently selected at each occurrence from one or more hydroxy, halogen, oxo, —$C_{1-10}$ haloalkyl, and —N$H_2$.

In some embodiments, R¹ is selected from

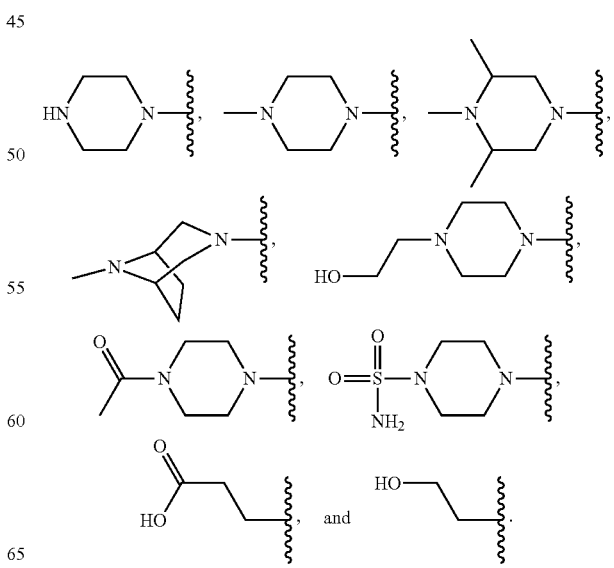

In some embodiments, R¹ is selected from optionally substituted 6 to 8-membered saturated heterocycle; wherein the optional substituents are independently selected at each occurrence from one or more —S(O₂)NH₂, and optionally substituted C₁₋₁₀ alkyl, wherein the optional substituents on the C₁₋₁₀ alkyl are independently selected at each occurrence from one or more hydroxy, halogen, oxo, —C₁₋₁₀ haloalkyl, and —NH₂.

In some embodiments, R¹ is selected from

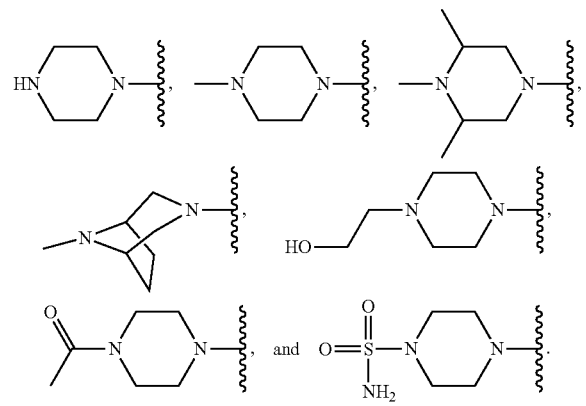

In some embodiments, R¹ is selected from substituted C₁-C₆ alkyl, wherein the substituents on C₁-C₆ alkyl are independently selected at each occurrence from one or more halogen, —OH, oxo, —C₁₋₁₀ haloalkyl, and —O—C₁₋₁₀ alkyl.

In some embodiments, R¹ is selected from

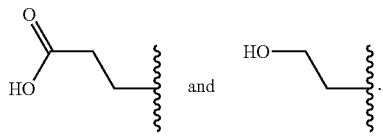

In some embodiments, R¹ is selected from:

substituted C₁-C₆ alkyl, wherein the substituents on C₁-C₆ alkyl are independently selected at each occurrence from one or more —OH, oxo, and —O—C₁₋₁₀ alkyl;

optionally substituted 6 to 8-membered saturated heterocycle; wherein the optional substituents are independently selected at each occurrence from one or more optionally substituted C₁₋₁₀ alkyl, wherein the optional substituents on the C₁₋₁₀ alkyl are independently selected at each occurrence from one or more hydroxy, oxo, —C₁₋₁₀ haloalkyl, and —NH₂.

In some embodiments, R¹ is selected from:

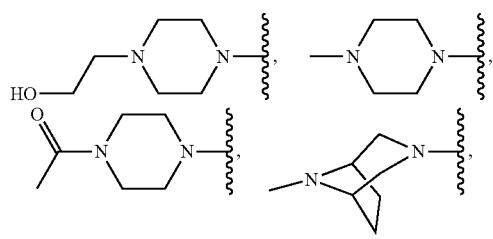

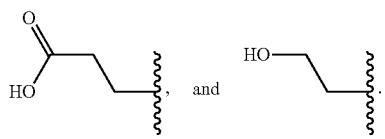

In some embodiments, the compound is

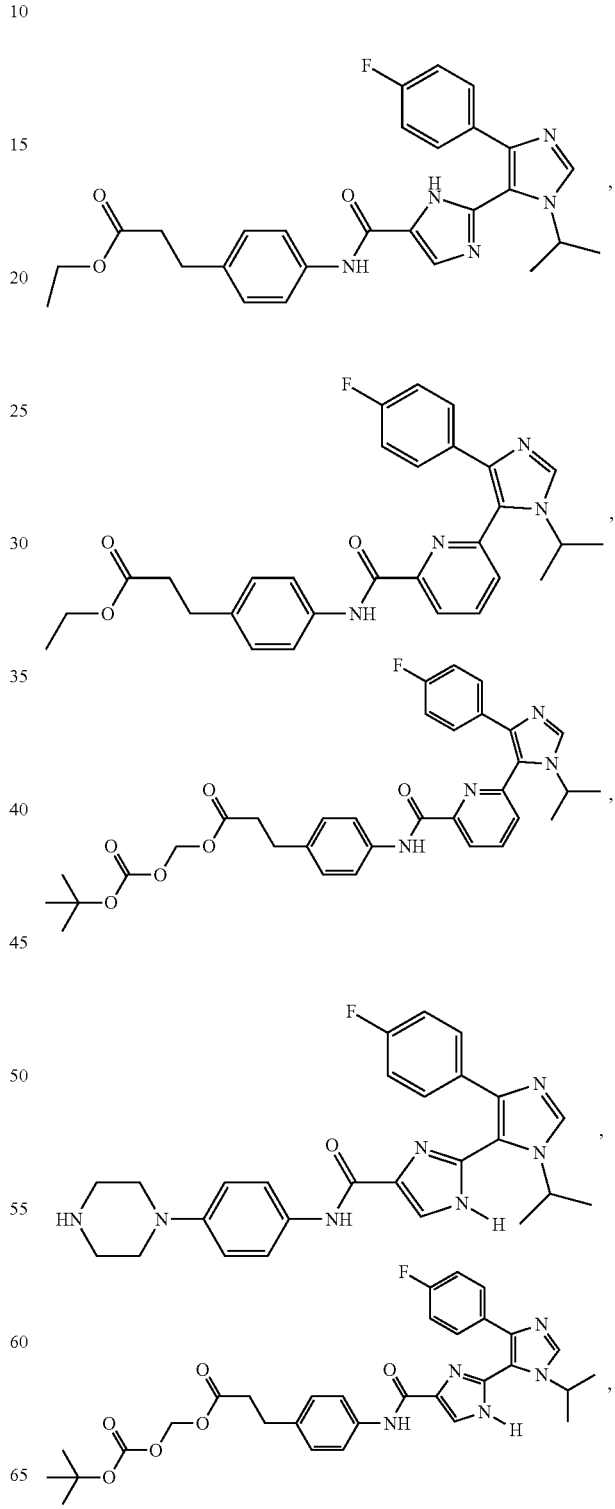

77
-continued
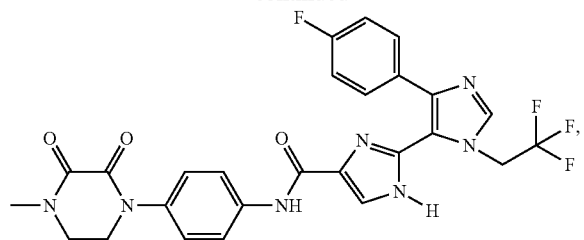
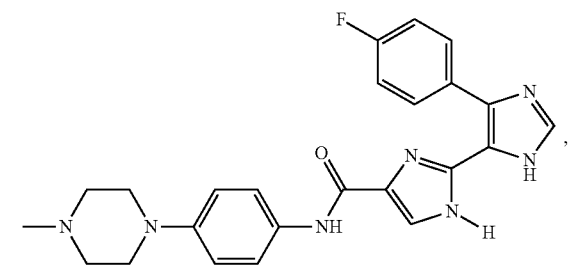
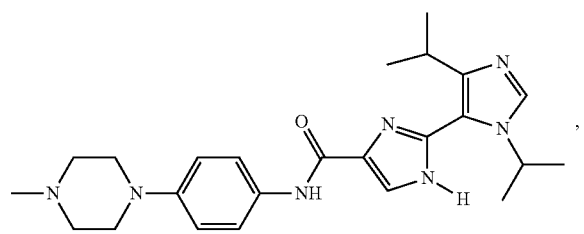
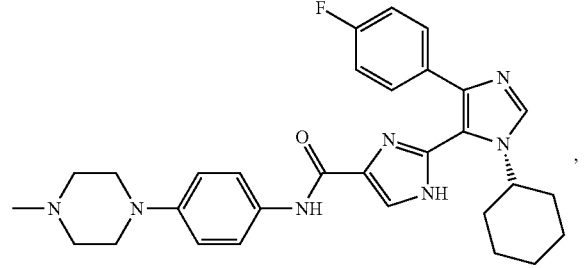
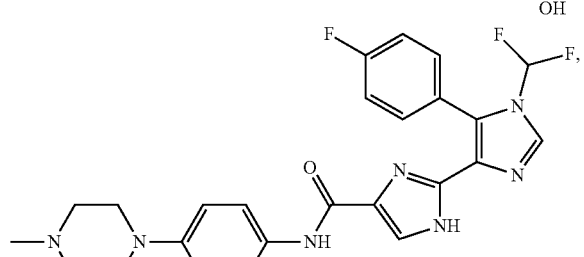
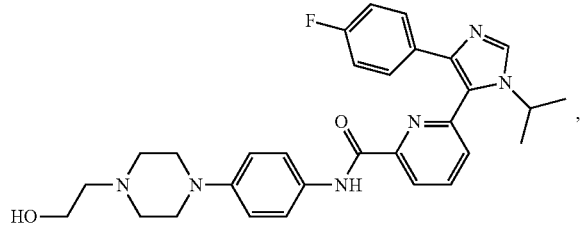
78
-continued
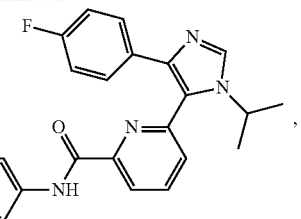
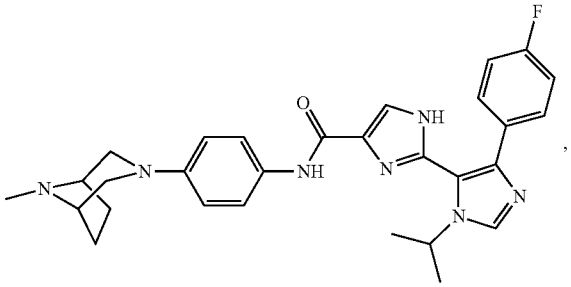
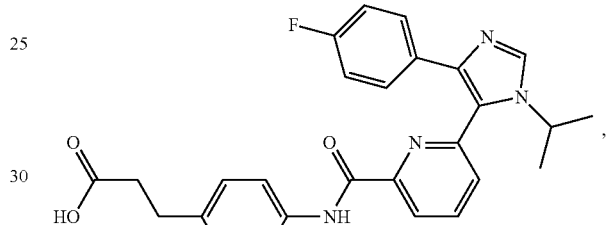
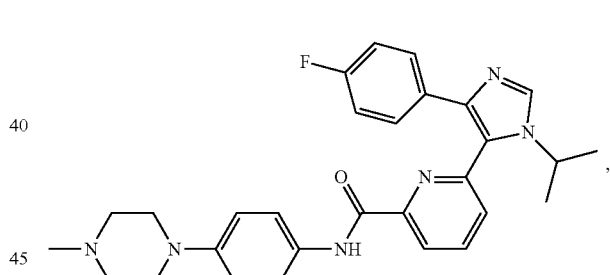
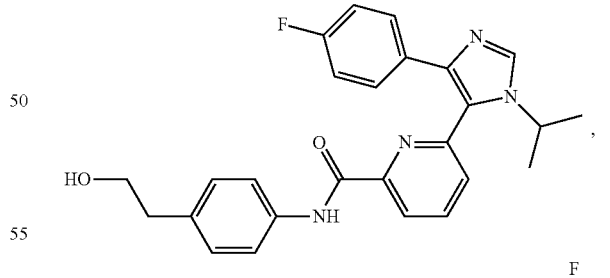
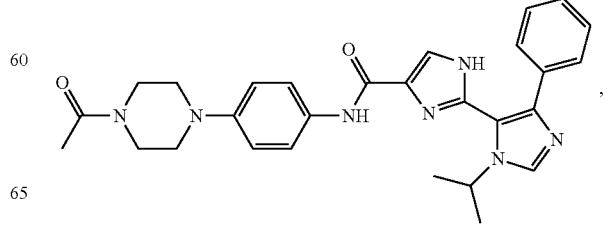

-continued
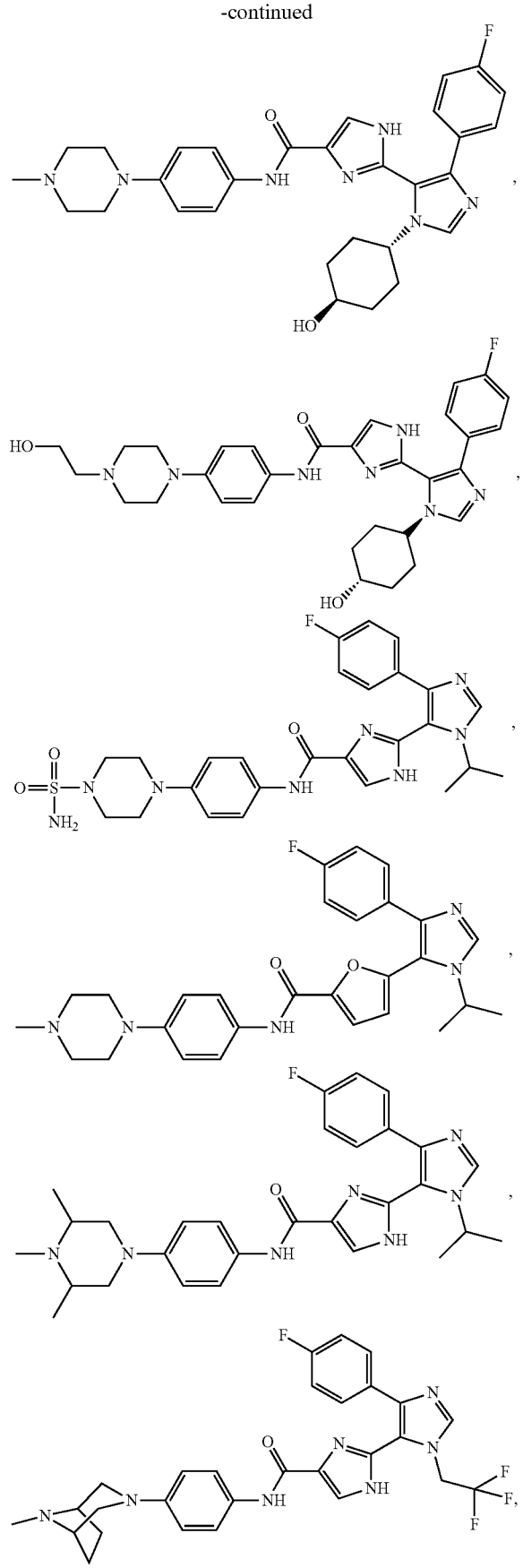
-continued
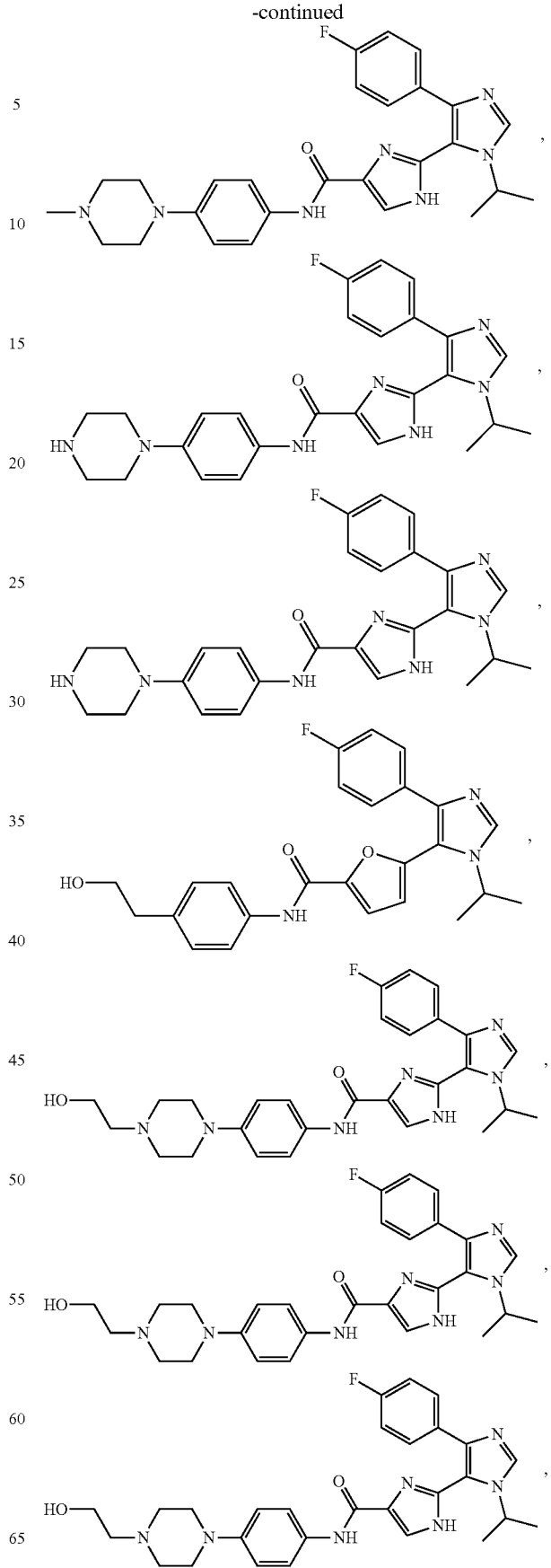

-continued
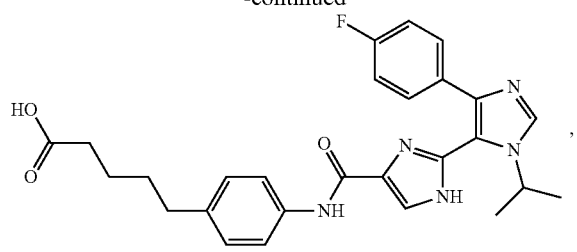
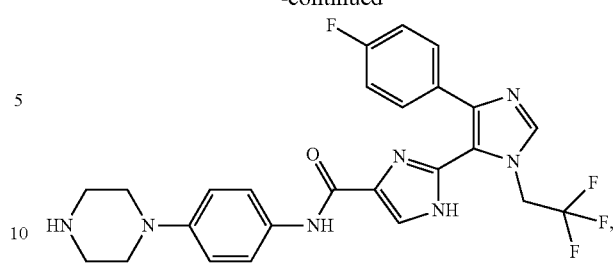
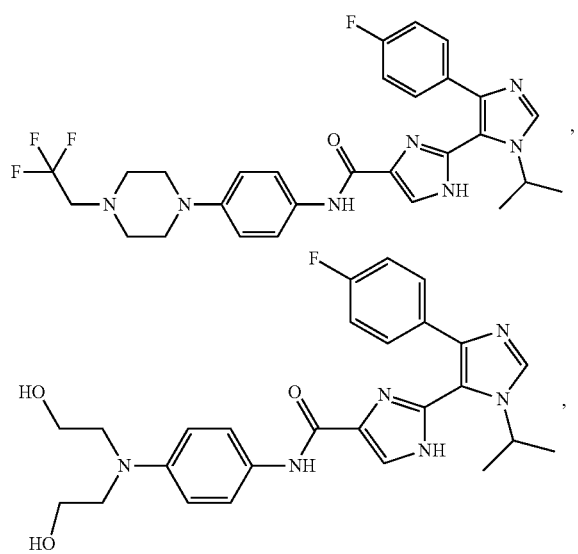
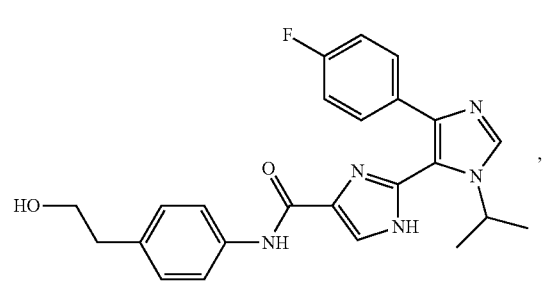
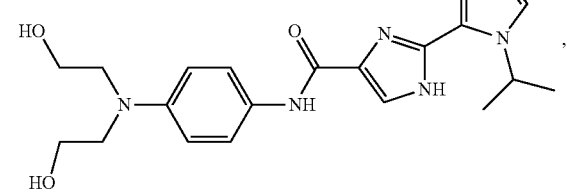
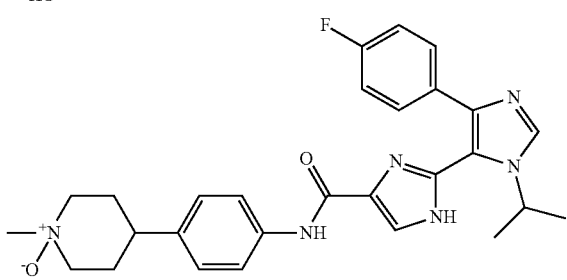
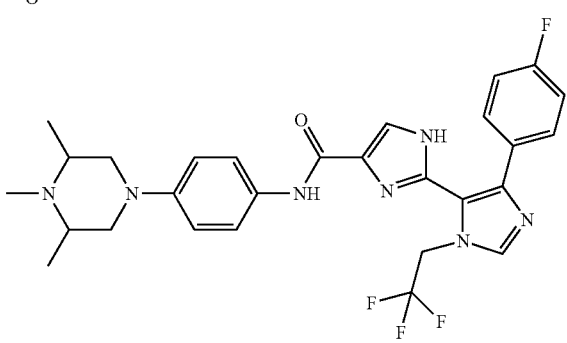
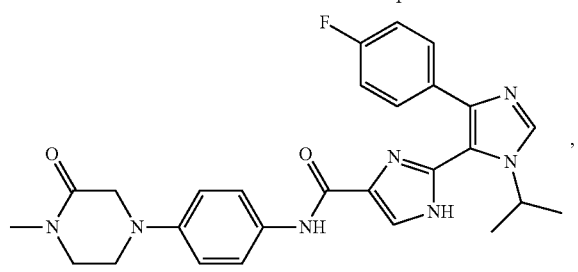

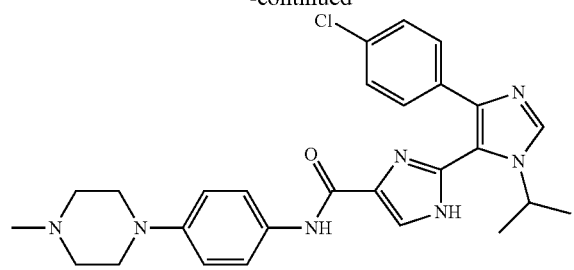
,
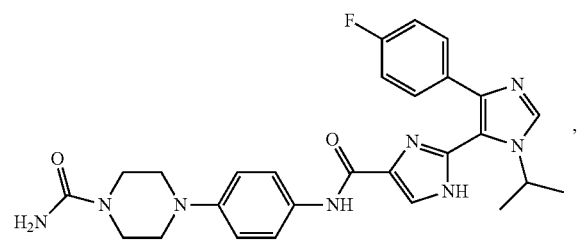
,
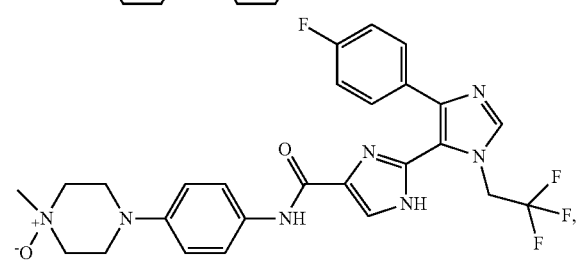
,
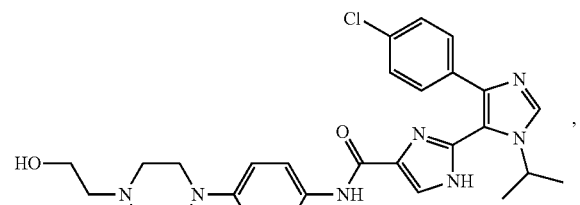
,
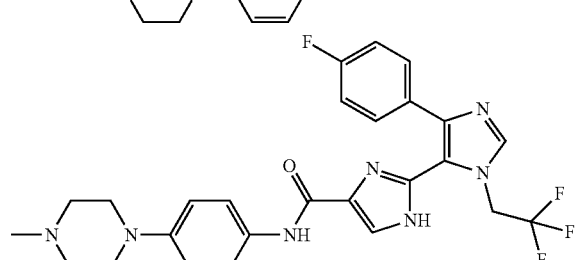
,
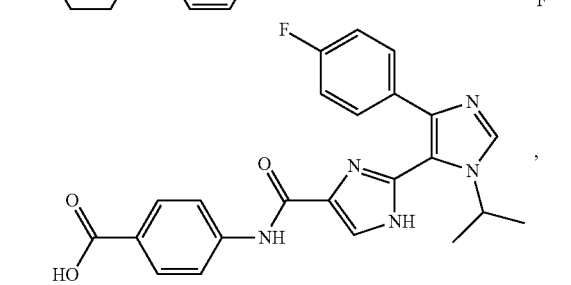
,
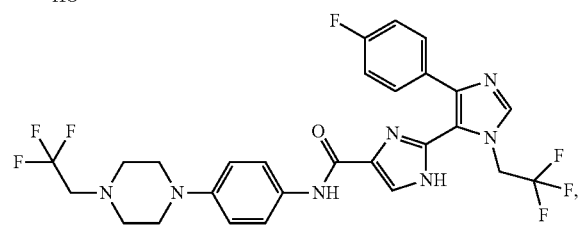
,
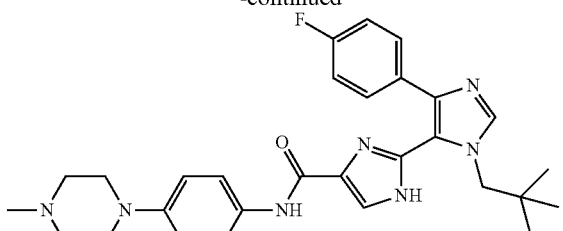
,
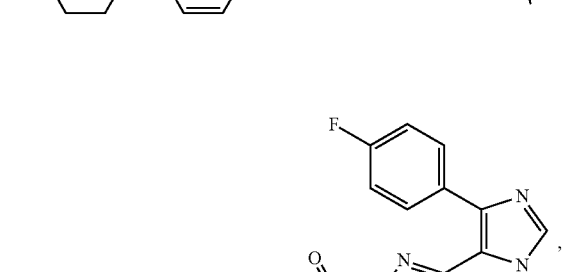
,
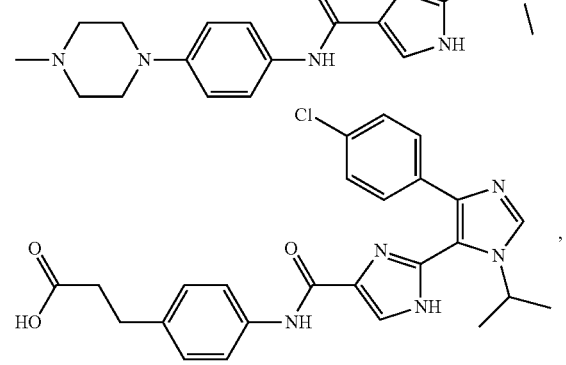
,
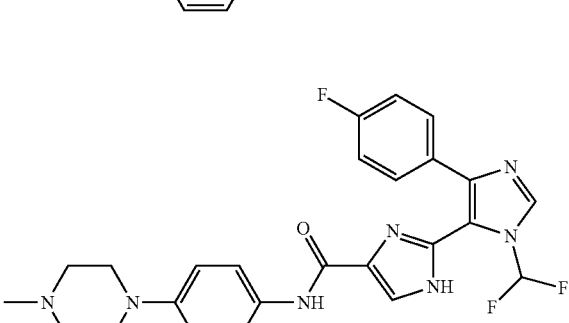
,
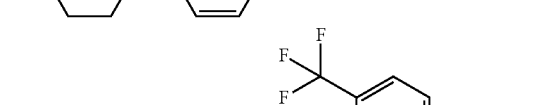
,
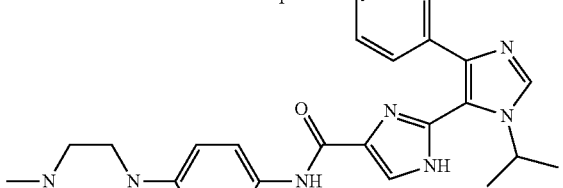
,
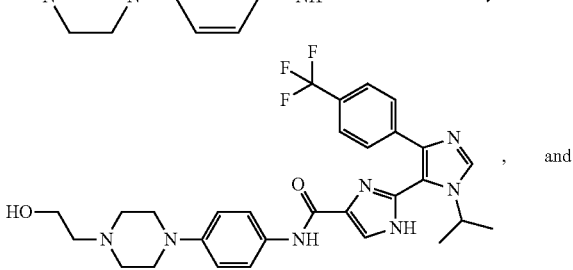
, and

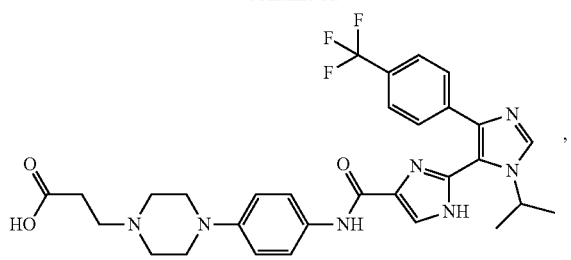
or a pharmaceutically acceptable salt of any one thereof.
In some embodiments, the compound is
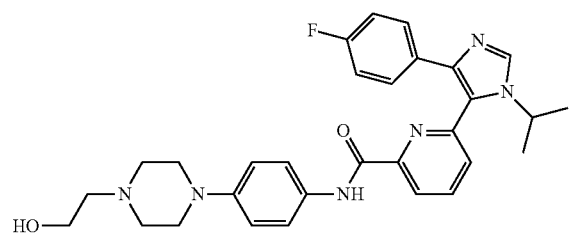
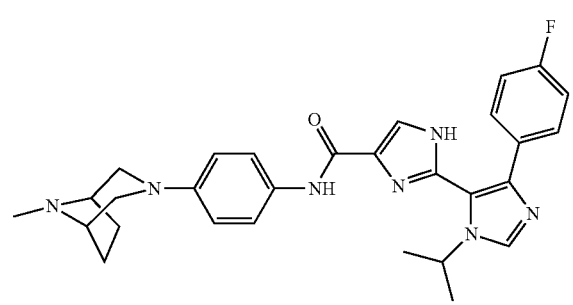
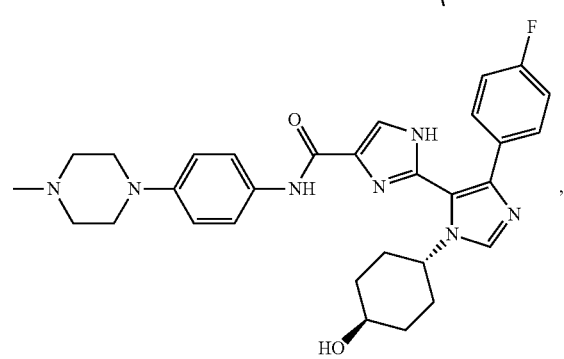
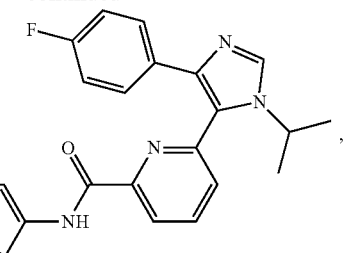
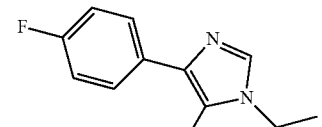
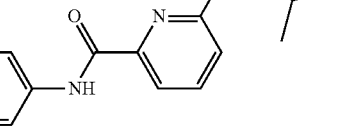
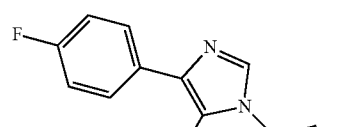
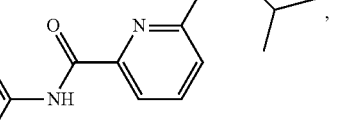
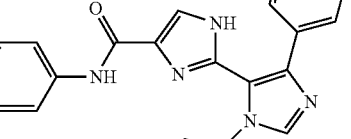
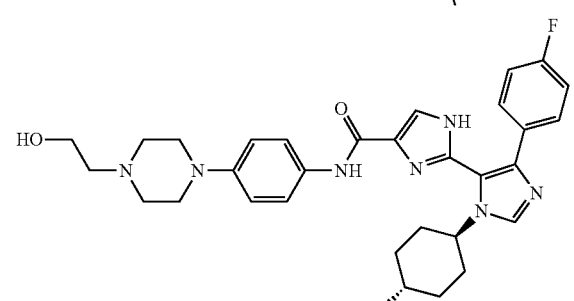
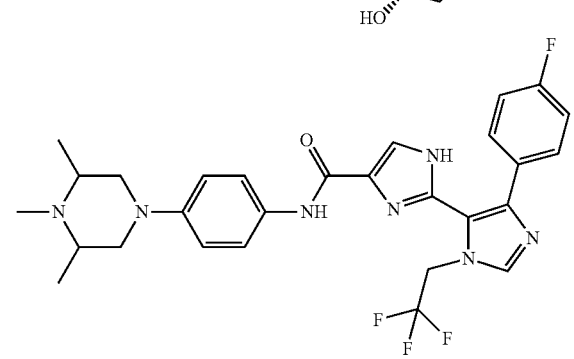

87
-continued
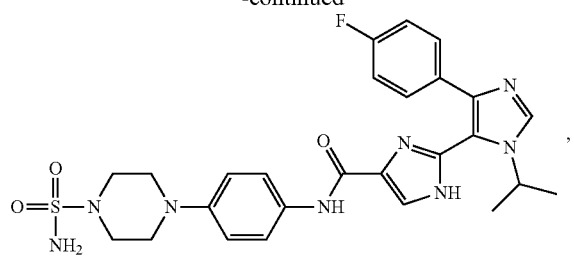
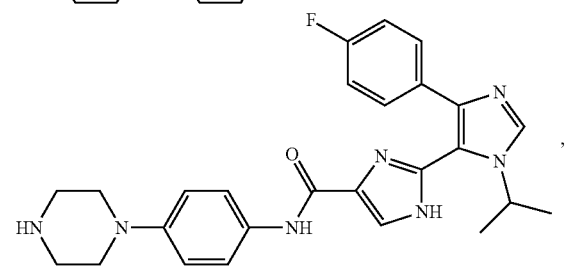
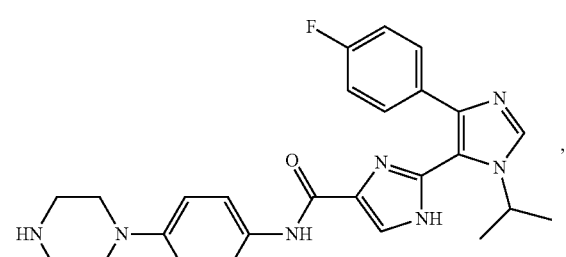
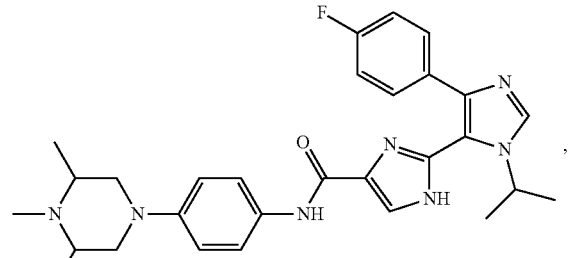
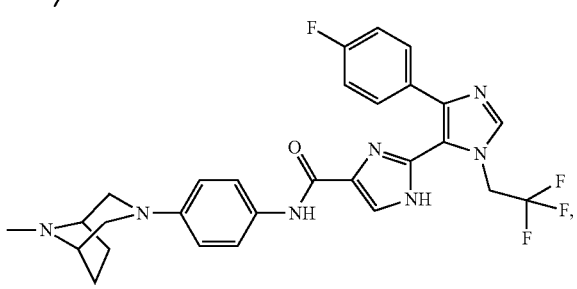
88
-continued
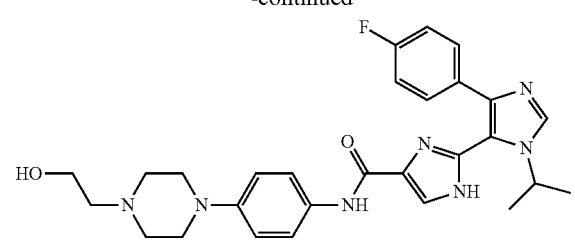
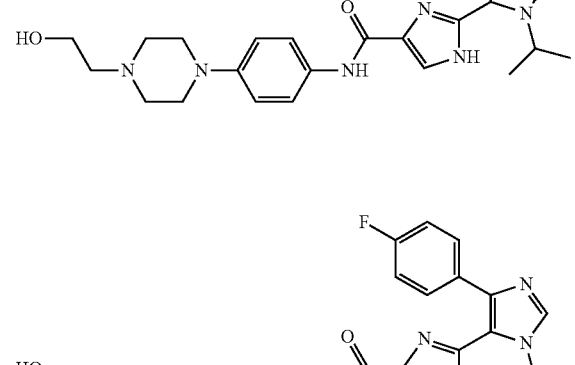
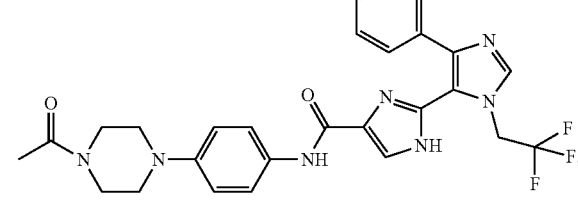
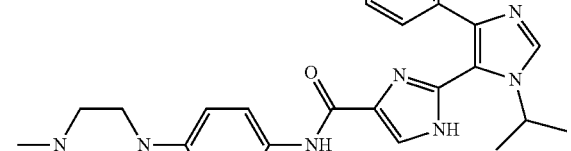
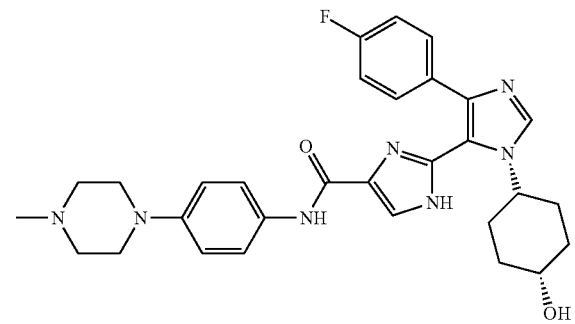

89
-continued
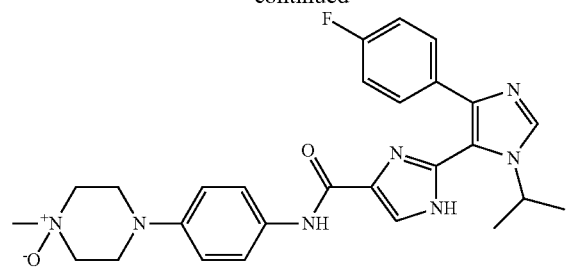
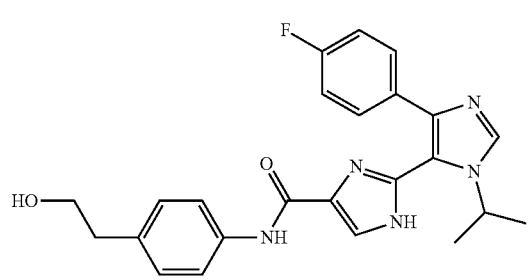
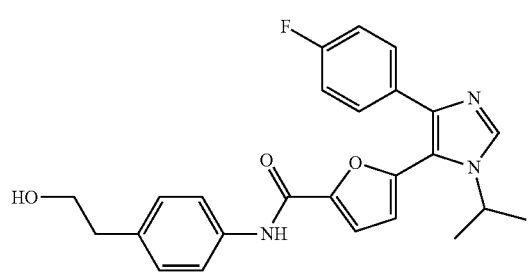
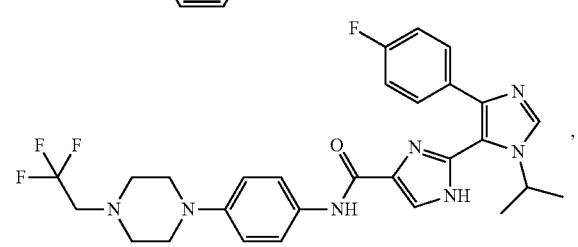
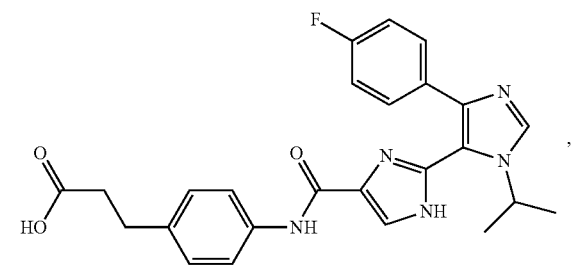
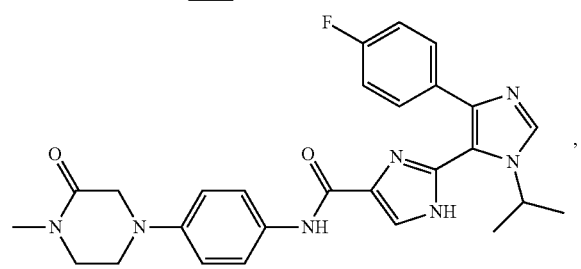
90
-continued
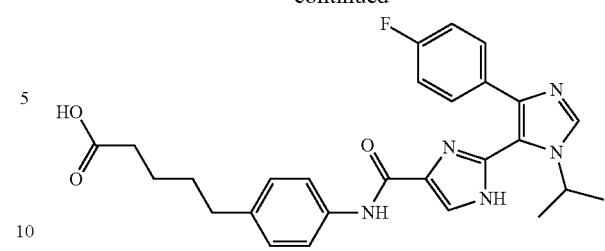
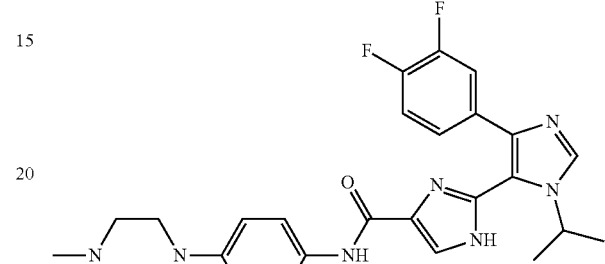
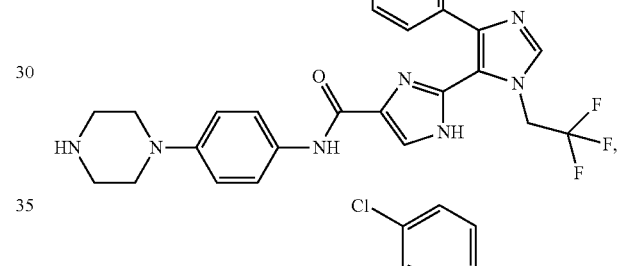
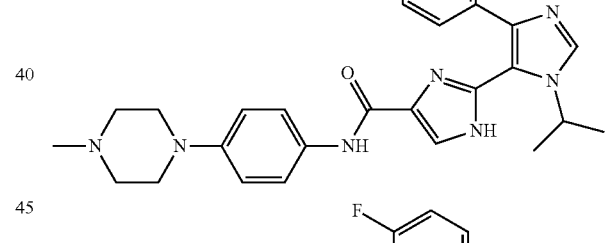
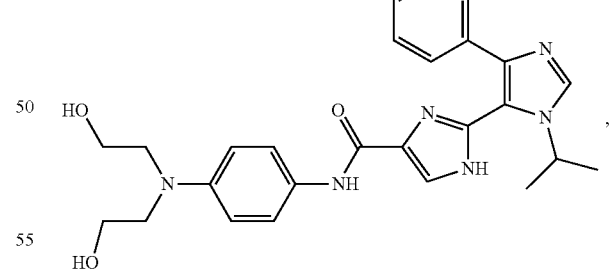
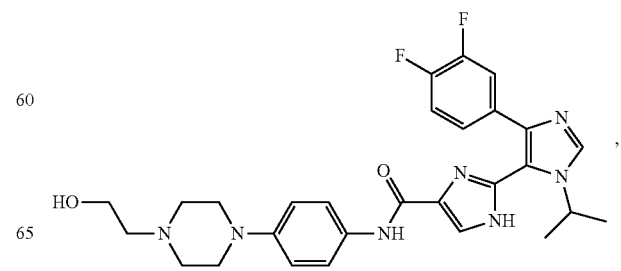

91
-continued
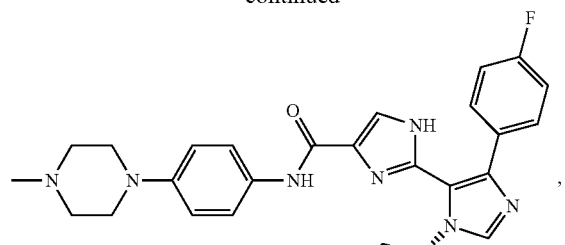
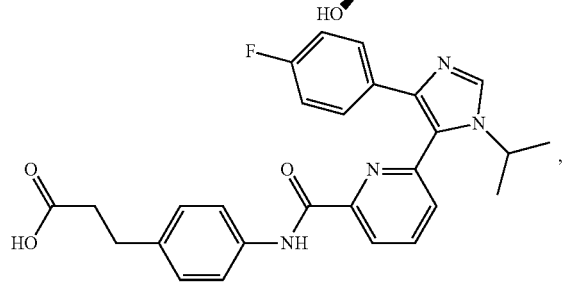
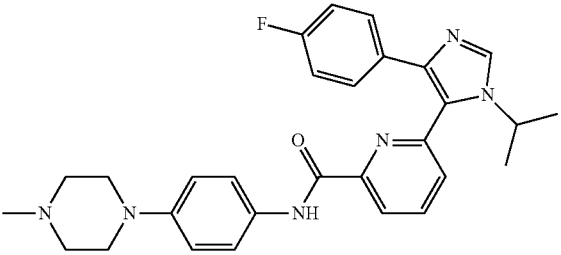
or a pharmaceutically acceptable salt of any one thereof.
In some embodiments, the compound is
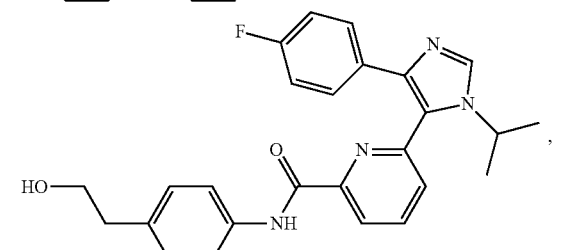
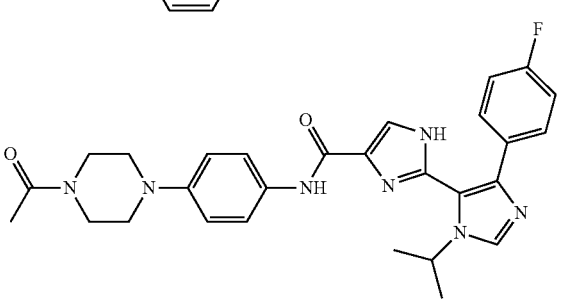
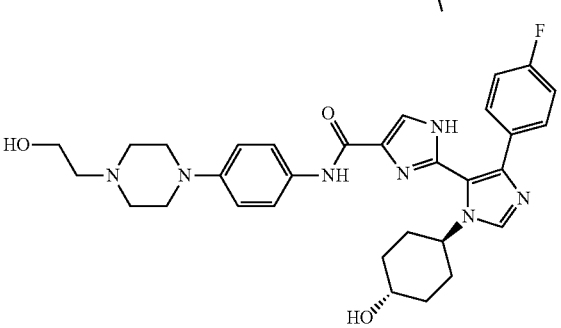
92
-continued

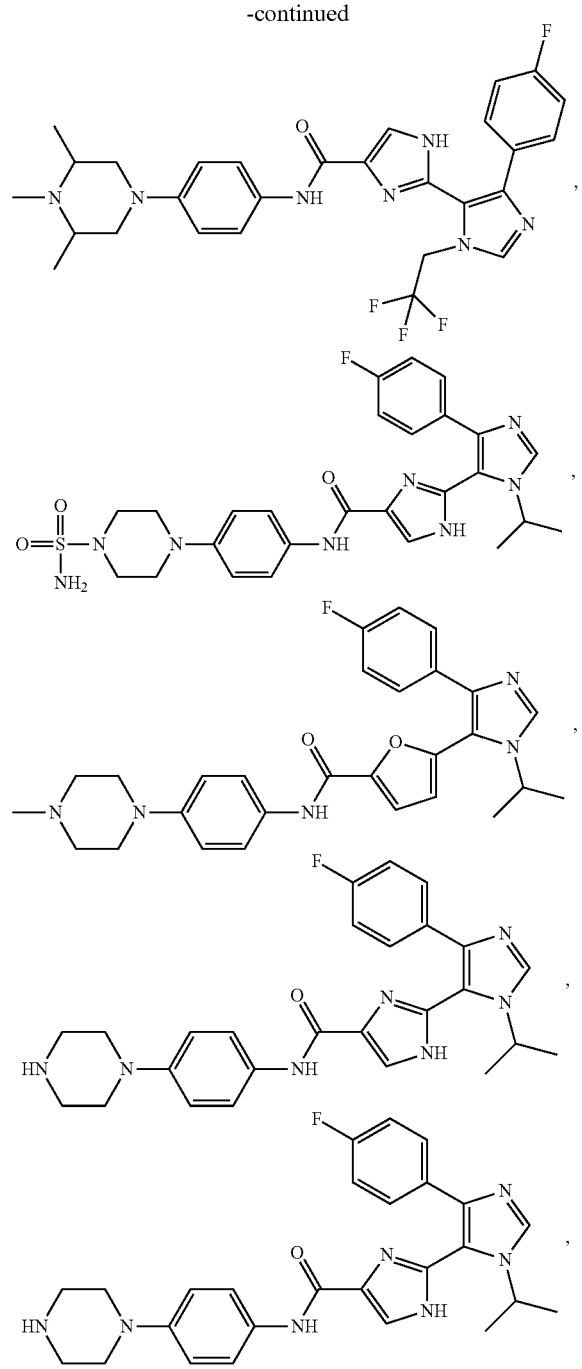
or a pharmaceutically acceptable salt of any one thereof.
In some embodiments, the compound is
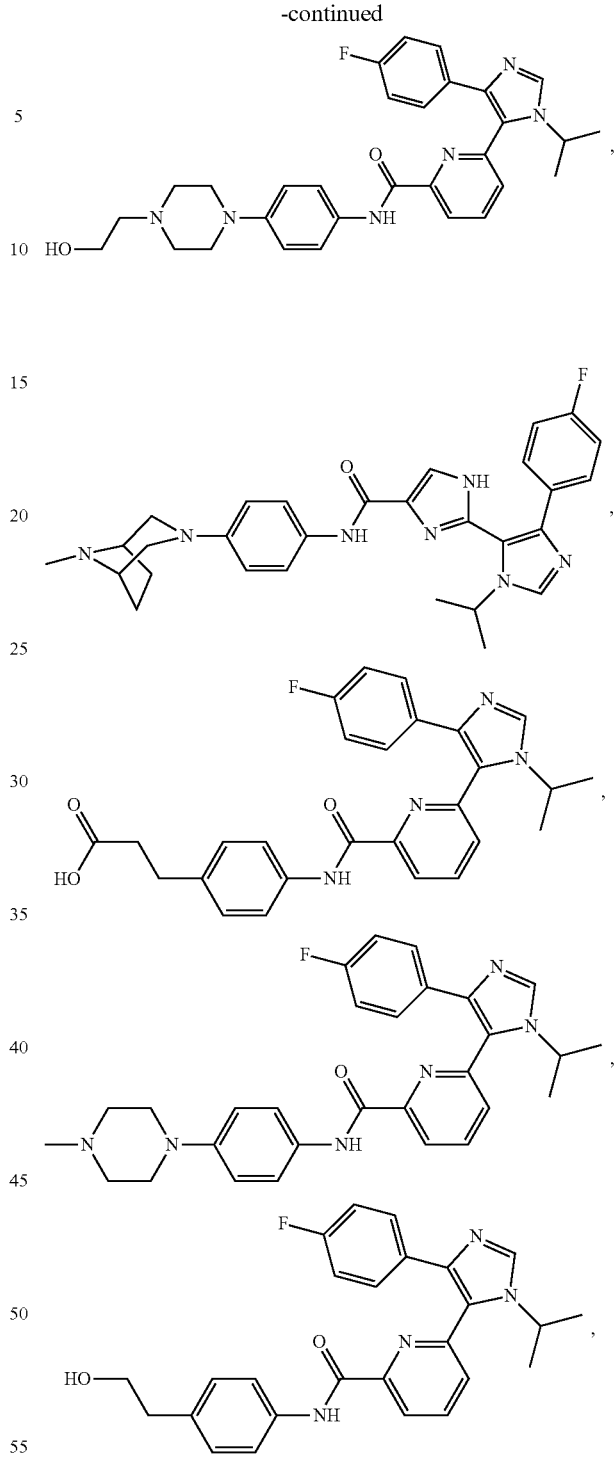

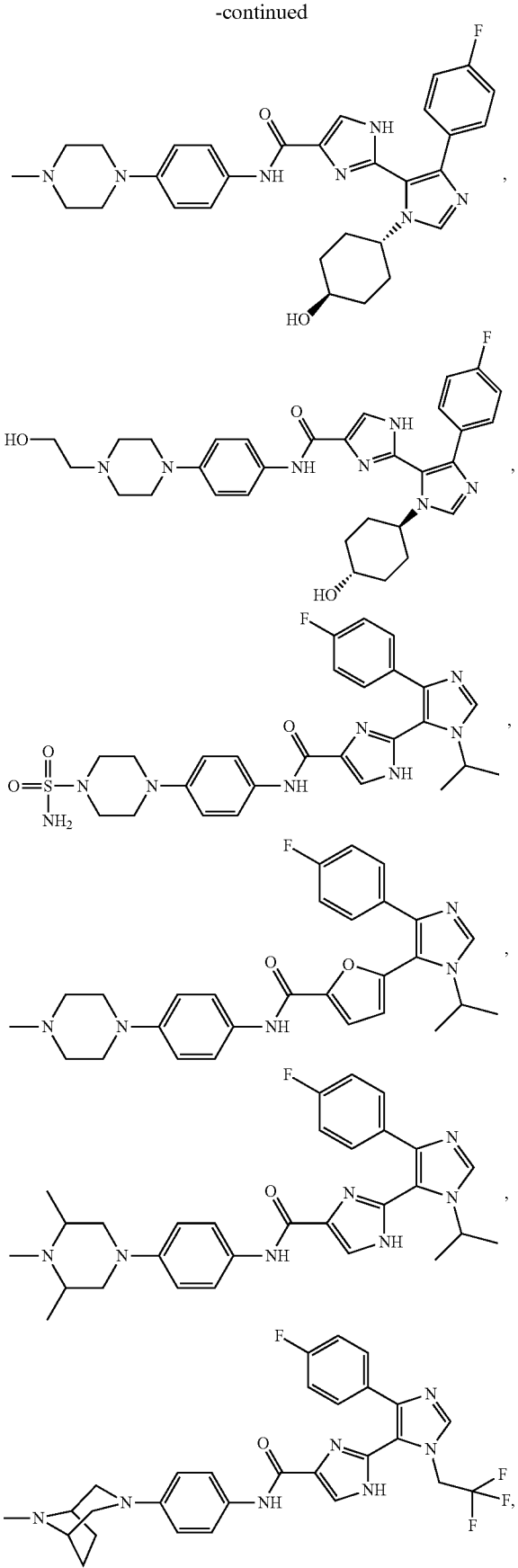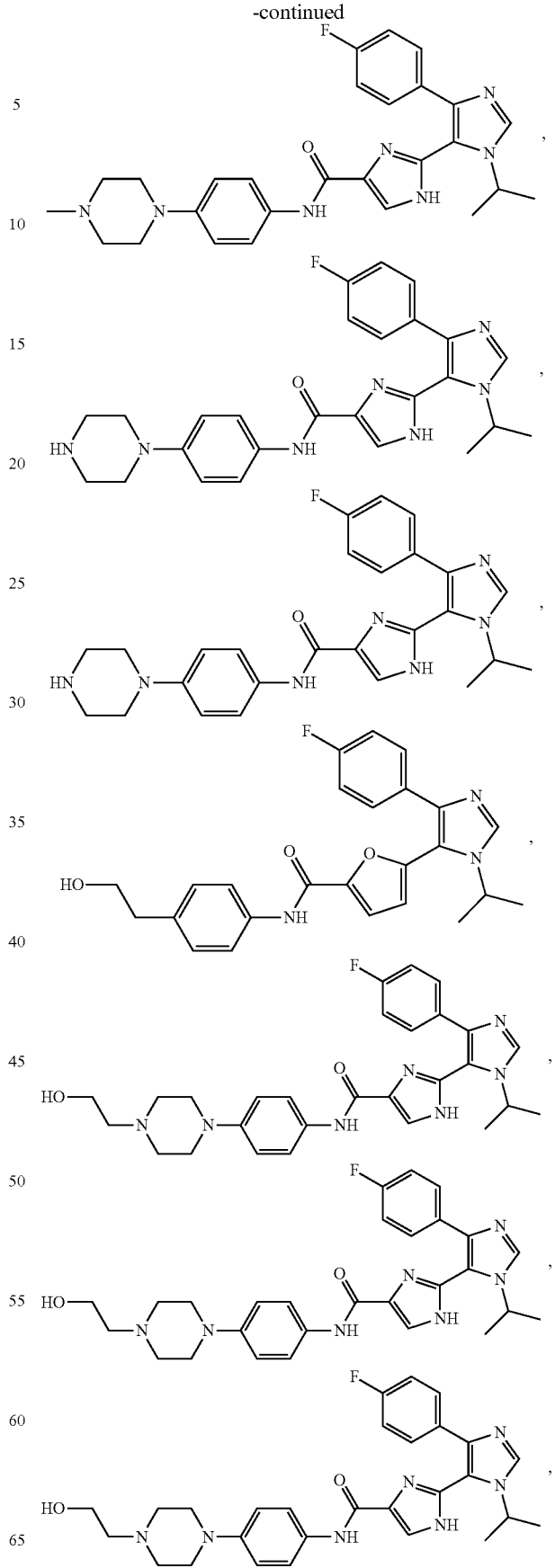

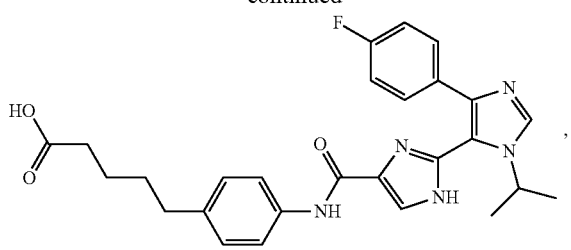
,
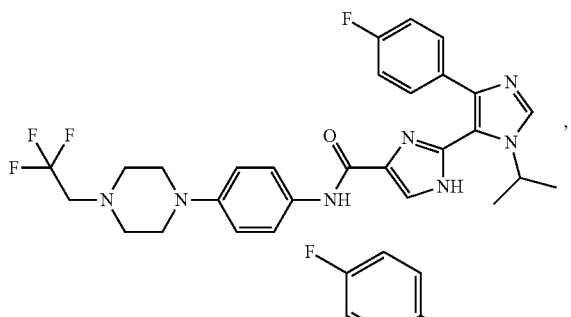
,
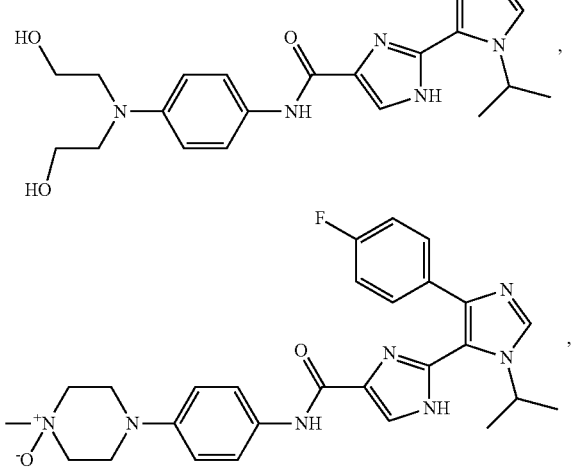
,
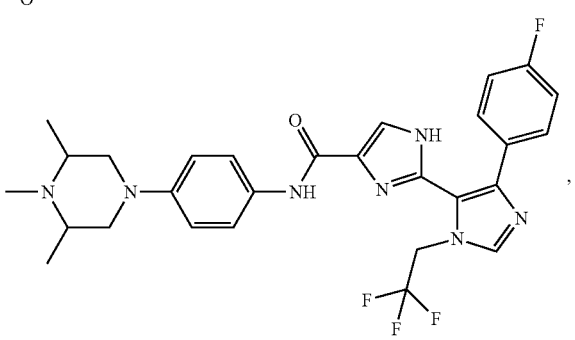
,
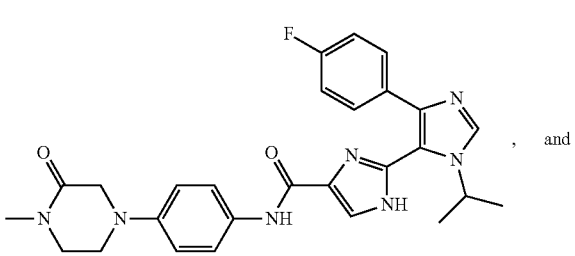
, and
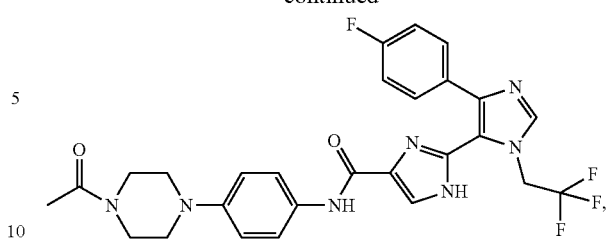
,
or a pharmaceutically acceptable salt of any one thereof.
In some embodiments, the compound is
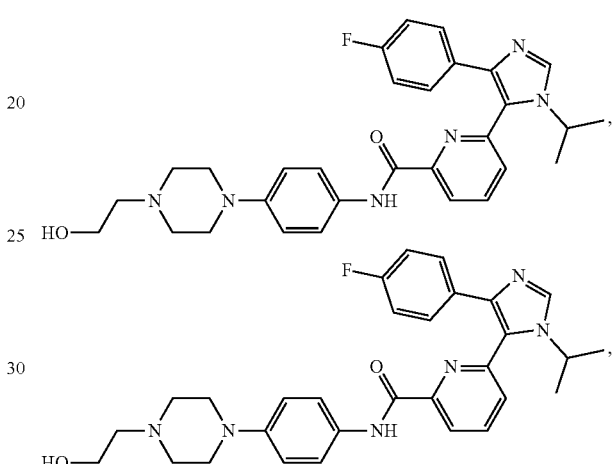
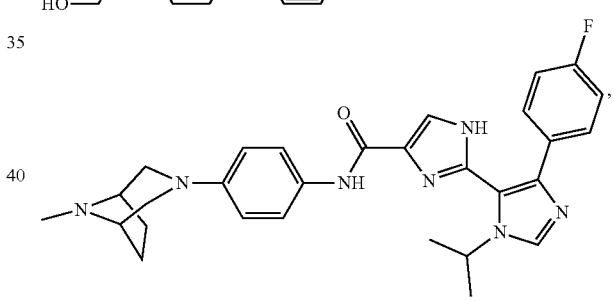
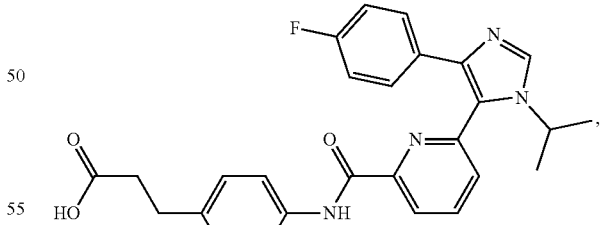
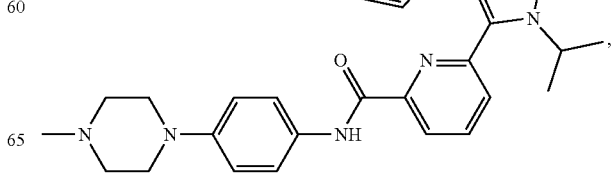

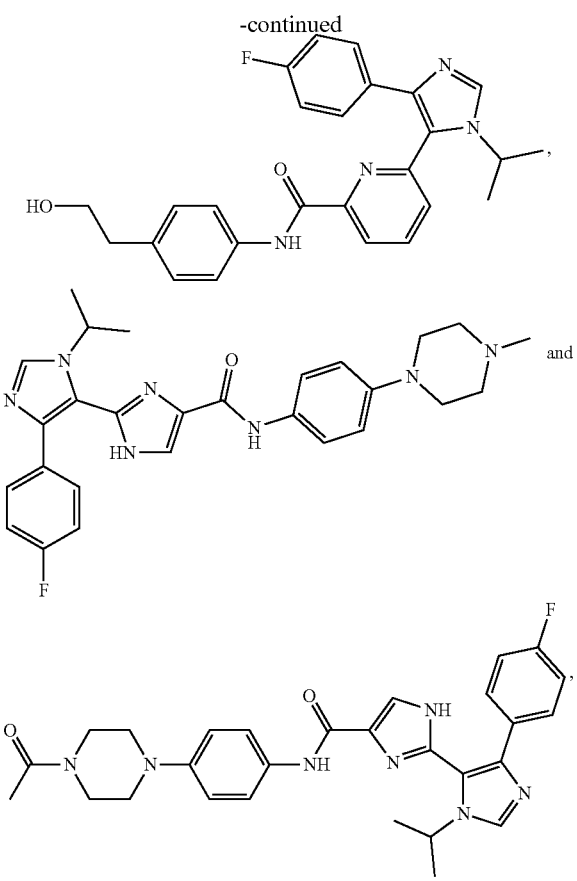

or a pharmaceutically acceptable salt of any one thereof.

In another aspect, provided herein is a pharmaceutical composition comprising a compound of Formula (I) or salt thereof, and a pharmaceutically acceptable excipient.

In another aspect, provided herein is a method of treating or preventing a disease, comprising administering a compound of Formula (I), or salt thereof, to a subject in need thereof.

In some embodiments, the disease is cancer.

In some embodiments, the cancer is selected from colorectal cancer, gastric cancer, breast cancer, lung cancer, pancreatic cancer, prostate cancer, multiple myeloma, chronic myelogenous leukemia, cancer metastasis, fibrosis, and psychiatric disorder.

In some embodiments, the disease is a fibrotic disease or condition selected from liver cirrhosis, pulmonary fibrosis, renal interstitial fibrosis, myocardial infarction, systemic sclerosis (SSc), and graft-versus-host disease (GVHD).

In some embodiments, the disease is kidney fibrosis.

In some embodiments, the disease is skin fibrosis.

In some embodiments, the disease is idiopathic pulmonary fibrosis (IPF).

In some embodiments, the disease is associated with TNIK kinase.

In another aspect, provided herein is a method of treating or preventing a disease comprising inhibiting TNIK kinase by administering a compound of Formula (I), or a pharmaceutically acceptable salt thereof.

In another aspect, provided herein is a method of treating or preventing disease comprising inhibiting MAP4K4 kinase by administering a compound of Formula (I), or a pharmaceutically acceptable salt thereof.

In another aspect, provided herein is a compound represented by Formula (A):

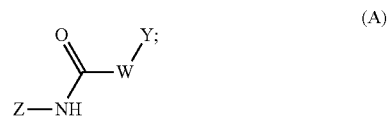

or a pharmaceutically acceptable salt thereof, wherein:

Z is selected from optionally substituted 3- to 12-membered heterocycle and optionally substituted $C_3$-$C_{12}$ carbocycle, wherein the substituents on each are independently selected at each occurrence from one or more —$N(R^{10})_2$, halogen, —OH, —CN, —$NO_2$, —$NH_2$, oxo, =S, —$C_{1-10}$ haloalkyl, —O—$C_{1-10}$ alkyl, $C_{2-10}$ alkenyl, $C_{2-10}$ alkynyl, $C_1$-$C_{10}$ alkyl, $C_{3-12}$ carbocycle, and 3- to 12-membered heterocycle;

wherein the $C_1$-$C_{10}$ alkyl is optionally substituted with one or more substituents independently selected at each occurrence from halogen, —OH, —CN, —$NO_2$, —$NH_2$, oxo, =S, —$C_{1-10}$ haloalkyl, —O—$C_{1-10}$ alkyl, —O—$C_{1-6}$alkyl-O—C(O)(O—$C_{1-10}$ alkyl), $C_{2-10}$ alkenyl, $C_{2-10}$ alkynyl, $C_{3-12}$ carbocycle, and 3- to 12-membered heterocycle;

wherein the $C_{3-12}$ carbocycle and 3- to 12-membered heterocycle are each optionally substituted at each occurrence from one or more substituents independently selected from halogen, —OH, —CN, —$NO_2$, —$NH_2$, oxo, =S, —$S(O_2)NH_2$, —$C_{1-10}$ haloalkyl, —O—$C_{1-10}$ alkyl, $C_{2-10}$ alkenyl, $C_{2-10}$ alkynyl, $C_{3-12}$ carbocycle, and 3- to 12-membered heterocycle, and optionally substituted $C_{1-10}$ alkyl, wherein the optional substituents on the $C_{1-10}$ alkyl are independently selected at each occurrence from one or more hydroxy, halogen, oxo, —$C_{1-10}$ haloalkyl, —$NH_2$, —CN, and —$NO_2$;

$R^{10}$ is selected from optionally substituted $C_1$-$C_6$ alkyl, wherein the optional substituents on $C_1$-$C_6$ alkyl are independently selected at each occurrence from one or more halogen, —OH, —CN, —$NO_2$, —$NH_2$, oxo, =S, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle;

W is selected from optionally substituted 5- to 8-membered heterocycle and optionally substituted $C_3$-$C_8$ carbocycle, wherein the substituents on each are independently selected at each occurrence from one or more halogen, —OH, —CN, —$NO_2$, —$NH_2$, oxo, =S, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, wherein the $C_{3-12}$ carbocycle and 3- to 12-membered heterocycle are each optionally substituted with one or more substituents independently selected at each occurrence from halogen, —OH, —CN, —$NO_2$, —$NH_2$, oxo, =S, $C_{1-10}$ alkyl, —$C_{1-10}$ haloalkyl, and —O—$C_{1-10}$ alkyl; and Y is selected from optionally substituted 5- to 8-membered heterocycle and optionally substituted $C_3$-$C_8$ carbocycle, wherein the substituents on each are independently selected at each occurrence from one or more halogen, —OH, —CN, —$NO_2$, —$NH_2$, oxo, =S, —$C_{1-10}$ haloalkyl, —O—$C_{1-10}$ alkyl, $C_{2-10}$ alkenyl, $C_{2-10}$ alkynyl, $C_{3-12}$ carbocycle, 3- to 12-membered heterocycle, wherein the $C_{3-12}$ carbocycle and 3- to 12-membered heterocycle are each optionally substituted with one or more substituents independently selected at each occurrence from halogen, —OH, —CN, —NO$_2$, —NH$_2$, oxo, =S, C$_{1-10}$ alkyl, —C$_{1-10}$ haloalkyl, and —O—C$_{1-10}$ alkyl.

In another aspect, provided herein is a compound represented by Formula (A*):

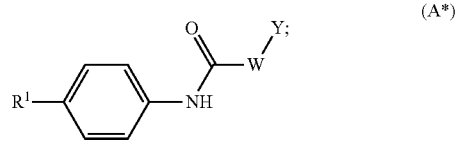

or a pharmaceutically acceptable salt thereof, wherein:
R$^1$ is selected from:
- —N(R$^5$)$_2$, wherein R$^5$ is selected from hydrogen, and optionally substituted C$_1$-C$_6$ alkyl, wherein the optional substituents on C$_1$-C$_6$ alkyl are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle;
- substituted C$_1$-C$_6$ alkyl, wherein the substituents on C$_1$-C$_6$ alkyl are independently selected at each occurrence from one or more halogen, —OH, —CN, —NO$_2$, —NH$_2$, oxo, =S, —C$_{1-10}$ haloalkyl, —O—C$_{1-10}$ alkyl, —O—C$_{1-6}$alkyl-O—C(O)(O—C$_{1-10}$ alkyl), C$_{2-10}$ alkenyl, C$_{2-10}$ alkynyl, C$_{3-12}$ carbocycle, 3- to 12-membered heterocycle;
- optionally substituted 3 to 8-membered heterocycle; wherein the optional substituents on the 3 to 8-membered heterocycle are independently selected at each occurrence from one or more halogen, —OH, —CN, —NO$_2$, —NH$_2$, oxo, =S, —S(O$_2$)NH$_2$, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, and optionally substituted C$_{1-10}$ alkyl, wherein the optional substituents on the C$_{1-10}$ alkyl are independently selected at each occurrence from one or more hydroxy, halogen, oxo, —C$_{1-10}$ haloalkyl, —NH$_2$, —CN, and —NO$_2$;

W is selected from optionally substituted 5- to 8-membered heterocycle and optionally substituted C$_3$-C$_8$ carbocycle, wherein the substituents on each are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, wherein the C$_{3-12}$ carbocycle and 3- to 12-membered heterocycle are each optionally substituted with one or more substituents independently selected at each occurrence from halogen, —OH, —CN, —NO$_2$, —NH$_2$, oxo, =S, C$_{1-10}$ alkyl, —C$_{1-10}$ haloalkyl, and —O—C$_{1-10}$ alkyl; and Y is selected from optionally substituted 5- to 8-membered heterocycle and optionally substituted C$_3$-C$_8$ carbocycle, wherein the substituents on each are independently selected at each occurrence from one or more halogen, —OH, —CN, —NO$_2$, —NH$_2$, oxo, =S, —C$_{1-10}$ haloalkyl, —O—C$_{1-10}$ alkyl, C$_{2-10}$ alkenyl, C$_{2-10}$ alkynyl, C$_{3-12}$ carbocycle, 3- to 12-membered heterocycle, wherein the C$_{3-12}$ carbocycle and 3- to 12-membered heterocycle are each optionally substituted with one or more substituents independently selected at each occurrence from halogen, —OH, —CN, —NO$_2$, —NH$_2$, oxo, =S, C$_{1-10}$ alkyl, —C$_{1-10}$ haloalkyl, and —O—C$_{1-10}$ alkyl.

In another aspect, provided herein is a pharmaceutical composition comprising a compound of Formula (A) or (A*), or a salt thereof, and a pharmaceutically acceptable excipient.

In another aspect, provided herein is a method of treating or preventing a disease, comprising administering a compound of Formula (A) or (A*), or a salt thereof, to a subject in need thereof.

In some embodiments, the disease is cancer.

In some embodiments, the cancer is selected from colorectal cancer, gastric cancer, breast cancer, lung cancer, pancreatic cancer, prostate cancer, multiple myeloma, chronic myelogenous leukemia, cancer metastasis, fibrosis, and psychiatric disorders, In some embodiments, the disease is a fibrotic disease or condition selected from pulmonary fibrosis, cystic fibrosis, liver fibrosis, myocardial fibrosis, kidney fibrosis, brain fibrosis, arterial fibrosis, arthrofibrosis, intestinal fibrosis, Dupytren's contracture fibrosis, keloid fibrosis, mediastinal fibrosis, myelofibrosis, peyronie's disease fibrosis, progressive massive fibrosis, retroperitoneal fibrosis, scleroderma sclerosis fibrosis, and adhesive capsulitis fibrosis.

In some embodiments, the disease is a fibrotic disease or condition selected from liver cirrhosis, pulmonary fibrosis, renal interstitial fibrosis, myocardial infarction, systemic sclerosis (SSc), and graft-versus-host disease (GVHD).

In some embodiments, the disease is kidney fibrosis.

In some embodiments, the disease is skin fibrosis.

In some embodiments, the disease is idiopathic pulmonary fibrosis (IPF).

In some embodiments, the disease is associated with TNIK kinase.

In another aspect, provided herein is a method of treating or preventing a disease comprising inhibiting TNIK kinase by administering a compound of Formula (A) or (A*), or a salt thereof to a subject in need thereof.

In another aspect, provided herein is a method of treating or preventing disease comprising inhibiting MAP4K4 kinase by administering a compound of Formula (A) or (A*), or salt thereof to a subject in need thereof.

EXAMPLES

The following examples are offered to illustrate, but not to limit the claimed invention. The following examples further illustrate the invention but, of course, should not be construed as in any way limiting its scope.

The following synthetic schemes are provided for purposes of illustration, not limitation. The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

Illustrative Synthesis Schemes

The compounds and salts of Formulas (A), (A*), (I), (IIA), or (IIB) can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in the synthesis schemes below, the steps in some cases may be performed in a different order than the order shown below. Numberings or R groups in each scheme do not necessarily correspond to that of the claims or other schemes or tables herein.

In some embodiments, compounds of Table 1 may be prepared according to the synthesis schemes below.

Example 1: Synthesis of Compound 102

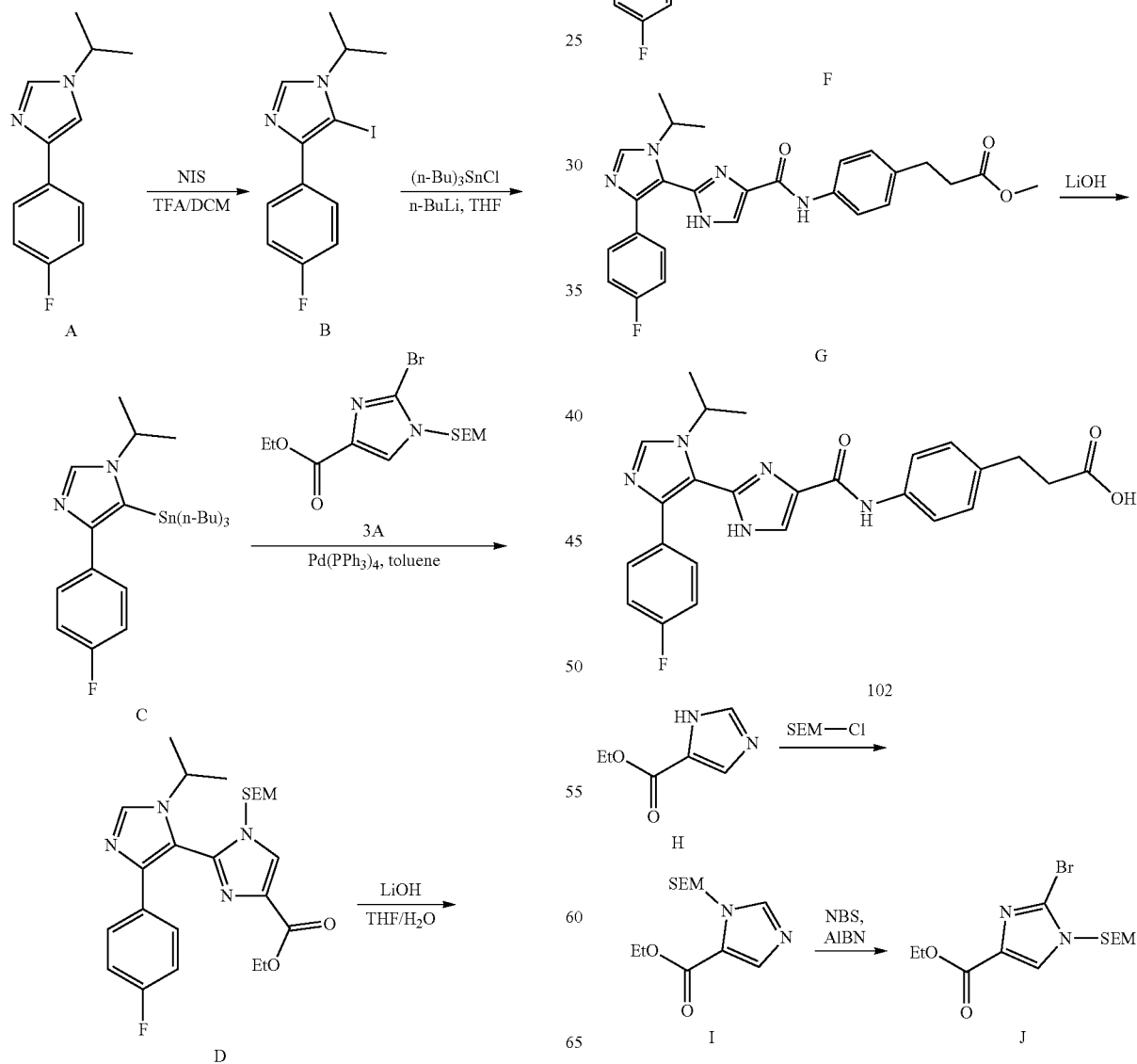

Example 2: General Procedure for Preparation of 4-(4-fluorophenyl)-5-iodo-1-isopropyl-1H-imidazole (Compound B)

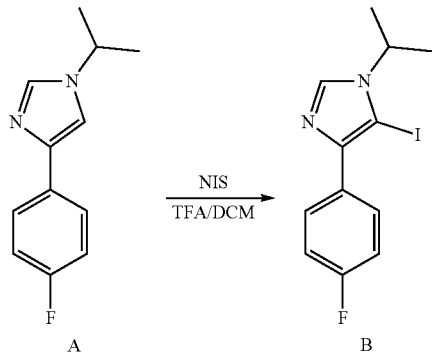

To a solution of Compound A (35 g, 171.36 mmol, 1 eq) and NIS (115.66 g, 514.09 mmol, 3 eq) in DCM (210 mL) was added TFA (5.86 g, 51.41 mmol, 3.81 mL, 0.3 eq) at 20° C. The mixture was stirred at 20° C. for 16 h. TLC (PE:EA=1:1) showed reactant 1 (Rf=0.4) was consumed and a new spot (Rf=0.6) was detected. The mixture was poured to aq NaNO$_2$ (1000 mL). The mixture was extracted with EA (500 mL×3). The combined organic layers were washed with brine (500 mL), dried over Na$_2$SO$_4$, filtered and concentrated under reduced pressure to give a residue. The residue was purified by column chromatography (SiO2, PE:EA=5:1~1:1) to afford desired compound. Compound B (14 g, 37.74 mmol, 22.02% yield, 89% purity) was obtained as yellow solid, which was determined by $^1$HNMR and LCMS. LCMS: Retention time: 0.743 min, (M+H)=331.1. $^1$HNMR: (400 MHz, DMSO-d$_6$), δ=8.15 (s, 1H), 7.92-7.85 (m, 2H), 7.29-7.19 (m, 2H), 4.50-4.31 (m, 1H), 1.47 (d, J=6.8 Hz, 6H).

Example 3: General Procedure for Preparation of 4-(4-fluorophenyl)-1-isopropyl-5-(tributylstannyl)-1H-imidazole (Compound C)

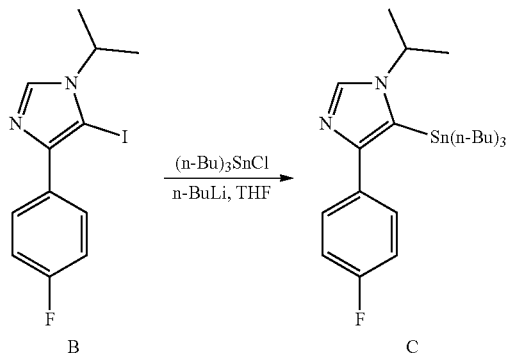

To a solution of Compound B (2 g, 6.06 mmol, 1 eq) in THF (20 mL) was added n-BuLi (2.5 M, 3.15 mL, 1.3 eq) and tributyl(chloro)stannane (2.96 g, 9.09 mmol, 2.44 mL, 1.5 eq) slowed at −70° C. The mixture was stirred at −70° C. for 0.5 h. LCMS showed reactant 1 was consumed and 74% of desired mass was detected. The mixture was poured to aq NH$_4$Cl (100 mL) and aq KF (100 mL). The mixture was extracted with EA (100 mL*3). The combined organic layers were washed with brine (100 mL), dried over Na$_2$SO$_4$, filtered and concentrated under reduced pressure to give a residue. The residue was purified by column chromatography (SiO2, PE:EA=50:1-3:1) to afford desired compound. Compound C (2 g, 4.05 mmol, 66.93% yield) was obtained as colorless oil, which was determined by $^1$HNMR. LCMS: Retention time: 0.982 min, (M+H)=492.9. $^1$H NMR: (400 MHz, DMSO-d$_6$), δ=8.05 (s, 1H), 7.46-7.31 (m, 2H), 7.27-7.07 (m, 2H), 4.18 (s, 1H), 1.48 (d, J=6.8 Hz, 6H), 1.39-1.30 (m, 5H), 1.29-1.10 (m, 8H), 0.97-0.90 (m, 5H), 0.80 (t, J=7.4 Hz, 9H).

Example 4: General Procedure for Preparation of ethyl 1-((2-(trimethylsilyl)ethoxy)methyl)-1H-imidazole-4-carboxylate (Compound I)

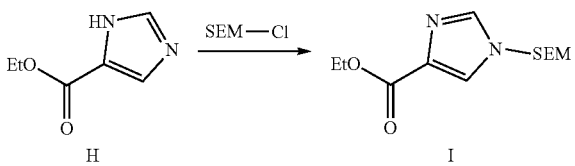

To a solution of NaH (8.56 g, 214.07 mmol, 60% purity, 1.5 eq) in THF (200 mL) was added a mixture of Compound H (20 g, 142.71 mmol, 1 eq) in THF (100 mL) at 0° C. The mixture was stirred at 0° C. for 20 min, and then stirred at 20° C. for 30 min. SEM-Cl (35.69 g, 214.07 mmol, 37.89 mL, 1.5 eq) was added to the mixture at 0° C. The mixture was stirred at 20° C. for 16 hrs. TLC (PE:EA=1:1) showed reactant 1 (Rf=0.1) consumed and a new spot (Rf=0.2) was observed. The mixture was poured into sat. NH$_4$Cl (200 mL), and then extracted with EA (100 mL×2). The combined organic layers were washed with brine (20 mL×2), dried over Na$_2$SO$_4$, filtered and concentrated in vacuo to give a residue. The residue was purified by silica gel chromatography (PE:EA=5:1-1:1). Compound I (15.9 g, 58.80 mmol, 41.20% yield) was obtained as yellow oil, which was determined by HNMR. $^1$H NMR: (400 MHz, CHLOROFORM-d), δ=7.72 (d, J=1.4 Hz, 1H), 7.61 (d, J=1.4 Hz, 1H), 5.30 (s, 2H), 4.37 (q, J=7.2 Hz, 2H), 3.49 (dd, J=7.8, 8.7 Hz, 2H), 1.39 (t, J=7.2 Hz, 3H), 0.98-0.85 (m, 2H), 0.04--0.06 (m, 10H).

Example 5: General Procedure for Preparation of ethyl 2-bromo-1-((2-(trimethylsilyl)ethoxy)methyl)-1H-imidazole-4-carboxylate (Compound J)

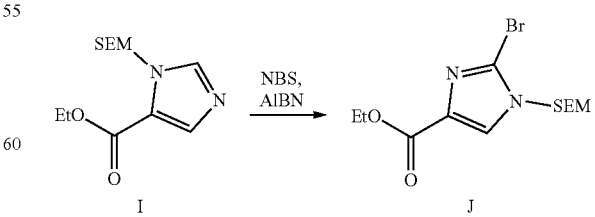

To a solution of Compound I (14.5 g, 53.62 mmol, 1 eq) in CHCl$_3$ (150 mL) was added NBS (9.54 g, 53.62 mmol, 1 eq) and AIBN (880.56 mg, 5.36 mmol, 0.1 eq) at 20° C. The mixture was stirred at 60° C. for 5 hrs. TLC (PE:EA=1:1) showed reactant 1 (Rf=0.2) consumed and a new spot (Rf=0.5) was observed. The mixture was concentrated in vacuo to give a residue. The residue was purified by silica gel chromatography (PE:EA=5:1-1:1). Compound J (11 g, 31.49 mmol, 58.73% yield) was obtained as yellow solid, which was determined by HNMR. $^1$H NMR: (400 MHz, CHLOROFORM-d), δ=7.76 (s, 1H), 5.31 (s, 2H), 4.38 (q, J=7.2 Hz, 2H), 3.61-3.49 (m, 2H), 1.38 (t, J=7.2 Hz, 3H), 1.01-0.85 (m, 2H), 0.05--0.07 (m, 9H).

Example 6: General Procedure for Preparation of ethyl 5'-(4-fluorophenyl)-3'-isopropyl-1-((2-(trimethylsilyl)ethoxy)methyl)-1H,3'H-[2,4'-biimidazole]-4-carboxylate (Compound D)

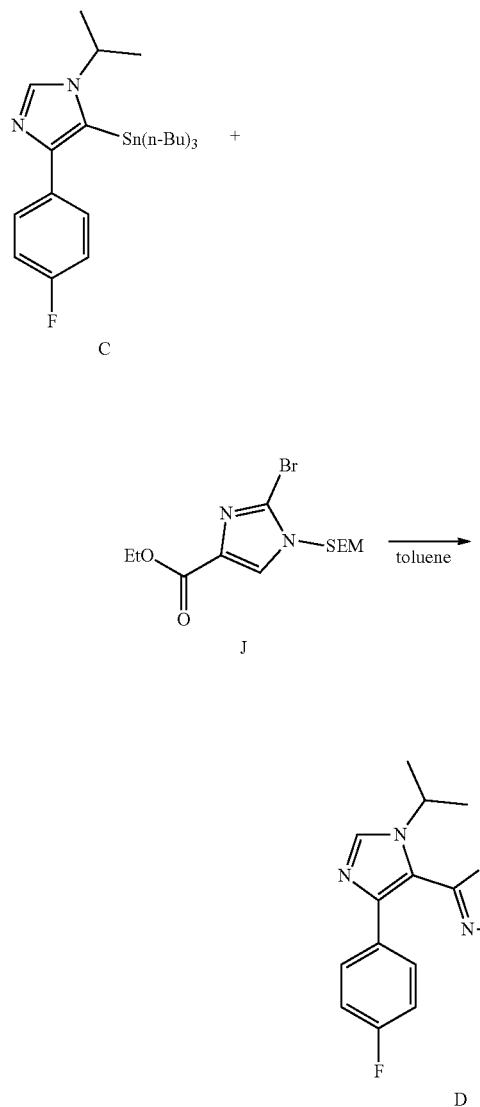

To a solution of Compound C (300 mg, 608.17 μmol, 1 eq) and Compound J (318.64 mg, 912.25 μmol, 1.5 eq) in toluene (2 mL) was added [2-(2-aminophenyl)phenyl]-chloro-palladium; bis(1-adamantyl)-butyl-phosphane (120.00 mg, 179.47 μmol, 2.95e-1 eq) under N2 at 20° C. The mixture was stirred at 110° C. for 16 h. LCMS showed reactant 1 was consumed and 58% of desired mass was detected. The mixture was concentrated in vacuo to afford residue. The residue was purified by prep-HPLC (column: Phenomenex luna C18 150*40 mm*15 um; mobile phase: [water (0.225% FA)-ACN]; B %: 54%-64%, 14 min) to afford desired compound. Compound D (60 mg, 125.68 μmol, 20.67% yield, 99% purity) was obtained as brown oil, which was determined by $^1$HNMR and LCMS. Compound D (100 mg, 84.63 μmol, 13.92% yield, 40% purity) was obtained as brown oil, which was determined by LCMS. LCMS: Retention time: 0.920 min, (M+H)=473.1. LCMS: Retention time: 0.823 min, (M+H)=473.3. LCMS: Retention time: 0.842 min, (M+H)=473.3. $^1$H NMR: (400 MHz, DMSO-d$_6$), δ=8.41 (s, 1H), 8.24 (s, 1H), 7.42-7.34 (m, 2H), 7.27-7.19 (m, 2H), 5.17-4.92 (m, 2H), 4.51-4.34 (m, 2H), 4.24-4.07 (m, 1H), 3.37-3.30 (m, 2H), 1.54-1.41 (m, 9H), 0.67 (br d, J=2.6 Hz, 2H), 0.02--0.02 (m, 9H).

Example 7: General Procedure for Preparation of 5'-(4-fluorophenyl)-3'-isopropyl-1-((2-(trimethylsilyl)ethoxy)methyl)-1H,3'H-[2,4'-biimidazole]-4-carboxylic acid (Compound E)

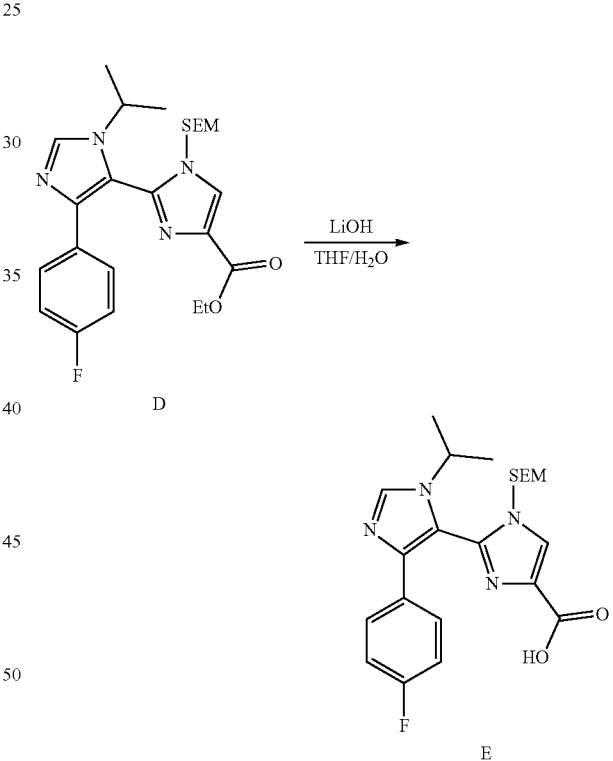

To a solution of Compound D (50.00 mg, 105.79 μmol, 1 eq) in THF (1 mL) and H$_2$O (1 mL) was added LiOH.H$_2$O (8.88 mg, 211.58 μmol, 2 eq) at 20° C. The mixture was stirred at 20° C. for 4 h. LCMS showed reactant 1 was consumed and 93% of desired mass was detected. To the mixture was added 1N HCl (10 mL). The mixture was extracted with EA (20 mL*3). The combined organic layers were washed with brine (20 mL), dried over Na$_2$SO$_4$, filtered and concentrated under reduced pressure to give crude product. Compound E (50 mg, crude) was obtained as colorless oil. LCMS: Retention time: 0.778 min, (M+H)= 445.3.

Example 8: General Procedure for Preparation of methyl 3-(4-(5'-(4-fluorophenyl)-3'-isopropyl-1-((2-(trimethylsilyl)ethoxy)methyl)-1H,3'H-[2,4'-biimidazole]-4-carboxamido)phenyl)propanoate (Compound F)

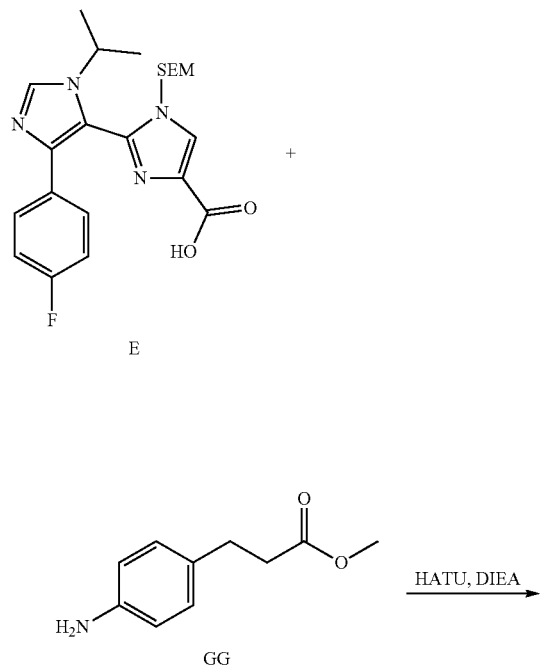

To a solution of Compound E (50 mg, 112.47 μmol, 1 eq) and Compound GG (30.23 mg, 168.70 μmol, 1.5 eq) in DMF (2 mL) was added HATU (64.15 mg, 168.70 μmol, 1.5 eq) and DIPEA (43.61 mg, 337.40 μmol, 58.77 μL, 3 eq) at 20° C. The mixture was stirred at 20° C. for 2 h. LCMS showed reactant 1 was consumed and 82% of desired mass was detected. The mixture was poured to H$_2$O (20 mL). The mixture was extracted with EA (20 mL*3). The combined organic layers were washed with brine (20 mL), dried over Na$_2$SO$_4$, filtered and concentrated under reduced pressure to give crude product. Compound F (65 mg, crude) was obtained as colorless oil. LCMS: Retention time: 0.978 min, (M+H)=606.1.

Example 9: General Procedure for Preparation of methyl 3-(4-(5'-(4-fluorophenyl)-3'-isopropyl-1H,3'H-[2,4'-biimidazole]-4-carboxamido)phenyl)propanoate (Compound G)

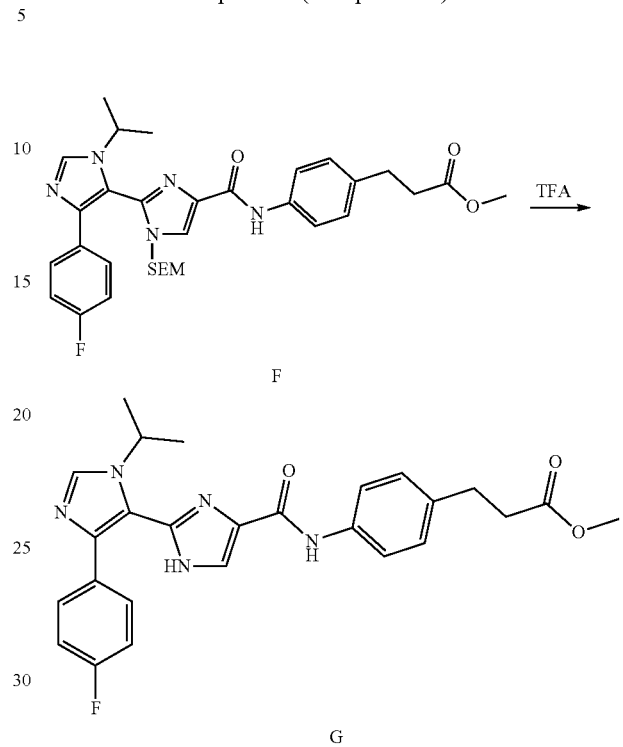

To a solution of Compound F (60 mg, 99.05 μmol, 1 eq) in DCM (2 mL) was added TFA (1.54 g, 13.51 mmol, 1 mL, 136.36 eq) at 20° C. The mixture was stirred at 20° C. for 8 h. LCMS showed reactant 1 was consumed and 80% of desired mass was detected. The mixture was poured to aq NaHCO$_3$ (20 mL). The mixture was extracted with EA (20 mL*3). The combined organic layers were washed with brine (20 mL), dried over Na$_2$SO$_4$, filtered and concentrated under reduced pressure to give crude product. Compound G (50 mg, crude) was obtained as colorless oil. LCMS: Retention time: 0.748 min, (M+H)=476.3.

Example 10: General Procedure for Preparation of 3-(4-(5'-(4-fluorophenyl)-3'-isopropyl-1H,3'H-[2,4'-biimidazole]-4-carboxamido)phenyl)propanoic acid (Compound 102)

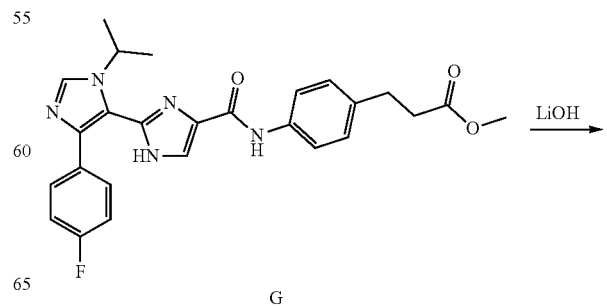

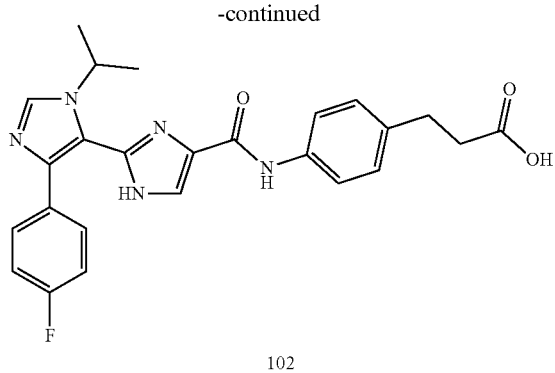

102

To a solution of Compound G (40 mg, 84.12 μmol, 1 eq) in THF (1 mL) and H2O (1 mL) was added LiOH.H2O (35.30 mg, 841.20 μmol, 10 eq) at 20° C. The mixture was stirred at 20° C. for 2 h. LCMS showed reactant 1 was consumed and 74% of desired mass was detected. The mixture was poured to 1N HCl (100 mL). The mixture was extracted with EA (20 mL*3). The combined organic layers were washed with brine (20 mL), dried over Na$_2$SO$_4$, filtered and concentrated under reduced pressure to give a residue. The residue was purified by prep-HPLC (column: Unisil 3-100 C18 Ultra 150*50 mm*3 μm; mobile phase: [water (0.225% FA)-ACN]; B %: 18%-38%, 10 min) to afford desired compound. Compound 102 (14.8 mg, 31.59 μmol, 37.55% yield, 98.5% purity) was obtained as yellow solid, which was determined by $^1$HNMR, LCMS and HPLC and F NMR. LCMS: Retention time: 0.692 min, (M+H)=462.3. LCMS: Retention time: 0.673 min, (M+H)=462.3. HPLC: Retention time: 1.434 min. HNMR: (400 MHz, DMSO-d$_6$), δ=13.30-12.87 (m, 1H), 9.86 (br s, 1H), 8.06 (s, 1H), 8.02 (s, 1H), 7.72 (br d, J=7.8 Hz, 2H), 7.43-7.35 (m, 2H), 7.25-7.07 (m, 5H), 4.30-4.18 (m, 1H), 2.79 (t, J=7.6 Hz, 2H), 2.53 (br s, 2H), 1.40 (d, J=6.8 Hz, 6H).

Example 11: Synthesis of Compound 112

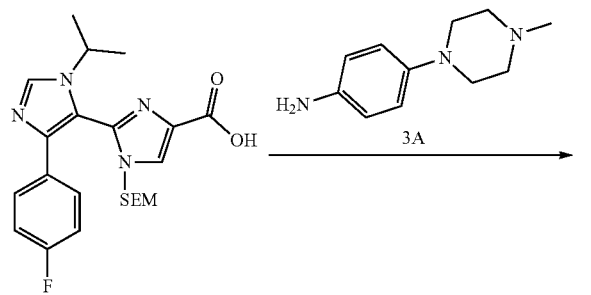

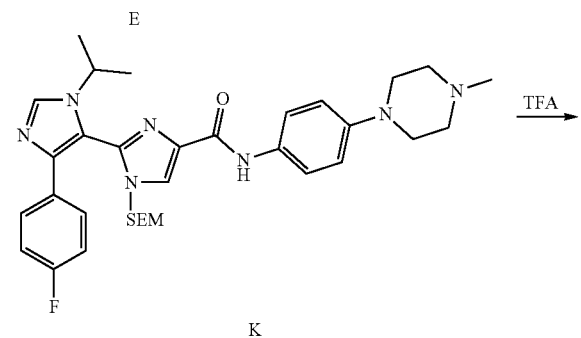

K

Example 12: General Procedure for Preparation of 5'-(4-fluorophenyl)-3'-isopropyl-N-(4-(4-methylpiperazin-1-yl)phenyl)-1-((2-(trimethylsilyl)ethoxy)methyl)-1H,3'H-[2,4'-biimidazole]-4-carboxamide (Compound K)

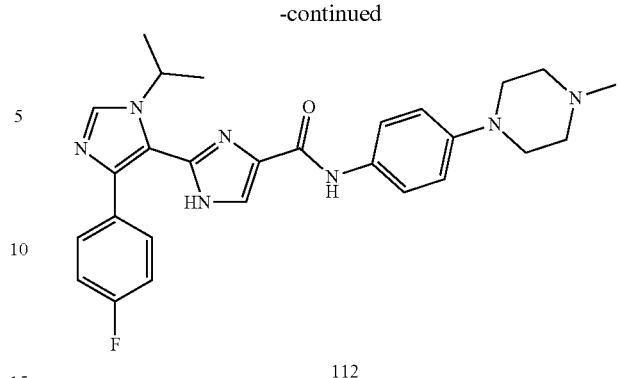

K

To a mixture of Compound E (6.5 g, 14.62 mmol, 1 eq) and Compound 3A (4.19 g, 21.93 mmol, 1.5 eq) in DMF (50 mL) was added HATU (8.34 g, 21.93 mmol, 1.5 eq) and DIEA (5.67 g, 43.86 mmol, 7.64 mL, 3 eq). The mixture was stirred at 20° C. for 3 hours. LCMS showed Compound E was consumed and desired mass was detected. The residue was poured into water (500 mL) and extracted with ethyl acetate (150 mL×3). The combined organic phase was washed with brine (200 mL), dried with anhydrous Na$_2$SO$_4$, filtered and concentrated in vacuum. The crude compound was used into the next step without further purification. Compound K (9 g, crude) was obtained as brown oil. LCMS: Retention time: 0.753 min, (M+H)=618.4.

Example 13: General Procedure for Preparation of 5'-(4-fluorophenyl)-3'-isopropyl-N-(4-(4-methylpiperazin-1-yl)phenyl)-1H,3'H-[2,4'-biimidazole]-4-carboxamide (compound 112)

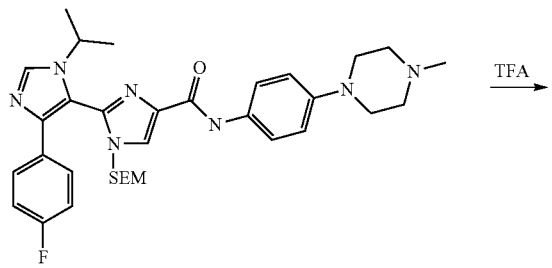

K

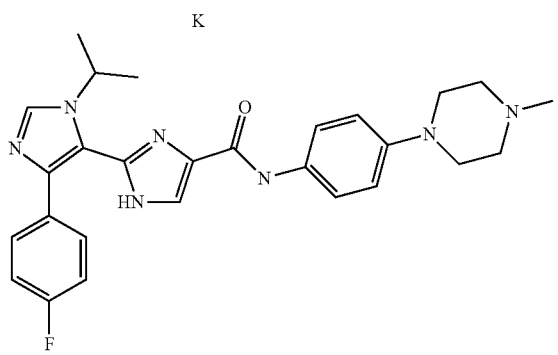

112

To a mixture of Compound K (9 g, 14.57 mmol, 1 eq) in CH2Cl2 (2 mL) was added TFA (30.80 g, 270.12 mmol, 20.00 mL, 18.54 eq). The mixture was stirred at 20° C. for 5 hours. LCMS showed Compound K was consumed and desired mass was detected. The mixture was basified with saturated $NaHCO_3$ to pH=8 and extracted with ethyl acetate (200 mL×4). The combined organic phase was washed with brine (100 mL), dried with anhydrous $Na_2SO_4$, filtered and concentrated in vacuum. The residue was purified by reversed-phase HPLC (0.1% $NH_3.H_2O$). Compound 112 (3.04 g, 6.20 mmol, 42.58% yield, 99.492% purity) was obtained as off-white solid, which was checked with HNMR, LCMS, HPLC. LCMS: Retention time: 0.683 min, (M+H)=488.2. HPLC: Retention time: 1.157 min. HPLC: Retention time: 1.155 min. HNMR: (400 MHz, DMSO-$d_6$) δ=13.14-12.98 (m, 1H), 9.72 (s, 1H), 8.07 (s, 1H), 7.98 (s, 1H), 7.67 (d, J=9.2 Hz, 2H), 7.44-7.34 (m, 2H), 7.14 (t, J=8.8 Hz, 2H), 6.90 (d, J=9.0 Hz, 2H), 4.30-4.18 (m, 1H), 3.13-3.04 (m, 4H), 2.47-2.42 (m, 4H), 2.22 (s, 3H), 1.40 (d, J=6.4 Hz, 6H).

Example 14: Synthesis of Compound 113

4-(5'-(4-fluorophenyl)-3'-isopropyl-1H,3'H-[2,4'-biimidazole]-4-carboxamido)benzoic acid (Compound 113) was synthesized under the same synthetic route as for Compound 112 as white solid, which was determined by $^1$HNMR, F NMR, LCMS and HPLC. LCMS: Retention time: 0.750 min, (M+H)=434.2. LCMS: Retention time: 0.760 min, (M+H)=434.2. HPLC: Retention time: 1.384 min. $^1$HNMR: (400 MHz, DMSO-$d_6$), δ=10.27 (s, 1H), 9.41 (s, 1H), 8.15 (s, 1H), 7.91-7.81 (m, 4H), 7.45-7.39 (m, 2H), 7.30-7.21 (m, 2H), 4.46 (br d, J=6.6 Hz, 1H), 1.40 (d, J=6.8 Hz, 6H).

Example 15: Synthesis of Compound 111

5'-(4-fluorophenyl)-N-(4-(2-hydroxyethyl)phenyl)-3'-isopropyl-1H,3'H-[2,4'-biimidazole]-4-carboxamide (Compound 111) was synthesized under the same synthetic route as for Compound 112 as white solid, which was determined by $^1$HNMR, F NMR, LCMS and HPLC. LCMS: Retention time: 0.745 min, (M+H)=434.3. LCMS: Retention time: 0.752 min, (M+H)=434.2. HPLC: Retention time: 1.472 min. $^1$HNMR: (400 MHz, DMSO-$d_6$), δ=13.08 (br s, 1H), 9.84 (s, 1H), 8.07 (s, 1H), 8.02 (s, 1H), 7.72 (d, J=8.4 Hz, 2H), 7.44-7.36 (m, 2H), 7.19-7.10 (m, 4H), 4.62 (t, J=5.2 Hz, 1H), 4.29-4.18 (m, 1H), 3.64-3.53 (m, 2H), 2.73-2.67 (m, 2H), 1.40 (d, J=6.8 Hz, 6H).

Example 16: Synthesis of Compound 116

N-(4-(bis(2-hydroxyethyl)amino)phenyl)-5'-(4-fluorophenyl)-3'-isopropyl-1H,3'H-[2,4'-biimidazole]-4-carboxamide (Compound 116) was synthesized under the same synthetic route as for Compound 112 as white solid, which was determined by $^1$HNMR, F NMR, LCMS and HPLC. LCMS: Retention time: 0.837 min, (M+H)=493.4. LCMS: Retention time: 0.790 min, (M+H)=493.1. HPLC: Retention time: 0.993 min. $^1$HNMR: (400 MHz, METHANOL-$d_4$), δ=9.53 (s, 1H), 8.19 (d, J=1.4 Hz, 1H), 8.07 (d, J=9.0 Hz, 2H), 7.71 (d, J=9.0 Hz, 2H), 7.56-7.40 (m, 2H), 7.36-7.20 (m, 2H), 4.90-4.80 (m, 1H), 3.84 (br t, J=5.2 Hz, 4H), 3.66 (br s, 4H), 1.62 (d, J=6.8 Hz, 6H).

Example 17: Synthesis of Compound 117

5'-(4-fluorophenyl)-N-(4-(4-(2-hydroxyethyl)piperazin-1-yl)phenyl)-3'-isopropyl-1H,3'H-[2,4'-biimidazole]-4-carboxamide (Compound 117) was synthesized under the same synthetic route as for Compound 112 as white solid, which was determined by $^1$HNMR, F NMR, LCMS and HPLC. LCMS: Retention time: 0.839 min, (M+H)=518.4. LCMS: Retention time: 0.670 min, (M+H)=518.3. HPLC: Retention time: 1.484 min. $^1$HNMR: (400 MHz, METHANOL-$d_4$), δ=9.13 (s, 1H), 7.98 (s, 1H), 7.66 (d, J=8.8 Hz, 2H), 7.51-7.39 (m, 2H), 7.21 (t, J=8.8 Hz, 2H), 7.08 (d, J=9.2 Hz, 2H), 4.82-4.74 (m, 1H), 3.96 (dd, J=4.6, 5.9 Hz, 2H), 3.91-3.58 (m, 4H), 3.43-3.33 (m, 4H), 3.29-3.03 (m, 2H), 1.58 (d, J=6.6 Hz, 6H).

Example 18: Synthesis of Compound 99

N-(4-(4-carbamoylpiperazin-1-yl)phenyl)-5'-(4-fluorophenyl)-3'-isopropyl-1H,3'H-[2,4'-biimidazole]-4-carboxamide (Compound 99) was synthesized under the same synthetic route as for Compound 112 as white solid, which was determined by $^1$HNMR, F NMR, LCMS and HPLC. LCMS: Retention time: 1.298 min, (M+H)=474.2. HPLC: Retention time: 0.732 min. 1H NMR (400 MHz, METHANOL-$d_4$) δ=8.06 (s, 1H), 7.89 (s, 1H), 7.60 (br d, J=8.6 Hz, 2H), 7.38 (dd, J=5.5, 9.0 Hz, 2H), 7.10-6.95 (m, 4H), 4.60-4.41 (m, 1H), 3.62-3.52 (m, 4H), 3.20-3.09 (m, 4H), 1.50 (d, J=6.7 Hz, 6H). $^{19}$F NMR (376 MHz, METHANOL-$d_4$) δ=-116.70 (br s, 1F).

Example 19: Synthesis of Compound 97

5'-(4-fluorophenyl)-3'-isopropyl-N-(4-(4-sulfamoylpiperazin-1-yl)phenyl)-1H,3'H-[2,4'-biimidazole]-4-carboxamide (Compound 97) was synthesized under the same synthetic route as for Compound 112 as white solid, which was determined by $^1$HNMR, F NMR, LCMS and HPLC. LCMS: Retention time: 0.956 min, (M+H)=553.3. HPLC: Retention time: 1.854 min. $^1$H NMR (400 MHz, DMSO-d$_6$) δ=9.90-9.65 (m, 1H), 8.06 (s, 1H), 7.99 (s, 1H), 7.69 (br d, J=8.2 Hz, 2H), 7.38 (dd, J=5.5, 9.0 Hz, 2H), 7.13 (t, J=9.0 Hz, 2H), 6.94 (br d, J=9.0 Hz, 2H), 6.86 (br s, 2H), 4.30-4.16 (m, 1H), 3.19 (br d, J=4.7 Hz, 4H), 3.09 (br d, J=5.1 Hz, 4H), 1.39 (s, 3H), 1.38 (s, 3H). $^{19}$F NMR (376 MHz, DMSO-d$_6$) δ=−115.64 (br s, 1F).

Example 20: Synthesis of Compound 181

5'-(4-fluorophenyl)-3'-isopropyl-N-(4-(piperazin-1-yl)phenyl)-1H,3'H-[2,4'-biimidazole]-4-carboxamide (Compound 181) was synthesized under the same synthetic route as for Compound 112 as white solid, which was determined by $^1$HNMR, F NMR, LCMS and HPLC. LCMS: Retention time: 0.825 min, (M+H)=474.2. HPLC: Retention time: 0.693 min. $^1$H NMR (400 MHz, DMSO-d$_6$) δ=9.76 (br s, 1H), 8.06 (s, 1H), 7.99 (s, 1H), 7.67 (br d, J=8.2 Hz, 2H), 7.44-7.31 (m, 2H), 7.13 (br t, J=9.0 Hz, 2H), 6.90 (br d, J=8.6 Hz, 2H), 4.30-4.14 (m, 1H), 3.09 (br s, 4H), 2.95 (br s, 4H), 1.39 (br d, J=6.7 Hz, 6H). $^{19}$F NMR (376 MHz, DMSO-d$_6$) δ=−115.66 (br s, 1F).

Example 22: Synthesis of Compound 119

5'-(4-fluorophenyl)-3'-methyl-N-(4-(4-methylpiperazin-1-yl)phenyl)-1H,3'H-[2,4'-biimidazole]-4-carboxamide (Compound 119) was synthesized under the same synthetic route as for Compound 112 as white solid, which was determined by $^1$HNMR, F NMR, LCMS and HPLC. LCMS: Retention time: 0.851 min, (M+H)=460.4. HPLC: Retention time: 0.981 min. 1H NMR (400 MHz, DMSO-d$_6$) δ=12.97 (br s, 1H), 9.71 (s, 1H), 8.04-7.80 (m, 2H), 7.66 (br d, J=8.7 Hz, 2H), 7.55-7.30 (m, 2H), 7.14 (br t, J=8.9 Hz, 2H), 6.89 (br d, J=8.9 Hz, 2H), 3.59 (s, 3H), 3.13-2.99 (m, 4H), 2.48-2.40 (m, 4H), 2.21 (s, 3H). $^{19}$F NMR (377 MHz, DMSO-d$_6$) δ=−115.52 (s, 1F).

Example 23: Synthesis of Compound 135

5'-(4-fluorophenyl)-N-(4-(4-methylpiperazin-1-yl)phenyl)-3'-neopentyl-1H,3'H-[2,4'-biimidazole]-4-carboxamide (Compound 135) was synthesized under the same synthetic route as for Compound 102 as white solid, which was determined by $^1$HNMR, LCMS and HPLC. LCMS: Retention time: 0.640 min, (M+H)=516.3. LCMS: Retention time: 0.715 min, (M+H)=516.3. HPLC: Retention time: 1.789 min. $^1$HNMR: (400 MHz, DMSO-d$_6$), δ=10.05 (br d, J=2.2 Hz, 1H), 9.84 (s, 1H), 8.37 (s, 1H), 7.99 (s, 1H), 7.72 (d, J=9.0 Hz, 2H), 7.44 (dd, J=5.4, 8.8 Hz, 2H), 7.22 (t, J=8.8 Hz, 2H), 7.00 (d, J=9.2 Hz, 2H), 4.07 (s, 2H), 3.79 (br d, J=12.2 Hz, 2H), 3.53 (br d, J=11.0 Hz, 2H), 3.17 (br s, 2H), 3.00-2.82 (m, 5H), 0.72 (s, 9H).

Example 24: Synthesis of Compound 130

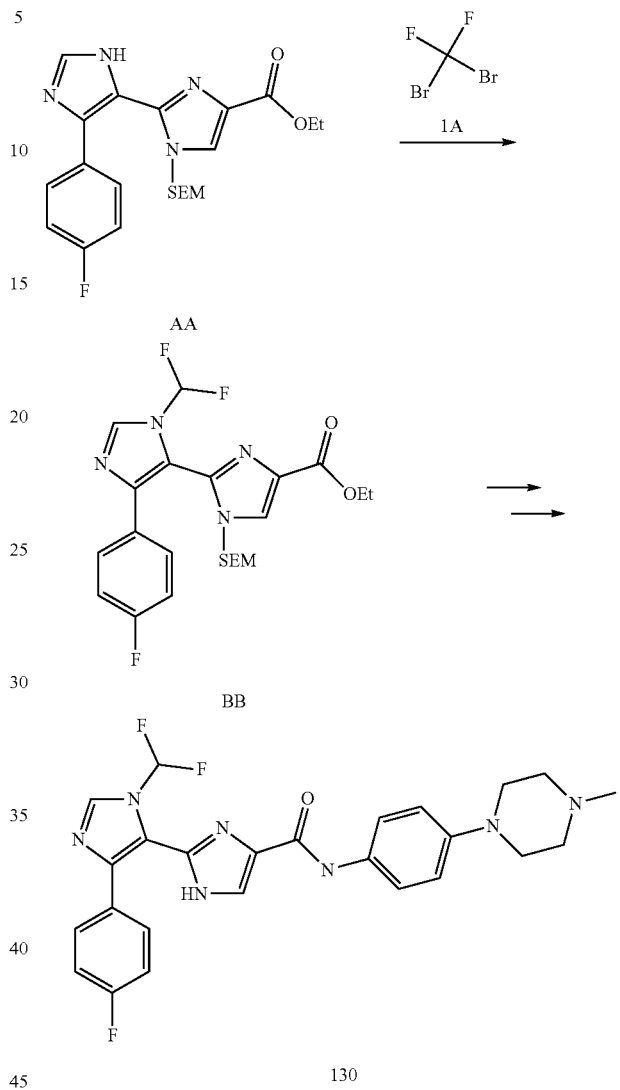

Example 25: General Procedure for Preparation of ethyl 3'-(difluoromethyl)-5'-(4-fluorophenyl)-1-((2-(trimethylsilyl)ethoxy)methyl)-1H,3'H-[2,4'-biimidazole]-4-carboxylate (Compound BB)

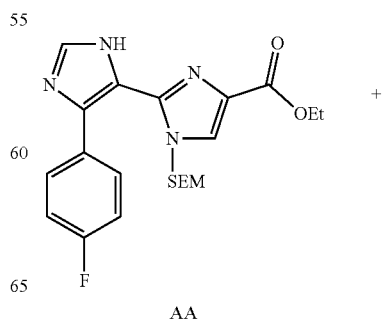

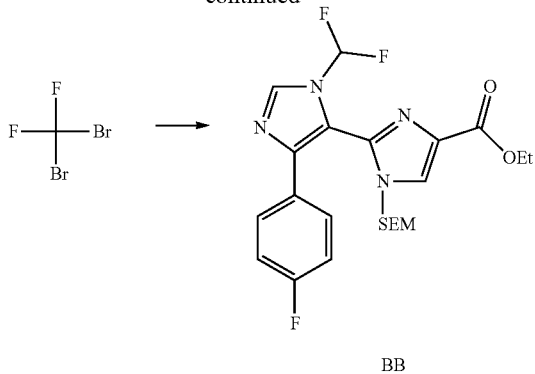

To a solution of Compound AA 500 mg, 1.16 mmol, 1 eq) in ACN (5 mL) was added NaH (46.45 mg, 1.16 mmol, 60% purity, 1 eq) at 20° C. The mixture was stirred at 20° C. for 1 hr. Dibromodifluoromethane (365.49 mg, 1.74 mmol, 161.01 µL, 1.5 eq) and Zn (9.80 mg, 149.81 µmol, 1.29e-1 eq) was added to the mixture at −15° C. The mixture was stirred at 20° C. for 16 h. LCMS showed 42% of Compound BB was remained and 17% of desired mass was detected. The mixture was poured to aq NH$_4$Cl (10 mL). The mixture was extracted with EA (20 mL×2). The combined organic layers were dried over Na$_2$SO$_4$, filtered and concentrated under reduced pressure to give a residue. The residue was purified by column chromatography (SiO$_2$, PE:EA=5:1-0:1) to afford desired compound and 200 mg of reactant 1 was recovered. Compound BB (40 mg, 72.42 µmol, 6.24% yield, 87% purity) was obtained as yellow oil, which was determined by LCMS. Ethyl 5'-(4-fluorophenyl)-1-((2-(trimethylsilyl)ethoxy)methyl)-1H,3'H-[2,4'-biimidazole]-4-carboxylate (200 mg, 464.53 µmol, 40.00% yield) was recovered. LCMS: Retention time: 0.958 min, (M+H)=481.3. LCMS: Retention time: 0.968 min, (M+H)=481.3.

3'-(difluoromethyl)-5'-(4-fluorophenyl)-N-(4-(4-methylpiperazin-1-yl)phenyl)-1H,3'H-[2,4'-biimidazole]-4-carboxamide (Compound 130) was synthesized from BB under the same synthetic route as for Compound 112 as oil, which was determined by $^1$HNMR, LCMS and HPLC. LCMS: Retention time: 0.691 min, (M+H)=496.3. LCMS: Retention time: 0.768 min, (M+H)=496.2. HPLC: Retention time: 2.175 min. HNMR: (400 MHz, DMSO-d$_6$), δ=10.44 (br s, 1H), 9.83 (s, 1H), 8.51 (s, 1H), 8.14-7.78 (m, 2H), 7.71 (d, J=9.2 Hz, 2H), 7.55-7.41 (m, 2H), 7.22 (t, J=8.9 Hz, 2H), 7.00 (d, J=9.0 Hz, 2H), 3.76 (br s, 2H), 3.48 (br s, 2H), 3.19-3.11 (m, 2H), 3.02 (br d, J=11.8 Hz, 2H), 2.83 (d, J=4.0 Hz, 3H).

Example 26: Synthesis of Compound 120

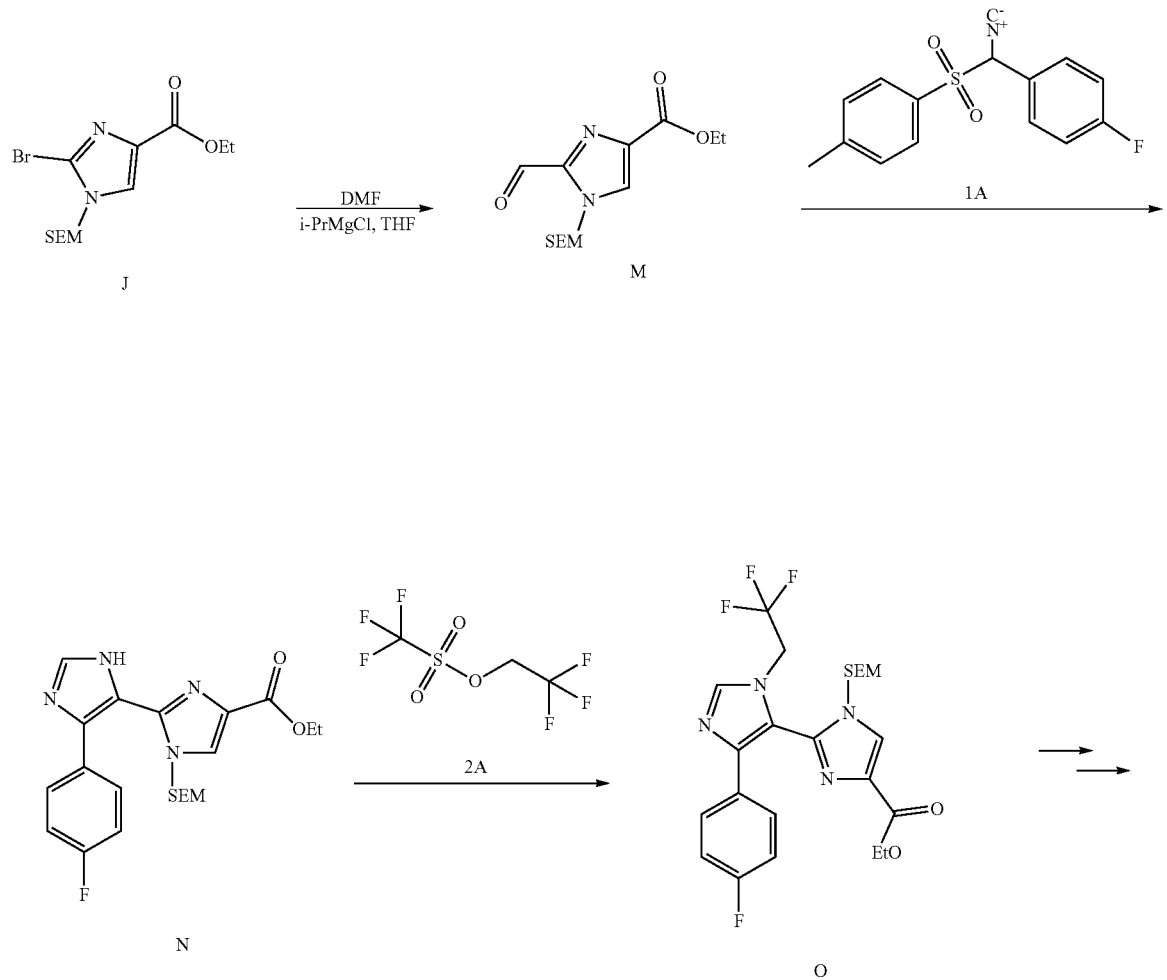

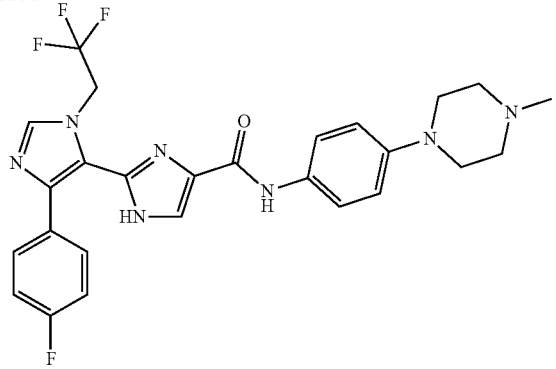

120

Example 27: General Procedure for Preparation of ethyl 2 formyl-1-((2-(trimethylsilyl)ethoxy)methyl)-JH-imidazole-4-carboxylate (Compound M)

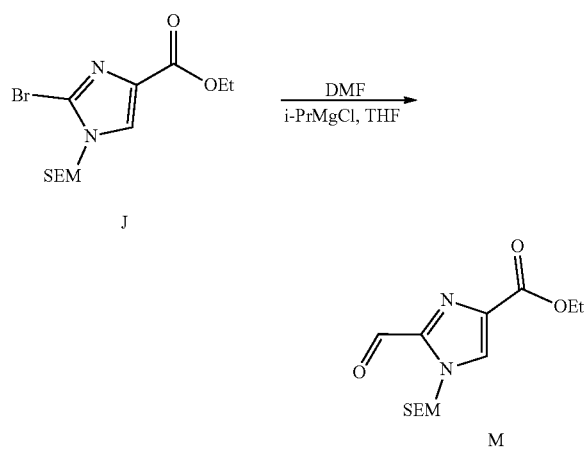

To a solution of Compound J (28 g, 80.16 mmol, 1 eq) in THF (300 mL) was added i-PrMgCl (2 M, 120.24 mL, 3 eq) at −40° C. The mixture was stirred at −40° C. for 10 min. To the mixture was added DMF (35.16 g, 480.97 mmol, 37.01 mL, 6 eq) at −70° C. The mixture was stirred at 20° C. for 1 hrs. LCMS showed desired mass was detected. The mixture was poured to 1N HCl (500 mL). The mixture was extracted with EA (300 mL×2). The combined organic layers were dried over $Na_2SO_4$, filtered and concentrated under reduced pressure to give a residue. The residue was purified by column chromatography on silica gel (PE: EA=10:1-3:1). Compound M (15 g, 50.27 mmol, 62.71% yield) was obtained as yellow oil, which was checked with HNMR. LCMS: Retention time: 0.955 min, (M+H)=299.2. HPLC: Retention time: 2.170 min. $^1$HNMR: (400 MHz, CHLOROFORM-d) δ=8.03-7.95 (m, 1H), 5.80 (s, 2H), 4.47-4.41 (m, 2H), 3.63-3.57 (m, 2H), 1.46-1.40 (m, 3H), 0.99-0.93 (m, 2H), 0.00 (s, 8H).

Example 28: General Procedure for Preparation of ethyl 5'-(4-fluorophenyl)-1-((2-(trimethylsilyl)ethoxy)methyl)-1H,3'H-[2,4'-biimidazole]-4-carboxylate (Compound N)

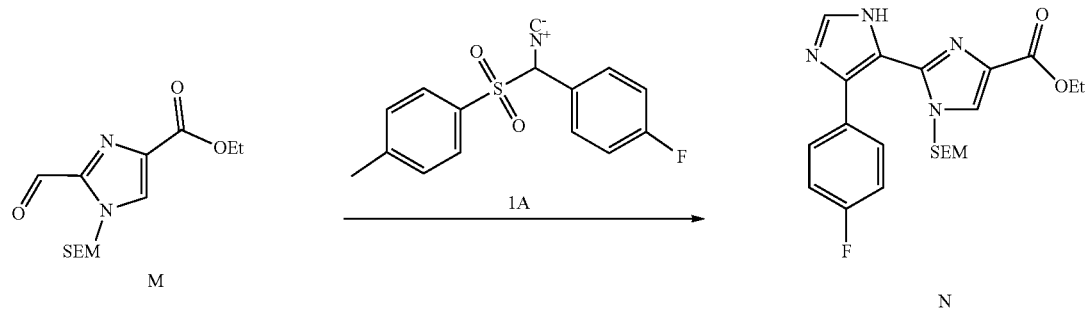

To a solution of Compound M (320 mg, 1.07 mmol, 1 eq) in THF (12 mL) was added NH$_3$.H$_2$O (582.40 mg, 4.15 mmol, 640.00 μL, 25% purity, 3.87 eq) at 20° C. The mixture was stirred at 20° C. for 3.5 h. To the mixture was added Compound 1A (372.31 mg, 1.29 mmol, 1.2 eq) and DIEA (415.78 mg, 3.22 mmol, 560.35 μL, 3 eq) at 20° C. The mixture was stirred at 20° C. for 1.5 h. LCMS showed Compound M was consumed and 31% of desired mass was detected. The mixture was poured to H$_2$O (20 mL). The mixture was extracted with DCM (20 mL×2). The combined organic layers were dried over Na$_2$SO$_4$, filtered and concentrated under reduced pressure to give a residue. The residue was purified by column chromatography (SiO$_2$, PE:EA=1:1-0:1) to afford desired compound. Compound N (330 mg, 490.54 μmol, 45.74% yield, 64% purity) was obtained as yellow oil, which was determined by LCMS. LCMS: Retention time: 0.803 min, (M+H)=431.3. LCMS: Retention time: 0.804 min, (M+H)=431.3.

Example 29: General Procedure for Preparation of ethyl 5'-(4-fluorophenyl)-3'-(2,2,2-trifluoroethyl)-1-((2-(trimethylsilyl)ethoxy)methyl)-1H,3'H-[2,4'-biimidazole]-4-carboxylate (Compound O)

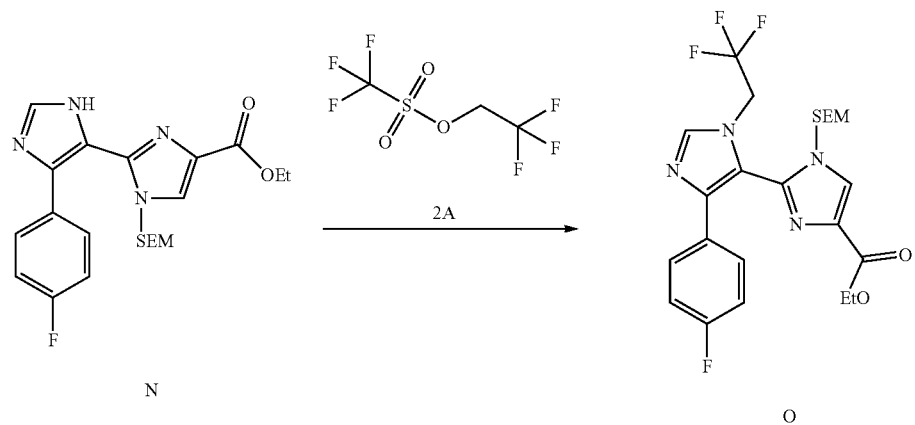

To a solution of ethyl Compound N (250 mg, 580.66 µmol, 1 eq) in DMF (5 mL) was added K$_2$CO$_3$ (240.75 mg, 1.74 mmol, 3 eq) and Compound 2A (404.31 mg, 1.74 mmol, 3 eq) at 20° C. The mixture was stirred at 20° C. for 16 h. LCMS showed Compound N was consumed and 86% of desired mass was detected. The mixture was poured to H$_2$O (20 mL). The mixture was extracted with DCM (20 mL×2). The combined organic layers were dried over Na$_2$SO$_4$, filtered and concentrated under reduced pressure to give a residue. The residue was purified by prep-TLC (PE:EA=1:1, product Rf=0.5) to afford desired compound. Compound O (80 mg, 156.08 µmol, 26.88% yield) was obtained as colorless oil. LCMS: Retention time: 0.976 min, (M+H)=513.3.

Example 30: General Procedure for Preparation of 5'-(4-fluorophenyl)-N-(4-(4-methylpiperazin-1-yl)phenyl)-3'-(2,2,2-trifluoroethyl)-1H,3'H-[2,4'-biimidazole]-4-carboxamide (Compound 120)

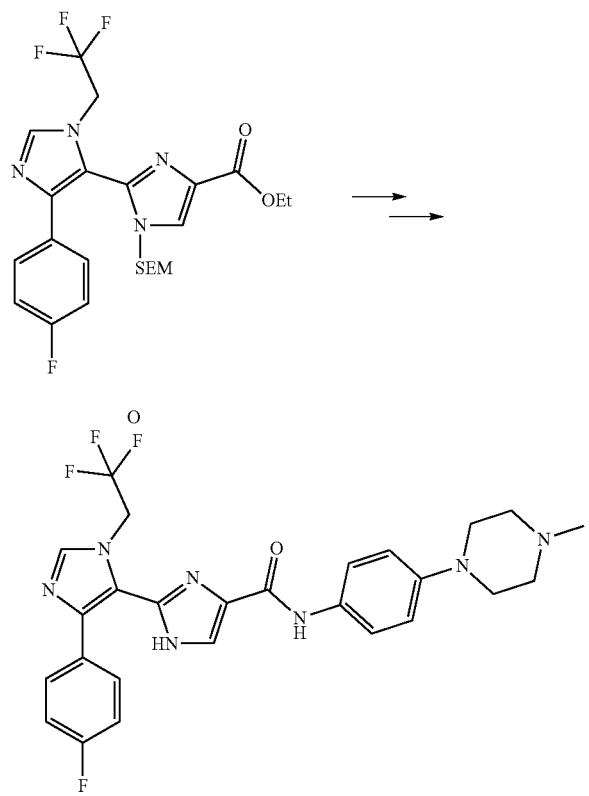

120

5'-(4-fluorophenyl)-N-(4-(4-methylpiperazin-1-yl)phenyl)-3'-(2,2,2-trifluoroethyl)-1H,3'H-[2,4'-biimidazole]-4-carboxamide (Compound 120) was synthesized from Compound O under the same synthetic route as for Compound 112 as white solid, which was determined by $^1$HNMR, LCMS and HPLC. LCMS: Retention time: 0.680 min, (M+H)=528.4. LCMS: Retention time: 0.747 min, (M+H)=528.2. HPLC: Retention time: 1.849 min. $^1$HNMR: (400 MHz, DMSO-d$_6$), δ=9.83 (s, 2H), 8.09 (s, 1H), 7.95 (s, 1H), 7.71 (d, J=9.0 Hz, 2H), 7.52-7.42 (m, 2H), 7.25-7.14 (m, 2H), 7.00 (d, J=9.2 Hz, 2H), 5.24 (br d, J=9.2 Hz, 2H), 3.80 (br d, J=12.7 Hz, 2H), 3.54 (br s, 2H), 3.20-3.11 (m, 2H), 2.93 (br t, J=12.2 Hz, 2H), 2.87 (br s, 3H).

Example 31: Synthesis of Compound 167

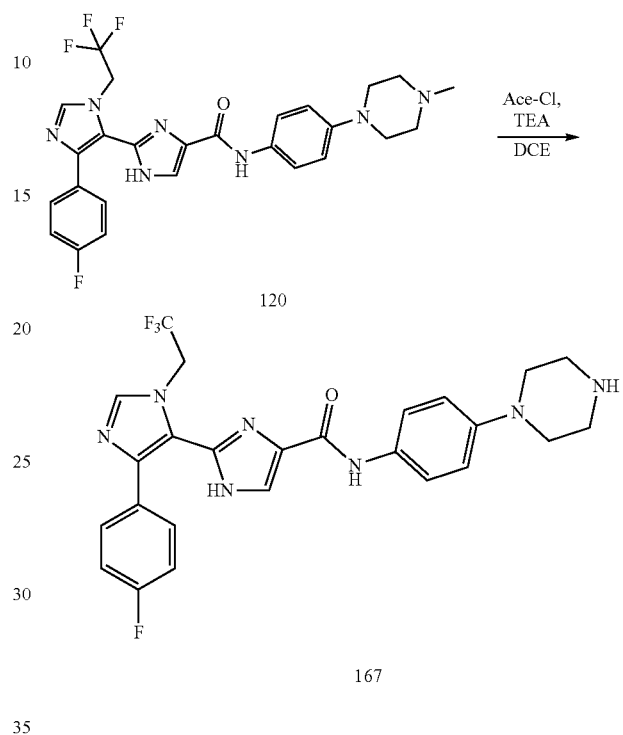

Example 32: General Procedure for Preparation of 5'-(4-fluorophenyl)-N-(4-(piperazin-1-yl)phenyl)-3'-(2,2,2-trifluoroethyl)-1H,3'H-[2,4'-biimidazole]-4-carboxamide (Compound 167)

To a solution of 2-[5-(4-fluorophenyl)-3-(2,2,2-trifluoroethyl)imidazol-4-yl]-N-[4-(4-methyl piperazin-1-yl)phenyl]-1H-imidazole-4-carboxamide (50 mg, 77.94 µmol, 1 eq, TFA salt) in DCE (1 mL) was added 1-chloroethyl chloroformate (55.71 mg, 389.69 µmol, 5 eq) and TEA (31.55 mg, 311.75 µmol, 43.39 µL, 4 eq), the mixture was stirred at 40° C. for 4 hrs. LCMS showed the reactant 1 was consumed and a main peak was detected, then MeOH (1.5 mL) was added to the reaction mixture, the mixture was stirred at 60° C. for 1 hr. LCMS showed 66% of desired mass was detected. The reaction mixture was concentrated in vacuum. The residue was purified with prep-HPLC (column: Phenomenex Gemini-NX C18 75×30 mm×3 µm; mobile phase: [water (10 mM NH$_4$HCO$_3$)-ACN]; B %: 12%-42%, 8 min). Compound 167 (2.99 mg, 5.24 µmol, 6.72% yield, 90% purity) was obtained as an off-white solid. LCMS, HPLC, HNMR and FNMR confirmed the structure. LCMS: Retention time: 0.742 min, (M+H+)=310.5. LCMS: Retention time: 0.913 min, (M+H+)=514.4. LCMS: Retention time: 0.720 min, (M+H+)=514.1. HPLC: Retention time: 1.582 min. 1H NMR: (400 MHz, METHANOL-d$_4$) δ=8.07 (s, 1H), 7.85 (s, 1H), 7.64 (d, J=8.8 Hz, 2H), 7.50-7.37 (m, 2H), 7.15-6.99 (m, 4H), 5.20 (q, J=8.8 Hz, 2H), 3.36-3.32 (m, 4H), 3.30-3.25 (m, 4H). $^{19}$F NMR: (377 MHz, METHANOL-d$_4$) δ=−73.58 (s, 1F).

Example 33: Synthesis of Compound 166

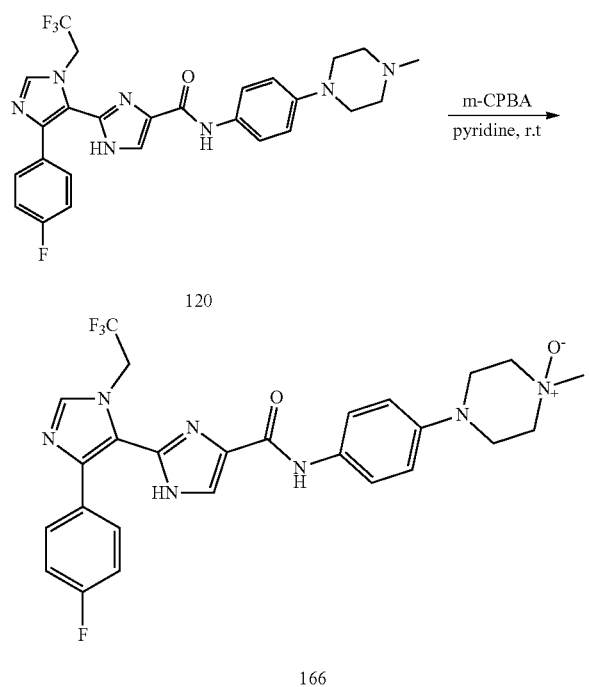

Example 34: General Procedure for Preparation of 4-(4-(5'-(4-fluorophenyl)-3'-(2,2,2-trifluoroethyl)-1H,3'H-[2,4'-biimidazole]-4-carboxamido)phenyl)-1-methylpiperazine 1-oxide (Compound 166)

To a solution of 2-[5-(4-fluorophenyl)-3-(2,2,2-trifluoroethyl)imidazol-4-yl]-N-[4-(4-methyl piperazin-1-yl)phenyl]-1H-imidazole-4-carboxamide (45 mg, 70.14 µmol, 1 eq, TFA salt) in DCM (0.3 mL) was added m-CPBA (14.24 mg, 70.14 µmol, 85% purity, 1 eq) and Pyridine (16.65 mg, 210.43 µmol, 16.98 µL, 3 eq) at 0° C., the mixture was stirred at 25° C. for 0.5 hr. LCMS showed 23% of desired mass was remained and 35% of desired mass was detected. The reaction mixture was concentrated in vacuum. The residue was purified with prep-HPLC (column: Phenomenex Gemini-NX C18 75×30 mm×3 um; mobile phase: [water (10 mM $NH_4HCO_3$)-ACN]; B %: 10%-40%, 8 min). Compound 166 (3.81 mg, 6.31 µmol, 8.99% yield, 89.98% purity) was obtained as a white solid. LCMS, HPLC, HNMR, and FNMR confirmed the structure. LCMS: Retention time: 0.632 min, (M+H+)=544.2. LCMS: Retention time: 0.777 min, (M+H+)=544.3. HPLC: Retention time: 1.447 min. $^1$HNMR: (400 MHz, METHANOL-$d_4$) δ=8.06 (s, 1H), 7.84 (s, 1H), 7.64 (d, J=9.0 Hz, 2H), 7.49-7.39 (m, 2H), 7.16-7.00 (m, 4H), 5.19 (q, J=8.8 Hz, 2H), 3.71-3.58 (m, 2H), 3.57-3.44 (m, 4H), 3.30-3.28 (m, 2H), 3.27 (s, 3H). $^{19}$F NMR: (377 MHz, METHANOL-$d_4$) δ=−73.57 (s, 1F).

Example 35: Synthesis of Compound 121

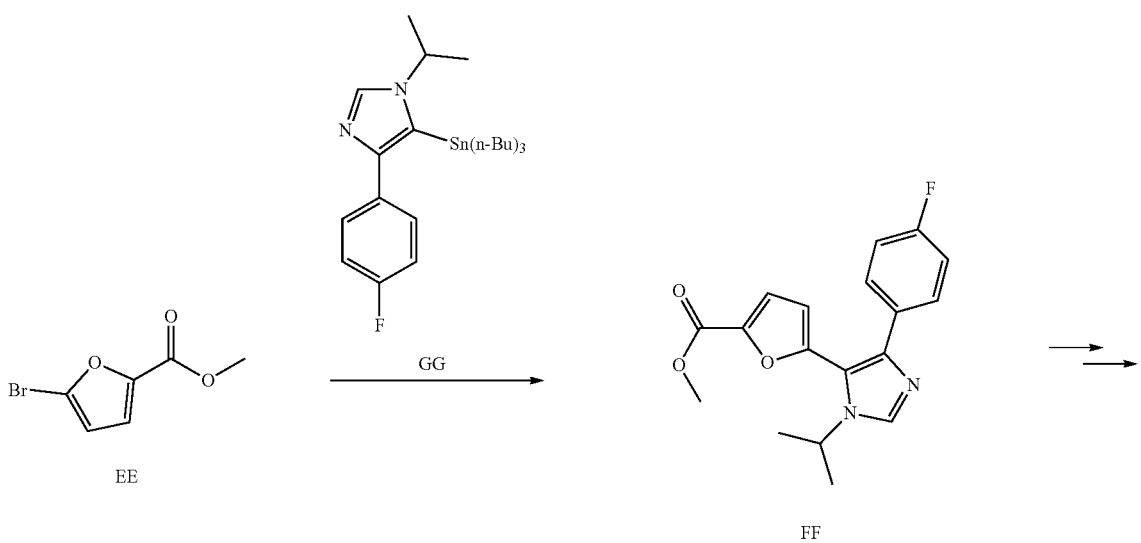

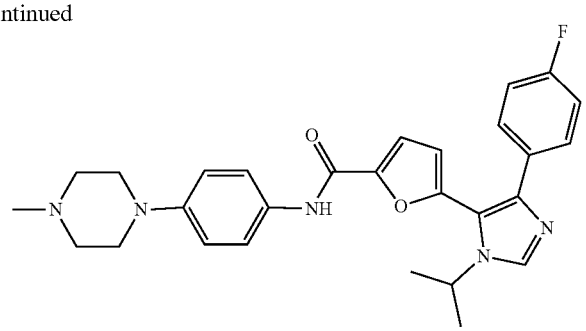

Example 36: General Procedure for Preparation of methyl 5-(4-(4-fluorophenyl)-1-isopropyl-1H-imidazol-5-yl)furan-2-carboxylate (Compound FF)

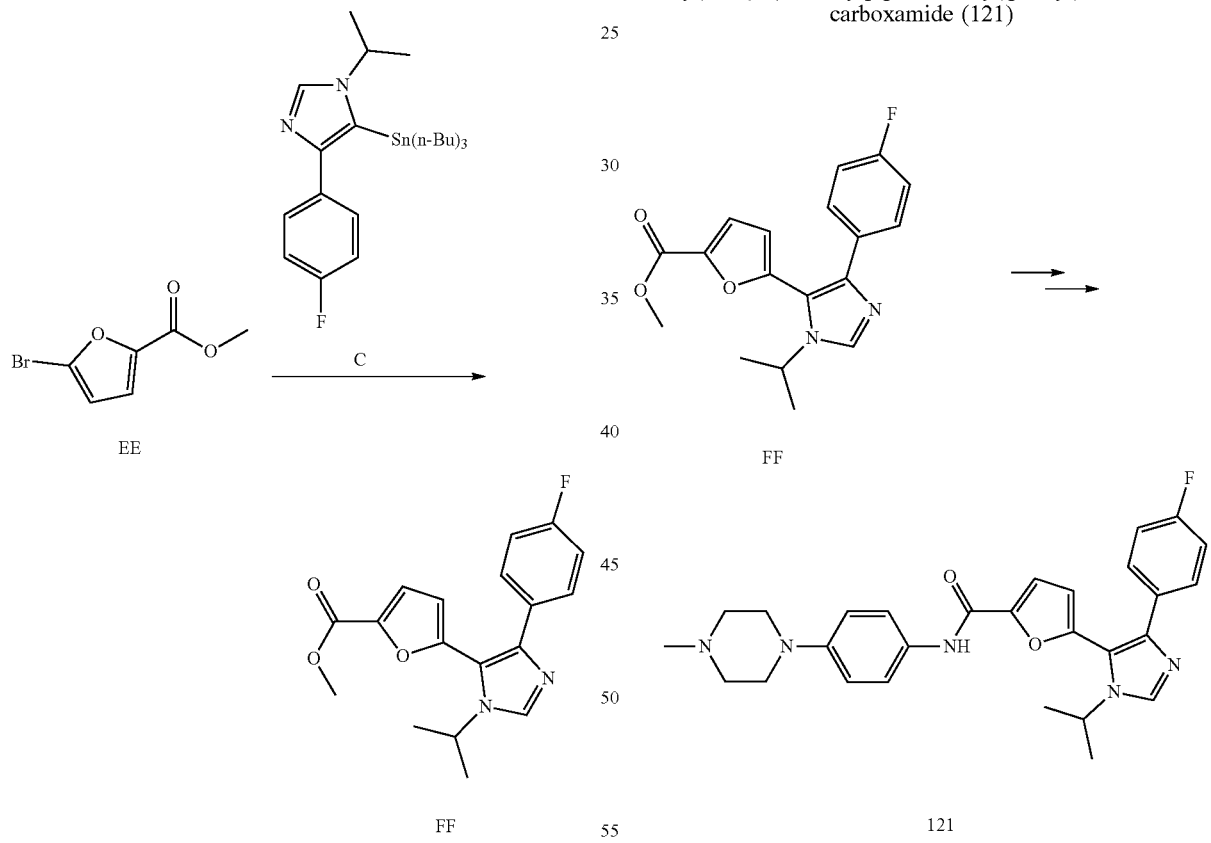

To a solution of Compound C (100 mg, 202.72 μmol, 1 eq) and Compound EE (83.12 mg, 405.44 μmol, 2 eq) in toluene (2 mL) was added methyl Chloro[(di(1-adamantyl)-N-butylphosphine)-2-(2-aminobiphenyl)]palladium(II) (20 mg, 60.91 μmol, 0.3 eq) under $N_2$ at 20° C. The mixture was stirred at 110° C. for 16 h. TLC showed Compound GG was consumed and a new spot was detected. The mixture was concentrated in vacuo to afford residue. The residue was purified by prep-TLC (PE:EA=1:1) to afford desired compound. Compound FF (65 mg, 181.54 μmol, 89.55% yield, 91.7% purity) was obtained as colorless oil, which was determined by LCMS. LCMS: Retention time: 0.715 min, (M+H)=329.2.

Example 37: General Procedure for Preparation of 5-(4-(4-fluorophenyl)-1-isopropyl-1H-imidazol-5-yl)-N-(4-(4-methylpiperazin-1-yl)phenyl)furan-2-carboxamide (121)

Compound 125 was synthesized from Compound FF under the same synthetic route as for Compound 112 as oil, which was determined by $^1$HNMR, LCMS and HPLC. LCMS: Retention time: 0.653 min, (M+H)=488.3. LCMS: Retention time: 0.718 min, (M+H)=488.3. HPLC: Retention time: 1.784 min. $^1$H NMR: (400 MHz, DMSO-$d_6$), δ=10.14 (s, 1H), 9.98-9.63 (m, 1H), 8.37 (br s, 1H), 7.63 (d, J=8.8 Hz, 2H), 7.54-7.46 (m, 3H), 7.19 (t, J=8.8 Hz, 2H), 7.04-6.97 (m, 3H), 4.27 (br d, J=6.4 Hz, 1H), 3.79 (br s, 2H), 3.53 (br d, J=11.4 Hz, 2H), 3.17 (br d, J=8.2 Hz, 2H), 2.93 (br s, 2H), 2.87 (s, 3H), 1.45 (d, J=6.8 Hz, 6H).

Example 38: Synthesis of Compound 102
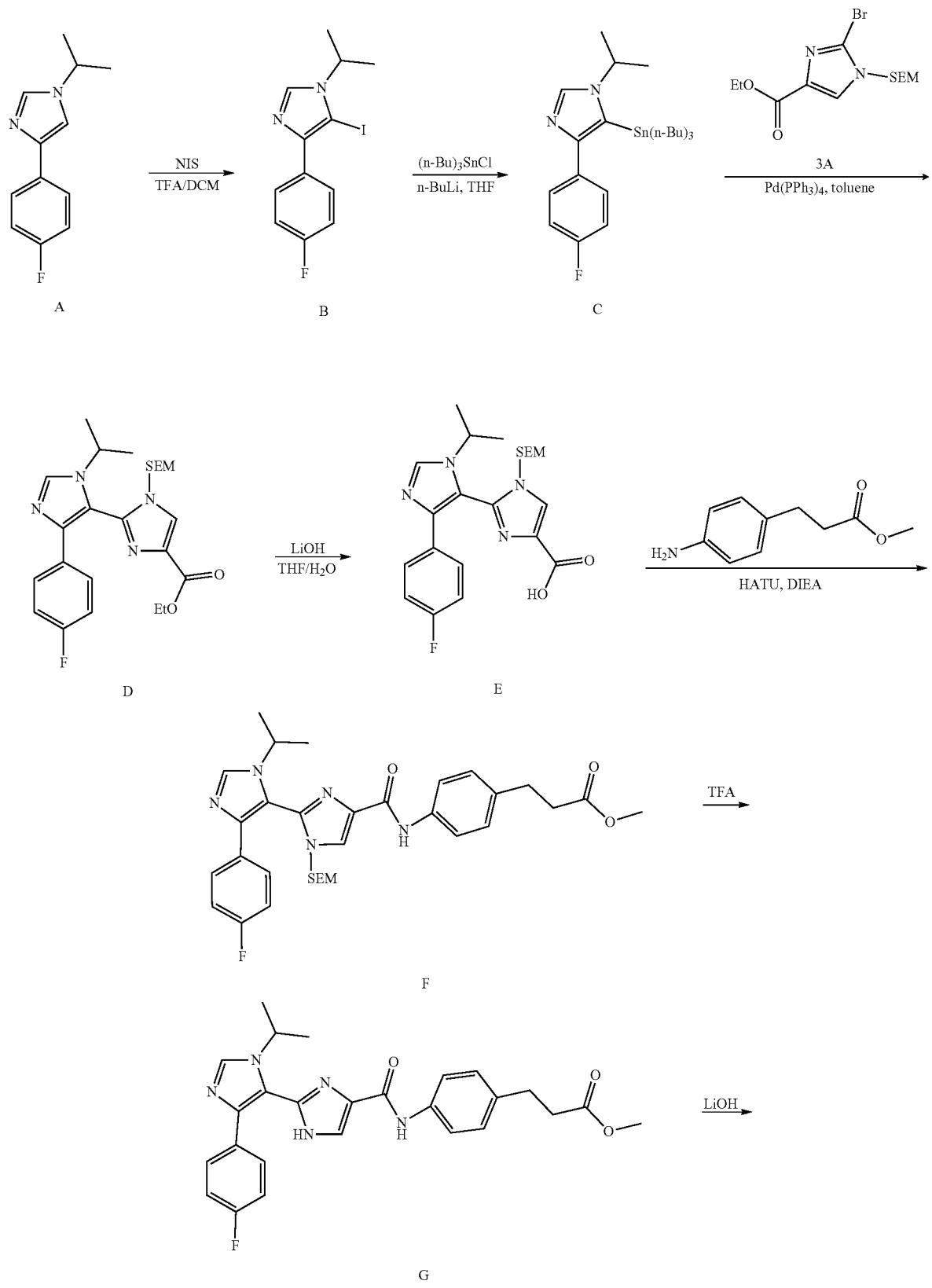

-continued

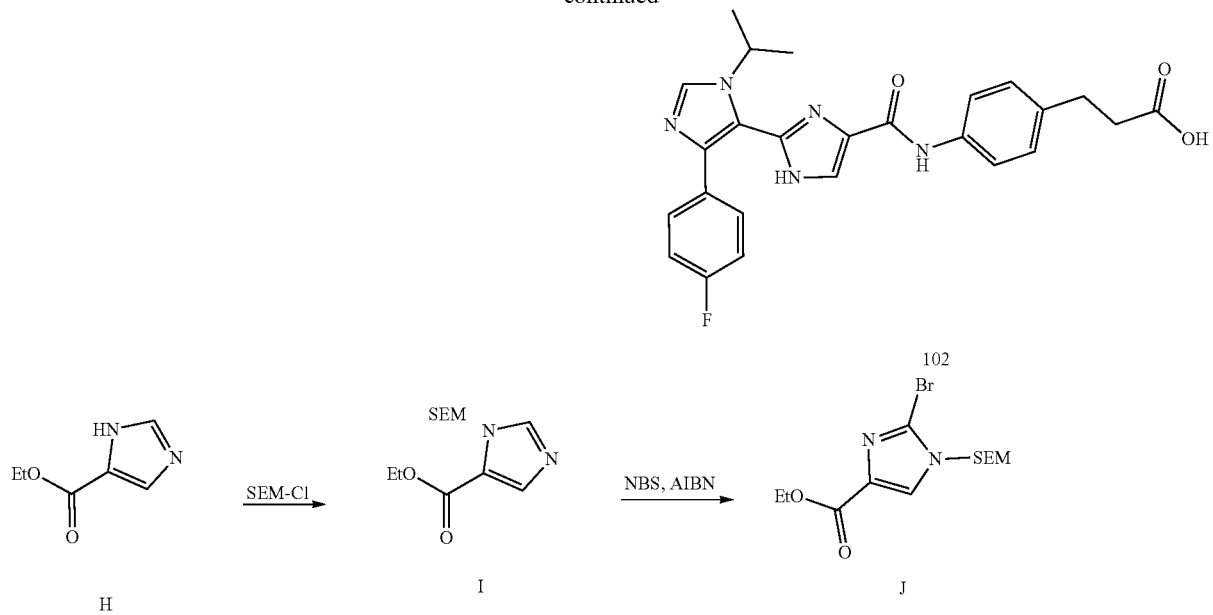

Example 39: Synthesis of Compound 132

5-(4-(5'-(4-fluorophenyl)-3'-isopropyl-1H,3'H-[2,4'-biimidazole]-4-carboxamido) phenyl)pentanoic acid (Compound 132) was synthesized under the similar synthetic route as for Compound 102 as white solid, which was determined by HNMR, LCMS and HPLC. LCMS: Retention time: 0.747 min, [M+H$^+$]=490.4. LCMS: Retention time: 0.801 min, [M+H$^+$]=490.4. HPLC: Retention time: 1.705 min. $^1$H NMR: (400 MHz, DMSO-d6), δ=9.85 (br s, 1H), 8.05 (s, 1H), 8.01 (s, 1H), 7.71 (d, J=8.4 Hz, 2H), 7.43-7.34 (m, 2H), 7.17-7.08 (m, 4H), 4.29-4.18 (m, 1H), 2.58-2.52 (m, 2H), 2.19 (t, J=7.0 Hz, 2H), 1.61-1.46 (m, 4H), 1.39 (d, J=6.7 Hz, 6H).

Example 40: Synthesis of Compound 126

5-(4-(4-fluorophenyl)-1-isopropyl-1H-imidazol-5-yl)-N-(4-(2-hydroxyethyl) phenyl)furan-2-carboxamide (Compound 126) was synthesized under the same synthetic route as for Compound 121 as white solid, which was determined by HNMR, FNMR, LCMS and HPLC. LCMS: Retention time: 0.794 min, [M+H$^+$]=434. LCMS: Retention time: 0.805 min, [M+H$^+$]=434.1. HPLC: Retention time: 1.506 min. HPLC: Retention time: 1.494 min. $^1$H NMR (400 MHz, DMSO-d$_6$) δ=10.19 (s, 1H), 8.66 (s, 1H), 7.61 (d, J=8.4 Hz, 2H), 7.56-7.47 (m, 3H), 7.28-7.14 (m, 4H), 7.01 (d, J=3.6 Hz, 1H), 4.33 (td, J=6.8, 13.2 Hz, 1H), 3.58 (s, 2H), 2.69 (t, J=7.0 Hz, 2H), 1.46 (d, J=6.8 Hz, 6H). $^{19}$F NMR (400 MHz, DMSO-d6) δ=74.404.

Example 41: Synthesis of Compound 162

6-(4-(4-fluorophenyl)-1-isopropyl-1H-imidazol-5-yl)-N-(4-(4-(2-hydroxyethyl) piperazin-1-yl)phenyl)picolinamide (Compound 162) was synthesized under the similar synthetic route as for Compound 121 as yellow solid, which was determined by HNMR, LCMS and HPLC. LCMS: Retention time: 0.913 min, [M+H$^+$]=529.5. LCMS: Retention time: 0.923 min, [M+H$^+$]=529.5. HPLC: Retention time: 1.992 min. $^1$H NMR: (400 MHz, DMSO-d$_6$), δ=10.23 (s, 1H), 8.18-8.03 (m, 3H), 7.69 (d, J=9.0 Hz, 2H), 7.54 (dd, J=1.0, 7.8 Hz, 1H), 7.41-7.34 (m, 2H), 7.10 (t, J=8.8 Hz, 2H), 6.94 (d, J=9.2 Hz, 2H), 4.58-4.39 (m, 2H), 3.54 (q, J=6.0 Hz, 2H), 3.10 (br d, J=4.8 Hz, 4H), 2.57 (br s, 4H), 2.46-2.41 (m, 2H), 1.44 (d, J=6.8 Hz, 6H).

Example 42: Synthesis of Compound 133

3-(4-(3'-isopropyl-5'-(4-(trifluoromethyl)phenyl)-1H,3'H-[2,4'-biimidazole]-4-carboxamido)phenyl)propanoic acid (Compound 133) was synthesized under the similar synthetic route as for Compound 102 as white solid, which was determined by HNMR, LCMS and HPLC. LCMS: Retention time: 0.752 min, (M+H)=512.2. LCMS: Retention time: 0.834 min, (M+H)=512.2, 5-95AB_R_220&254.lcm HPLC: Retention time: 2.301 min. $^1$H NMR: (400 MHz, DMSO-d$_6$), δ=9.91 (s, 1H), 8.45 (s, 1H), 8.09 (s, 1H), 7.79-7.66 (m, 4H), 7.56 (d, J=8.2 Hz, 2H), 7.18 (d, J=8.6 Hz, 2H), 4.38 (br d, J=6.6 Hz, 1H), 2.79 (t, J=7.6 Hz, 2H), 2.53 (br s, 2H), 1.43 (d, J=6.8 Hz, 6H).

Example 43: Synthesis of Compound 137

3-(4-(5'-(4-chlorophenyl)-3'-isopropyl-1H,3'H-[2,4'-biimidazole]-4-carboxamido) phenyl)propanoic acid (Compound 137) was synthesized under the similar synthetic route as for Compound 102 as white solid, which was determined by HNMR, LCMS and HPLC. LCMS: Retention time: 0.790 min, (M+H)=478.3. LCMS: Retention time: 0.788 min, (M+H)=478.3. HPLC: Retention time: 1.644 min. $^1$H NMR: (400 MHz, DMSO-d6) δ=9.89 (s, 1H), 8.52 (br s, 1H), 8.06 (s, 1H), 7.70 (d, J=8.4 Hz, 2H), 7.45-7.40 (m, 2H), 7.39-7.34 (m, 2H), 7.17 (d, J=8.4 Hz, 2H), 4.42-4.31 (m, 1H), 2.78 (t, J=7.6 Hz, 2H), 2.54-2.52 (m, 2H), 1.42 (d, J=6.8 Hz, 6H).

Example 44: Synthesis of Compound 134

3-(4-(5'-(4-chlorophenyl)-3'-isopropyl-1H,3'H-[2,4'-biimidazole]-4-carboxamido) phenyl)propanoic acid (Compound 134) was synthesized under the similar synthetic route as for Compound 102 as yellow oil, which was determined by HNMR, LCMS and HPLC. LCMS: Retention time: 0.671 min, (M+H)=568.3, 5-95AB_R_220&254.lcm. LCMS: Retention time: 0.755 min, (M+H)=568.2. HPLC: Retention time: 1.869 min. $^1$H NMR: (400 MHz, DMSO-d$_6$), δ=9.86 (s, 1H), 9.71 (br s, 1H), 8.36 (s, 1H), 8.05 (s, 1H), 7.71 (t, J=8.2 Hz, 4H), 7.56 (d, J=8.2 Hz, 2H), 6.99 (d, J=9.2 Hz, 2H), 4.38-4.31 (m, 1H), 3.83-3.71 (m, 4H), 3.60 (br d, J=11.2 Hz, 2H), 3.30-3.14 (m, 4H), 3.10-2.94 (m, 2H), 1.43 (d, J=6.8 Hz, 6H).

Example 45: Synthesis of Compound 139

5'-(4-chlorophenyl)-N-(4-(4-(2-hydroxyethyl)piperazin-1-yl)phenyl)-3'-isopropyl-1H,3'H-[2,4'-biimidazole]-4-carboxamide (Compound 139) was synthesized under the similar synthetic route as for Compound 137 as brown solid, which was determined by HNMR, LCMS and HPLC. LCMS: Retention time: 0.850 min, (M+H)=534.4. LCMS: Retention time: 0.713 min, (M+H)=534.4. HPLC: Retention time: 1.265 min. $^1$H NMR: (400 MHz, DMSO-d$_6$) δ=9.84 (s, 1H), 9.67 (br d, J=3.6 Hz, 1H), 8.43 (s, 1H), 8.03 (s, 1H), 7.70 (d, J=9.2 Hz, 2H), 7.48-7.29 (m, 4H), 6.98 (d, J=9.2 Hz, 2H), 4.37-4.27 (m, 1H), 3.80-3.75 (m, 4H), 3.32-3.14 (m, 6H), 3.07-2.97 (m, 2H), 1.41 (d, J=6.8 Hz, 6H).

Example 46: Synthesis of Compound 146

5'-(3,4-difluorophenyl)-N-(4-(4-(2-hydroxyethyl)piperazin-1-yl)phenyl)-3'-isopropyl-1H,3'H-[2,4'-biimidazole]-4-carboxamide (Compound 146) was synthesized under the similar synthetic route as for Compound 102 as yellow solid, which was determined by HNMR, LCMS and HPLC. LCMS: Retention time: 0.717 min, [M+H$^+$]=536.2. LCMS: Retention time: 0.627 min, [M+H$^+$]=536.3. HPLC: Retention time: 1.252 min. $^1$H NMR: (400 MHz, DMSO-d$_6$), δ=9.85 (s, 1H), 9.65 (br s, 1H), 8.28 (s, 1H), 8.04 (s, 1H), 7.71 (d, J=9.2 Hz, 2H), 7.45-7.32 (m, 2H), 7.10 (ddd, J=1.8, 4.2, 8.4 Hz, 1H), 6.98 (d, J=9.2 Hz, 2H), 4.32-4.21 (m, 1H), 3.77 (br d, J=5.0 Hz, 4H), 3.57 (brs, 2H), 3.29-3.16 (m, 4H), 3.07-2.96 (m, 2H), 1.40 (d, J=6.8 Hz, 6H).

Example 47: Synthesis of Compound 158

5'-(4-fluorophenyl)-3'-((1r,4r)-4-hydroxycyclohexyl)-N-(4-(4-(2-hydroxyethyl) piperazin-1-yl)phenyl)-1H,3'H-[2,4'-biimidazole]-4-carboxamide (Compound 158) was synthesized under the similar synthetic route as for Compound 120 as white solid, which was determined by HNMR, LCMS and HPLC. LCMS: Retention time: 0.683 min, (M+H)=574.3. HPLC: Retention time: 1.600 min. $^1$H NMR: (400 MHz, DMSO-d$_6$), δ=9.85 (s, 2H), 8.76 (s, 1H), 8.06 (s, 1H), 7.71 (d, J=9.0 Hz, 2H), 7.49-7.36 (m, 2H), 7.24 (t, J=8.9 Hz, 2H), 7.00 (d, J=9.0 Hz, 2H), 4.03-3.95 (m, 1H), 3.82-3.72 (m, 4H), 3.60 (br d, J=9.9 Hz, 2H), 3.49-3.44 (m, 1H), 3.31-3.17 (m, 4H), 3.05 (br d, J=11.0 Hz, 2H), 2.04-1.78 (m, 6H), 1.30-1.13 (m, 2H).

Example 48: Synthesis of Compound 156

5'-(3,4-difluorophenyl)-3'-isopropyl-N-(4-(4-methylpiperazin-1-yl)phenyl)-1H,3'H-[2,4'-biimidazole]-4-carboxamide (Compound 156) was synthesized under the similar synthetic route as for Compound 102 as white solid, which was determined by HNMR, LCMS and HPLC. LCMS: Retention time: 0.886 min, (M+H)=506.4. LCMS: Retention time: 0.890 min, (M+H)=506.4. LCMS: Retention time: 0.713 min, (M+H)=506.2. HPLC: Retention time: 1.254 min. $^1$H NMR: (400 MHz, DMSO-d$_6$) δ=9.73 (s, 1H), 8.10 (s, 1H), 8.01 (s, 1H), 7.66 (br d, J=8.8 Hz, 2H), 7.42-7.31 (m, 2H), 7.08 (br d, J=1.6 Hz, 1H), 6.90 (br d, J=8.8 Hz, 2H), 4.30-4.16 (m, 1H), 3.09 (br d, J=4.4 Hz, 4H), 2.52 (br s, 2H), 2.24 (s, 3H), 2.07 (s, 2H), 1.39 (d, J=6.8 Hz, 6H).

Example 49: Synthesis of Compound 159

5'-(4-fluorophenyl)-3'-((1r,4r)-4-hydroxycyclohexyl)-N-(4-(4-methylpiperazin-1-yl)phenyl)-1H,3'H-[2,4'-biimidazole]-4-carboxamide (Compound 159) was synthesized under the similar synthetic route as for 158 as yellow solid, which was determined by HNMR, LCMS and HPLC. LCMS: Retention time: 0.613 min, (M+H)=544.2. LCMS: Retention time: 0.690 min, (M+H)=544.3. HPLC: Retention time: 1.614 min. $^1$H NMR: (400 MHz, DMSO-d$_6$) δ=9.81 (br s, 2H), 8.48-8.20 (m, 1H), 8.02 (d, J=2.0 Hz, 1H), 7.72 (br d, J=8.8 Hz, 2H), 7.44-7.35 (m, 2H), 7.20-7.10 (m, 2H), 6.99 (br d, J=9.2 Hz, 2H), 3.79 (br d, J=13.2 Hz, 6H), 3.19-3.13 (m, 2H), 2.97-2.84 (m, 6H), 1.99-1.82 (m, 6H), 1.17 (br d, J=12.4 Hz, 2H). HNMR: (400 MHz, DMSO-d$_6$+D$_2$O) δ=8.75-8.49 (m, 1H), 8.01 (d, J=1.2 Hz, 1H), 7.67 (br d, J=7.2 Hz, 2H), 7.47-7.32 (m, 2H), 7.28-7.09 (m, 2H), 6.99 (d, J=9.2 Hz, 2H), 3.99-3.91 (m, 1H), 3.77 (br d, J=12.4 Hz, 2H), 3.55-3.44 (m, 3H), 3.16 (br t, J=10.8 Hz, 2H), 3.00-2.84 (m, 5H), 2.06-1.77 (m, 6H), 1.27-1.13 (m, 2H).

Example 50: Synthesis of Compound 142

3'-isopropyl-N-(4-(4-methylpiperazin-1-yl)phenyl)-5'-(4-(trifluoromethyl)phenyl)-1H,3'H-[2,4'-biimidazole]-4-carboxamide (Compound 142) was synthesized under the similar synthetic route as for Compound 102 as white solid, which was determined by HNMR, LCMS and HPLC. LCMS: Retention time: 0.678 min, (M+H)=538.3. LCMS: Retention time: 0.663 min, (M+H)=538.3. HPLC: Retention time: 1.889 min. $^1$H NMR: (400 MHz, DMSO-d$_6$), δ=9.85 (s, 2H), 8.27 (s, 1H), 8.04 (s, 1H), 7.71 (dd, J=8.8, 12.9 Hz, 4H), 7.56 (d, J=8.2 Hz, 2H), 6.99 (d, J=9.0 Hz, 2H), 4.30 (br s, 1H), 3.79 (br d, J=13.2 Hz, 2H), 3.53 (br d, J=12.2 Hz, 2H), 3.17 (br d, J=10.4 Hz, 2H), 3.09-2.78 (m, 5H), 1.42 (d, J=6.8 Hz, 6H)

Example 51: Synthesis of Compound 150

5'-(4-chlorophenyl)-3'-isopropyl-N-(4-(4-methylpiperazin-1-yl)phenyl)-1H,3'H-[4,4'-biimidazole]-2-carboxamide (Compound 150) was synthesized under the same synthetic route as for Compound 120 as white solid, which was determined by $^1$H NMR, LCMS and HPLC. LCMS: Retention time: 0.714 min, [M+H$^+$]=504.3. HPLC: Retention time: 1.992 min. $^1$H NMR: (400 MHz, DMSO-d$_6$), δ=9.67 (br s, 1H), 8.05 (s, 1H), 7.94 (s, 1H), 7.64 (br d, J=8.8 Hz, 2H), 7.44-7.30 (m, 4H), 6.89 (d, J=9.1 Hz, 2H), 4.31-4.21 (m, 1H), 3.11-3.04 (m, 4H), 2.46-2.42 (m, 4H), 2.21 (s, 3H), 1.38 (d, J=6.8 Hz, 6H).

Example 52: Synthesis of Compound 153

4-(4-(5'-(4-fluorophenyl)-3'-isopropyl-1H,3'H-[2,4'-biimidazole]-4-carboxamido)phenyl)-1-methylpiperazine 1-oxide (Compound 153) was synthesized under the same synthetic route as for Compound 166 as white solid, which was determined by $^1$HNMR, LCMS and HPLC. LCMS: Retention time: 0.782 min, (M+H)=504.5. LCMS: Retention time: 0.615 min, (M+H)=504.2. HPLC: Retention time: 1.225 min. ¹H NMR: 1H NMR (400 MHz, DMSO-d$_6$) δ=9.85-9.61 (m, 1H), 8.05 (s, 1H), 7.97 (s, 1H), 7.69 (br d, J=7.6 Hz, 2H), 7.41 (dd, J=6.0, 8.4 Hz, 2H), 7.18-7.08 (m, 2H), 6.95 (d, J=9.2 Hz, 2H), 4.24 (td, J=6.8, 13.2 Hz, 1H), 3.56-3.39 (m, 6H), 3.10 (s, 3H), 2.98 (br d, J=10.4 Hz, 2H), 1.40 (d, J=6.8 Hz, 6H).

Example 53: Synthesis of Compound 205

3',5'-diisopropyl-N-(4-(4-methylpiperazin-1-yl)phenyl)-1H,3'H-[2,4'-biimidazole]-4-carboxamide (Compound 205) was synthesized under the same synthetic route as for Compound 120 as white solid, which was determined by ¹HNMR, LCMS and HPLC. LCMS: Retention time: 0.853 min, [M+H$^+$]=436.5. LCMS: Retention time: 0.850 min, [M+H$^+$]=436.5. LCMS: Retention time: 0.863 min, [M+H$^+$]= 436.4. HPLC: Retention time: 1.605 min. ¹H NMR: (400 MHz, DMSO-d$_6$), δ=13.02-12.24 (m, 1H), 9.59 (br s, 1H), 7.89 (s, 1H), 7.78 (s, 1H), 7.63 (br d, J=8.7 Hz, 2H), 6.89 (br d, J=9.0 Hz, 2H), 4.48-4.37 (m, 1H), 3.13-3.05 (m, 4H), 2.92-2.83 (m, 1H), 2.47-2.41 (m, 4H), 2.21 (s, 3H), 1.33 (d, J=6.7 Hz, 6H), 1.11 (d, J=6.8 Hz, 6H).

Example 54: Synthesis of Compound 196

5'-(4-fluorophenyl)-3'-isopropyl-N-(4-(3,4,5-trimethylpiperazin-1-yl)phenyl)-1H,3'H-[2,4'-biimidazole]-4-carboxamide (Compound 196) was synthesized under the same synthetic route as for Compound 112 as white solid, which was determined by ¹HNMR, LCMS and HPLC. LCMS: Retention time: 0.965 min, [M+H$^+$]=516.4. LCMS: Retention time: 0.711 min, [M+H$^+$]=516.4. HPLC: Retention time: 1.075 min, 10-80AB_4 min.lcm, EW25973-78-P1A6. ¹H NMR: (400 MHz, DMSO-d$_6$) δ=13.28-12.82 (m, 1H), 9.69 (br s, 1H), 8.05 (s, 1H), 7.97 (s, 1H), 7.66 (br d, J=8.0 Hz, 2H), 7.39 (dd, J=5.6, 8.7 Hz, 2H), 7.13 (t, J=8.9 Hz, 2H), 6.89 (br d, J=8.9 Hz, 2H), 4.38-4.17 (m, 1H), 3.50 (br d, J=10.9 Hz, 2H), 2.39-2.31 (m, 2H), 2.29-2.14 (m, 5H), 1.39 (d, J=6.7 Hz, 6H), 1.07 (d, J=5.9 Hz, 6H).

Example 55: Synthesis of Compound 185

5'-(4-fluorophenyl)-3'-isopropyl-N-(4-(4-methyl-3-oxopiperazin-1-yl)phenyl)-1H,3'H-[2,4'-biimidazole]-4-carboxamide (Compound 185) was synthesized under the same synthetic route as for Compound 112 as white solid, which was determined by 1HNMR, LCMS and HPLC. LCMS: Retention time: 0.846 min, (M+H)=502.5. LCMS: Retention time: 0.763 min, (M+H)=502.2. HPLC: Retention time: 1.499 min. ¹H NMR: (400 MHz, DMSO-d$_6$) δ=13.18-12.93 (m, 1H), 9.76 (s, 1H), 8.07 (s, 1H), 7.99 (s, 1H), 7.71 (d, J=9.2 Hz, 2H), 7.44-7.33 (m, 2H), 7.20-7.07 (m, 2H), 7.00-6.85 (m, 2H), 4.29-4.18 (m, 1H), 3.71 (s, 2H), 3.46-3.40 (m, 4H), 2.90 (s, 3H), 1.40 (d, J=6.8 Hz, 6H).

Example 56: Synthesis of Compound 188

N-(4-(4-acetylpiperazin-1-yl)phenyl)-5'-(4-fluorophenyl)-3'-isopropyl-1H,3'H-[2,4'-biimidazole]-4-carboxamide (Compound 188) was synthesized under the same synthetic route as for Compound 112 as white solid, which was determined by ¹HNMR, LCMS and HPLC. LCMS: Retention time: 0.851 min, [M+H$^+$]=516.5. LCMS: Retention time: 0.756 min, [M+H$^+$]=516.1. HPLC: Retention time: 1.475 min. ¹H NMR (400 MHz, DMSO-d$_6$), δ=13.03 (br s, 1H), 9.74 (s, 1H), 8.05 (s, 1H), 7.98 (s, 1H), 7.69 (br d, J=8.8 Hz, 2H), 7.42-7.33 (m, 2H), 7.13 (t, J=8.9 Hz, 2H), 6.93 (br d, J=8.8 Hz, 2H), 4.29-4.17 (m, 1H), 3.57 (br d, J=3.7 Hz, 4H), 3.14-3.08 (m, 2H), 3.06-3.00 (m, 2H), 2.04 (s, 3H), 1.39 (d, J=6.7 Hz, 6H).

Example 57: Synthesis of Compound 189

5'-(4-fluorophenyl)-3'-isopropyl-N-(4-(4-(2,2,2-trifluoroethyl)piperazin-1-yl)phenyl)-1H,3'H-[2,4'-biimidazole]-4-carboxamide (Compound 189) was synthesized under the same synthetic route as for Compound 112 as white solid, which was determined by 1HNMR, LCMS and HPLC. LCMS: Retention time: 0.726 min, (M+H)=556.3. LCMS: Retention time: 0.805 min, (M+H)=556.3. HPLC: Retention time: 1.635 min. HNMR: (400 MHz, DMSO-d$_6$), δ=9.84 (s, 1H), 8.88 (br s, 1H), 8.07 (s, 1H), 7.68 (d, J=8.8 Hz, 2H), 7.51-7.38 (m, 2H), 7.32-7.21 (m, 2H), 6.99 (br d, J=8.8 Hz, 2H), 4.45 (s, 1H), 3.30 (d, J=10.2 Hz, 2H), 3.22-3.12 (m, 4H), 2.89-2.76 (m, 4H), 1.45 (d, J=6.8 Hz, 6H).

Example 58: Synthesis of Compound 186

5'-(4-fluorophenyl)-3'-isopropyl-N-(4-((1R,5S)-8-methyl-3,8-diazabicyclo[3.2.1]octan-3-yl)phenyl)-1H,3'H-[2,4'-biimidazole]-4-carboxamide (Compound 186) was synthesized under the same synthetic route as for Compound 112 as white solid, which was determined by ¹HNMR, LCMS and HPLC. LCMS: Retention time: 0.635 min, (M+H)=514.3. LCMS: Retention time: 0.712 min, (M+H)=514.3. HPLC: Retention time: 1.285 min. ¹HNMR: (400 MHz, DMSO-d$_6$), δ=8.77 (s, 1H), 8.03 (s, 1H), 7.65 (br d, J=9.0 Hz, 2H), 7.48-7.35 (m, 2H), 7.23 (t, J=8.8 Hz, 2H), 6.90 (d, J=9.2 Hz, 2H), 4.40 (s, 1H), 4.04 (br s, 2H), 3.78-3.70 (m, 2H), 3.06 (br d, J=12.0 Hz, 2H), 2.77 (s, 3H), 2.26-2.15 (m, 2H), 2.00 (br d, J=8.2 Hz, 2H), 1.43 (d, J=6.8 Hz, 6H).

Example 59: Synthesis of Compound 190

5'-(4-fluorophenyl)-3'-(2,2,2-trifluoroethyl)-N-(4-(3,4,5-trimethylpiperazin-1-yl)phenyl)-1H,3'H-[2,4'-biimidazole]-4-carboxamide (Compound 190) was synthesized under the same synthetic route as for Compound 120 as white solid, which was determined by ¹HNMR, LCMS and HPLC. LCMS: Retention time: 0.937 min, (M+H)=556.5. HPLC: Retention time: 1.519 min. ¹H NMR: (400 MHz, CHLOROFORM-d) δ=8.75 (s, 1H), 7.74 (br d, J=14.3 Hz, 2H), 7.60 (br d, J=8.4 Hz, 2H), 7.52-7.47 (m, 2H), 7.12 (br t, J=7.5 Hz, 2H), 6.96 (br d, J=8.7 Hz, 2H), 5.14-5.07 (m, 2H), 3.47 (br d, J=11.2 Hz, 2H), 2.61 (br t, J=11.0 Hz, 2H), 2.44 (br s, 2H), 2.36 (s, 3H), 1.21 (d, J=6.1 Hz, 6H).

Example 60: Synthesis of Compound 194

5'-(4-fluorophenyl)-N-(4-(4-methyl-3-oxopiperazin-1-yl)phenyl)-3'-(2,2,2-trifluoroethyl)-1H,3'H-[2,4'-biimidazole]-4-carboxamide (Compound 194) was synthesized under the same synthetic route as for Compound 120 as white solid, which was determined by ¹HNMR, LCMS and HPLC. LCMS: Retention time: 0.832 min, (M+H)=542.4. HPLC: Retention time: 1.704 min. ¹H NMR: (400 MHz, CHLOROFORM-d) δ=8.78 (s, 1H), 7.76 (d, J=12.5 Hz, 2H), 7.65 (d, J=9.0 Hz, 2H), 7.53-7.49 (m, 2H), 7.13 (t, J=8.7 Hz, 2H), 6.94 (d, J=9.0 Hz, 2H), 5.12 (q, J=8.4 Hz, 2H), 3.87 (s, 2H), 3.50 (s, 4H), 3.06 (s, 3H).

Example 61: Synthesis of Compound 191

N-(4-(4-acetylpiperazin-1-yl)phenyl)-5'-(4-fluorophenyl)-3'-(2,2,2-trifluoroethyl)-1H,3'H-[2,4'-biimidazole]-4- carboxamide (Compound 191) was synthesized under the same synthetic route as for Compound 120 as white solid, which was determined by 1HNMR, LCMS and HPLC. LCMS: Retention time: 0.847 min, (M+H)=556.5. HPLC: Retention time: 1.706 min. ¹H NMR: (400 MHz, CHLOROFORM-d) δ=9.67 (br s, 1H), 8.79 (s, 1H), 7.77-7.71 (m, 2H), 7.63 (d, J=8.9 Hz, 2H), 7.52-7.47 (m, 2H), 7.12 (t, J=8.6 Hz, 2H), 6.98 (d, J=9.0 Hz, 2H), 5.10 (q, J=8.5 Hz, 2H), 3.81-3.76 (m, 2H), 3.67-3.63 (m, 2H), 3.21-3.17 (m, 2H), 3.17-3.13 (m, 2H), 2.15 (s, 3H).

Example 62: Synthesis of Compound 192

5'-(4-fluorophenyl)-3'-(2,2,2-trifluoroethyl)-N-(4-(4-(2,2,2-trifluoroethyl)piperazin-1-yl)phenyl)-1H,3'H-[2,4'-biimidazole]-4-carboxamide (Compound 192) was synthesized under the same synthetic route as for Compound 120 as white solid, which was determined by 1HNMR, LCMS and HPLC. LCMS: Retention time: 0.943 min, (M+H)=596.5. HPLC: Retention time: 1.965 min. ¹H NMR: (400 MHz, CHLOROFORM-d) δ=9.78 (br d, J=0.7 Hz, 1H), 8.76 (s, 1H), 7.70 (d, J=14.1 Hz, 2H), 7.59 (d, J=8.8 Hz, 2H), 7.47 (dd, J=5.6, 8.2 Hz, 2H), 7.10 (t, J=8.6 Hz, 2H), 6.96 (d, J=8.9 Hz, 2H), 5.08 (q, J=8.4 Hz, 2H), 3.24-3.20 (m, 4H), 3.07 (q, J=9.6 Hz, 2H), 2.89-2.86 (m, 4H).

Example 63: Synthesis of Compound 193

5'-(4-fluorophenyl)-N-(4-((1R,5S)-8-methyl-3,8-diazabicyclo[3.2.1]octan-3-yl)phenyl)-3'-(2,2,2-trifluoroethyl)-1H,3'H-[2,4'-biimidazole]-4-carboxamide (Compound 193) was synthesized under the same synthetic route as for Compound 120 as white solid, which was determined by ¹HNMR, LCMS and HPLC. LCMS: Retention time: 1.036 min (M+H)=554.5. HPLC: Retention time: 1.544 min 10-80AB_4 min.lcm. ¹H NMR: (400 MHz, CHLOROFORM-d) δ=8.73 (br s, 1H), 7.71 (br d, J=14.4 Hz, 2H), 7.55 (br d, J=8.6 Hz, 2H), 7.48 (br dd, J=5.9, 7.4 Hz, 2H), 7.09 (br t, J=8.3 Hz, 2H), 6.81 (br d, J=8.8 Hz, 2H), 5.05 (br d, J=7.7 Hz, 2H), 4.76 (s, 1H), 3.35 (br d, J=9.7 Hz, 2H), 3.26 (br s, 2H), 3.00 (br d, J=10.5 Hz, 2H), 2.34 (s, 3H), 2.07-2.02 (m, 2H), 1.81 (br d, J=7.6 Hz, 2H).

Certain compounds of Table 1 can be prepared employing alternative reagents in the examples above. Exemplary compounds may include, but are not limited to, a compound or salt thereof selected from Table 1 which may be prepared using the examples above and the accompanying procedures described herein.

TABLE 1

Compounds and Assay Data

| Compound # | Compound Structure | Human Liver Microsome (μM/min/mg) | TNIK (IC50, nM) | MAP4K4 (IC50, nM) |
|---|---|---|---|---|
| 172 | 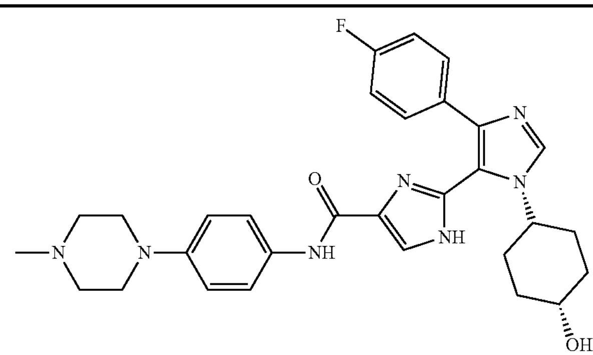 | | +++ | ++ |
| 175 | 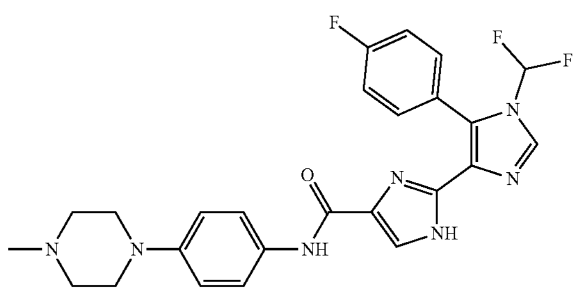 [SMILES: CN1CCN(c2ccc(NC(=O)c3c[nH]c(-c4ncn(C(F)F)c4-c4ccc(F)cc4)n3)cc2)CC1] | | | +++ |
| 128 | 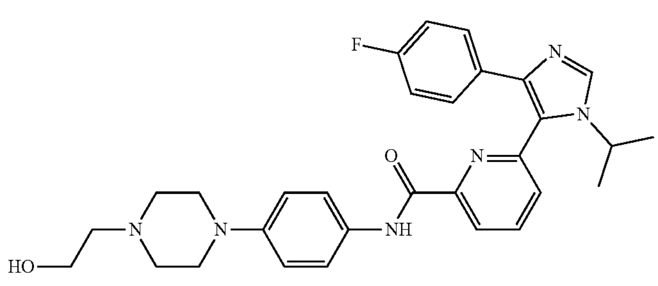 [SMILES: CC(C)n1cnc(-c2ccc(F)cc2)c1-c1cccc(C(=O)Nc2ccc(N3CCN(CCO)CC3)cc2)n1] | + | +++ | +++ |

TABLE 1-continued
Compounds and Assay Data
| Compound # | Compound Structure | Human Liver Microsome (μM/min/mg) | TNIK (IC50, nM) | MAP4K4 (IC50, nM) |
|---|---|---|---|---|
| 186 | 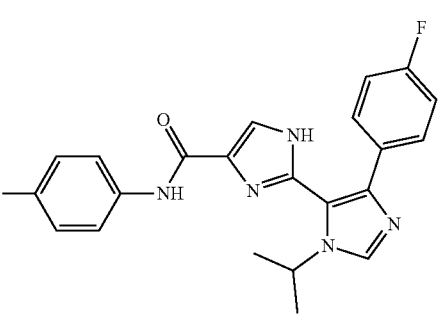 | | +++ | +++ |
| 131 | 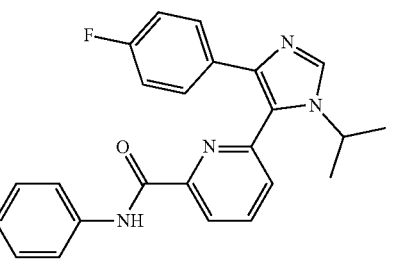 | +++ | +++ | ++ |
| 127 | 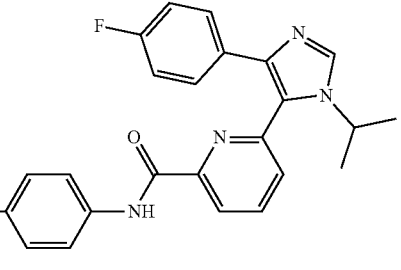 | + | +++ | +++ |
| 125 | 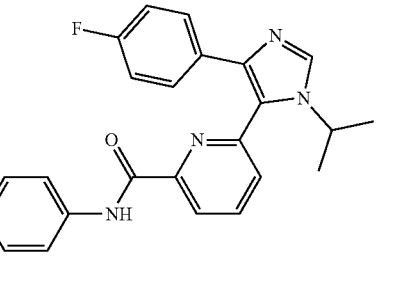 | ++ | +++ | +++ |
| 188 | 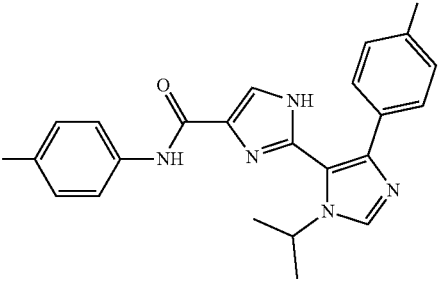 | | +++ | ++ |

TABLE 1-continued

Compounds and Assay Data

| Compound # | Compound Structure | Human Liver Microsome (µM/min/mg) | TNIK (IC50, nM) | MAP4K4 (IC50, nM) |
|---|---|---|---|---|
| 159 | 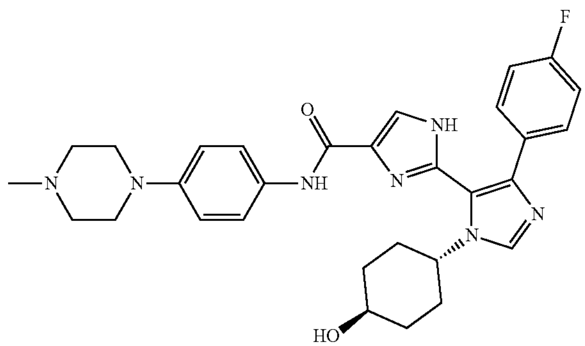 [SMILES: CN1CCN(c2ccc(NC(=O)c3c[nH]c(-c4c(-c5ccc(F)cc5)ncn4[C@H]4CC[C@H](O)CC4)n3)cc2)CC1] | ++ | +++ | ++ |
| 158 | 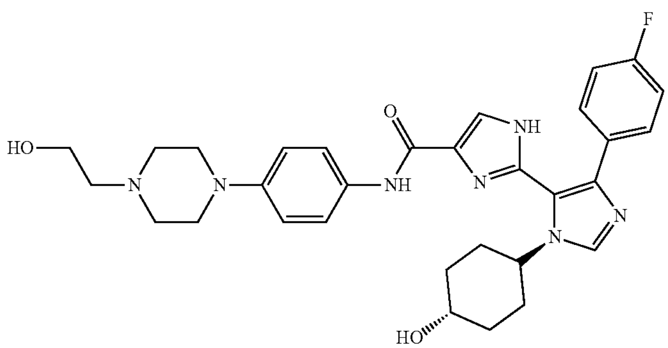 | +++ | +++ | ++ |
| 97 | 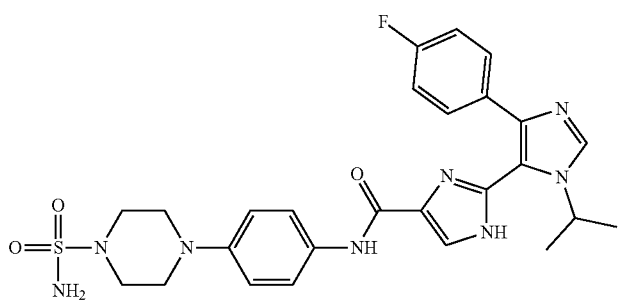 [SMILES: CC(C)n1cnc(-c2ccc(F)cc2)c1-c1nc(C(=O)Nc2ccc(N3CCN(S(N)(=O)=O)CC3)cc2)c[nH]1] | + | ++ | ++ |
| 121 | 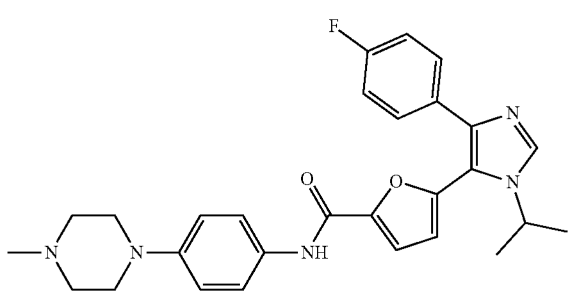 [SMILES: CC(C)n1cnc(-c2ccc(F)cc2)c1-c1ccc(C(=O)Nc2ccc(N3CCN(C)CC3)cc2)o1] | + | +++ | ++ |

TABLE 1-continued
Compounds and Assay Data
| Compound # | Compound Structure | Human Liver Microsome (µM/min/mg) | TNIK (IC50, nM) | MAP4K4 (IC50, nM) |
| --- | --- | --- | --- | --- |
| 196 | 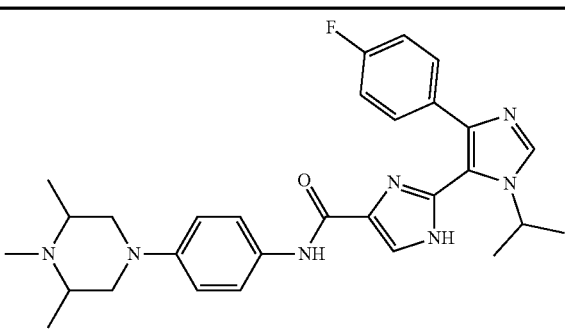 | | ++ | ++ |
| 193 | 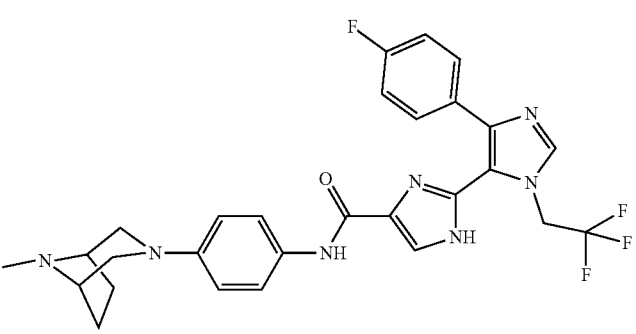 [SMILES: CN1C2CCC1CN(c1ccc(NC(=O)c3c[nH]c(-c4c(-c5ccc(F)cc5)ncn4CC(F)(F)F)n3)cc1)C2] | | ++ | ++ |
| 112 | 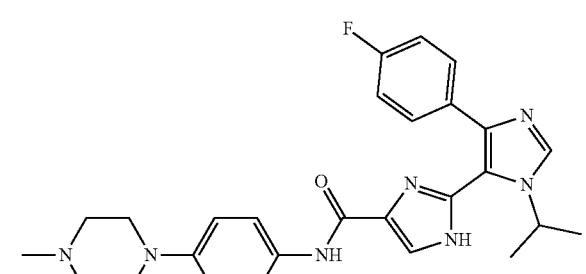 | ++ | ++ | ++ |
| 181 | 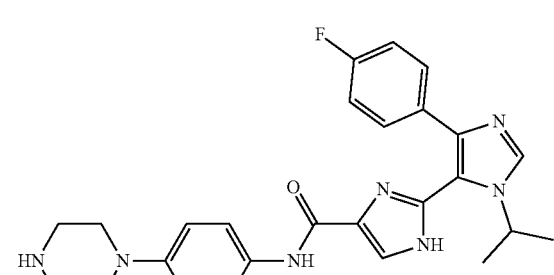 | ++ | ++ | ++ |
| 126 | 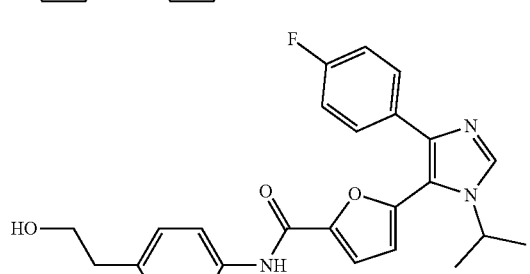 | + | ++ | ++ |

TABLE 1-continued

Compounds and Assay Data

| Compound # | Compound Structure | Human Liver Microsome (µM/min/mg) | TNIK (IC50, nM) | MAP4K4 (IC50, nM) |
|---|---|---|---|---|
| 117 | 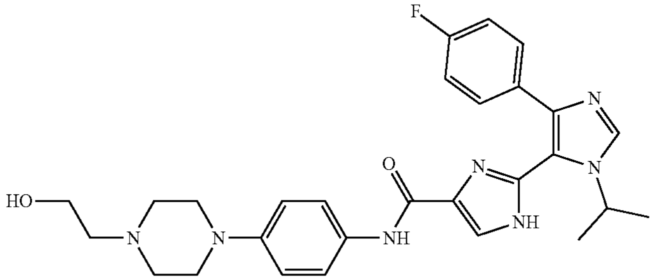 | ++ | ++ | ++ |
| 132 | 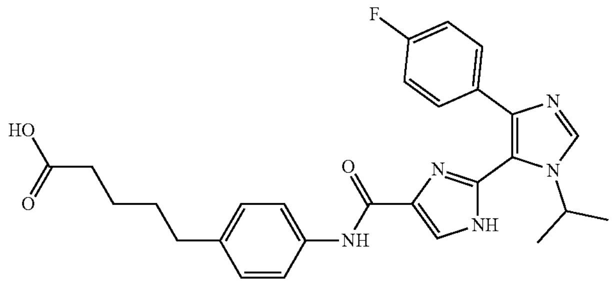 [SMILES: CC(C)n1cnc(-c2ccc(F)cc2)c1-c1nc(C(=O)Nc2ccc(CCCCC(=O)O)cc2)c[nH]1] | +++ | ++ | ++ |
| 189 | 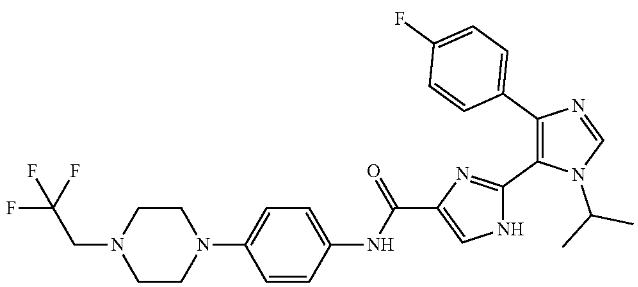 [SMILES: CC(C)n1cnc(-c2ccc(F)cc2)c1-c1nc(C(=O)Nc2ccc(N3CCN(CC(F)(F)F)CC3)cc2)c[nH]1] | | ++ | ++ |
| 116 | 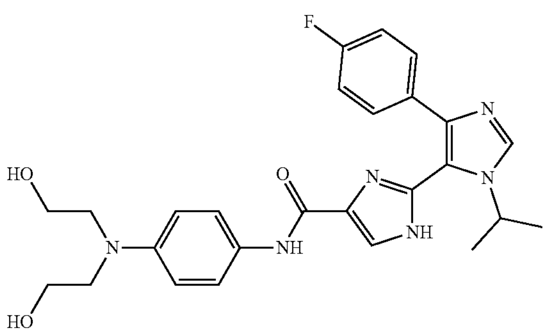 [SMILES: CC(C)n1cnc(-c2ccc(F)cc2)c1-c1nc(C(=O)Nc2ccc(N(CCO)CCO)cc2)c[nH]1] | +++ | ++ | ++ |
| 153 | 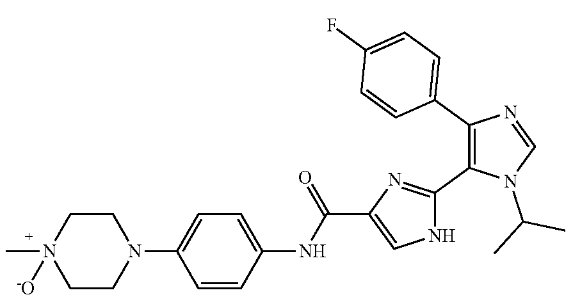 | +++ | ++ | ++ |

TABLE 1-continued
Compounds and Assay Data
| Compound # | Compound Structure | Human Liver Microsome (µM/min/mg) | TNIK (IC50, nM) | MAP4K4 (IC50, nM) |
|---|---|---|---|---|
| 190 | 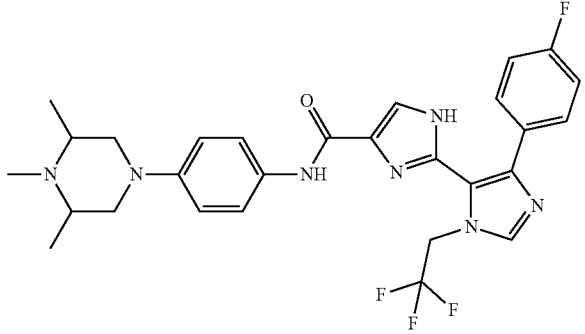 [SMILES: CC1CN(c2ccc(NC(=O)c3c[nH]c(-c4c(-c5ccc(F)cc5)ncn4CC(F)(F)F)n3)cc2)CC(C)N1C] | | +++ | ++ |
| 185 | 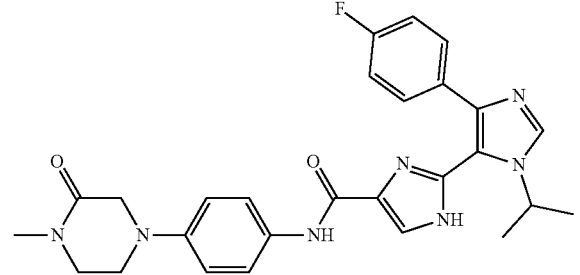 [SMILES: CC(C)n1cnc(-c2ccc(F)cc2)c1-c1nc(C(=O)Nc2ccc(N3CCN(C)C(=O)C3)cc2)c[nH]1] | | ++ | ++ |
| 191 | 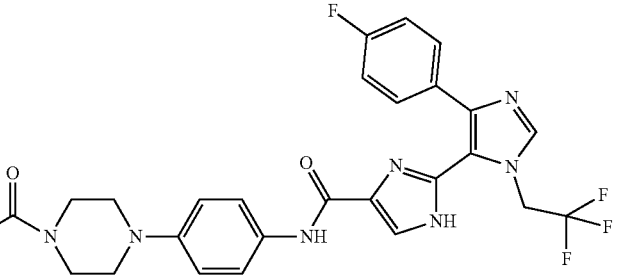 | | ++ | ++ |
| 167 | 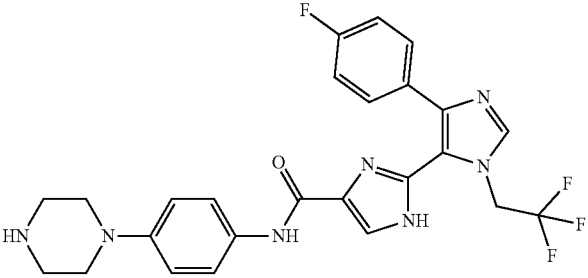 [SMILES: O=C(Nc1ccc(N2CCNCC2)cc1)c1c[nH]c(-c2c(-c3ccc(F)cc3)ncn2CC(F)(F)F)n1] | | ++ | ++ | + |
| 111 | 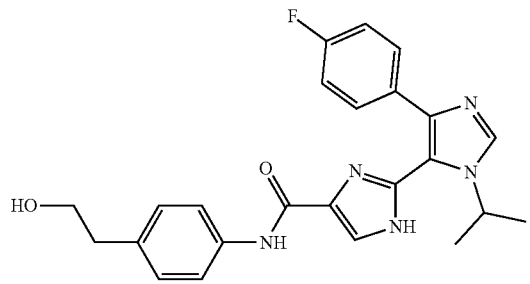 [SMILES: CC(C)n1cnc(-c2ccc(F)cc2)c1-c1nc(C(=O)Nc2ccc(CCO)cc2)c[nH]1] | | ++ | ++ | + |

TABLE 1-continued

Compounds and Assay Data

| Compound # | Compound Structure | Human Liver Microsome (μM/min/mg) | TNIK (IC50, nM) | MAP4K4 (IC50, nM) |
|---|---|---|---|---|
| 156 | 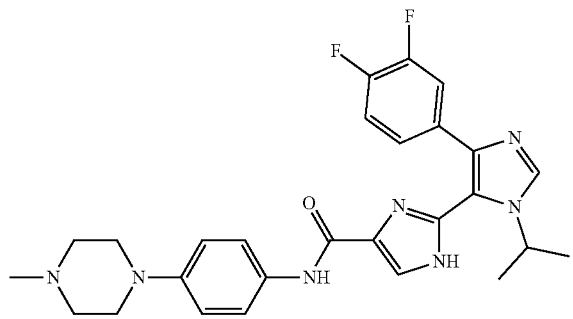 [SMILES: CC(C)n1cnc(-c2ccc(F)c(F)c2)c1-c1nc(C(=O)Nc2ccc(N3CCN(C)CC3)cc2)c[nH]1] | ++ | ++ | + |
| 194 | 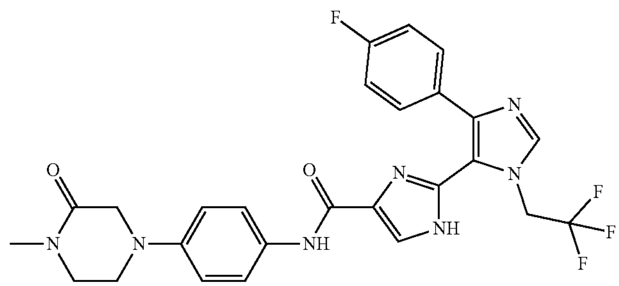 [SMILES: CN1CCN(c2ccc(NC(=O)c3c[nH]c(-c4c(-c5ccc(F)cc5)ncn4CC(F)(F)F)n3)cc2)CC1=O] | | ++ | + |
| 146 | 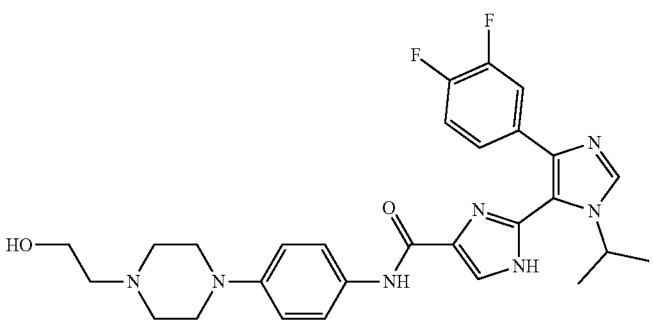 [SMILES: CC(C)n1cnc(-c2ccc(F)c(F)c2)c1-c1nc(C(=O)Nc2ccc(N3CCN(CCO)CC3)cc2)c[nH]1] | ++ | ++ | + |
| 102 | 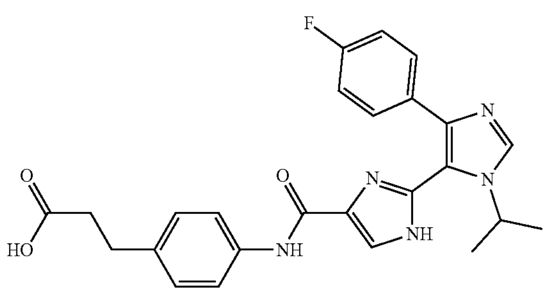 | +++ | ++ | + |
| 150 | 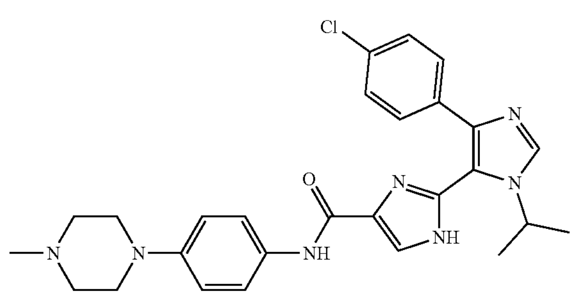 [SMILES: CC(C)n1cnc(-c2ccc(Cl)cc2)c1-c1nc(C(=O)Nc2ccc(N3CCN(C)CC3)cc2)c[nH]1] | ++ | ++ | + |

TABLE 1-continued

Compounds and Assay Data

| Compound # | Compound Structure | Human Liver Microsome (µM/min/mg) | TNIK (IC50, nM) | MAP4K4 (IC50, nM) |
|---|---|---|---|---|
| 99 | 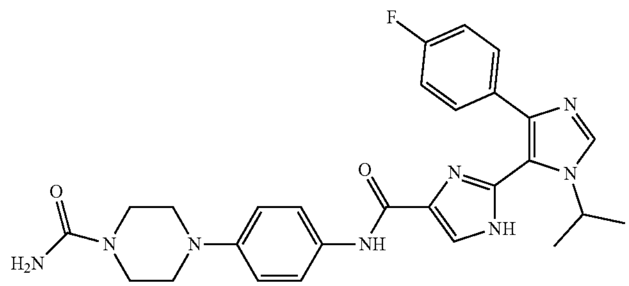 [SMILES: CC(C)n1cnc(-c2ccc(F)cc2)c1-c1nc(C(=O)Nc2ccc(N3CCN(C(N)=O)CC3)cc2)c[nH]1] | ++ | + | + |
| 166 | 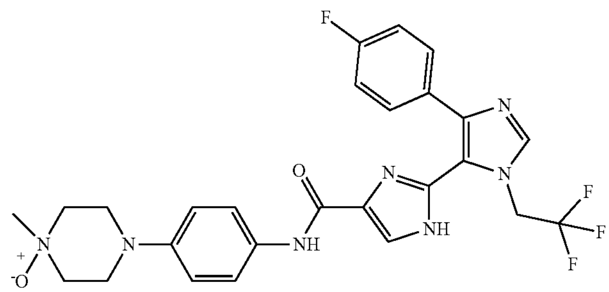 | +++ | + | + |
| 139 | 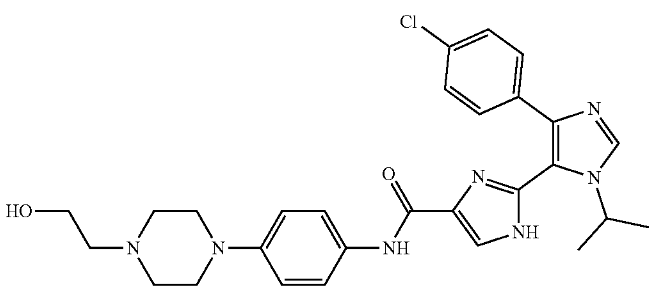 [SMILES: CC(C)n1cnc(-c2ccc(Cl)cc2)c1-c1nc(C(=O)Nc2ccc(N3CCN(CCO)CC3)cc2)c[nH]1] | ++ | ++ | + |
| 120 | 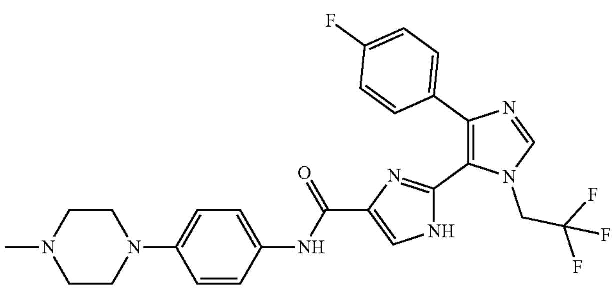 [SMILES: CN1CCN(c2ccc(NC(=O)c3c[nH]c(-c4c(-c5ccc(F)cc5)ncn4CC(F)(F)F)n3)cc2)CC1] | ++ | ++ | + |
| 113 | 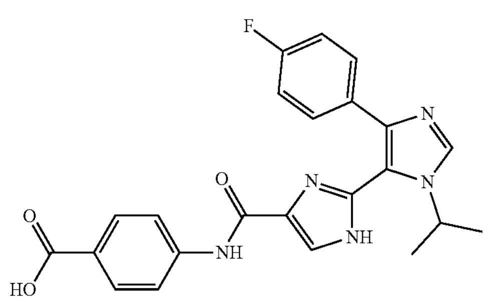 [SMILES: CC(C)n1cnc(-c2ccc(F)cc2)c1-c1nc(C(=O)Nc2ccc(C(=O)O)cc2)c[nH]1] | +++ | +++ | + |

TABLE 1-continued

Compounds and Assay Data

| Compound # | Compound Structure | Human Liver Microsome (μM/min/mg) | TNIK (IC50, nM) | MAP4K4 (IC50, nM) |
|---|---|---|---|---|
| 192 | 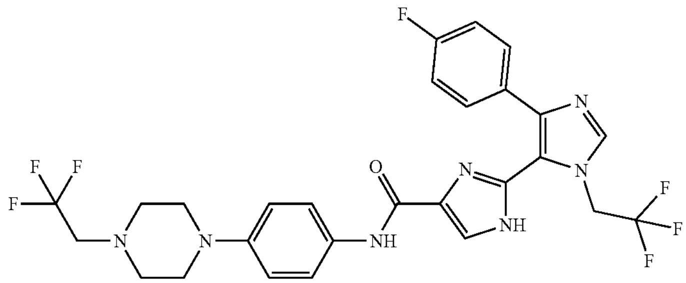 [SMILES: O=C(Nc1ccc(N2CCN(CC(F)(F)F)CC2)cc1)c1c[nH]c(-c2c(-c3ccc(F)cc3)ncn2CC(F)(F)F)n1] | | ++ | + |
| 135 | 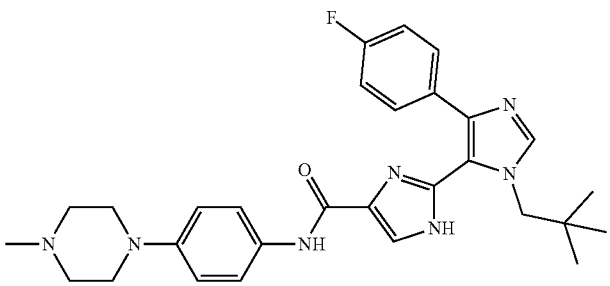 [SMILES: CN1CCN(c2ccc(NC(=O)c3c[nH]c(-c4c(-c5ccc(F)cc5)ncn4CC(C)(C)C)n3)cc2)CC1] | + | ++ | + |
| 119 | 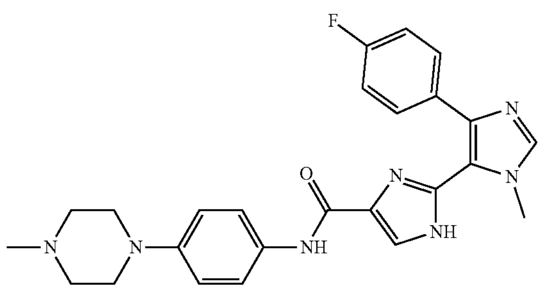 [SMILES: CN1CCN(c2ccc(NC(=O)c3c[nH]c(-c4c(-c5ccc(F)cc5)ncn4C)n3)cc2)CC1] | ++ | + | + |
| 137 | 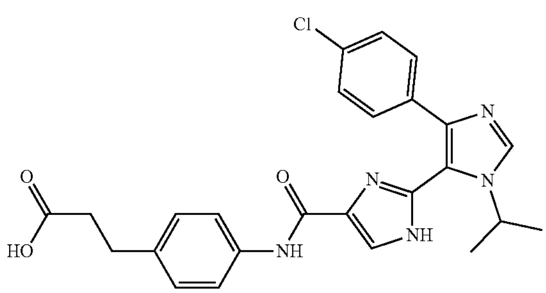 [SMILES: CC(C)n1cnc(-c2ccc(Cl)cc2)c1-c1nc(C(=O)Nc2ccc(CCC(=O)O)cc2)c[nH]1] | +++ | +++ | + |
| 130 | 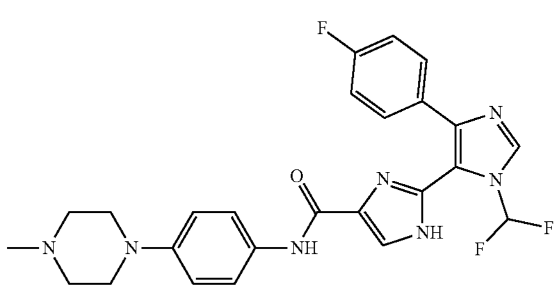 | ++ | ++ | + |

TABLE 1-continued

Compounds and Assay Data

| Compound # | Compound Structure | Human Liver Microsome (μM/min/mg) | TNIK (IC50, nM) | MAP4K4 (IC50, nM) |
|---|---|---|---|---|
| 142 | 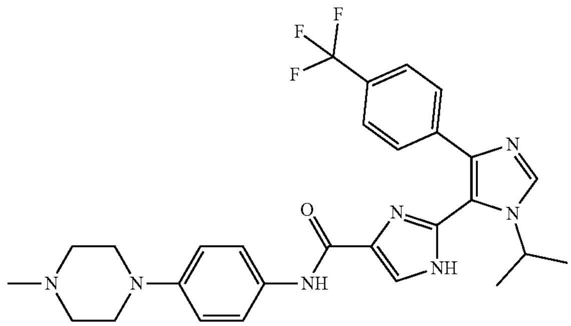 [SMILES: CC(C)n1cnc(-c2ccc(C(F)(F)F)cc2)c1-c1nc(C(=O)Nc2ccc(N3CCN(C)CC3)cc2)c[nH]1] | + | + | + |
| 134 | 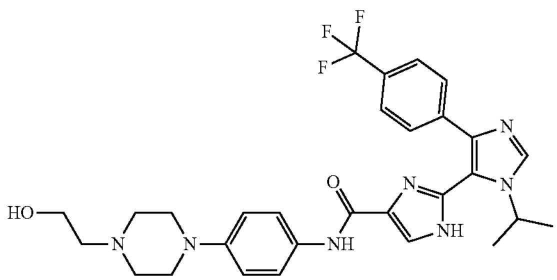 [SMILES: CC(C)n1cnc(-c2ccc(C(F)(F)F)cc2)c1-c1nc(C(=O)Nc2ccc(N3CCN(CCO)CC3)cc2)c[nH]1] | ++ | + | + |
| 133 | 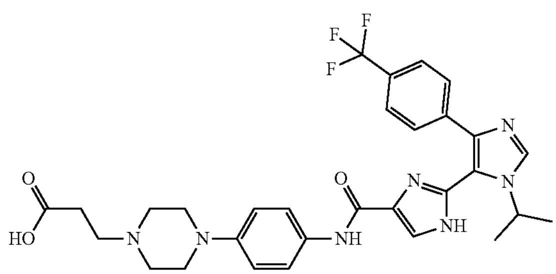 [SMILES: CC(C)n1cnc(-c2ccc(C(F)(F)F)cc2)c1-c1nc(C(=O)Nc2ccc(N3CCN(CCC(=O)O)CC3)cc2)c[nH]1] | +++ | + | + |
| 164 | 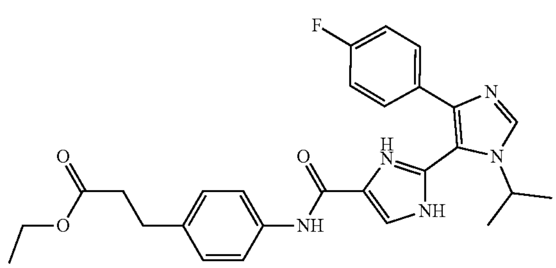 | | | |
| 168 | 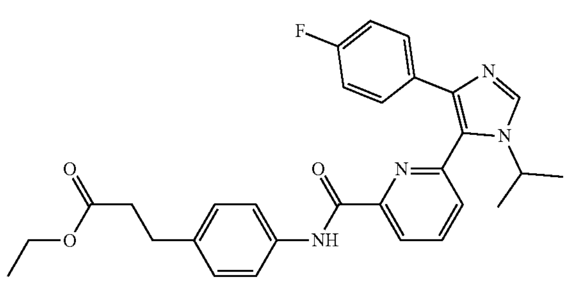 [SMILES: CCOC(=O)CCc1ccc(NC(=O)c2cccc(-c3c(-c4ccc(F)cc4)ncn3C(C)C)n2)cc1] | | | |

TABLE 1-continued

Compounds and Assay Data

| Compound # | Compound Structure | Human Liver Microsome (µM/min/mg) | TNIK (IC50, nM) | MAP4K4 (IC50, nM) |
|---|---|---|---|---|
| 171 | 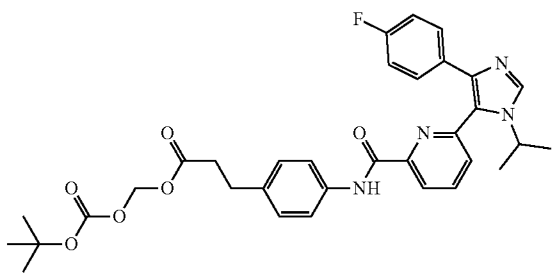 [SMILES: CC(C)n1cnc(-c2ccc(F)cc2)c1-c1cccc(C(=O)Nc2ccc(CCC(=O)OCOC(=O)OC(C)(C)C)cc2)n1] | | | |
| 198 | 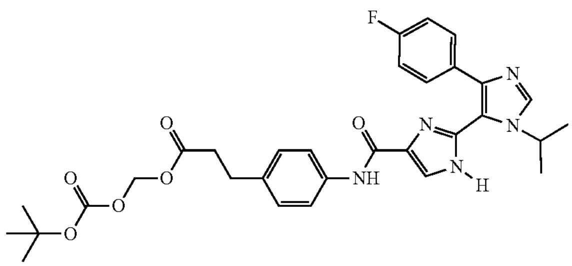 [SMILES: CC(C)n1cnc(-c2ccc(F)cc2)c1-c1nc(C(=O)Nc2ccc(CCC(=O)OCOC(=O)OC(C)(C)C)cc2)c[nH]1] | | | |
| 199 | 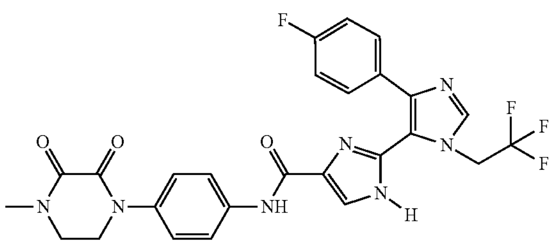 [SMILES: CN1CCN(c2ccc(NC(=O)c3c[nH]c(-c4c(-c5ccc(F)cc5)ncn4CC(F)(F)F)n3)cc2)C(=O)C1=O] | | | |
| 200 | 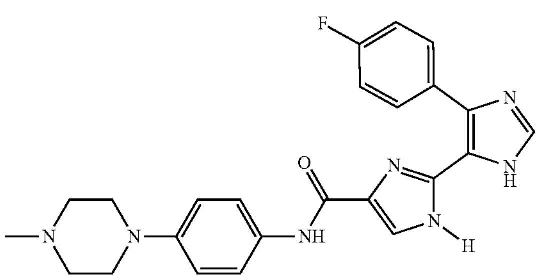 [SMILES: CN1CCN(c2ccc(NC(=O)c3c[nH]c(-c4[nH]cnc4-c4ccc(F)cc4)n3)cc2)CC1] | | | |
| 205 | 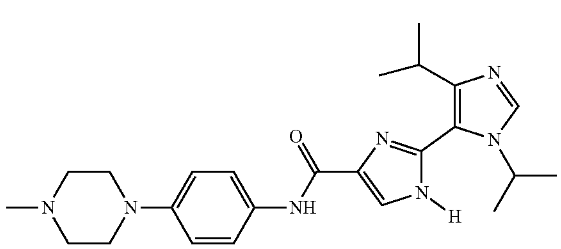 [SMILES: CC(C)c1ncn(C(C)C)c1-c1nc(C(=O)Nc2ccc(N3CCN(C)CC3)cc2)c[nH]1] | | | |

Example 64: Metabolic Stability in Human and Mouse Liver Microsomes

TABLE 1.1

Compound Information

| Compound No. | Compound ID | Batch No. | Exact Mass | Stock Concentration (mM) |
|---|---|---|---|---|
| 172 | 172 | | | 10 |
| Control | Testosterone | | 288.42 | 10 |
| Control | Diclofenac | | 295.14 | 10 |
| Control | Propafenone | | 341.44 | 10 |

2.1. Test Compound and Control Working Solution Preparation: Working solution: 5 μL of compound and control stock solution (10 mM in dimethyl sulfoxide (DMSO)) were diluted with 495 L of acetonitrile (ACN) (intermediate solution concentration: 100 μM, 99% ACN).

2.2. NADPH Cofactor Preparation 2.2.1. Materials: NADPH powder: β-Nicotinamide adenine dinucleotide phosphate reduced form, tetrasodium salt; NADPH.4Na (Vendor: Chem-Impex International, Cat. No. 00616).

2.2.2. Preparation Procedure: The appropriate amount of NADPH powder was weighed and diluted into a 10 mM $MgCl_2$ solution (working solution concentration: 10 unit/mL; final concentration in reaction system: 1 unit/mL).

2.3. Liver Microsomes Preparation:

2.3.1. Materials:

TABLE 2.1

Liver Microsomes Information

| Species | Product Information | Vendor | Abbreviation |
|---|---|---|---|
| Human | Cat No. 452117 Lot No. 38295 | Corning | HLM |
| CD-1 Mouse | Cat No. M00501 Lot No. WQP | BioIVT | MLM |

2.3.2. Preparation Procedure: The appropriate concentrations of microsome working solutions were prepared in 100 mM potassium phosphate buffer.

2.4. Stop Solution Preparation: Cold (4° C.) acetonitrile (ACN) containing 200 ng/mL tolbutamide and 200 ng/mL labetalol as internal standards (IS) was used as the stop solution.

2.5. Assay Procedure:

2.5.1. Pre-warm empty 'Incubation' plates T60 and NCF60 for 10 min minutes.

2.5.2. Dilute liver microsomes to 0.56 mg/mL in 100 mM phosphate buffer.

2.5.3. Transfer 445 μL microsome working solutions (0.56 mg/mL) into pre-warmed 'Incubation' plates T60 and NCF60, Then pre-incubate 'Incubation' plates T60 and NCF60 for 10 min at 37° C. with constant shaking. Transfer 54 μL liver microsomes to blank plate, then add 6 μL NAPDH cofactor to blank plate, and then add 180 μL quenching solution to blank plate.

2.5.4 Add 5 μL compound working solution (100 μM) into 'incubation' plates (T60 and NCF60) containing microsomes and mix 3 times thoroughly.

2.5.5. For the NCF60 plate, add 50 μL of buffer and mix 3 times thoroughly. Start timing; plate will be incubated at 37° C. for 60 min while shaking.

2.5.6. In 'Quenching' plate T0, add 180 μL quenching solution and 6 μL NAPDH cofactor. Ensure the plate is chilled to prevent evaporation.

2.5.7. For the T60 plate, mix 3 times thoroughly, and immediately remove 54 μL mixture for the 0-min time point to 'Quenching' plate. Then add 44 μL NAPDH cofactor to incubation plate (T60). Start timing; plate will be incubated at 37° C. for 60 min while shaking.

TABLE 2.2

Final Concentration of Each Component in Incubation Medium

| Component | Concentration |
|---|---|
| Microsome | 0.5 mg protein/mL |
| Test Compound | 1 μM |
| Control Compound | 1 μM |
| Acetonitrile | 0.99% |
| DMSO | 0.01% |

2.5.8. At 5, 10, 20, 30, and 60 min, add 180 μL quenching solution to 'Quenching' plates, mix once, and serially transfer 60 μL sample from T60 plate per time point to 'Quenching' plates.

TABLE 2.3

Reaction Plates Incubation

| Time Point | Start Time | End Time |
|---|---|---|
| Blank | 1:00:00 | 0:00:00 |
| T60 | 1:00:00 | 0:00:00 |
| T30 | 0:30:00 | 0:00:00 |
| T20 | 0:20:00 | 0:00:00 |
| T10 | 0:10:00 | 0:00:00 |
| T5 | 0:05:00 | 0:00:00 |
| T0 | | mix 3 times and out to 'Quenching' plate |

2.5.9. For NCF60: mix once, and transfer 60 μL sample from the NCF60 incubation to 'Quenching' plate containing quenching solution at the 60-min time point.

TABLE 2.4

NCF60 Incubation

| Time Point | Start Time | End Time |
|---|---|---|
| NCF60 | 1:00:00 | 0:00:00 |

2.5.10. All sampling plates are shaken for 10 min, then centrifuged at 4000 rpm for 20 minutes at 4° C.

2.5.11. Transfer 80 μL supernatant into 240 μL HPLC water, and mix by plate shaker for 10 min.

2.5.12. Each bioanalysis plate was sealed and shaken for 10 minutes prior to LC-MS/MS analysis.

3.1. The equation of first order kinetics was used to calculate T1/2 and Intrinsic clearance (CLint mic) in (μL/min/mg).

Equation of first order kinetic.

$$C_t = C_0 \cdot c^{-k_c \cdot 1} \text{ when}$$
$$C_t = \frac{1}{2}C_0,$$
$$T_{1/2} = \frac{\text{Ln}2}{k_c} = \frac{0.693}{k_c}$$
$$CL_{\text{int}(mic)} = \frac{0.693}{\text{In vitro } T_{1/2}} \cdot \frac{1}{\text{mg/mL microsomal protein in reaction system}}$$
$$CL_{\text{int}(liver)} = CL_{\text{int}(mic)} \cdot \frac{\text{mg microsomes}}{\text{g liver}} \cdot \frac{\text{g liver}}{\text{kg body weight}}$$

Table 1 include µM/min/mg values of selected compounds; compounds having a LM Clint of µM/min/mg of 1-10 µM/min/mg as +++, 10-100 µM/min/mg as ++, and >100 µM/min/mg as Example 65: TNIK Human STE Kinase Enzymatic Radiometric Assay Assay Information
ASSAY TYPE: Biochemical
ASSAY SUB TYPE: Enzymatic
FUNCTIONAL MODE: Antagonist
DETECTION METHOD: Radiometric
MEASURED RESPONSE: Scintillation
PROCEDURE SUMMARY: TNIK(h) is incubated with 8 mM MOPS pH 7.0, 0.2 mM EDTA, 250 µM RLGRDKYKTLRQIRQ, 10 mM Magnesium Acetate and [gamma-33P-ATP](specific activity and concentration as required). The reaction is initiated by the addition of the Mg/ATP mix. After incubation for 40 minutes at room temperature, the reaction is stopped by the addition of phosphoric acid to a concentration of 0.5%. 10 ul of the reaction is then spotted onto a P30 filter mat and washed four times for 4 minutes in 0.425% phosphoric acid and once in methanol prior to drying and scintillation counting.
SUBSTRATE: 250 µM RLGRDKYKTLRQI
TRACER: 33P
ATP CONCENTRATION: 70 µM
INCUBATION: 40 min at Room temperature
CONTROL INHIBITOR: 1-NM-PP1
COMPOUND CONCENTRATION: 10 µM, 3 µM, 1 µM, 0.3 µM, 0.1 µM, 0.03 µM, 0.01 µM, 0.003 µM, 0.001 µM
COMPOUND DILUTION SCHEME: All compounds supplied were prepared to a working stock of 50× final assay concentration in 100% DMSO. Where appropriate, more concentrated stocks were diluted manually to 50× using 100% DMSO. Compounds supplied as powders were reconstituted to a 10 mM stock in 100% DMSO before further dilution to 50×.
ASSAY PROCEDURE: The required volume of the 50× stock of test compound was added to the assay before a reaction mix containing the enzyme and substrate was added. The reaction was initiated by the addition of ATP at the selected concentration. There was no pre-incubation of the compound with the enzyme/substrate mix prior to ATP addition. For further details of each individual assay, please refer to the website or the accompanying protocol document.
DATA ANALYSIS: Data are handled using a custom built in-house analysis software. Results are expressed as kinase activity remaining, as a percentage of the DMSO control. This is calculated using the following formula:

Mean of Sample Counts−Mean of Blank Counts/
Mean of Control Counts

For IC50 determinations, data are analyzed using XLFit version 5.3 (ID Business Solutions).

Sigmoidal dose-response (variable slope) curves are fit based on the mean result for each test concentration using non-linear regression analysis. Where the top and/or bottom of the curve fall >10% out with 100 and 0, respectively, either or both of these limits may be constrained at 100 and 0, provided that the QC criterion on $R^2$ is met.

Table 1 include $IC_{50}$ values for TNIK of selected compounds; compounds having an IC50 value of 1-12 nM as +++, 12-120 nM as ++, and >120 nM as +. The $IC_{50}$ values can be found in Table 1.

Example 66: MAP4K4 Human STE Kinase Enzymatic Radiometric Assay

ASSAY TYPE: Biochemical
ASSAY SUB TYPE: Enzymatic
FUNCTIONAL MODE: Antagonist
DETECTION METHOD: Radiometric
MEASURED RESPONSE: Scintillation
PROCEDURE SUMMARY: MAP4K4 (h) is incubated with 8 mM MOPS pH 7.0, 0.2 mM EDTA, 250 µM RLGRDKYKTLRQIRQ, 10 mM Magnesium Acetate and [gamma-33P-ATP](specific activity and concentration as required). The reaction is initiated by the addition of the Mg/ATP mix. After incubation for 40 minutes at room temperature, the reaction is stopped by the addition of phosphoric acid to a concentration of 0.5%. 10 ul of the reaction is then spotted onto a P30 filter mat and washed four times for 4 minutes in 0.425% phosphoric acid and once in methanol prior to drying and scintillation counting.
SUBSTRATE: 250 µM RLGRDKYKTLRQI
TRACER: 33P
ATP CONCENTRATION: 200 µM
INCUBATION: 40 min at Room temperature
CONTROL INHIBITOR: Staurosporine
COMPOUND CONCENTRATION: 10 µM, 3 µM, 1 µM, 0.3 µM, 0.1 µM, 0.03 µM, 0.01 µM, 0.003 µM, 0.001 µM.
COMPOUND DILUTION SCHEME: All compounds supplied were prepared to a working stock of 50× final assay concentration in 100% DMSO. Where appropriate, more concentrated stocks were diluted manually to 50× using 100% DMSO. Compounds supplied as powders were reconstituted to a 10 mM stock in 100% DMSO before further dilution to 50×.
ASSAY PROCEDURE: The required volume of the 50× stock of test compound was added to the assay before a reaction mix containing the enzyme and substrate was added. The reaction was initiated by the addition of ATP at the selected concentration. There was no pre-incubation of the compound with the enzyme/substrate mix prior to ATP addition. For further details of each individual assay, please refer to the website or the accompanying protocol document.
DATA ANALYSIS: Data are handled using a custom built in-house analysis software. Results are expressed as kinase activity remaining, as a percentage of the DMSO control. This is calculated using the following formula:

$$\frac{\text{Mean of Sample Counts} - \text{Mean of Blank Counts}}{\text{Mean of Control Counts}}$$

For $IC_{50}$ determinations, data are analyzed using XLFit version 5.3 (ID Business Solutions). Sigmoidal dose-response (variable slope) curves are fit based on the mean result for each test concentration using non-linear regression analysis. Where the top and/or bottom of the curve fall >10% out with 100 and 0, respectively, either or both of these limits may be constrained at 100 and 0, provided that the QC criterion on $R^2$ is met.

Table 1 include $IC_{50}$ values for MAP4K4 of selected compounds; compounds having an IC50 value of 1-12 nM as +++, 12-120 nM as ++, and >120 nM as +.

Example 67: Masson's Trichrome (M&T) Staining and Ashcroft Score

Masson's Trichrome (M&T) Staining Protocol: Lung sections were cut at 4 µm in thickness, dried in an oven for 1 hour, and stained with M&T by a standard staining protocol. The sections were briefly stained with Weigert's iron hematoxylin working solution for 10 minutes. This was followed by staining in Biebrich scarlet-acid fuchsin solution for 10 minutes and differentiation in phosphomolybdic-phosphotungstic acid solution for 5 minutes or until collagen is not red. The sample was then transferred to aniline blue solution and stained for 1 minute followed by dedifferentiation in 1% acetic acid solution. This was followed by dehydration and placement of a cover-slip for the subsequent image analysis.

For image analysis of collagen deposition, Masson's trichrome stained slides were scanned using Aperio Scan Scope Model: CS2 (Leica), at 200× magnification. The area of fibrosis stained with Masson's trichrome stain was quantified with the HALO® image analysis platform from Indica Labs. The whole left lung section was selected as an annotation layer.

Fibrotic modifications were assessed morphologically and semi-quantitatively graded according to the scale of 0-8 defined by Ashcroft et al. and modified by Hubner et al. as described in the Table 3 below. The final score was expressed as a mean of individual scores observed across all microscopic fields.

TABLE 3

Modified Ashcroft Score.

Score Characterization Modified Ashcroft Score

0 Alveolar septa: No fibrotic burden at the flimsiest small fibers in some alveolar walls
  Lung structure: Normal lung
1 Alveolar septa: Isolated gentle fibrotic changes (septum ≤3× thicker than normal)
  Lung structure: Alveoli partly enlarged and rarefied, but no fibrotic masses present
2 Alveolar septa: Clearly fibrotic changes (septum >3× thicker than normal) with knot-like formation but not connected to each other
  Lung structure: Alveoli partly enlarged and rarefied, but no fibrotic masses
3 Alveolar septa: Contiguous fibrotic walls (septum >3× thicker than normal) predominantly in whole microscopic field
  Lung structure: Alveoli partly enlarged and rarefied, but no fibrotic masses
4 Alveolar septa: Variable
  Lung structure: Single fibrotic masses (≤10% of microscopic field)
5 Alveolar septa: Variable
  Lung structure: Confluent fibrotic mass (>10% and ≤50% of microscopic field). Lung structure severely damaged but still preserved
6 Alveolar septa: Variable, mostly not existent
  Lung structure: Large contiguous fibrotic masses (>50% of microscopic field). Lung architecture mostly no preserved
7 Alveolar septa: non-existent
  Lung structure: Alveoli nearly obliterated with fibrous masses but still up to five air bubbles
8 Alveolar septa: non-existent
  Lung structure: Microscopic field complete obliteration with fibrotic masses Example 68: Alpha-SMA IHC Assay Protocol: For immunohistochemical staining, 4 m thick-sections were placed on slides and after overnight drying, the paraffin was removed with xylene. The sections were placed in a graded ethanol series and immersed in distilled water. After heat-induced Citrate antigen (pH=6.0) unmasking, the sections were immersed in 3% hydrogen peroxide solution for 5 mins. To avoid nonspecific staining, the sections were then incubated in blocking serum for 15 mins at room temperature, followed by addition of primary rabbit polyclonal anti-α-SMA antibodies in a dilution 1:400 for 1 hour. This was followed by the addition of secondary goat polyclonal antibodies conjugated to HRP.

For image analysis of fibrosis, α-SMA stained sections were scanned via Aperio CS2 Scan machine. The area of fibrosis were quantified with the HALO® image analysis platform from Indica Labs. The whole left lung section was selected as an annotation layer. The bronchus was excluded in the annotation layer. The area occupied by collagen fibers was measured using "Area Quantification v2.1.3" module. The percentage of positive areas in the selected annotation was then calculated by the program. The fibrosis was expressed as percentage per lung section.

Example 69: Bleomycin-Induced Lung Fibrosis Mouse Model

Protocol: Eight-week-old C57BL/6 male mice were anaesthetized with Pentobarbital (60 mg/kg body weight, i.p.) and received bleomycin on day 1 at a dose of 0.66 mg/kg (equivalent to 1 U/kg) by intra-tracheal administration. Compound treatment started on day 7 after the induction of lung fibrosis when the initial lung injury and inflammation were already abating.

Example 70: Bleomycin-Induced Rat Model for Skin Fibrosis

Protocol: Five to six-week-old Sprague Dawley male rats were transiently anesthetized using isoflurane and their dorsal regions were shaved using a Wahl pet trimmer. Bleomycin (BLM) will be diluted to 1 mg/ml with sterile phosphate-buffered saline (PBS). Using a 1 ml syringe containing a 27-gauge needle, 100 µl of BLM solution will be injected subcutaneously into two sites on the shaved regions, once daily for 4 weeks. Naive controls will be injected daily with an equivalent volume of sterile PBS.

Example 71: Unilateral Ureteral Obstruction Renal Fibrosis Model

Protocol: On Day 0, UUO surgery was performed onto seven-week-old female $C_{57}BL/6$ mice under three types of mixed anesthetic agents (medetomidine, midazolam, butorphanol). After shaving the hair, the abdomen was cut open and the left ureter will be exteriorized. The ureter was ligated 4-0 silk sutures at two points. The peritoneum and the skin were closed with sutures, and the mice were transferred to a clean cage and kept until recovery from anesthesia. Mice were divided into two slots based on their body weight before the day of the surgery. Compounds were administered orally from Day 0 to 13. On Day 14. The ligated left kidney and right kidney weight were measured at sacrifice.

Example 72: Collagen and Alpha-SMA in LX-2

Method: Culture medium was prepared with DMEM supplemented with 2% FBS and 1% P/S. The medium was removed from culture flask containing the confluent layer of LX-2 cells. 3 ml of 0.25% Trypsin-EDTA solution was then added and cells were incubated at 37° C. for 5 min for each T150-flask. 7 ml of culture medium was added to stop trypsinization. The cells were centrifuged at 300×g for 5 min. Supernatant medium was discarded and cells were re-suspended with fresh culture medium. The cells were counted with Cell viability analyzer. 5.0E+05 cells/well were seeded into 6-well plate containing 2.0 mL of culture medium. The cells were cultured overnight at 37° C. The next day, the complete medium was replaced with medium with 0.4% FBS for starvation. After 24 h incubation in medium with reduced serum, LX-2 cells were treated with compounds (8 concentrations, 3-fold dilution) in duplicate for 30 minutes before being stimulated with 4 ng/ml of TGF-β for additional 48 hours. In parallel, medium containing only DMSO and TGF-β was used as blank control and positive control, respectively. TGF-β induction was used as maximum induction positive control. The culture medium was discarded at the end of induction. Cells were washed once using ice-cold DPBS. RIPA buffer was added to lyse the cells for 20 min. The cells were then scraped off the culture plate, collected in a tube and centrifuged. The supernatant was stored at −80° C. The total amount of protein in the lysate was determined using BCA Protein Assay kit. The cell treatment of fibrosis assay was performed in three independent experiments for each compound.

All the lysate samples were adjusted to the same protein concentration with RIPA buffer after BCA assay. The samples with the same protein amount were mixed with 4×LDS sample buffer and boiled at 95° C. for 5 min. The denatured samples were used for electrophoresis. Western blot was performed according to the standard protocols. The same volume of protein was loaded onto 4-12% Bis-Tris gel. Duplicate lysates of samples were loaded onto two gels. The gels were run for 0.5 h at 80 V and 120 V for another 1 h. When the electrophoresis was completed, the gels containing target protein Collagen I (COL1A1) were transferred onto NC membrane using Trans-Blot Electrophoretic Transfer Cell for 90 min at 100 V. The iBlot™ 2 Gel Transfer Device was used to transfer α-SMA and GAPDH at 20 V for 7 min. All the membranes were blocked in TBST buffer with 5% nonfat dry milk in at RT for 1 h and then incubated with primary antibody anti-COL1A1 and anti-α-SMA in TBST buffer containing 5% BSA at 4° C. overnight. For GAPDH detection, the membrane with α-SMA immunoblots were stripped with Restore™ Western Blot Stripping Buffer after detection. And the membranes were re-blocked and then re-probed with primary antibody anti-GAPDH antibody at room temperature (RT) for 2 h. After incubation with primary antibodies, membranes were washed with TBST, then incubated with the secondary antibody at RT for 1 h. Blots were visualized using the instrument Image Quant LAS-4000. The chemiluminescent signals derived from ECL Western blotting reagents were captured. The bands integrated intensity from 16-bit blot images was used for quantitation with the software (1D component of ImageQuant TL). The quantification raw data of the two duplicated gels was obtained from ImageQuant TL. Collagen I and α-SMA proteins expression level was normalized to GAPDH for each gel. The average normalization data of the two duplicated gels was calculated and applied to calculate $IC_{50}$ using an equation for a sigmoidal dose response (variable slope) of GraphPad™ Prism software. The equation is Y=Bottom+(Top−Bottom)/(1+10^((Log IC50−X)*Hillslope). Note: X is the logarithm of compound concentration, Y is the average normalization data Table 4 include $IC_{50}$ values for collagen of selected compounds; compounds having an $IC_{50}$ value of <0.1 nM as +++, 0.1-1.0 nM as ++, and >1.0 nM as +.

TABLE 4

ICso data for collagen in LX-2 cells

| Compound # | Collagen in LX-2 ($IC_{50}$, nM) |
|---|---|
| 172 | +++ |
| 128 | ++ |
| 131 | ++ |
| 127 | ++ |
| 125 | ++ |
| 188 | ++ |
| 159 | ++ |
| 121 | .+++ |
| 196 | +++ |
| 193 | +++ |
| 112 | +++ |
| 126 | ++ |
| 117 | ++ |
| 189 | ++ |
| 116 | ++ |
| 153 | .++ |
| 190 | +++ |
| 185 | ++ |
| 191 | ++ |
| 167 | +++ |
| 111 | ++ |
| 156 | +++ |
| 194 | ++ |
| 146 | ++ |
| 150 | ++ |
| 139 | ++ |
| 120 | +++ |
| 192 | +++ |
| 130 | ++ |
| 1 | + |

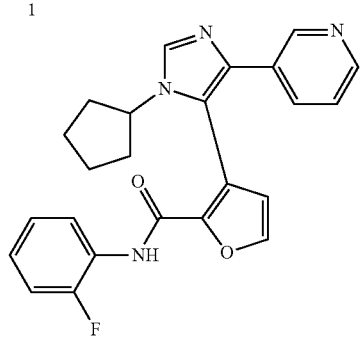

| 4 | + |

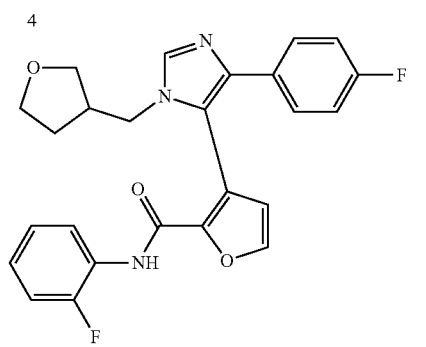

TABLE 4-continued

ICso data for collagen in LX-2 cells

| Compound # | Collagen in LX-2 (IC$_{50}$, nM) |
|---|---|
| 39 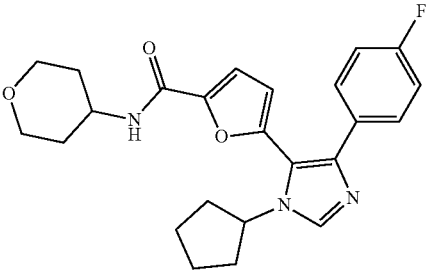 [SMILES: O=C(NC1CCOCC1)c1ccc(-c2c(-c3ccc(F)cc3)ncn2C2CCCC2)o1] | + |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound represented by Formula (IIA),

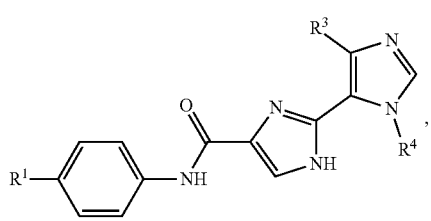

(IIA)

or a pharmaceutically acceptable salt thereof, wherein:

$R^1$ is piperazine, wherein the piperazine is optionally substituted with one or more substituents independently selected at each occurrence from oxo and $C_{1-10}$ alkyl, wherein the $C_{1-10}$ alkyl is optionally substituted with one or more substituents independently selected at each occurrence from hydroxy, halogen, oxo, and —NH$_2$;

$R^3$ is phenyl, wherein the phenyl is optionally substituted with one or more halogen; and $R^4$ is

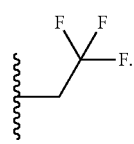 [SMILES: *CC(F)(F)F]

2. The compound of claim 1, or a pharmaceutically acceptable salt thereof, wherein $R^3$ is selected from 3. The compound of claim 1, or a pharmaceutically acceptable salt thereof, wherein $R^1$ is piperazine substituted with one or more $C_{1-3}$ alkyl, wherein the $C_{1-3}$ alkyl is optionally substituted with one or more halogen.

4. The compound of claim 1, or a pharmaceutically acceptable salt thereof, wherein $R^1$ is selected from 5. The compound of claim 1, or a pharmaceutically acceptable salt thereof, wherein $R^1$ is selected from

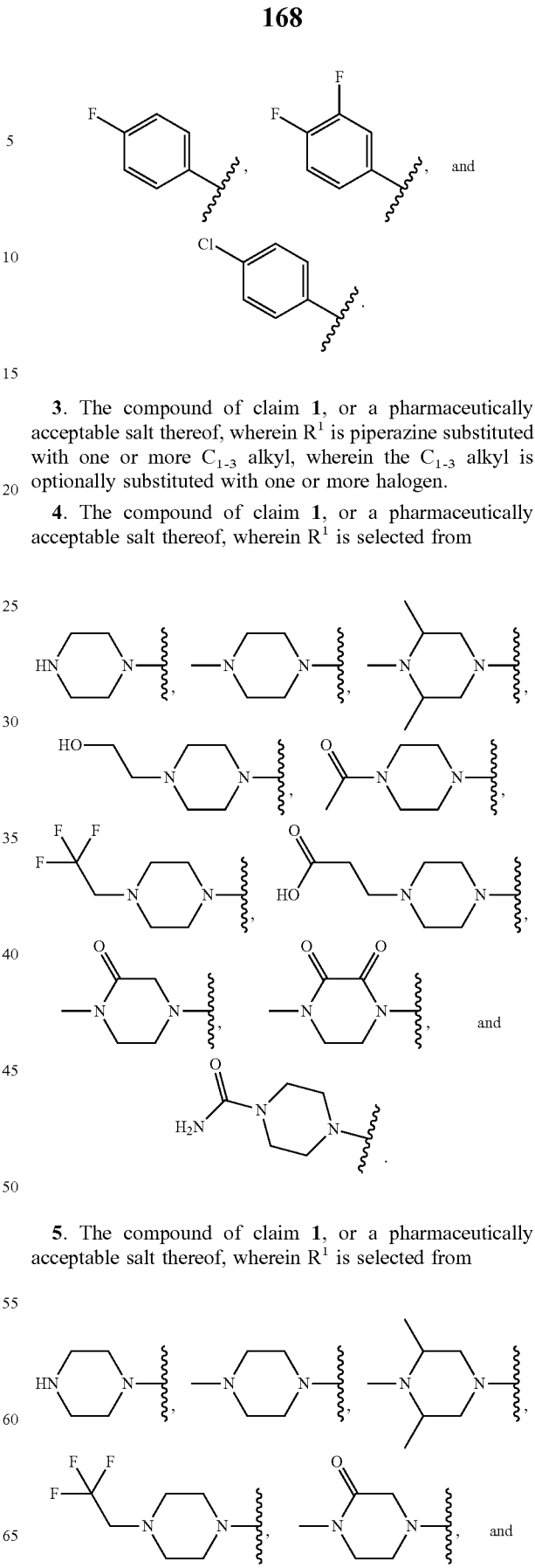

-continued

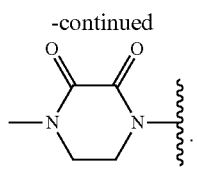

6. The compound of claim 1, or a pharmaceutically acceptable salt thereof, wherein the compound is selected from:

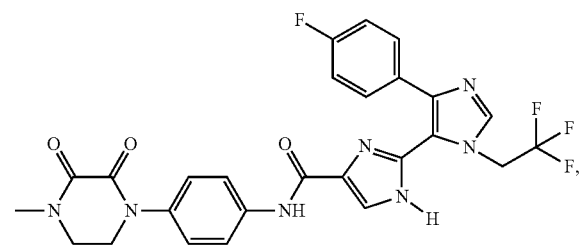 [SMILES: CN1CCN(c2ccc(NC(=O)c3c[nH]c(-c4c(-c5ccc(F)cc5)ncn4CC(F)(F)F)n3)cc2)C(=O)C1=O]

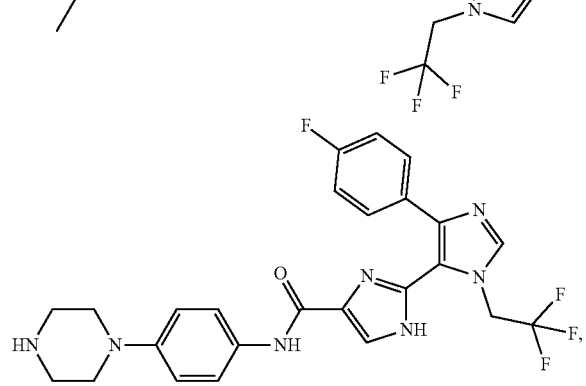

and

-continued

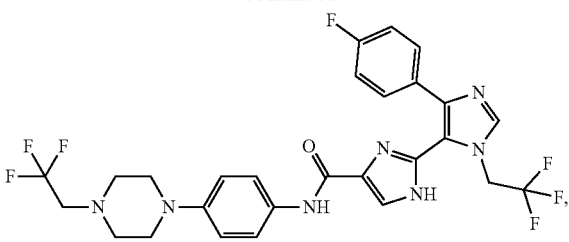 [SMILES: O=C(Nc1ccc(N2CCN(CC(F)(F)F)CC2)cc1)c1c[nH]c(-c2c(-c3ccc(F)cc3)ncn2CC(F)(F)F)n1]

or a pharmaceutically acceptable salt thereof.

7. The compound of claim 1, or a pharmaceutically acceptable salt thereof, wherein the compound is

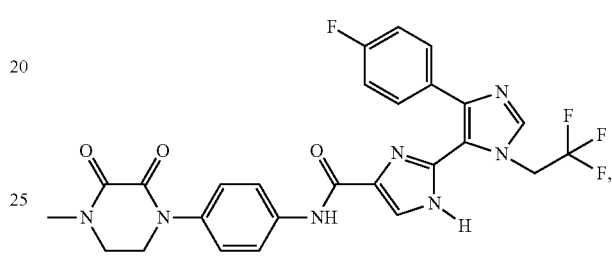

or a pharmaceutically acceptable salt thereof.

8. The compound of claim 1, or a pharmaceutically acceptable salt thereof, wherein the compound is

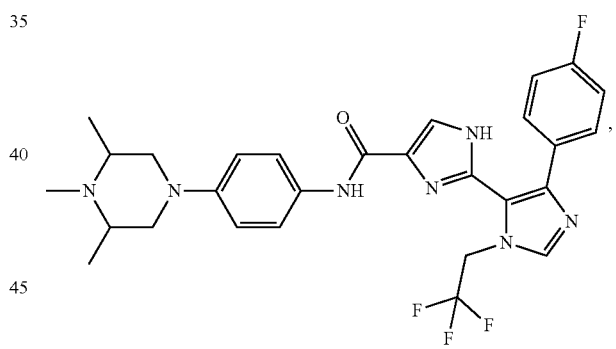

or a pharmaceutically acceptable salt thereof.

9. The compound of claim 1, or a pharmaceutically acceptable salt thereof, wherein the compound is

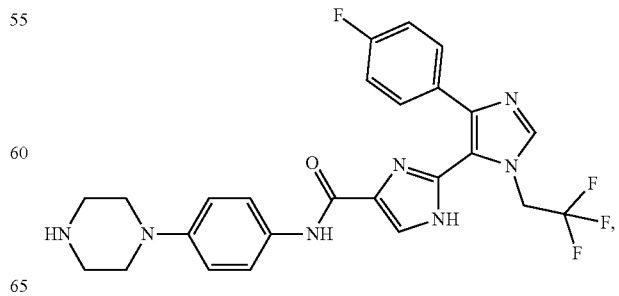

or a pharmaceutically acceptable salt thereof.

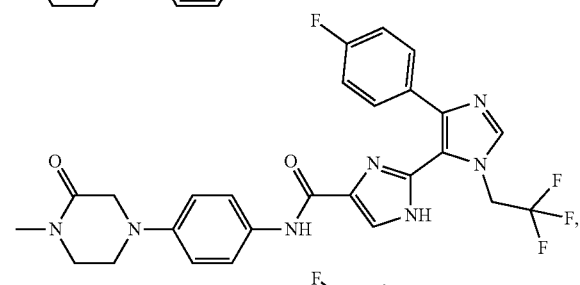

10. The compound of claim 1, or a pharmaceutically acceptable salt thereof, wherein the compound is

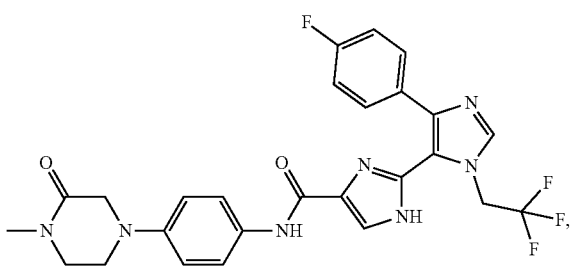 [SMILES: CN1CCN(c2ccc(NC(=O)c3c[nH]c(-c4c(-c5ccc(F)cc5)ncn4CC(F)(F)F)n3)cc2)CC1=O]

or a pharmaceutically acceptable salt thereof.

11. The compound of claim 1, or a pharmaceutically acceptable salt thereof, wherein the compound is

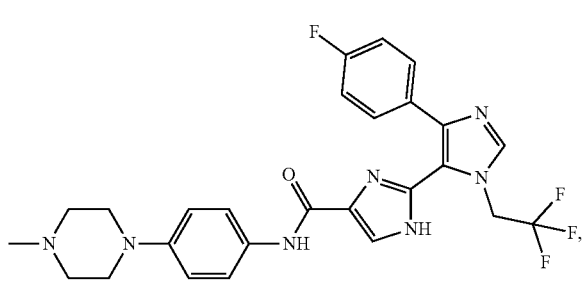 [SMILES: CN1CCN(c2ccc(NC(=O)c3c[nH]c(-c4c(-c5ccc(F)cc5)ncn4CC(F)(F)F)n3)cc2)CC1]

or a pharmaceutically acceptable salt thereof.

12. The compound of claim 1, or a pharmaceutically acceptable salt thereof, wherein the compound is

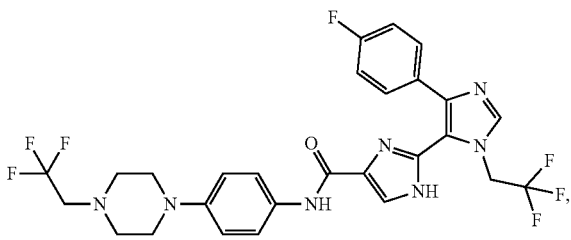 [SMILES: O=C(Nc1ccc(N2CCN(CC(F)(F)F)CC2)cc1)c1c[nH]c(-c2c(-c3ccc(F)cc3)ncn2CC(F)(F)F)n1]

or a pharmaceutically acceptable salt thereof.

13. A method of treating a fibrotic disease or condition, comprising administering a compound of claim 6 or a pharmaceutically acceptable salt thereof, to a subject in need thereof, wherein the fibrotic disease or condition is kidney fibrosis.

14. The method of claim 13, wherein the fibrotic disease or condition is associated with TNIK kinase.

15. A pharmaceutical composition comprising (i) a compound represented by Formula (IIA),

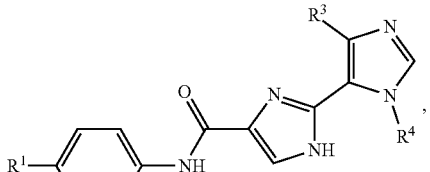

(IIA)

or a pharmaceutically acceptable salt thereof, wherein:

$R^1$ is piperazine, wherein the piperazine is optionally substituted with one or more substituents independently selected at each occurrence from oxo and $C_{1-10}$ alkyl, wherein the $C_{1-10}$ alkyl is optionally substituted with one or more substituents independently selected at each occurrence from hydroxy, halogen, oxo, and —$NH_2$;

$R^3$ is phenyl, wherein the phenyl is optionally substituted with one or more halogen; and $R^4$ is

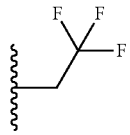

and (ii) a pharmaceutically acceptable excipient.

16. The pharmaceutical composition of claim 15, wherein $R^1$ is piperazine substituted with one or more $C_{1-3}$ alkyl, wherein the $C_{1-3}$ alkyl is optionally substituted with one or more halogen.

17. The pharmaceutical composition of claim 15, wherein:

$R^1$ is selected from

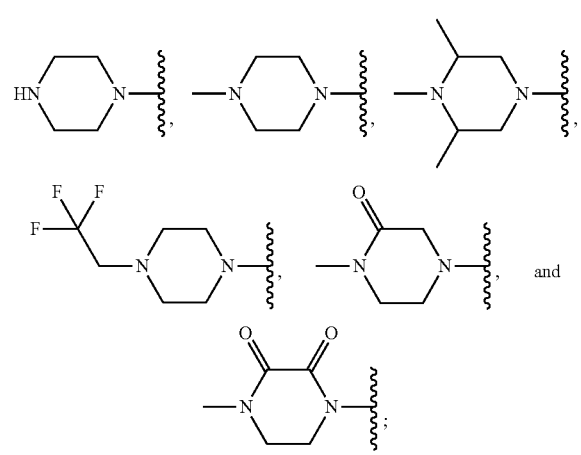

and

R³ is selected from

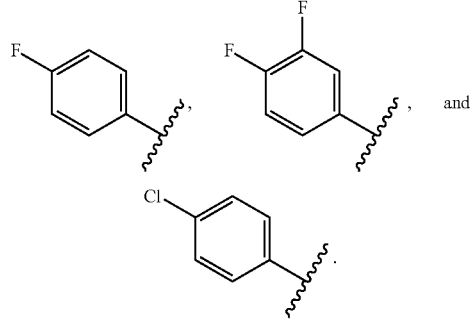

18. The pharmaceutical composition of claim 15, wherein the compound is selected from:

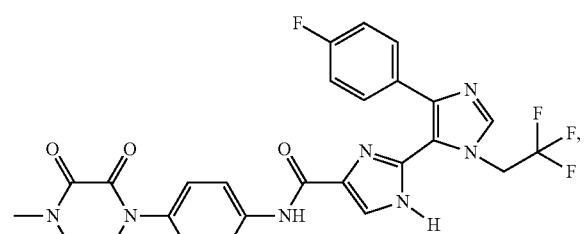

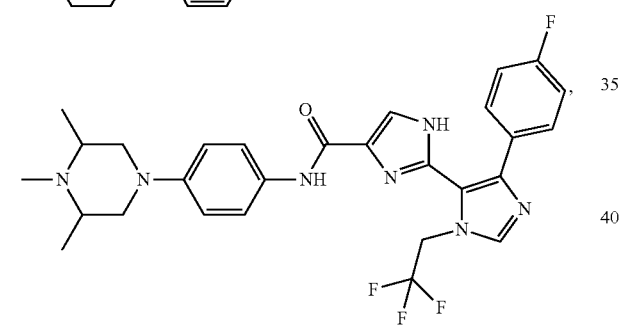

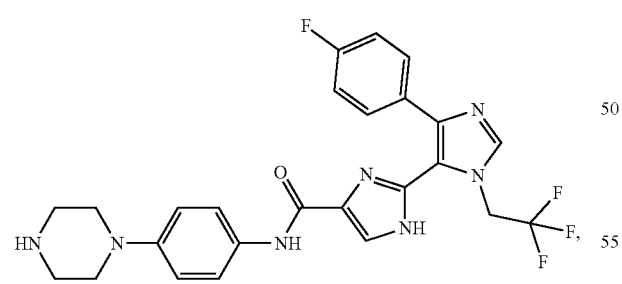

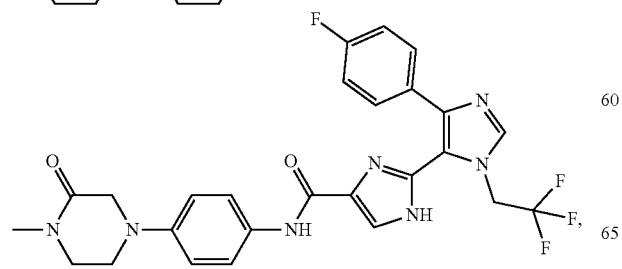

-continued

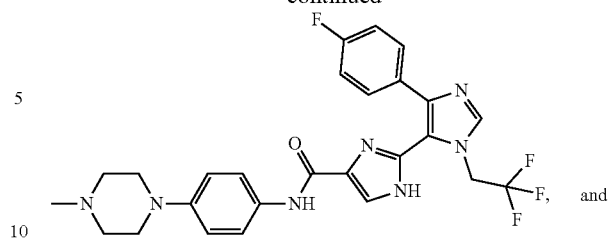

or a pharmaceutically acceptable salt thereof.

19. The pharmaceutical composition of claim 15, wherein the compound is

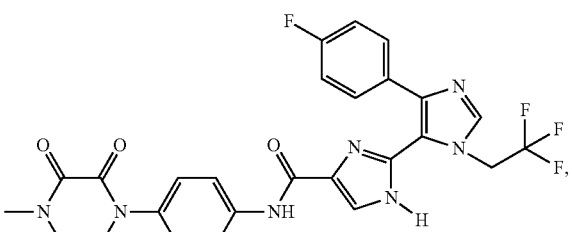

or a pharmaceutically acceptable salt thereof.

20. The pharmaceutical composition of claim 15, wherein the compound is

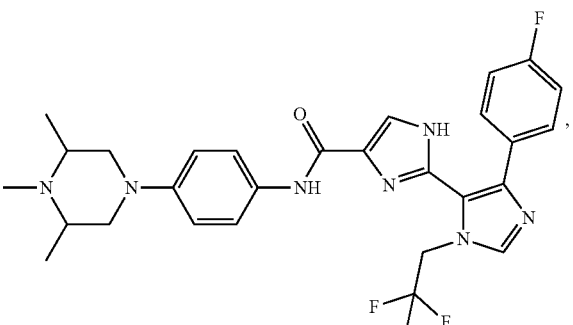

or a pharmaceutically acceptable salt thereof.

21. The pharmaceutical composition of claim 15, wherein the compound is

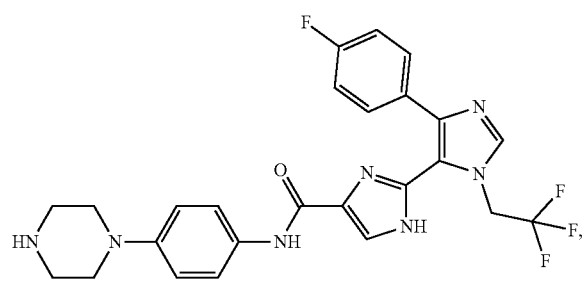 [SMILES: O=C(Nc1ccc(N2CCNCC2)cc1)c1c[nH]c(-c2c(-c3ccc(F)cc3)ncn2CC(F)(F)F)n1]

or a pharmaceutically acceptable salt thereof.

22. The pharmaceutical composition of claim 15, wherein the compound is

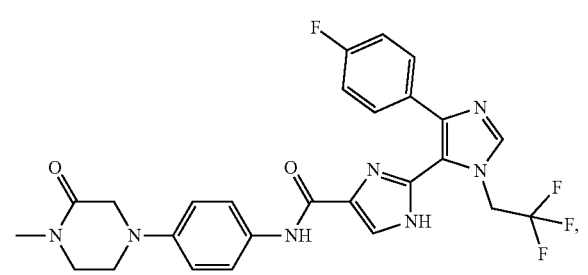 [SMILES: CN1CCN(c2ccc(NC(=O)c3c[nH]c(-c4c(-c5ccc(F)cc5)ncn4CC(F)(F)F)n3)cc2)CC1=O]

or a pharmaceutically acceptable salt thereof.

23. The pharmaceutical composition of claim 15, wherein the compound is

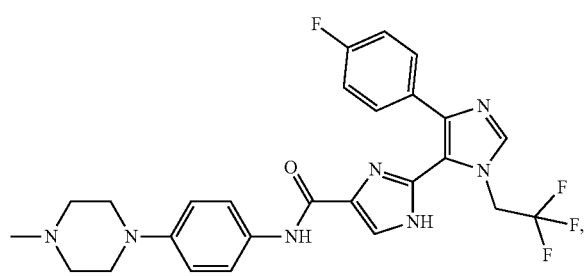 [SMILES: CN1CCN(c2ccc(NC(=O)c3c[nH]c(-c4c(-c5ccc(F)cc5)ncn4CC(F)(F)F)n3)cc2)CC1]

or a pharmaceutically acceptable salt thereof.

24. The pharmaceutical composition of claim 15, wherein the compound is

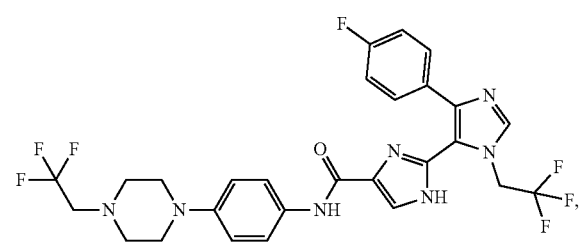 [SMILES: O=C(Nc1ccc(N2CCN(CC(F)(F)F)CC2)cc1)c1c[nH]c(-c2c(-c3ccc(F)cc3)ncn2CC(F)(F)F)n1]

or a pharmaceutically acceptable salt thereof.

25. The compound of claim 1, or a pharmaceutically acceptable salt thereof, wherein the compound or a pharmaceutically acceptable salt thereof is

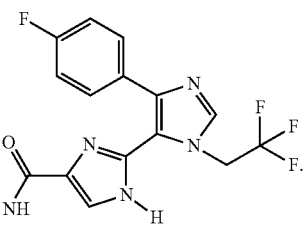

26. The compound of claim 1, or a pharmaceutically acceptable salt thereof, wherein the compound or a pharmaceutically acceptable salt thereof is

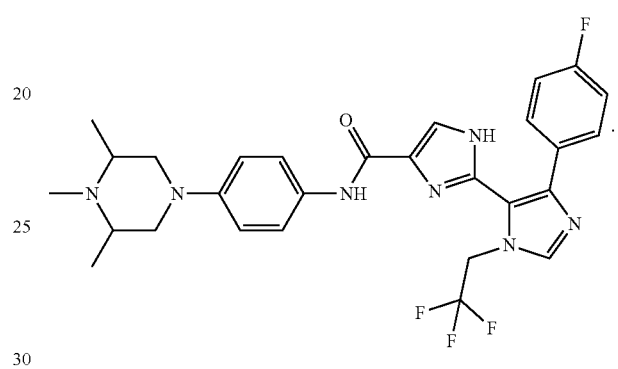

27. The compound of claim 1, or a pharmaceutically acceptable salt thereof, wherein the compound or a pharmaceutically acceptable salt thereof is

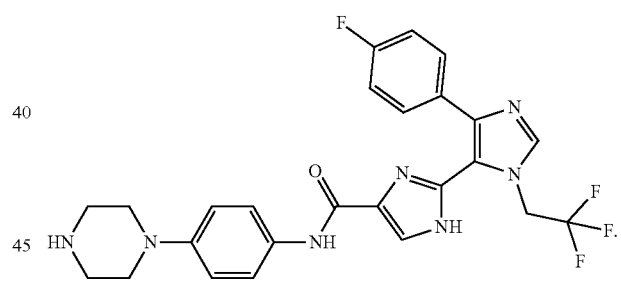

28. The compound of claim 1, or a pharmaceutically acceptable salt thereof, wherein the compound or a pharmaceutically acceptable salt thereof is

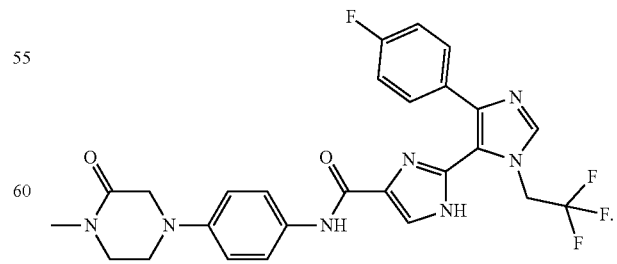

29. The compound of claim 1, or a pharmaceutically acceptable salt thereof, wherein the compound or a pharmaceutically acceptable salt thereof is

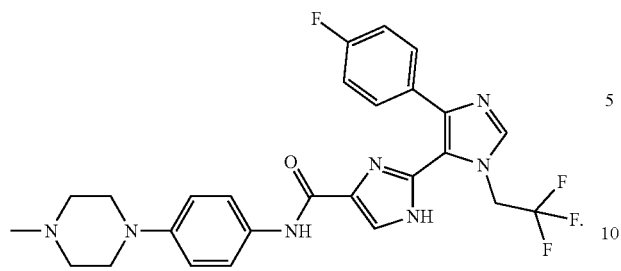
30. The compound of claim 1, or a pharmaceutically acceptable salt thereof, wherein the compound or a pharmaceutically acceptable salt thereof is
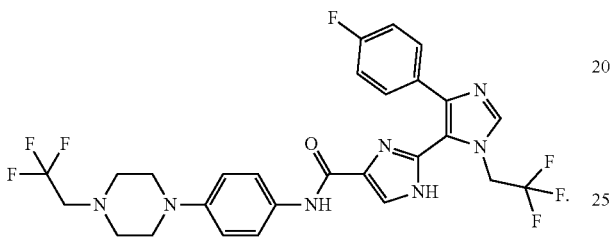
* * * * *